US012516347B2

(12) United States Patent
Paul et al.

(10) Patent No.: US 12,516,347 B2
(45) Date of Patent: Jan. 6, 2026

(54) LINKAGE OF A DISTAL PROMOTER TO A GENE OF INTEREST BY GENE EDITING TO MODIFY GENE EXPRESSION

(71) Applicant: LIMAGRAIN EUROPE, Saint Beauzire (FR)

(72) Inventors: Wyatt Paul, Pont-du-Chateau (FR); Pascual Perez, Chanonat (FR); Jean-Philippe Pichon, Clermont Ferrand (FR)

(73) Assignee: LIMAGRAIN EUROPE, Saint-Beauzire (FR)

( * ) Notice: Subject to any disclaimer, the term of this patent is extended or adjusted under 35 U.S.C. 154(b) by 169 days.

(21) Appl. No.: 18/274,023

(22) PCT Filed: Feb. 1, 2022

(86) PCT No.: PCT/EP2022/052357
§ 371 (c)(1),
(2) Date: Jul. 25, 2023

(87) PCT Pub. No.: WO2022/167421
PCT Pub. Date: Aug. 11, 2022

(65) Prior Publication Data

US 2024/0425873 A1 Dec. 26, 2024

(30) Foreign Application Priority Data

Feb. 2, 2021 (EP) .................................... 21305141

(51) Int. Cl.
*C12N 15/82* (2006.01)

(52) U.S. Cl.
CPC ..... *C12N 15/8289* (2013.01); *C12N 15/8213* (2013.01); *C12N 15/8216* (2013.01)

(58) Field of Classification Search
None
See application file for complete search history.

(56) References Cited

U.S. PATENT DOCUMENTS

2015/0132269 A1 5/2015 Orkin et al.

FOREIGN PATENT DOCUMENTS

| | | | | |
|---|---|---|---|---|
| CN | 106947750 A | 7/2017 | | |
| EP | 3 690 047 A2 | 8/2020 | | |
| WO | 2019/023291 A2 | 1/2019 | | |
| WO | WO-2019086510 A1 | * | 5/2019 | ......... C12N 15/8287 |
| WO | 2020/117553 A1 | 6/2020 | | |

OTHER PUBLICATIONS

Ling, Jia, et al. "Bicoid-dependent activation of the target gene hunchback requires a two-motif sequence code in a specific basal promoter." Molecular cell 75.6 (2019): 1178-1187 (Year: 2019).*

May 13, 2022 International Search Report issued in International Patent Application No. PCT/EP2022/052357.

May 13, 2022 Written Opinion issued in International Patent Application No. PCT/EP2022/052357.

Li et al., "Interrogation of enhancer function by enhancer-targeting CRISPR epigenetic editing", Nature Communications, vol. 11, No. 1, Jan. 24, 2020.

Hay et al., "Disruption of an enhancer associated with addictive behaviour within the cannabinoid receptor-1 gene suggests a possible role in alcohol intake, cannabinoid response and anxiety-related behaviour", Psychoneuroendocrinology, vol. 109, Aug. 13, 2019.

Krishnan et al., "CRISPR deletion of the C9ORF72 promoter in ALS/FTD patient motor neurons abolishes production of dipeptide repeat proteins and rescues neurodegeneration", Acta Neuropathologica, 2020, vol. 140, pp. 81-84.

Cermak et al., "A Multipurpose Toolkit to Enable Advanced Genome Engineering in Plants", The Plant Cell, vol. 29, Jun. 2017, pp. 1196-1217.

Shou et al., "Precise and Predictable CRISPR Chromosomal Rearrangements Reveal Principles of Cas9-Mediated Nucleotide Insertion", Molecular Cell, vol. 71, Aug. 16, 2018, pp. 489-509.

Schmidt et al., "Efficient induction of heritable inversions in plant genomes using the CRISPR/Cas system", The Plant Journal, 2019, vol. 98, pp. 577-589.

Ordon et al., "Generation of chromosomal deletions in dicotyledonous plants employing a user-friendly genome editing toolkit", The Plant Journal, 2017, vol. 89, pp. 155-168.

Li et al., "Efficient inversions and duplications of mammalian regulatory DNA elements and gene clusters by CRISPR/Cas9", Journal of Molecular Cell Biology, 2015, vol. 7, No. 4, pp. 284-298.

Korablev et al., "Generation of megabase-scale deletions, inversions and duplications involving the contactin-6 gene in mice by CRISPR/Cas9 Technology", BMC Genetics, 2017, vol. 18, pp. 53-60.

Durr et al., "Highly efficient heritable targeted deletions of gene clusters and non-coding regulatory regions in *Arabidopsis* using CRISPR/Cas9", Scientific Reports, 2018, pp. 1-11.

Cai et al., "CRISPR/Cas9-Mediated Deletion of Large Genomic Fragments in Soybean", International Journal of Molecular Sciences, 2018, vol. 19, pp. 1-13.

* cited by examiner

*Primary Examiner* — Weihua Fan
(74) *Attorney, Agent, or Firm* — Oliff PLC

(57) ABSTRACT

Gene editing to link a distal promoter to a gene of interest in order to modify the expression of the gene. The desired gene editing is a deletion or inversion. The invention relates to a method to enhance the expression of a fertility-restorer gene of interest in a plant. The invention also relates to the plant obtained by such methods.

23 Claims, 8 Drawing Sheets

Specification includes a Sequence Listing.

LINKAGE OF A DISTAL PROMOTER TO A GENE OF INTEREST BY GENE EDITING TO MODIFY GENE EXPRESSION

The invention relates to gene editing, preferably in a plant, to link a distal promoter to a gene of interest in order to modify the expression of said gene. The desired gene editing is preferably a deletion or inversion. More specifically, said invention relates to a method to enhance the expression of a fertility-restorer gene of interest in a plant.

BACKGROUND

The expression pattern and the strength of a promoter are key elements in the expression of genes. Genetic modification approaches highlighted the fact that the use of a strong constitutive promoter to drive the expression of a plant gene was necessary to boost the expression of a gene in order to improve a specific trait of interest. Other possibilities offered by genetic engineering involved the use of a promoter with a different pattern of expression in the plant or a promoter with a different pattern of expression throughout the plant development cycle.

The recent gene editing technologies are offering new possibilities for researchers to modify the expression of genes. It is now possible to activate or repress target genes by using inactivated endonucleases coupled with activator or repressor domains. Some technologies also target promoters to add specific domains within the regulatory regions of genes by homologous recombination. But some of these gene editing technologies are relatively similar to technologies previously used to obtain GMO as they require the insertion of heterologous DNA within the plant genomes.

The use of gene editing to create deletions or inversions in the genome of plants or mammals has already been disclosed. For example, Cai et al. disclose a CRISPR/Cas9-mediated deletion of large genomic fragments in soybean, Durr et al. disclose deletions of gene clusters and non-coding regulatory regions in *Arabidopsis* using CRISPR/Cas9 for functional genomic studies, and Ordon et al. describe chromosomal deletions in dicotyledonous plants by gene editing. Relative to mammals, Korablev et al. mention deletions, inversions and duplications involving the Contactin-6 gene, using a CRISPR-Cas9 technology, to develop new mouse lines. Li et al. also disclose inversions and duplications of mammalian regulatory DNA elements and gene clusters by CRISPR/Cas9. The use of gene editing to create chromosome inversions has also been described, as in WO2020/117553, but only to reduce the expression of a gene of interest.

Therefore, deletions or inversions into a genome by gene editing have already been disclosed in the prior art. However, none of these deletions and/or inversions aims to operably link a distal endogenous promoter to a gene of interest.

Fertility-restorer (Rf) genes are essential today for the development of hybrids, especially in autogamous species like wheat. To avoid self-pollination, the plant that is used as the female parent has to be male sterile. The male parent is generally a fertility restorer line. The hybrid progeny of the cross will have normal restored pollen fertility.

It is a goal of breeders to move towards hybrid wheat since hybrid varieties usually outperform inbreds. Since wheat is dioecious and largely autogamous, the production of hybrid seed requires systems to facilitate crossing and reduce the cost of hybrid seed production. Such a system is the use of male-sterile 'female' plant line crossed to a male fertile line such that all the seed harvested from the female, male-sterile plants will be F1 hybrid seed. Male-sterile plants can be produced using cytoplasmic male sterility (CMS) where the female plant carries 'defective' mitochondria that often express novel ORFs leading to the production of no or defective pollen. Use of CMS systems for hybrid seed production requires that the male line used in the hybrid seed production cross carries a nuclear gene or genes that repair the defective mitochondria in the F1. This leads to full male-fertility of the F1 plants that are grown by the farmer. These nuclear genes in the male line are referred to as CMS restorer genes. One potential CMS system for hybrid wheat production is that using *T. timopheevii* CMS (Bohra A, Jha U C, Adhimoolam P, et al (2016) Cytoplasmic male sterility (CMS) in hybrid breeding in field crops. Plant Cell Rep 35:967-993. doi: 10.1007/s00299-016-1949-3). A drawback of this system is that a combination of several restorer genes (Rf1, Rf3, Rf4 and Rf7) is required to give full male fertility to the F1. For the breeder this makes the system more complex to use since each male line has to be converted to contain 3 or 4 independently segregating restorer genes.

It is thus desirable to identify or create a single effective restorer locus.

In this context, the development of modified organisms which do not require the insertion of heterologous DNA within their genomes is of high interest, notably in plants. A method to obtain hybrid plant, more specifically hybrid wheat, which requires the use of only one fertility restorer gene is also of major importance.

It is therefore the object of this invention to provide a method to meet these needs. Preferably, it is an object of this invention to modify the expression of a gene of interest, more preferably a fertility restorer gene, to obtain hybrid plants useful for the seed industry.

SUMMARY

The inventors have shown that the expression of a gene of interest can be modified, preferably enhanced, using gene editing to operably link a distal endogenous promoter, or part of an endogenous promoter, to said gene of interest.

Therefore, in a first aspect, it is disclosed herein a method to modify the expression of a gene of interest in an organism, said method comprising the steps of: a) introducing into said organism at least one gene editing system; b) allowing the said gene editing system to perform the desired editing at a target genomic site; and wherein the said gene editing system is designed so that, after the desired editing, the gene of interest is operably linked to an endogenous promoter, or part of an endogenous promoter, said endogenous promoter being distal from a naturally occurring promoter of the gene of interest in the genome of a non-modified organism.

In a specific embodiment, said organism is a eukaryotic organism, provided that the organism is not a human or an animal. In specific embodiments that may be combined with the previous embodiments, the organism is a plant, preferably a polyploid plant, such as wheat, oat, rapeseed, potato, sugar cane, . . . .

In a specific embodiment that may be combined with the previous embodiments, the performance of the desired editing as recited in step b) comprises two or more DNA breaks within said target genomic site.

In a specific embodiment that may be combined with the previous embodiments, the desired editing is a deletion or an inversion, the deletion preferably having a size from 10 kb to 10 Mb and the size of said inversion being from 10 kb to 100 Mb.

In a specific embodiment that may be combined with the previous embodiments, said deletion is a deletion of a genomic region comprising the full naturally occurring promoter or of a genomic region comprising only a part of the naturally occurring promoter. Alternatively, in a specific embodiment that may be combined with the previous embodiments, said inversion is an inversion of a genomic region resulting in the replacement of the naturally occurring promoter by said endogenous promoter or is an inversion of a genomic region resulting in the replacement of a part of the naturally occurring promoter by a part of said endogenous promoter.

In a specific embodiment that may be combined with the previous embodiments, said gene of interest is a fertility-restorer gene, preferably an RFL29 gene, more preferably represented by the coding sequence of SEQ ID NO:14. In another specific embodiment that may be combined with the previous embodiments, said fertility-restorer gene is an RFL79 gene, more preferably represented by SEQ ID NO:58.

In a specific embodiment that may be combined with the previous embodiments, said endogenous promoter drives a higher expression of the gene of interest, changes the pattern of expression of the gene of interest during the development cycle of a plant, changes the spatial pattern of expression of the gene of interest or is a promoter which is activated by biotic or abiotic stress.

In a specific embodiment that may be combined with the previous embodiments, the modification of the expression is an enhancement, said endogenous promoter being notably a strong promoter.

In a specific embodiment that may be combined with the previous embodiments, the gene editing system is designed to maintain the Kozak sequence of the gene of interest.

In a specific embodiment that may be combined with the previous embodiments, the break occurs in a promoter, in an untranslated region, in gene-gene junction region, in exon or in intron, preferably in a promoter or in an untranslated region.

In a specific embodiment that may be combined with the previous embodiments, said gene editing system is chosen among a zinc finger nuclease (ZFN) gene editing system, a transcription activator-like effector nucleases (TALEN) gene editing system, a clustered regularly interspaced short palindromic repeats (CRISPR) gene editing system, or a meganuclease gene editing system, preferably a CRISPR gene editing system. In a more specific embodiment, said gene editing system comprises at least one enzyme chosen among: meganuclease, zinc-finger nuclease, transcription-activator like effector nuclease, CRISPR-nickase or CRISPR-nuclease.

In a specific embodiment that may be combined with the previous embodiments, the CRISPR gene editing system comprises multiple guide sequences capable of hybridizing to multiple target sequences within the target genomic site.

In a specific embodiment that may be combined with the previous embodiments, the method comprises the steps of:

a) identifying an endogenous promoter, distal from a naturally occurring promoter of a gene of interest in a non-modified organism, which is capable of modifying the expression of said gene of interest;
b) identifying the deletion or insertion of a genomic region to be performed in order to operably link said endogenous promoter, or part of an endogenous promoter, to said gene of interest;
c) introducing into said organism at least one gene editing system designed to perform the deletion or insertion identified in step b);
d) allowing said gene-editing system to perform the desired editing at the target genomic site;
e) optionally selecting an organism with the desired editing.

It is also disclosed herein, as a second aspect, a method to enhance the expression of a fertility-restorer gene of interest, in a plant, said method comprising the steps of: a) introducing into said plant, at least one gene-editing system, preferably a CRISPR gene-editing system; b) allowing the said gene-editing system to perform the desired editing at a target genomic site; and wherein the said gene editing system is designed so that, after the desired editing, the fertility-restorer gene of interest is operably linked to an endogenous promoter, or part of an endogenous promoter, said endogenous promoter being distal from a naturally occurring promoter of the fertility-restorer gene of interest in the genome of a non-modified plant.

This second aspect is a particular embodiment of the first aspect, wherein the organism is a plant, more specifically a wheat plant. Consequently, all the specific embodiments disclosed above in relation to the first aspect also apply and may also be combined with this second aspect.

In a specific embodiment that may be combined with the previous embodiments, after the desired editing, the fertility-restorer gene of interest is operably linked to an endogenous promoter, said endogenous promoter being a strong promoter.

In a specific embodiment that may be combined with the previous embodiments, the fertility-restorer gene is RFL29, and preferably said endogenous promoter identified to replace the naturally-occurring promoter of RFL29 is chosen among PK-like promoter (notably PK-like promoter in *T. aestivum* represented by SEQ ID NO:10), RAE1-like promoter (notably RAE1-like promoter in *T. aestivum* represented by SEQ ID NO:11) or At5g02240-like promoter (notably At5g02240-like promoter in *T. aestivum* represented by SEQ ID NO:59).

In another specific embodiment, that may be combined with the previous embodiments, the fertility-restorer gene is RFL79.

In a specific embodiment that may be combined with the previous embodiments, the gene editing system is a CRISPR gene-editing system which is a delivery system comprising and operably configured to deliver into a plant cell, either CRISPR-Cas complex components, or one or more polynucleotide sequences comprising or encoding said components, wherein said CRISPR-Cas complex components, comprises:

(i) at least two guide sequences capable of hybridizing to the two ends of the target genomic site to effect two breaks, thereby allowing a deletion of said target genomic site or an inversion at said target genomic site;
(ii) a CRISPR-associated protein, and wherein said CRISPR-Cas complex is operable in a plant cell.

The present disclosure also relates to a plant useful in the above-mentioned methods. It is thus disclosed, in a third aspect, a plant, or a plant part, comprising a gene editing system designed to perform a desired editing at a target genomic site, so that after the desired editing occurred, a gene of interest in the plant is operably linked to an endogenous promoter, or part of an endogenous promoter, said endogenous promoter being distal from a naturally occurring promoter of the gene of interest in the genome of a non-modified plant.

The present disclosure, in a fourth aspect, further relates to the plant as obtained with the above-mentioned methods, as well a method to identify such a plant. Such identification method comprises a step of PCR after the desiring editing was performed, in order to detect bands corresponding to the desired editing, notably inversion or deletion. To evaluate the result of the gene editing, such an identification method can also be used to detect the expression level of the gene of interest, as well as the level of the protein encoded by said gene. A phenotypic analysis can also be performed in order to determine if the modified plant has a fertility restoration phenotype.

The present disclosure, in a fifth aspect, also relates to a method to restore fertility in wheat, comprising a step of crossing a sterile wheat plant with a plant wherein the expression of a fertility-restorer gene has been enhanced according to the above-mentioned methods.

BRIEF DESCRIPTION OF THE FIGURES

The FIG. 1 shows genomic deletions or inversions to alter the expression of a gene of interest (GOI).

The FIG. 1A presents the genomic context of the target region. GOI stands for Gene Of Interest. a, b, c, e represents the cutting/cleavage sites. Genes 1, 2, 3 are genes in the GOI region. Prom G1, G2, G3 are the promoters of Genes 1, 2, 3 respectively.

The FIG. 1B shows the deletion obtained with a cleavage at both “a” sites. Because of the deletion, the GOI is now under the control of endogenous distal promoter Prom G1 instead of its naturally-occurring promoter.

The FIG. 1C shows the deletion obtained with a cleavage at both “b” sites. Because of the deletion, the GOI is now under the control of a chimeric promoter Prom GOI::G1 comprising a region of its naturally-occurring promoter and a region of endogenous distal promoter Prom G1.

The FIG. 1D shows the inversion obtained with a cleavage at sites “a” and “c”. Because of the inversion, the GOI is now under the control of endogenous distal promoter Prom G2 instead of its naturally-occurring promoter.

The FIG. 1E shows the inversion obtained with a cleavage at sites “a” and “e”. Because of the inversion, the GOI is now under the control of endogenous distal promoter Prom G3 instead of its naturally-occurring promoter.

The FIG. 2 shows RNAseq expression data for RFL29, PK-like (or TaPK-like), RAE1-like (or TaRAE1-like) and CHSL1 in wheat spikes.

Figure 2A:
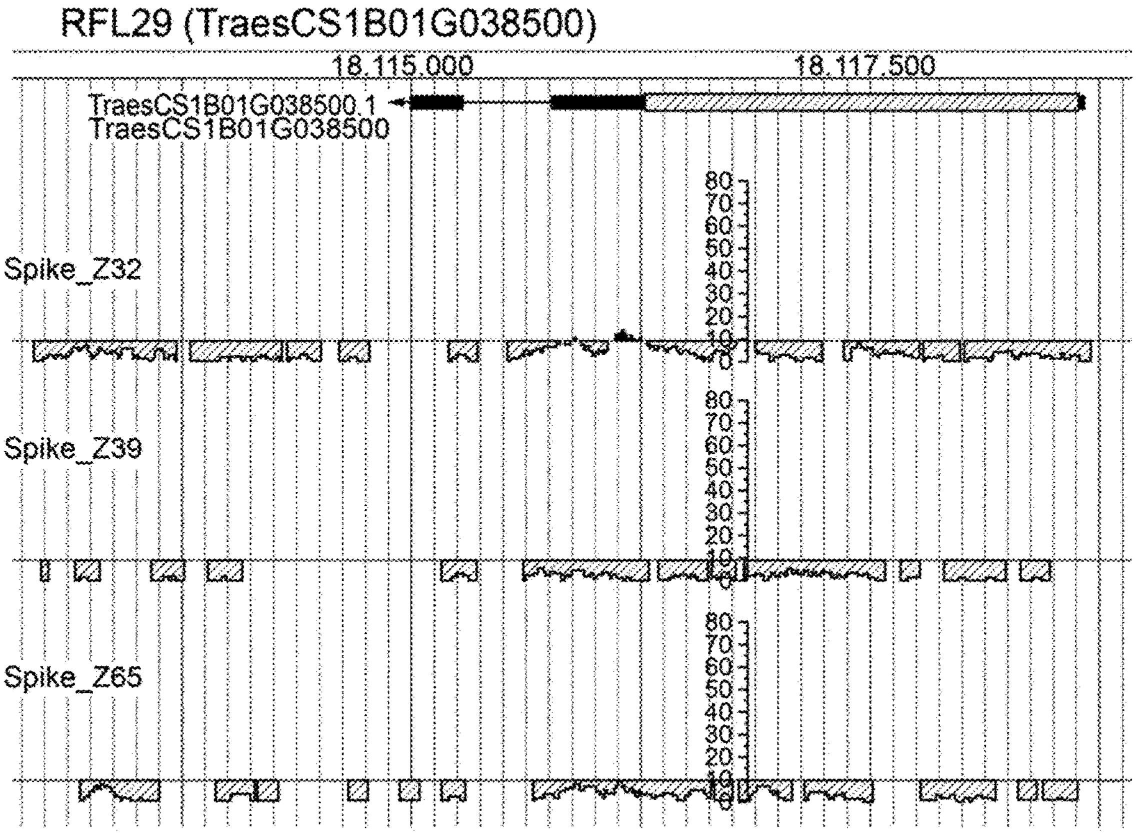
Figure 2B:
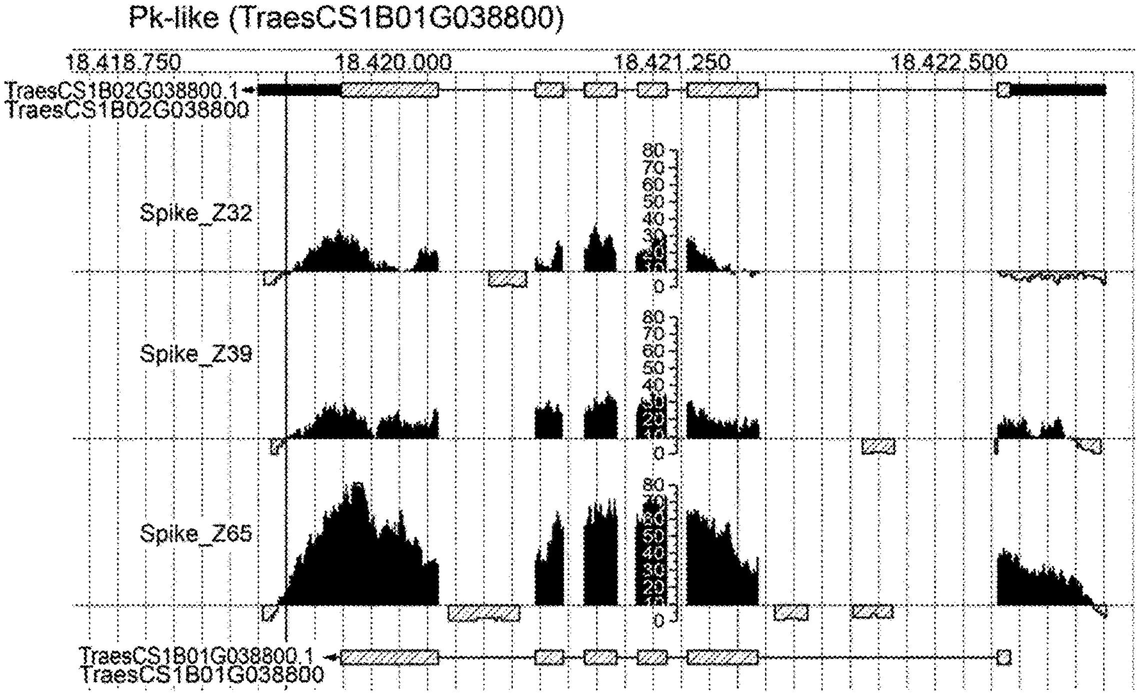
Figure 2C:
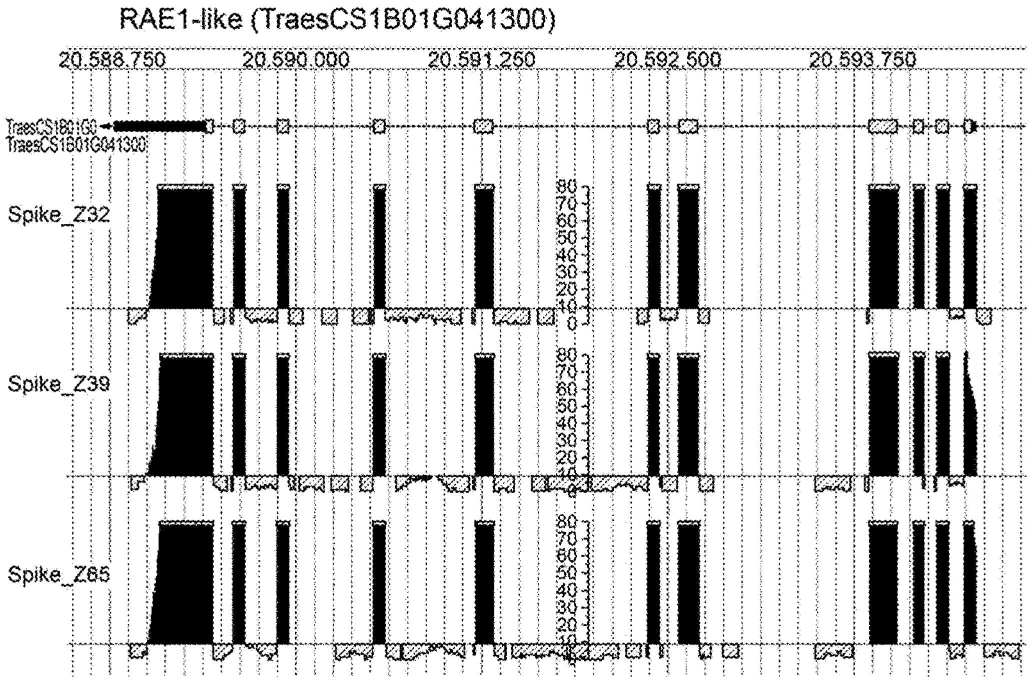

The FIG. 2A shows the RNAseq expression data for RFL29 (FIG. 2A), PK-like (or TaPK-like) (FIG. 2B), RAE1-like (or TaRAE1-like) (FIG. 2C) and CHSL1 (FIG. 2D) in wheat spikes.

Figure 2D:
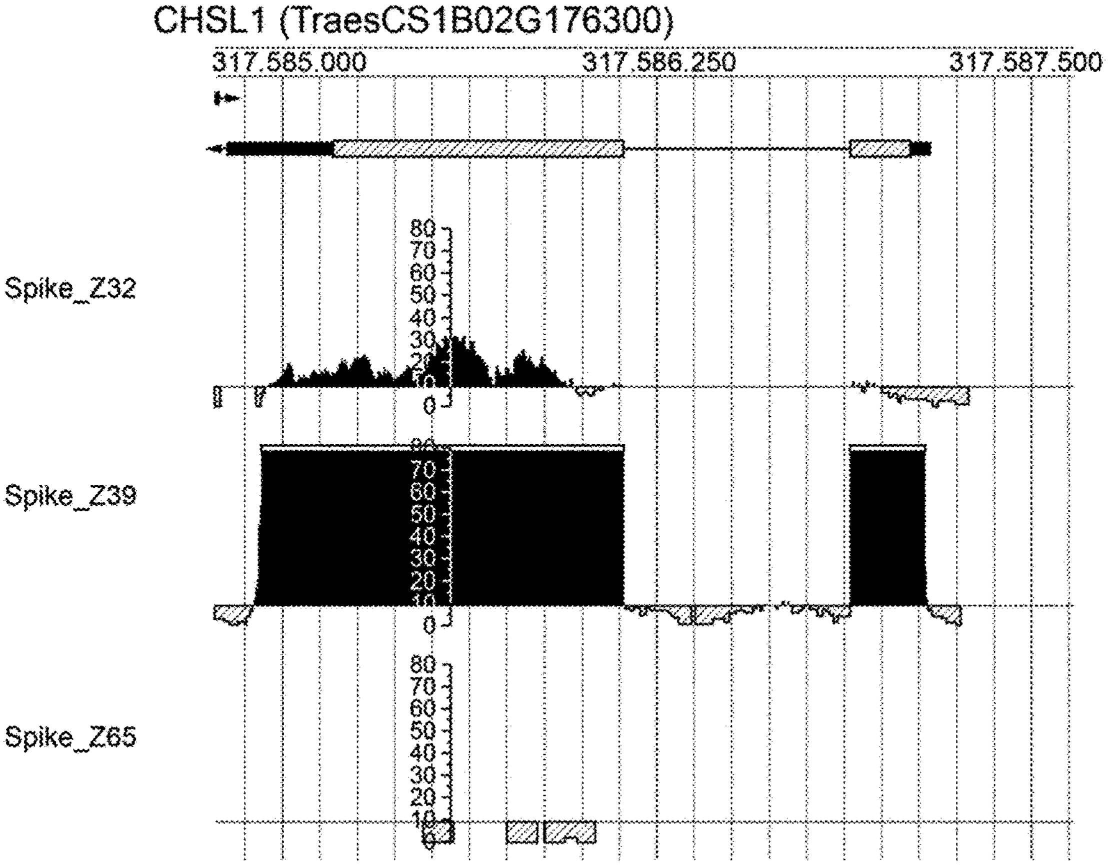
Figure 2E:
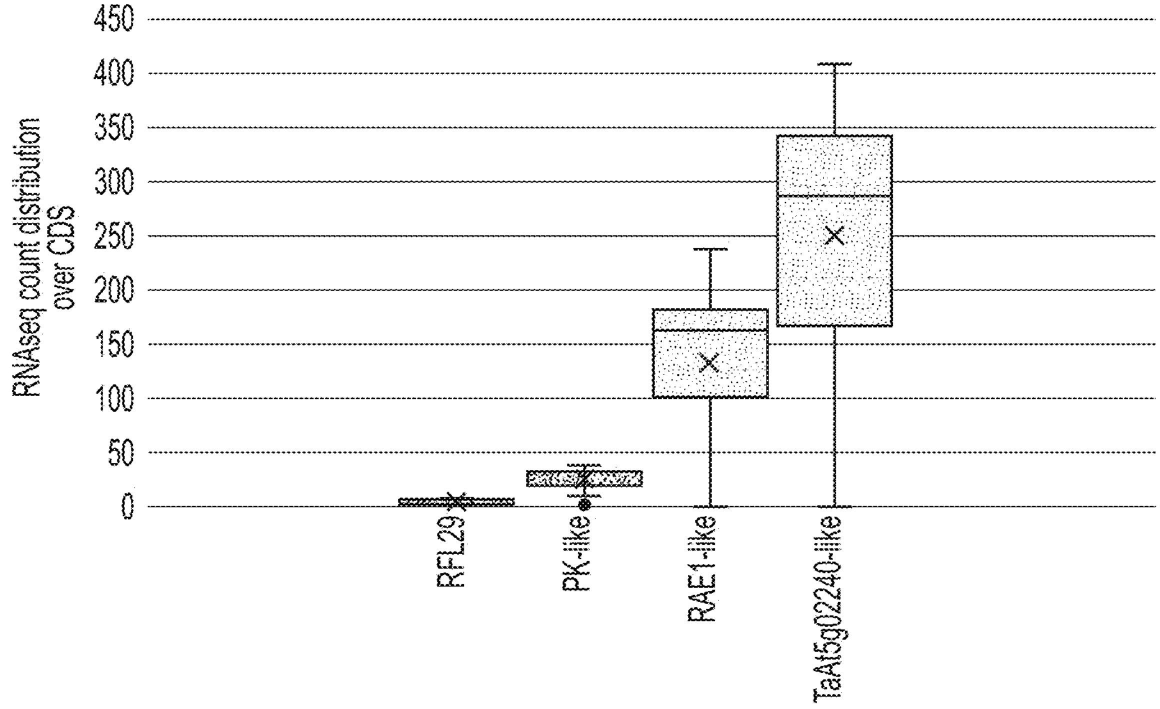

The FIG. 2E shows the expression in Z39 spikes.

Figure 3:
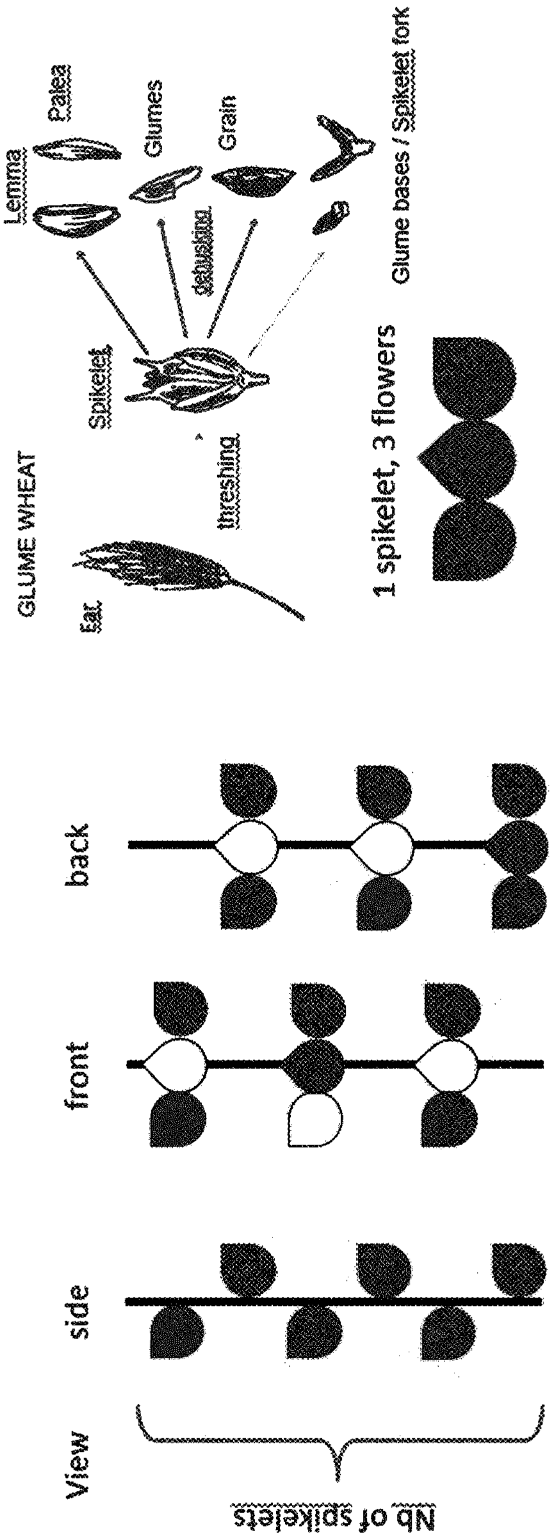

The FIG. 3 shows the procedure of fertility scoring.

The FIG. 4 shows the candidate gRNA targets for RFL29 to PK-like (or TaPK-like) and RFL29 to RAE1-like (or TaRAE1-like) deletions. The arrows represent the cleavage sites.

Figure 4A:
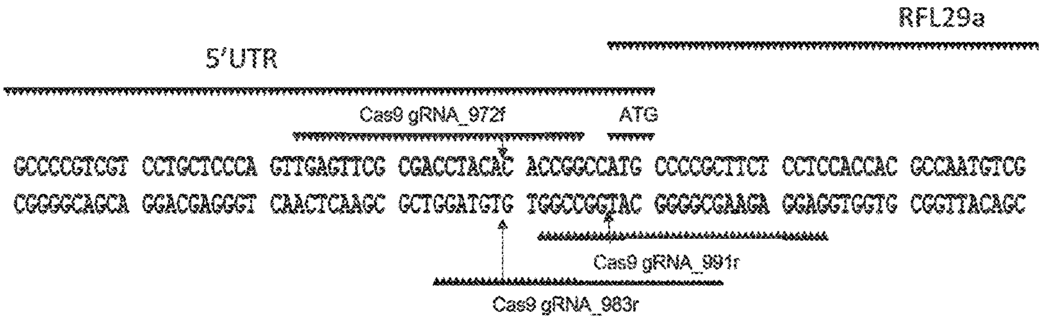

The FIG. 4A shows the positions on RFL29 gene.

Figure 4B:
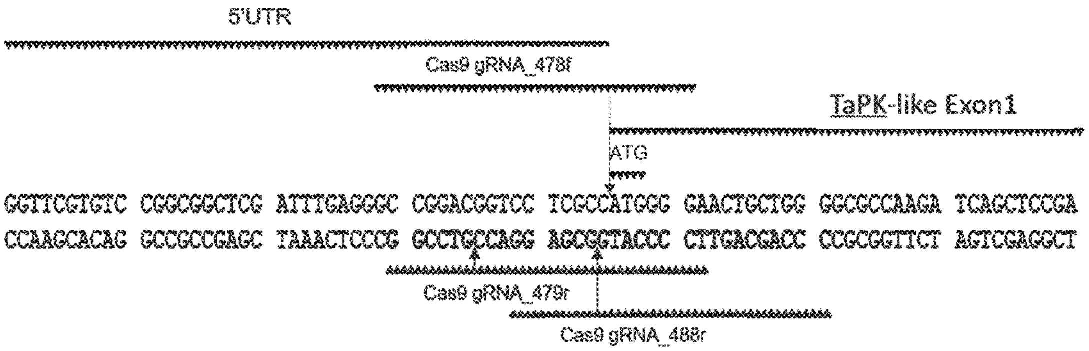

The FIG. 4B shows the positions on PK-like (or TaPK-like) gene.

Figure 4C:
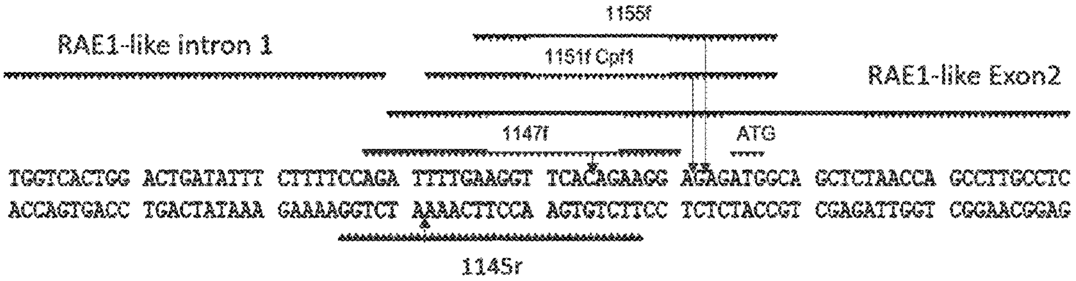

The FIG. 4C shows the positions on RAE1-like (or TaRAE1-like) gene.

Figure 5:
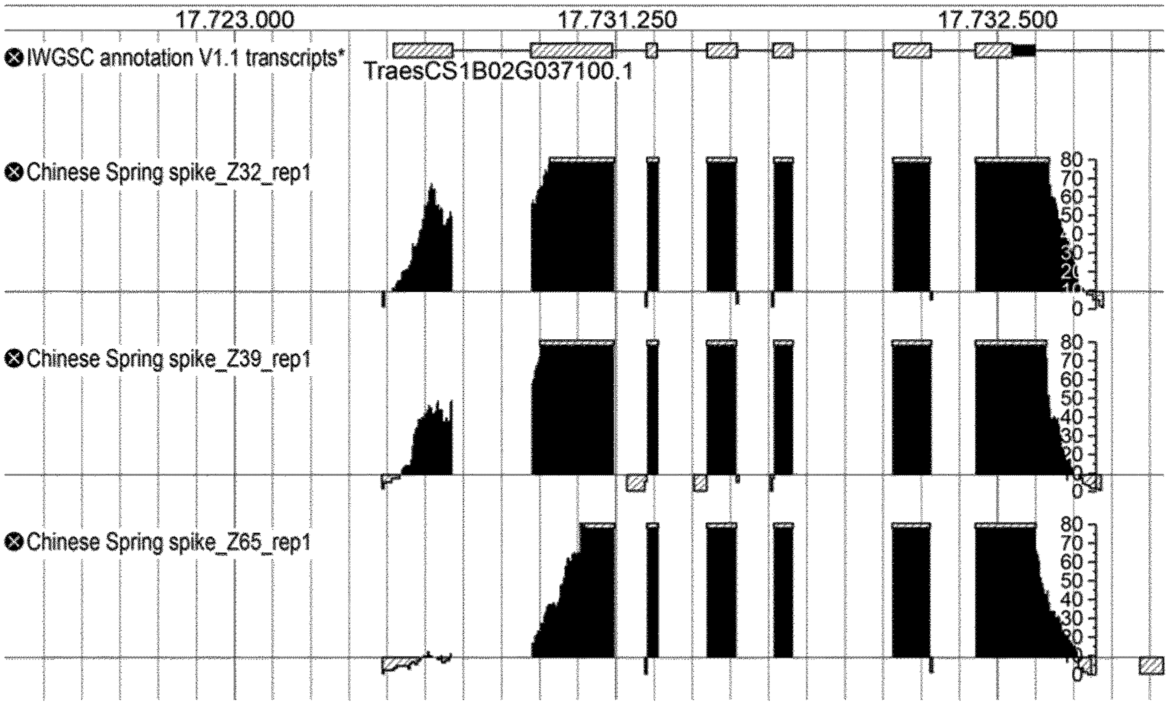

The FIG. 5 shows RNAseq expression data for TaAt5g02240-like in spikes.

The FIG. 6 shows the candidate gRNA targets for RFL29-TaAt5g02240-like inversion. The arrows represent the cleavage sites.

Figure 6A:
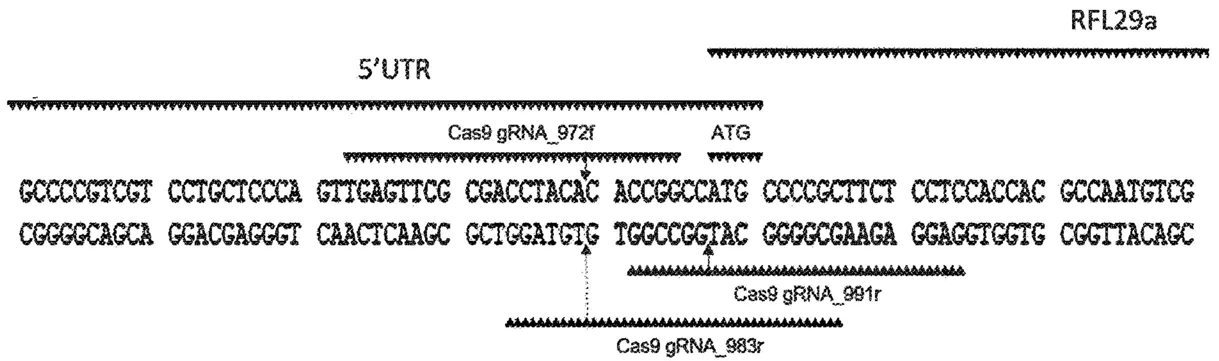

The FIG. 6A shows the positions on RFL29 gene.

Figure 6B:
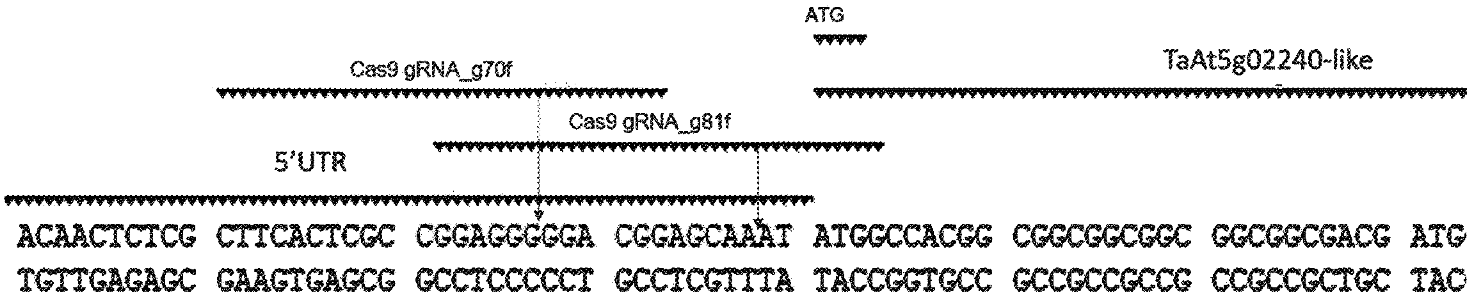

The FIG. 6B shows the positions on At5g02240-like (or Ta At5g02240-like) gene.

DETAILED DESCRIPTION

Organism According to the Present Disclosure

In specific embodiments of the disclosure, the organism is a eukaryotic organism, provided that the organism is not a human or other animal.

Preferably, the organism is a plant. As used herein, the term “plant” or “plants” refer to the entire plant but also plant parts (cells, tissues or organs, seed pods, seeds, severed parts such as roots, leaves, flowers, pollen, etc.), progeny of the plants which retain the distinguishing characteristics of the parents (i.e. the modification of the expression of the gene of interest), such as seed obtained by selfing or crossing, e.g. hybrid seeds (obtained by crossing two inbred parent plants), hybrid plants and plant parts derived there from are encompassed herein, unless otherwise indicated. The plant can be a monocotyledon or a dicotyledonous plant.

In specific embodiments, said plant is a polyploid plant such as wheat, oat, rapeseed, potato, sugar cane, . . . .

As used herein, the term “wheat” refers to a plant of *Triticum* gender, as for example *T. aestivum, T. aethiopicum, T. araraticum, T. boeoticum, T. carthlicum, T. compactum, T. dicoccoides, T. dicoccon, T. durum, T. ispahanicum, T. karamyschevii, T. macha, T. militinae, T. monococcum, T. polonicum, T. spelta, T. sphaerococcum, T. timopheevii, T. turanicum, T. turgidum, T. urartu, T. vavilovii, T. zhukovskyi* Faegi. Preferably, the wheat plant is *T. aestivum*. Wheat plant also refers to *Aegilops* gender and Triticale.

As used herein, the term “oat” refers to a plant of *Avena* gender, as for example *A. sativa*.

As used herein, the term “rapeseed” refers to a plant of *Brassica* gender, as for example *B. napus, B. juncea* and *B. rapa*; preferably *B. napus*.

As used herein, the term “potato” refers to a plant of *Solanum* gender, as for example *Solanum tuberosum*.

As used herein, the term “sugar cane” refers to a plant of *Saccharum* gender, as for example *S. officinarum, S. sponteneum, S. robustum, S. sinense* and *S. barberi*.

Method to Modify the Expression of a Gene of Interest in an Organism

A first aspect of the present disclosure relates to a method to modify the expression of a gene of interest in an organism, said method comprising the steps of:

a) introducing into said organism at least one gene editing system;

b) allowing the said gene-editing system to perform the desired editing at a target genomic site;

and wherein the said gene editing system is designed so that, after the desired editing, the gene of interest is operably linked to an endogenous promoter, or part of an endogenous promoter, said endogenous promoter being distal from a naturally occurring promoter of the gene of interest in the genome of a non-modified organism.

As used herein, the term “modify the expression of a gene” refers to an enhancement of the expression, or a modification of an expression pattern. In a preferred embodiment that may be combined with the previous embodiments, said modification is an enhancement. In such a case, the endogenous promoter can be considered as a strong promoter. In a specific embodiment, the gene expression modification can include modification at a precursor mRNA level, at a mature mRNA level or at translation level.

As used herein, the term "enhancement of the expression" means that the gene of interest is more expressed compared to a non-modified organism. Preferably the gene expression is increased by at least 2 fold, preferably between 2 and 100 fold, such as, at least 5, 10, 15, 20, 25, 30, 35, 40, 45, 50, 55, 60, 65, 70, 75, 80, 85, 90, 95 or 100. The term "enhancement of the expression" also means that the gene of interest is expressed when operably linked to the endogenous promoter. Indeed, in this specific embodiment, the gene of interest is not expressed in a non-modified organism, but gene expression of said gene of interest can be detected in a modified organism, after the desired editing. Relative gene expression can be measured by a q-RT-PCR method. Gene expression can also be measured by RNA-Seq.

As used herein, the term "modification of an expression pattern" means that the gene is expressed under different conditions by comparison with a non-modified organism, for example at a different time during the development cycle of a plant, in a different tissue, in presence of biotic or abiotic stress, . . . .

As used herein, the term "gene of interest" refers to an endogenous gene of the organism whose modification of the expression confers a desired characteristic to the organism, such as improved performance in the fields, improved performance in an industrial process, improved nutritional value, or improved reproductive capability. The gene of interest can encode for a protein of interest, but can also encode for a functional RNA of interest, such as antisense RNA, rRNA, tRNA, . . . . The gene of interest can be a gene which is not expressed in a non-modified organism and which becomes expressed when operably linked to an endogenous promoter, or part of an endogenous promoter. The gene of interest can be dominant, recessive or semi-dominant. As used herein "expression of a gene" means that the coding sequence of the gene is transcribed, and optionally translated.

As used herein, the term "operably linked" means that the gene of interest is linked to said endogenous promoter in a manner that allows for expression of the gene of interest.

As used herein, the term "introducing" means that the gene editing system penetrates into the cell of the organism, so that the system can enter the nucleus for targeted gene editing.

As used herein, the term "allowing the said gene-editing system to perform the desired editing at a target genomic site" means that two or more DNA breaks are made within the target genomic site, and that the strand cuts are then repaired. In other words, it also means "making two or more DNA breaks and then selecting for an organism (more specifically a cell) wherein the target genomic site has been edited" (in such edited cell, the gene of interest is operably linked to an endogenous distal promoter, or part of an endogenous distal promoter, whereas in non-edited cell, the gene of interest is operably linked to its naturally occurring promoter).

As used herein, the term "target genomic site" refers to the genomic region wherein the gene editing occurs, i.e. the genomic region between the two cleavage sites, or the genomic region between the most remote cleavage sites if there are more than two cleavage sites. As used herein, the term "cleavage site" corresponds to genomic DNA region which comprises a sequence recognized by a specific enzyme used in gene editing system, such as nickase or nuclease, which cleave the genomic DNA region in one or both strands.

As used herein, the term "gene of interest is operably linked to an endogenous promoter, or part of an endogenous promoter" means that the coding sequence is under the transcriptional control of the endogenous promoter or part of endogenous promoter. In other words, the promoter, or part, controls the expression of the gene of interest. The said promoter sequence does not need to be contiguous with the sequence of the gene of interest, as long as the promoter still controls the expression of the gene (e.g. a transcribed sequence which is not translated, can be interposed between the promoter and the coding sequence of the gene of interest). In a preferred embodiment, after the gene editing occurred, the endogenous promoter is contiguous to the gene of interest.

As used herein, the term "endogenous promoter" means that the promoter is native to the organism.

As used herein, the term "the said promoter distal from a naturally occurring promoter of the gene of interest" means that the endogenous promoter is distant from the gene of interest in a non-modified organism. The distance can be kilobase-sized or megabase-sized between the naturally occurring promoter of the gene of interest and the distal promoter. Said distal promoter can be located in 5' or 3' from the naturally occurring promoter. In other words, the endogenous promoter is distal compared to the naturally occurring promoter which is a proximal promoter. As used herein, the term "proximal" refers more specifically to a nucleotide sequence, upstream (5') to the coding sequence of the gene, generally from 1 base to about 500 base of the start site. The term "from 1 base to 500 base" means every value of this range, even if not explicitly recited, such as 1, 2, 3, 4, 5, 6, 7, 8, 9, 10, 20, 30, 40, 50, 60, 70, 80, 90, 100, 150, 200, 250, 300, 350, 400, 450, 500.

As used herein, the term "distal promoter" refers also to a promoter which is distant from the gene of interest in a non-modified organism, and which regulates the expression of a gene different from the gene of interest in a non-modified organism. It is only after the gene-editing that the said distal promoter regulates the expression of the gene of interest. In other words, in a non-modified organism, the gene of interest is operably linked to its naturally occurring promoter and not to the distal endogenous promoter or part of it, whereas after the gene-editing the gene of interest is operably linked to the distal endogenous promoter or part of it.

In a specific embodiment of the disclosure that may be combined with the previous embodiments, the desired editing is a deletion or an inversion.

As used herein "deletion" means that the genetic material which represents the target genomic site is lost on a chromosome. According to a specific embodiment of the disclosure that may be combined with the previous embodiments, the deletion is a deletion of a genomic region comprising the full naturally occurring promoter. In this embodiment, the full naturally occurring promoter is either replaced by the full distal endogenous promoter or by a functional part of the full distal endogenous promoter. Alternatively, said deletion is a deletion of a genomic region comprising only a part of the naturally occurring promoter. In this last embodiment, the gene editing creates thus a chimeric promoter containing two parts: one part comprising the naturally occurring promoter and one part comprising the endogenous promoter, with the proviso that such chimeric promoter is a functional promoter.

As used herein "inversion" means that the genomic region is reversed end to end within the target region site. In other words, it corresponds to a rearrangement within a single chromosome. According to a specific embodiment of the disclosure that may be combined with the previous embodiments, the inversion is an inversion of a genomic region resulting in the replacement of the naturally occurring promoter by said endogenous promoter. Alternatively, said inversion is an inversion of a genomic region resulting in the replacement of a part of the naturally occurring promoter by a part of said endogenous promoter. In this last embodiment, the gene editing creates thus two chimeric promoters containing two parts: one part comprising the naturally occurring promoter and one part comprising the endogenous promoter. In an embodiment, the two chimeric promoters can be functional and in another embodiment only one chimeric promoter is functional: the one which is operably linked to the gene of interest.

In a specific embodiment that may be combined with the previous embodiments, the size of said deletion is from 10 kb to 10 Mb. In a specific embodiment that may be combined with the previous embodiments, the size of said inversion is from 10 kb to 100 Mb. As used herein, "from 10 kb to 10 Mb" or "from 10 kb to 100 Mb" mean every value of this range, even if not explicitly recited, for example from 100 kb to 10 Mb, from 1000 kb to 10 Mb, from 100 kb to 1 Mb, from 1000 kb to 1 Mb, from 10 kb to 5 Mb, from 100 kb to 5 Mb, from 200 kb to 10 Mb, from 300 kb to 10 Mb, from 400 kb to 10 Mb, from 500 kb to 10 Mb, from 600 kb to 10 Mb, from 700 kb to 10 Mb, from 800 kb to 10 Mb, from 900 kb to 10 Mb, from 200 kb to 5 Mb, from 300 kb to 5 Mb, from 400 kb to 5 Mb, from 500 kb to 5 Mb, from 600 kb to 5 Mb, from 700 kb to 5 Mb, from 800 kb to 5 Mb, from 900 kb to 5 Mb, from 1 Mb to 10 Mb, from 2 Mb to 10 Mb, from 3 Mb to 10 Mb, from 4 Mb to 10 Mb, from 5 Mb to 10 Mb, from 6 Mb to 10 Mb, from 7 Mb to 10 Mb, from 8 Mb to 10 Mb, from 9 Mb to 10 Mb, from 10 kb to 9 Mb, from 10 kb to 8 Mb, from 10 kb to 7 Mb, from 10 kb to 6 Mb, from 10 kb to 5 Mb, from 10 kb to 4 Mb, from 10 kb to 3 Mb, from 10 kb to 2 Mb, from 10 kb to 1 Mb, or from 100 kb to 100 Mb, from 1000 kb to 100 Mb, from 10 kb to 1 Mb, from 10 kb to 10 Mb, from 10 kb to 20 Mb, from 10 kb to 30 Mb, from 10 kb to 40 Mb, from 10 kb to 50 Mb, from 10 kb to 60 Mb, from 10 kb to 70 Mb, from 10 kb to 80 Mb, from 10 kb to 90 Mb, from 100 kb to 20 Mb, from 100 kb to 30 Mb, from 100 kb to 40 Mb, from 100 kb to 50 Mb, from 100 kb to 60 Mb, from 100 kb to 70 Mb, from 100 kb to 80 Mb, from 100 kb to 90 Mb, from 1 Mb to 20 Mb, from 1 Mb to 30 Mb, from 1 Mb to 40 Mb, from 1 Mb to 50 Mb, from 1 Mb to 60 Mb, from 1 Mb to 70 Mb, from 1 Mb to 80 Mb, or from 1 Mb to 90 Mb.

In a specific embodiment of the disclosure that may be combined with the previous embodiments, the endogenous promoter drives a higher expression of the gene of interest, changes the pattern of expression of the gene of interest during the development cycle of a plant, changes the spatial pattern of expression of the gene of interest or is a promoter which is activated by biotic or abiotic stress. Abiotic stress is for example light or drought stress. Biotic stress is for example viral, bacterial or fungal invasion of the plant.

Gene Editing System Used According to the Present Disclosure

According to the disclosure, a gene editing is performed to create at least two breaks in the genomic targeted site. As used herein, the term "break" refers to a cleavage on both DNA strands. The double-stranded break can result of two separate single-stranded breaks. One double strand break on each side of the target genomic site is necessary to perform the desired editing at the target genomic site. Two single strand breaks (a single strand break on each DNA strand) on each side of the target genomic site are necessary to perform the desired editing at the target genomic site.

In a specific embodiment, the at least two breaks occur in a promoter, in an untranslated region, in gene-gene junction region, in exon or in intron. The term "untranslated region" preferably refers to a 5'UTR region. For example, one of the breaks can occur in front of the initiating Methionine ATG of the coding sequence of the gene of interest. In a specific embodiment, the gene-editing system is designed to maintain the Kozak sequence of the gene of interest.

The gene editing system which can be used are preferably chosen among a zinc finger nuclease (ZFN) gene editing system, a transcription activator-like effector nucleases (TALEN) gene editing system, a clustered regularly interspaced short palindromic repeats (CRISPR) gene editing system, or a meganuclease gene editing system. Such gene editing system comprises at least one enzyme, preferably chosen among: meganuclease, zinc-finger nuclease, transcription-activator like effector nuclease, CRISPR-nickase or CRISPR-nuclease. Such enzymes may be a wild-type protein, or a mutant with the proviso that the enzyme still possesses its nuclease or nickase activity. In a more preferred embodiment, the enzyme is chosen among Cas3, Cas9, Cas12a, or dCas9-Fokl, dCpf1-Fokl, chimeric FENI-Fokl, a nickase Cas9, chimeric dCas9 non-Fokl nuclease and dCpf1 non-Fokl nuclease.

According to the disclosure, the most preferred gene editing system is a CRISPR gene editing system. As used herein, the term "CRISPR gene editing system", which can also be called "CRISPR-Cas system" in an embodiment refers to a system which relies on two components: (i) a guide sequence which is a specific RNA sequence which hybridize to a target DNA region and direct the enzyme (the 'CRISPR-associated protein') to the target DNA region to perform the gene editing, and (ii) the CRISPR-associated protein which is a non-specific nuclease or nickase.

As used herein, the term "guide sequence" refers to a "guide RNA", also called "gRNA". Preferably, said guide sequence comprises a crRNA and optionally a tracrRNA. The 'crispr RNA', also called crRNA is a 17-20 nucleotide sequence complementary to the target DNA, and a "tracrRNA", is a binding scaffold for the Cas9 nuclease. For Cas12a, the guide RNA comprises only the crRNA.

The crRNA and the tracrRNA may be present on the same molecule or may be present on two physically distinct molecules. According to the disclosure, the guide sequence may refer to a single guide, so that the crRNA and the tracrRNA form a single molecule.

In specific embodiments of the disclosure, the CRISPR system may comprise multiple guide sequences capable of hybridizing to multiple target sequences within the target genomic site.

Preferably, the said "CRISPR-associated protein" binds to the target DNA region only in presence of a specific sequence, called protospacer adjacent motif (PAM), on the non-targeted DNA strand. The nuclease cuts 3-4 nucleotides upstream of the PAM sequence or around 18-19 nucleotides downstream of the PAM sequence. Therefore, in a preferred embodiment, each end of the target genomic site (i.e. each end of the target DNA region) is adjacent to a Protospacer Adjacent Motif (PAM) recognized by a CRISPR-associated protein, such as 5'NGG3' (with N representing either A, T, C or G) for Cas9 of *Streptococcus pyogenes* or T-rich PAM for Cas12a such 5'TTN or 5'TTTN (with N representing either A, T, C or G). In this embodiment, the locations in the genome that can be targeted by the CRISPR-associated proteins are limited by the locations of these PAM sequences.

In specific embodiments of the disclosure that may be combined with the previous embodiments, the CRISPR system may comprise at least one nuclear localization system (NLS). Preferably, said CRISPR-associated protein, more preferably the nuclease, is operably linked to the NLS.

According to the disclosure, several strategies are available to deliver the CRISPR gene editing system: a DNA delivery format, a RNA delivery format or a ribonucleoprotein delivery format.

In the DNA delivery format, the system is provided as one or several DNA molecules which enters the cell and translocates to the nucleus where the sequences encoding for CRISPR-associated protein and the guide sequence are transcribed. After translation of the CRISPR-associated protein said CRISPR-associated protein, preferably a nuclease, and the guide sequence assembles into the cell cytoplasm to form a ribonucleoprotein (RNP) complex. Next, said RNP complex enters the nucleus to perform the desired gene editing.

In the RNA delivery format, the system is provided as one or several RNA molecules. The sequences comprising the guide RNA and the mRNA corresponding to the CRISPR-associated protein are co-transfected into the cell cytoplasm. The mRNA is then translated to produce a CRISPR-associated protein, preferably a nuclease. Then, a RNP complex is formed and it enters the nucleus to perform the desired gene editing.

In the ribonucleoprotein delivery format, a RNP complex comprising a guide RNA and a CRISPR-associated protein are provided. Next, said RNP complex enters the nucleus to perform the desired gene editing.

In a specific embodiment of the disclosure, the CRISPR gene editing system comprises then a delivery system comprising and operably configured to deliver into an eukaryotic cell, either CRISPR-Cas complex components, or one or more polynucleotide sequences comprising or encoding said components, wherein said CRISPR-Cas complex components, comprises:

(i) at least two guide sequences capable of hybridizing to the two ends of the target genomic site to effect two breaks, thereby allowing a deletion of said target genomic site or an inversion at said target genomic site;
(ii) a CRISPR-associated protein, and wherein said CRISPR-Cas complex is operable in an eukaryotic cell.

As used herein, the term "CRISPR-Cas complex components" refers to the components required to form a RNP complex (i.e. at least one guide sequence and a functional nuclease or a nickase, preferably a nuclease);

Preferably, the CRISPR gene editing system is a CRISPR-Cas vector system encoding a CRISPR-Cas complex, said vector system comprising:

(i) a first regulatory element operably linked to a polynucleotide sequence encoding a first guide sequence, said first guide sequence being capable of hybridizing to a first end of the target genomic site;
(ii) a second regulatory element operably linked to a polynucleotide sequence encoding a second guide sequence, said second guide sequence being capable of hybridizing to a second end of the target genomic site;
(iii) a third regulatory element operably linked to a polynucleotide sequence encoding a CRISPR-associated protein;

wherein said components (i), (i) and (iii) are located on the same or different vectors of the system, and wherein said CRISPR-Cas complex is operable in an eukaryotic cell.

As used herein, the term "vector" refers to DNA sequence in which it is possible to insert fragments of foreign nucleic acid, the vectors making it possible to introduce foreign DNA into the eukaryotic cell. Examples of vectors are plasmids, cosmids, yeasts, yeast artificial chromosomes (YACs), bacteria artificial chromosomes (BACs), artificial chromosomes derived from the P1 bacteriophage (PACs), and viral vectors such as lentiviral, baculoviral or adenoviral, adeno-associated viral vectors or plant viral vectors. In a specific embodiment, the CRISPR-Cas complex is delivered via liposomes, nanoparticles, exosomes, microvesicles, or a gene-gun. In a specific embodiment, the CRISPR-Cas complex is delivered in plants via electroporation, *Agrobacterium* transformation, direct precipitation by means of PEG.

As used herein, the term "regulatory element linked to a polynucleotide sequence" means that the polynucleotide sequence is linked to the regulatory element in a manner that allows for expression of said polynucleotide. Said regulatory element is preferably a promoter. In a specific embodiment, the said vector system can comprise one or several regulatory elements, such as promoter, enhancer, internal ribosomal entry sites, polyadenylation signals, poly U sequences, . . . . Said regulatory elements may direct constitutive expression of the polynucleotide sequence in many types of host cells or only in certain types (i.e. tissue specific regulatory sequences). A tissue-specific promoter may direct expression primarily in a desired tissue of interest or in a particular type of cells. Regulatory elements may also direct expression in a temporal-dependent manner, such as in a cell-cycle dependent or developmental stage-dependent manner, which may or may not also be tissue or cell-type specific.

In other embodiment, the CRISPR gene editing system is a vector system encoding a CRISPR-Cas complex, said vector system comprising:

i) a first regulatory element operably linked to a polynucleotide sequence encoding the first guide sequence and the second guide sequence; and
ii) a second regulatory element operably linked to a polynucleotide sequence encoding a CRISPR-associated protein;

wherein said components (i) and (ii) are located on the same or different vectors of the system.

In a specific embodiment, the said vector system comprises one or more expression cassettes for driving the expression of one or more guide RNA and CRISPR-associated protein. Each of the expression cassettes comprise a promoter sequence, a polynucleotide sequence encoding for at least one guide sequence, and a terminator.

In a specific embodiment, the disclosure relates to of the disclosure a method to modify the expression of a gene of interest in an organism, as mentioned above, which the steps of:

a) identifying an endogenous promoter, distal from a naturally occurring promoter of the gene of interest in a non-modified organism, which is capable of modifying the expression of said gene of interest;
b) identifying the deletion or insertion of a genomic region to be performed in order to operably link said endogenous promoter, or part of an endogenous promoter, to said gene of interest;
c) introducing into said organism at least one gene-editing system designed to perform the deletion or insertion identified in step b);

d) allowing said gene-editing system to perform the desired editing at the target genomic site;

e) optionally selecting an organism with the desired editing.

In a specific embodiment, some steps can be performed before the step a) mentioned above. Such steps can be:

a step of analyzing the region surrounding the gene of interest to identify the presence of at least one distal promoter, notably the position of at least one distal promoter and/or its orientation, and/or a step of operably linking the distal promoter to the coding region of said gene of interest, and a step of selecting the distal promoter as an endogenous promoter capable of being used in step a) if the expression of said gene of interest is modified.

Said "step of analyzing the region surrounding the gene of interest" is any method known in the art.

In a specific embodiment, the disclosure relates to a method to modify the expression of a gene of interest, as mentioned above, wherein said gene of interest is a fertility-restorer gene, preferably RFL29 gene, more preferably represented by SEQ ID NO:14 (RFL29a). In another embodiment, the fertility-restorer gene is RFL79, more preferably represented by SEQ ID NO:58. In another embodiment, the fertility-restorer gene is RFL29b, more preferably represented by SEQ ID NO: 2. Such embodiment corresponds to a second aspect of the disclosure.

Method to Enhance the Expression of a Fertility-Restorer Gene of Interest in a Plant In a second aspect, the disclosure then relates to a method to enhance the expression of a fertility-restorer gene of interest in a plant, said method comprising the steps of:

a) introducing into said plant, at least one gene-editing system, preferably a CRISPR gene-editing system;

b) allowing the said gene-editing system to perform the desired editing at a target genomic site;

and wherein the said gene-editing system is designed so that, after the desired editing, the fertility-restorer gene of interest is operably linked to an endogenous promoter, or part of an endogenous promoter, said endogenous promoter being distal from a naturally occurring promoter of the fertility-restorer gene of interest in the genome of a non-modified plant.

In a specific embodiment, said method aims to enhance the expression of a fertility-restorer gene of interest in a wheat plant.

In a specific embodiment, the desired editing to enhance the expression of a fertility-restorer gene of interest is preferably a deletion or an inversion. SEQ ID NO:14 notably refers to a RFL29a gene in *Triticum aestivum* (var. Spelt) P1190962. In a specific embodiment, the distal promoter to drive RFL29 is expressed (active) in Z32 and Z39 spikes. In a specific embodiment, the fertility-restorer gene is RFL29 gene and said endogenous promoter identified to replace the naturally-occurring promoter of RFL29 is chosen among PK-like promoter, RAE1-like promoter or At5g02240-like promoter. PK-like promoter is notably represented by SEQ ID NO:10 (TaPK-like promoter), RAE1-like promoter by SEQ ID NO:11 (TaRAE1-like promoter) and At5g02240-like promoter by SEQ ID NO:59 (TaAt5g02240-like promoter).

In another specific embodiment, the fertility-restorer gene is an RFL79 gene, more preferably represented by SEQ ID NO:58 in *Triticum aestivum.*

In a specific embodiment, said CRISPR gene-editing system is a delivery system comprising and operably configured to deliver into a plant cell, either CRISPR-Cas complex components, or one or more polynucleotide sequences comprising or encoding said components, wherein said CRISPR-Cas complex components, comprises:

(i) at least two guide sequences capable of hybridizing to the two ends of the target genomic site to effect two breaks, thereby allowing a deletion of said target genomic site or an inversion at said target genomic site;

(ii) a CRISPR-associated protein, and wherein said CRISPR-Cas complex is operable in a plant cell.

In a specific embodiment of this method, the fertility-restorer gene is a RFL29 gene and the two guide sequences hybridize to the following targets:

991r+478f, represented respectively by the following sequences SEQ ID NO: 35 and SEQ ID NO: 39, 991r+488r, represented respectively by the following sequences SEQ ID NO: 35 and SEQ ID NO: 38, 972f+479r, represented respectively by the following sequences SEQ ID NO: 36 and SEQ ID NO: 37, 983r+479r, represented respectively by the following sequences SEQ ID NO: 34 and SEQ ID NO: 37, 991r+1155f, represented respectively by the following sequences SEQ ID NO: 35 and SEQ ID NO: 42, 991r+1151f, represented respectively by the following sequences SEQ ID NO: 35 and SEQ ID NO: 43, 972f+1147f, represented respectively by the following sequences SEQ ID NO: 36 and SEQ ID NO: 41, 972f+1145r, represented respectively by the following sequences SEQ ID NO: 36 and SEQ ID NO: 40, 983r+1147f, represented respectively by the following sequences SEQ ID NO: 34 and SEQ ID NO: 41, 983r+1145r, represented respectively by the following sequences SEQ ID NO: 34 and SEQ ID NO: 40, 991r+81f, represented respectively by the following sequences SEQ ID NO: 35 and SEQ ID NO: 57, 972f+70f, represented respectively by the following sequences SEQ ID NO: 36 and SEQ ID NO: 56, 983r+70f, represented respectively by the following sequences SEQ ID NO:34 and SEQ ID NO: 56.

In a specific embodiment of this method, the fertility-restorer gene is RFL29 gene and the said CRISPR gene-editing system comprises the following components:

(1) a first guide sequence which hybridizes to SEQ ID NO: 24 (991r) or a polynucleotide sequence comprising or encoding said first guide, and a second guide sequence which hybridizes to SEQ ID NO: 28 (478f) or a polynucleotide sequence comprising or encoding said second guide sequence, and a Cas9 or a polynucleotide sequence encoding said Cas9, or (2) a first guide which hybridizes to SEQ ID NO: 24 (991r) or a polynucleotide sequence comprising or encoding said first guide, and a second guide which hybridizes to SEQ ID NO: 27 (488r) or a polynucleotide sequence comprising or encoding said second guide sequence, and a Cas9 or a polynucleotide sequence encoding said Cas9, or (3) a first guide which hybridizes to SEQ ID NO: 25 (972f) or a polynucleotide sequence comprising or encoding said first guide, and a second guide which hybridizes to SEQ ID NO: 26 (479r) or a polynucleotide sequence comprising or encoding said second guide sequence, and a Cas9 or a polynucleotide sequence encoding said Cas9, or (4) a first guide which hybridizes to SEQ ID NO: 23 (983r) or a polynucleotide sequence comprising or encoding said first guide, and a second guide which hybridizes to SEQ ID NO: 26 (479r) or a polynucleotide sequence comprising or encoding said second guide sequence, and a Cas9 or a polynucleotide sequence encoding said Cas9, or (5) a first guide which hybridizes to SEQ ID NO: 24 (991r) or a polynucleotide sequence comprising or encoding said first guide, and a second guide which hybridizes to SEQ ID NO: 31 (1155f) or a polynucleotide sequence comprising or encoding second first guide, and a Cas9 or a polynucleotide sequence encoding said Cas9, or (6) a first guide which hybridizes to SEQ ID NO: 24 (991r) or a polynucleotide sequence comprising or encoding said first guide, and a second guide which hybridizes to SEQ ID NO: 32 (1151f) or a polynucleotide sequence comprising or encoding said second guide sequence, and a Cas9 or a polynucleotide sequence encoding said Cas9, and a Cas12a or a polynucleotide sequence encoding said Cas12a, or (7) a first guide which hybridizes to SEQ ID NO: 25 (972f) or a polynucleotide sequence comprising or encoding said first guide, and a second guide which hybridizes to SEQ ID NO: 30 (1147f) or a polynucleotide sequence comprising or encoding said second guide sequence, and a Cas9 or a polynucleotide sequence encoding said Cas9, or (8) a first guide which hybridizes to SEQ ID NO: 25 (972f) or a polynucleotide sequence comprising or encoding said first guide, and a second guide which hybridizes to SEQ ID NO: 29 (1145r) or a polynucleotide sequence comprising or encoding said second guide sequence, and a Cas9 or a polynucleotide sequence encoding said Cas9, or (9) a first guide which hybridizes to SEQ ID NO: 23 (983r) or a polynucleotide sequence comprising or encoding said first guide, and a second guide which hybridizes to SEQ ID NO: 30 (1147f) or a polynucleotide sequence comprising or encoding said second guide sequence, and a Cas9 or a polynucleotide sequence encoding said Cas9, or

(10) a first guide which hybridizes to SEQ ID NO: 23 (983r), or a polynucleotide sequence comprising or encoding said first guide and a second guide which hybridizes to SEQ ID NO: 29 (1145r) or a polynucleotide sequence comprising or encoding said second guide sequence, a Cas9 or a polynucleotide sequence encoding said Cas9, or

(11) a first guide which hybridizes to SEQ ID NO: 24 (991r) or a polynucleotide sequence comprising or encoding said first guide, and a second guide which hybridizes to SEQ ID NO: 55 (81f) or a polynucleotide sequence comprising or encoding said second guide sequence, and a Cas9 or a polynucleotide sequence encoding said Cas9, or

(12) a first guide which hybridizes to SEQ ID NO: 25 (972f) or a polynucleotide sequence comprising or encoding said first guide, and a second guide which hybridizes to SEQ ID NO: 54 (70f) or a polynucleotide sequence comprising or encoding said second guide sequence, and a Cas9 or a polynucleotide sequence encoding said Cas9, or

(13) a first guide which hybridizes to SEQ ID NO: 23 (983r) or a polynucleotide sequence comprising or encoding said first guide, and a second guide which hybridizes to SEQ ID NO: 54 (70f) or a polynucleotide sequence comprising or encoding said second guide sequence, and a Cas9 or a polynucleotide sequence encoding said Cas9.

Plant Used in the Methods of the Disclosure or Obtained by Such Methods

The present disclosure also relates to a plant, or a plant part, which comprises a gene-editing system designed to perform a desired editing at a target genomic site, so that after the desired editing, a gene of interest in the plant is operably linked to an endogenous promoter, said endogenous promoter being distal from a naturally occurring promoter of the gene of interest in the genome of a non-modified plant.

The present disclosure further relates to a plant obtained by the method to modify the expression of a gene of interest in an organism as mentioned above, notably the method to enhance the expression of a fertility-restorer gene of interest in a plant. In a specific embodiment, the disclosure relates thus to a wheat plant wherein the RFL29 gene is preferably linked to an endogenous promoter being distal from the naturally occurring promoter of RFL29 gene in the genome of a non-modified plant, such as PK-like promoter, RAE1-like promoter or At5g02240-like promoter.

Several techniques can be used to identify whether a plant was obtained by a method according to the present disclosure, and/or to determine of the gene editing was correctly performed. Any method known in the art may be used. Some suitable methods include, but are not limited to, sequencing, hybridization assays, polymerase chain reaction (PCR), ligase chain reaction (LCR), or combinations thereof. For example, such a method of identification can comprise a step of PCR after the desiring editing was performed, in order to detect bands corresponding to the desired editing, notably inversion or deletion. The step of PCR amplification is generally followed by a sequencing step. Alternatively, the method of identification can comprise a step to determine the expression level of the gene of interest, in order to compare the expression of a gene of interest by comparison with the expression of a gene of interest in a non-modified plant, thereby verifying the modification of the expression of the gene of interest, preferably a higher expression of the gene of interest. In another alternative embodiment, said identification method can comprise a step to determine the level of the expressed protein encoded by the gene of interest, in order to compare said expression level by comparison with the level of the expressed protein encoded by the gene of interest in a non-modified plant, thereby verifying the modification of the expression level of the protein encoded by the gene of interest, preferably a higher level of the protein.

When said plant was obtained by a method to enhance the expression of a fertility-restorer gene of interest, as disclosed above, a further step of phenotypic analysis can be performed in order to determine if said plant has a fertility restoration phenotype.

A Method to Restore Fertility

As mentioned above, plant having a fertility restoration phenotype can be obtained according to the methods of the disclosure. It is then desirable to cross such plant with another plant, preferably when the plant is wheat.

Therefore, the present disclosure also relates to a method to restore fertility in wheat, comprising a step of crossing a sterile wheat plant with a plant wherein the expression of a fertility-restorer gene has been enhanced, as mentioned above. Preferably the sterile wheat plant is female wheat and the plant with an enhanced fertility restorer gene is male wheat.

SEQUENCES OF THE PRESENT DISCLOSURE

| Sequence number | Sequence |
|---|---|
| SEQ ID NO: 1_<br>Traes-<br>CS1B01G038500<br>(RFL29b)CDS | atgccccgcttctcctccaccacgccaatgtcgccaccccgcctccgcctccgcctccgactctgcgcccgccactcctcctccacctctcatccctcacgcatctgggatccccacgccgc<br>cttcgccgccgcggcacagcgggcgagctctggcacgctcactacggaggacgcacaccacctgtttgacgaattgctgcggcggggcaatcctgtccaggagcgtcccttgaataaatttc<br>tggctgccctcgcccgcgcgcccgcgtccgcatcctgctgcgatggccccgccctggcagtcaccctcttcggccgtttgtcccgagacgtcggacgacgggggcgcagccaaatgtcttca<br>cctatggcgtcctcatggactgctgctgccgcgcttgccgcacagatctggtgctcgccttctttggccgtctcctcaagacgggcctggaggcaaaccaagtcgtcttcaacaccctcctc<br>aagggcctttgccacacaaagcgggcggatgaggctctggacgtgctgcttcacaggatgcctgagctgggctgcactcctaatgtggtggcgtataacaccgttatccatggcttctttaa<br>ggaaggccatgtaagcaaggcctgcaatctgttccatgaaatggcgcagcagggcgttaagcctaatgtggtgacatataactcagttattgatgcgctgtgcaaggccagagccatggaca<br>aggcagaggtggtccttcgtcagatgattgatgatggtgttggacctgataatgtgacgtatagtagcctcatccatggatattcctcttcaggccactggaaggaggcagttagggtattc<br>aaagagatgacaagtcggagggttacagcagatgtgcatacttacaacatgtttatgacctttctttgcaaacatggaagaagcaaagaagctgcaggaattttttgataccatggctatcaa<br>gggcctgaaacctgacaacgtttcatatgctattcgccttcatgggtatgccaccgaaggatgcctagttgacatgatcaatctcttcaattccatggcaacacactgcattctacctaact<br>gtcatatattcaacatactgattaatgcatatgctaaatctgggaagcttgataaggctatgcttatcttcaatgaaatgcagaaacaaggagtgagtccaaatgcagtcacatattcaacc<br>gtaatacatgcattttgcaagaagggtaggttggatgatgctgtgataaagtttaatcagatgattgatacaggagtacgaccggacgcatctgtttatcgtcccctaatccagggtttttg<br>tacacatggcgatttggtgaaagcaaaggaatatgttactgaaatgatgaagaaaggtatgcctcctcctgatattatgttcttcagttcaatcatgcagaacctatgcacagaaggaaggg<br>taacagaagcacgggatatccttgacttgatagtgcacattggtatgaggcctaatgttatcatatttaatttgctgatcggtggatactgcctagtccgcaagatggcagatgcattgaaa<br>gtatttgatgatatggtgtcatatggtttagaaccttgtaactttacgtatggtatacttattaatggctattgcaaaaatagaaggattgatgacgggcttattctgttcaaagagatgct<br>gcacaagggacttaaacctacaacttttaattataacgtcatactggatggattatttctggctggacaaactgttgctgcaaaagagaagtttgatgagatggttgaatctggagtaagtg<br>tgtgcattgatacatactctataattcttggtggactttgtagaaatagctgcagtagcgaagcgatcacccttttccggaaattaagcgcaatgaatgtgaaatttgatattacaattgtc<br>aatatcattattggtgccttatacagggtcgagagaaaccaagaggctaaggatttgtttgctgctatgccagccaatggcttggttcctaatgctgttacctacaccgtaatgatgacaaa<br>tcttataaaagaaggttcagtggaagaagctgacaatcttttcttatccatggagaagagcggctgtactgccaactcttgcctgttaaatcatatcatcagaaggttactggaaaaaggag<br>agatagtcaaggctggaaattatatgtctaaagttgatgcaaagagctactcacttgaagctaaaactgtttcgctgctgatctctctgttttcaaggaaagggaaatatagagaacacatc<br>aaattgcttcctacaaagtatcagtttctggaagaagcagccacagttgaatag |
| SEQ ID NO: 2_<br>Traes-<br>CS1B01G038500<br>(RFL29b) | mprfssttpmspprlrlrlrlcarhssstshpsriwdphaafaaaaqrassgtlttedahhlfdellrrgnpvqerpinkflaalarapasasccdgpalavtlfgrlsrdvgrrvaqpnvf<br>tygvlmdcccracrtdlvlaffgrllktgleanqvvfntllkglchtkradealdvllhrmpelgctpnvvayntvihgffkeghvskacnlfhemaqqgvkpnvvtynsvidalckaramd<br>kaevvlrqmiddgvgpdnvtysslihgysssghwkeavrvfkemtsrrvtadvhtynmfmtflckhgrskeaagifdtmaikglkpdnvsyairlhgyategclvdminlfnsmathcilpn<br>chifnilinayaksgkldkamlifnemqkqgvspnavtystvihafckkgrlddavikfnqmidtgvrpdasvyrpliqgfcthgdlvkakeyvtemmkkgmpppdimffssimqnlctegr<br>vteardildlivhigmrpnviifnlliggyclvrkmadalkvfddmvsyglepcnftygilingycknrriddglilfkemlhkglkpttfnynvildglflagqtvaakekfdemvesgvs<br>vcidtysiilgglcrnscsseaitlfrklsamnvkfditivniiigalyrvernqeakdlfaampanglvpnavtytvmmtnlikegsveeadnlflsmeksgctanscllnhiirrllekg<br>eivkagnymskvdaksysleaktvsllislfsrkgkyrehikllptkyqfleeaatve |
| SEQ ID NO: 3_<br>Traes-<br>CS1B01G038500<br>(RFL29b)<br>genomic | GCACCTTTAGGTCCTAATTCTTTATTAATTGGTTCACCCGAGGTCCTTTTCCACGAGCGCTCGCTGACCAGCACACGTGCCGCATTGACCCATGCCA<br>CATCGATAGAGGGTCTAACCGCCAGGCGAGAAGCTTCGCAAAGAGACCCCCCCCCCTCTTAGTGGCACCCTCTCTCCTCTTTCACGGTACTTTGGC<br>GACATTGGAGGCGAGCGACAGAGGCAACCGGAGGTGATCTGGAGGTAATTTGTGTGGGTGCCCGTGAAGATGCCCCTTCTATGACGGCCAGTGAG<br>CAATCCTCCTCCATGTTACCGTAAGAACCCTAATCTTGTCGATGATCTTCTCCTGTAGCTCTTCTAATATGTCATAACTTTGTCATAATCAATAGTTGTA<br>GTCCTTGATTTACTTTGATTTGCATAACGGTGATACGGACACGGCAAAAAGGACACACCACCAGCGGCAACATACCCGCCGAAGTTGGAGCTTGCTT<br>CGCCGCGCCGGGGGGGTGCTGAGGATGTTGCCATGCTCCTCATCTTAGTTGTTTCCTTGCCGAGGAGCTTGAAGTTCCGGCCATGGATAGGTTTA<br>GGGGACGCGCGCGCCGAGAGAGAGAGCAGATTTGGGGAAGAAATAAAGCCAGGGACTGGGGAATGAGAAGATAATGTTTATAAGGGGTTTTCTGTA<br>AAAAGAAAGAGCAACCTACGCAGCCCTTCTGTCGATTTGGCATGGGTCAACGCACCACACGAGCAGGTCAACGAGCGCTCGTGAGAAAAAGGACCT<br>AGGGTAAACCACTTACTAAAGAATTAGGACCTAAAGGTGCATTTTGGACGAAATAAGACTAAAGTGACACCCTGACGAATTTTTTAGGACCTTGAGTG<br>CATTTAACTCTTTCAAAAAATAAAGATGCTAAAAAAACTAAATGCTTAAAAATACATTTTTCTATGGGAATACTTAAAAATACTAGTATAATTTGATGGCT<br>TCCTAGTATATTTCTAGGGCTTACAACTAAATTTATATTCTTGGTCTAAATAAAATTATAATCTGATAAATTATGTGATATGAATATAGCCATATGAGACC<br>ATAATTTAATTTTACCTGCAAAAAGTAAGTAATAGTAGTAGTAGTACTACATACTCCCTCCGTCCGGAAATACTTGTCGAAGAATTTGATGAAAATGGAT<br>GCATCTAGAACAAGAATACATCTAGATACATCAATCTCCCTGACAAGTATTTCCGAGCGGAGGGAGTACTAGATAATACTCCCTCCGTTCCTAAATAAT<br>TGTCTTTCTAGCTATCTCAAATAAACTACAACATACGGATGTATGTAGACATGTTTTAGAGTGTAGATTCACTCATTTTGTTCCGTATGTAGTCATTTGT<br>TGAAATCTCTAGAGAGACAATTATTTAGGAACGGAGGGAGTAAGATAACTACCCTAAAAAAAAAGATAACTGAAGGTTGCCACCTAGCACATTCACAT<br>TGGTACAACTTGGAAAAGCACAGCCCCGTCGTCCTGCTCCCAGTTGAGTTCGCGACCTACACACCGGCCATGCCCCGCTTCTCCTCCACCACGCCA<br>ATGTCGCCACCCCGCCTCCGCCTCCGCCTCCGACTCTGCGCCCGCCACTCCTCCTCCACCTCTCATCCCTCACGCATCTGGGATCCCCACGCCGCC<br>TTCGCCGCCGCGGCACAGCGGGCGAGCTCTGGCACGCTCACTACGGAGGACGCACACCACCTGTTTGACGAATTGCTGCGGCGGGGCAATCCTGT |

-continued

SEQUENCES OF THE PRESENT DISCLOSURE

| Sequence number | Sequence |
|---|---|
| | CCAGGAGCGTCCCTTGAATAAATTTCTGGCTGCCCTCGCCCGCGCGCCCGCGTCCGCATCCTGCTGCGATGGCCCCGCCCTGGCAGTCACCCTCT<br>TCGGCCGTTTGTCCCGAGACGTCGGACGACGGGTGGCGCAGCCAAATGTCTTCACCTATGGCGTCCTCATGGACTGCTGCTGCCGCGCTTGCCGC<br>ACAGATCTGGTGCTCGCCTTCTTTGGCCGTCTCCTCAAGACGGGCCTGGAGGCAAACCAAGTCGTCTTCAACACCCTCCTCAAGGGCCTTTGCCAC<br>ACAAAGCGGGGGGATGAGGCTCTGGACGTGCTGCTTCACAGGATGCCTGAGCTGGGCTGCACTCCTAATGTGGTGGCGTATAACACCGTTATCCAT<br>GGCTTCTTTAAGGAAGGCCATGTAAGCAAGGCCTGCAATCTGTTCCATGAAATGGCGCAGCAGGGCGTTAAGCCTAATGTGGTGACATATAACTCAG<br>TTATTGATGCGCTGTGCAAGGCCAGAGCCATGGACAAGGCAGAGGTGGTCCTTCGTCAGATGATTGATGATGGTGTTGGACCTGATAATGTGACGTA<br>TAGTAGCCTCATCCATGGATATTCCTCTTCAGGCCACTGGAAGGAGGCAGTTAGGGTATTCAAAGAGATGACAAGTCGGAGGGTTACAGCAGATGTG<br>CATACTTACAACATGTTTATGACCTTTCTTTGCAAACATGGAAGAAGCAAAGAAGCTGCAGGAATTTTTGATACCATGGCTATCAAGGGCCTGAAACCT<br>GACAACGTTTCATATGCTATTCGCCTTCATGGGTATGCCACCGAAGGATGCCTAGTTGACATGATCAATCTCTTCAATTCCATGGCAACACACTGCAT<br>TCTACCTAACTGTCATATATTCAACATACTGATTAATGCATATGCTAAATCTGGGAAGCTTGATAAGGCTATGCTTATCTTCAATGAAATGCAGAAACAA<br>GGAGTGAGTCCAAATGCAGTCACATATTCAACCGTAATACATGCATTTTGCAAGAAGGGTAGGTTGGATGATGCTGTGATAAAGTTTAATCAGATGAT<br>TGATACAGGAGTACGACCGGACGCATCTGTTTATCGTCCCCTAATCCAGGGTTTTGTACACATGGCGATTTGGTGAAAGCAAAGGAATATGTTACTG<br>AAATGATGAAGAAAGGTATGCCTCCTCCTGATATTATGTTCTTCAGTTCAATCATGCAGAACCTATGCACAGAAGGAAGGGTAACAGAAGCACGGGAT<br>ATCCTTGACTTGATAGTGCACATTGGTATGAGGCCTAATGTTATCATATTTAATTTGCTGATCGGTGGATACTGCCTAGTCCGCAAGATGGCAGATGC<br>ATTGAAAGTATTTGATGATATGGTGTCATATGGTTTAGAACCTTGTAACTTTACGTATGGTATACTTATTAATGGCTATTGCAAAAATAGAAGGATTGAT<br>GACGGGCTTATTCTGTTCAAAGAGATGCTGCACAAGGGACTTAAACCTACAACTTTTAATTATAACGTCATACTGGATGGATTATTTCTGGCTGGACAA<br>ACTGTTGCTGCAAAAGAGAAGTTTGATGAGATGGTTGAATCTGGAGTAAGTGTGTGCATTGATACATACTCTATAATTCTTGGTGGACTTTGTAGAAAT<br>AGCTGCAGTAGCGAAGCGATCACCCTTTTCCGGAAATTAAGCGCAATGAATGTGAAATTTGATATTACAATTGTCAATATCATTATTGGTGCCTTATAC<br>AGGGTCGAGAGAAACCAAGAGGCTAAGGATTTGTTTGCTGCTATGCCAGCCAATGGCTTGGTTCCTAATGCTGTTACCTACACCGTAATGATGACAA<br>ATCTTATAAAAGAAGGTTCAGTGGAAGAAGCTGACAATCTTTTCTTATCCATGGAGAAGAGCGGCTGTACTGCCAACTCTTGCCTGTTAAATCATATCA<br>TCAGAAGGTTACTGGAAAAAGGAGAGATAGTCAAGGCTGGAAATTATATGTCTAAAGTTGATGCAAAGAGCTACTCACTTGAAGCTAAAACTGTTTCG<br>CTGCTGATCTCTCTGTTTTCAAGGAAAGGGAAATATAGAGAACACATCAAATTGCTTCCTACAAAGTATCAGTTTCTGGAAGAAGCAGCCACAGTTGA<br>ATAGTTGGTACATGATATCTGAAATTTAATTTGCATCGCTTGCCATGGGTCCGTCTGCTTGTACAAGAAATGCATTTTCTATTTGTAAATAGGAAGTCA<br>GTTTAGAACAAGCCATCAGGATGACGCAAAGAGTACAATTCAGTTGCACCACCAATAAAAAGGCAGAACTAGGGCTGCCAAAACAACACTGAATCAA<br>AACTCAAACAGAAGGAGCAGCAAACTTTTTTTTTGAAGCTGGACAGTCTGCTAGCCAAACAACTACAGGAGACTGTCAGGCGGGGCATGTAGTGGC<br>TGGCGTCTAAGCGCCTTTGCTTCTTCCACCATCCATGGCTTAGCCTCACACGGAATCGAGTCAACCAATTCCCGTCGGTTTTGGGTGGCTCCCTTGA<br>AGATGCAATTGTTTTCAGCGGCCAGATACGCATGGTCAGATTAATCAGCGAGTGTGCCCCTTCTGTCTGGTTCGAGAAAGAATTTGAAGAGCTGAGC<br>TTGTCCCAGCTGGAACCAGTTTGAGGTTAGTTAATCATAACAGGGTACTAGAGAGGTGTTTTATTGACTGTTGATGTGTAATATGTTATATGCCATCCT<br>CTTGATGATTACGGTGATCTGTGAAGAGGCAGCATGCAAAAGTCTGAATCACATATGCTTATGTAATTGTGTTATTATTTGTGCAGCTTCTAGACCTTT<br>TGCCTTGTAGATGGCTACATGGATCTAGTTGTAGCAATCTGTAACTGTTAGTGTTTTGTATATGCTGGCATTGATGATTAGGGTGACTTGTGAAGCATG<br>CAGAAGTCTGAATCATACATGCTTGTCTAGTTATTTTTGGGGCTCTCTCTTTGCCATGTACATGTTTTATGGATGCAGTTGTAGTCTGTATGTGCTGGC<br>ATTTAATATGAGGGCTGGTCTGCAATTTTTCTGTTTTGATCGATACAGCGCCATGTTGAGTTTAACCCTGTAACTTGGCTTAACTAGATCATGCTGGTG<br>TTATCTCTAGGAATCACAATATCAATACTCTCTGTTGTTGCACAAACTGACGCAGATCAATGTCCAGAGGTAATATGGTTCTGCCCGTAATTTTCATCG<br>ACTGTCAGCATGTTCCTTTTTTATTTAGTACTCTGTATATCACGGCGGTATGACTATAATAAGGATATACGGCTGGTGCATTTTGAGCTTCTCTGTTTCT<br>TGGGATAAAGCTGATAAATTTCTATTCTTGTTGGCTTTGGTAGTATGAACAGAAAGCAGGCAGTAATAAACTGATATGTGGTACTATTTTGTTAGTGAA<br>ACAGGGTCCTTTTTATTATCTATTTTATCCAGCAATAGTGTTCCATAAAATTATAGATCGGTTCATTCATCTCATATGGATTTCGGTGAGCTTCGCCCGT<br>CCTTGGTACATTTTGTTACTATAGAACAATTGGTGTGCGCTTTTTTTCTTTTGGCTGTACGTTATAGAACAACAAAACCTGTTTATTTCATTAATTCATTG<br>TCTAATTTATTTTCTTACGAGAGCTCAGAAGTTCAGCATTTTATTTTATCTTGTTCCTTCCGCGTAATTTTTCATTTACTCACTGAGTAGTACAGGTCTTG<br>GACCTGAAATTCTTGTACTAATTTAGTAGAACCATTCTTCGAGAAACACTCCAAAAATGGTTTGTCTTGGGTCTGAATCATATTGTCTCTGAACAAACA<br>GGTGTGACTCATGCATGGAAAGATCCCCAAGAAACATTGCACATTTGGTAGATATGTCTATGCATGAATACTATTTTTTGAAAAAGAATTTAGTAAATAT<br>TTTGGTAGCATTTTTTATACGTATGATGCTTTTTCTTCTTCCCGAAATAAGGGTTTTGATTTTTGAATTTTTGTAAAGCAACATGGTTTGTAGTACGTACG<br>AAAGAACGCTAGTGTGTTTTCGCGATCGTAAGAATGTTATAAACTGTTTTCCTGGGTCATGTAGGTGTAAGCTATAGAAGGAATTCAATATCGTCCTAA<br>ACATCCTTGGCAGTGGCCAGTGAAAGTCTTGGACCTGAAATCATACCAGTACTATTTTTCTGAAAGAGAACCCATTCTTGTATTCCATAAGTTGGCTG<br>GTGCCTGGGCATAATTGTCTAATCATATAGTACTATTTGCATCTCATAATTCCATTCAGTTTTGCACTATAGCTGAACTGAAGGAGTACCTAGCACAAA<br>ATATGTATGACTGTATTTCAGATCTTGCAATCGCAGCTGTAATGGAGTAGCACACCCTGTAGCAGCATATGGATGTACTCTGAATGTTGGGACTCTTT<br>GAAATGATAAATTGGTCTATTCTGGGAGCAGATTTTTTCCGGCTTTCGGAGATTCATTGATCTTTTTTTTTCAGAAAGTACAGTTGTAAGTTATAATCAA<br>ACATCCCGAACAAACCTCACTTGTACATGTAAGAATGCACTATGAATCAGTGGAAAGTAGATTTGTGGTGAACCAAAATAGCCAAGGAATAGGTTCAC<br>TTTCCTCCCTCCTTATGTCTAAAGTTGATGCAAAGAGCTACTCACTTGAAGCTAAAACTGTTTCGCTGCTGATCTCTCTCTTTTCAGGGAAAGGGAAAT |

-continued

SEQUENCES OF THE PRESENT DISCLOSURE

| Sequence number | Sequence |
|---|---|
| | ACAGAGAACAGATAAGATTGCTCCCCGCAAAGTATCAGTTTCGCGGAGAATGAGCTACAGTTGAATGGTTTTACATGATATCTGAACTTAACTCCTCA<br>GAAGGTAAGGTTGAATTATTGTTTGCCATGAGTTTATCTGCTTGTACAACAAGTGCAATTTCCATATGTAAATAGGAAGGCAGTTGAGAACAAGCCATC<br>AGGATGACGCAAAGAGTACAATTCAACTGTAGGACCAGCAATTGTTTTGAAGTTGTATGTCTGCTAGTAGAACACCTACGGGAGAGATTCAGGCGGC<br>CGGGCATGTAGTGGCACCTGTGTAAGTCCCTTTTCTGCTGCCAGCATCCATGGCTTGGCCTCACAGGGAATGGAGTCAACCAATTTCTCGGCGTAG<br>CTGTTGCAAATGTTTTCTCAGCCACCAGATACACCAAAGTTTCAGAGTAATCAGCGAGCGTGTCTCTTTTGTCTGGTTCGAGAAAGAATTTGAAAACG<br>CTGAGCAGCAACAGGTGCTTGACCAGCTTGTCCCTGCCGAAGCCAGTTTGAGGTTAGTTAATCATAACAGGGTACTAGACAGGTGTTTTGTTGACTG<br>TTGATGGGTAATACTCCTATGTTATATGCCAGCCACTTGATGAATAGGGTGATCTGTGAATCACATATGCTTATGTAATTGTGTTATTATTTGTGCAGCT<br>TCTAGACCTTCTGCCTTGTATGGCTACATGGATCACGTTGTAGCAGTCTGTGACTGTGACTGTTAGTGTTTTGTATATGCTGGCATTGATTAATTTAGG<br>GCCGGGCTCCAAATTATTTGTTTTGATCGATTCAGCACCATGTTGAGTTTAACCCTGTAACTTGGCTTAACCAGATCAATATCAGGGGCCTCGGCATT<br>TTTAAACGTTGAATTAAACATACTCTGTGGCATATCAATGTTCAGAGGTAATATGGTTCTGTCCATAATTTCATCGACTGTCAGCATGTTCCTTTGTTAT<br>TCAATACTCTGTATATCATGCCGGTATGACTATAATAAGGATATAGTATGTTTGATGCATTTTGAACTTCTCTATTCCGTCCGATAGAGGTGATAAATTC<br>TCTATTCTTTTTGGCTTTGGTAGTATGAACAGTAAGCAGGCAGTATATATTAAACTGATATGTGGTACTATTTTGTTAATGAAACAG |
| SEQ ID NO: 4_<br>ZTraes-<br>CS1B01G038800<br>(TaPK-like)<br>CDS | atggggaactgctggggcgccaagatcagctccgacacctcctcctcctcctccccttcagggacgaattccaagtatgctactaggaatggggcggccttgagcagctccagcagctatgc<br>acggagcgagggtgagattctggagtcagccaatgtcaaggccttctctttcaatgagctgaggaccgccacgagaaacttccgtccggacagtgtgctaggcgagggagggttcgggtcag<br>tcttcaaggggtggatcgatgagaagaccctcaccccaactaagccaggcaccgggatggtcattgctgtaaagaagcttaaccaggaaagctatcagggccatagggaatggctggctgaa<br>gtgaattaccttggacaactatcgcacccgaatcttgtaaagctcgttgggtactgtgtcgaagacgaacagcggcttctcgtctacgagttcatgccccgtgggagtttagagaatcatct<br>attcaggaggagtacacatttccagccgctctcctggaaccttcggatgaaaattgcccatggagcagcaaaagggctcgcgtttctccacagtgacaaggccaaagtcatctaccgcgatt<br>tcaaaacctctaatatcctcctagatgcgaactatgacgcaaagctctcagatttcggcctggcgaaggacggaccgacgggtgacaagagccatgtgtccacaagggtgatggggacatat<br>gggtatgctgcaccagaataccttgcaacaggccacctgaccacgaagagcgacgtgtacagcttcggcgtggtcctcctggagatgctctcggggcgtcgcgcggtggacaagaaccggcc<br>gaccggcgagcacaacctggtggagtgggcgcggccgtacctgacaagcaagcggcgcatcttccgcgtcctggacccccgtctgggggggcagtactccctcgccaaggcccagaaggcggc<br>gtcgctggcgctgcagtgcctctcggtggactcgaggaacaggccgagcatggagcaggtcgtcgtggtgctggagcagctccacgacgccaaggagggagggaacagccctcgcccgcagc<br>tgcagagaaagccgagcagcaaccggggcgtgaacggctcgagatcgtcgtcgaccaaggggaacaacaagaagcccgcctcaccgagaccggtttga |
| SEQ ID NO: 5_<br>Traes-<br>CS1B01G038800<br>(TaPK-like) | mgncwgakissdtsssssspsgtnskyatrngaalsssssyasaasvprsegeilesanvkafsfnelrtatrnfrpdsvlgeggfgsvfkgwidektltptkpgtgmviavkklnqesyqgh<br>rewlaevnylgqlshpnlvklvgycvedeqrllvyefmprgslenhlfrrsthfqplswnlrmkiahgaakglaflhsdkakviyrdfktsnilldanydaklsdfglakdgptgdkshvst<br>rvmgtygyaapeylatghlttksdvysfgvvllemlsgrravdknrptgehnlvewarpyltskrrifrvldprlggqyslakaqkaaslalqclsvdsrnrpsmeqvvvvleqlhdakegg<br>nsprpqlqrkpssnrgvngsrssstkgnnkkpasprpv |
| SEQ ID NO: 6_<br>Traes-<br>CS1B01G038800<br>(TaPK-like)<br>genomic | CACGGAGTGACAAATCCCAGTCTCGATCCGCATAAAACAATAGATACTTTCGGAGATACCTGTAGTGCACCTTTATAGTCACCCAATTACGTTGTGAC<br>GTTTGATACACCCAAAGCACTCCTACGGTATCCAGGAGTTACACGCTCTCATGGTCAAAGGAAGAGATACTTGACATTGGCAAAACTCTAGCAAATGA<br>ACTACACGATCTTTTGTGCTAGTCTTAGGATTGGGTCTTGTCCATCACATCATTCTCCTAATGATGTGATCCCGTTATCAACGACATCCAATGTCCATA<br>GCCAGGAAACCATGACTATCTGTTGATCACAACGAGCTAGTCAACTAGAGGCTCACTAGGGACATATTGTGGTCTATGTATTCACACATGTATTACTA<br>TTTCCGGATAATACAGTTATAGCATGAATAAAAGACAATTATCATGAACAAGGAAATATAATAATAATACTTTTATTATTTCCTCTAGGGCATATTTCCAA<br>CAAAAGTGTCGCAGGAAATAGAAAGTAGTATCCTACGGTATGTATTGCATTTATTAGTTGTAGGCTCAACTAAAAGCACTACTGCGTGGTGACAACCT<br>AAGACTAGCCACAGTGAGAGTAACTTTAGTAGTAACATCGAGTCCAACTCAGCAAATTTGCTTATGTGGCAATGAGTTAATGAGGAGAGATGTAATAC<br>AAGTAACTTAGCTAATTACTGTAACACTACATCTCCCAATGCATTATGAGGGGGTGTTTGGTTCAGAAGTCCTAGGACTTTTTCTAGTCCCAGGACTA<br>ATAAAAAAAAACTCTCTACTAGAGTCTTTTTCTAGTCCATGCATAAAAAGTCCCTTCCGTTTGGTTCATAGGAACTTTTTAGGGACCTTTTCTAGTCTCT<br>GAGACTAAAAAATCTCTGAACCAAACACCCCCTGAGTCTATAACCTAATAAATGAATCTTTGTATGTTACCATACTTATGTTACTACCCATAGCCTAGAA<br>ACGTGTGTATGTTACTCTCCATAGTGGTTAGTCTAATACGTGACTTTAAACATCTCTCTGCCCAAGTAGCTGCCACATAAGCAGATGGGCGTCTTAATA<br>TAATAATATAGAAATGTATCGGGGTAATATAATACTGTGGCGATAGGCTTGGGTTAATTTCTTTAGTCCCGCCGATAAGCTCGATTGGTCAGTGCTGG<br>TGCCCCTCTCGACTCCACACACACACACACAGAGGGCGAAAAATAAGGGCACACGAGGCCACGTCACGTGGGGCCCCCATGACCCACACGCGGGC<br>CCGCGCGCCATCGTGTCGACGCGCCGCGAGCAGAGACGGCCGGCGAGGCCAACCCGAACCACCACTCCGCGCGAGCCGCCCCTCCCTTTCTCTC<br>GCCTTTTCGGCCNNNNNNNNNNNNNNNNNNNNNNNNNNNNNNNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN<br>NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN<br>NNNNNNNNNNNNNNTAGCGGTAGTGTATCGGGTTCGCCTCCCTCCCCCTCCCCCTGCCTGCACTGTCCCATCGCTCGCTCGCTCGCTTTCTCGCCC<br>GCTCGGTGGCGGTCGTGGGGGAGAAAGTTGCCGGCCGGCCAGCGCACGGGGAAAAGGCGCACATACTTTCTTTCTTTCTTTCCACCGCCGCCCTC |

-continued

| SEQUENCES OF THE PRESENT DISCLOSURE | |
|---|---|
| Sequence number | Sequence |
| | CTCCTCCTCCCGGAGGAGTTCCGATTCCCCCTCTCTTTCTCTCTCTTCTTTCTCTCTCTCTTTCTTGCTCTGCTCTGGAAGCAGGGGGTCCTGATTTG<br>GGCGCGGGCGCCGTCCGCCGTGATTCGGTTCGGCTGATTTGGGAGGTCTGCTCGTTTGATCCGGGTTCGCTGATTGGTTGATTGATTGATTGGTTG<br>GTTCATCTCCGGCGGCTCGATTTGAGGGCCGGTCGGCTTGGTCGCCATGGGGAACTGCTGGGGCGCCAAGATCAGCTCCGACACCTCCTCCTCCT<br>CCTCCCCTTCAGGTGCGTGCGTCGTCCTCCCTCCCTCTCCTCATGCTACTATTTTGCAAAGATTTTTAATACTACGTACCAGCGGTACGACTAGTTCA<br>TAACTAATCTGTGCCCAGAGGGTCGAATAAATCCTGAATGAAAAATCTGGTGGTTTTTGGTTTGCGGCGACTTCGTGCTCTGCATCCCTTCTCTCCTT<br>CCCGAAACCAGTCCTCGGTCATGCTGATTCGATTTCGGTCCAATCCAACTGCTTCAACATAGGGCAAACACTAGGTTAGGTTCACTACTGTAGAAACT<br>TAATCTGGTTCCTACCAAATAGTACTCCCTCCGTAAACTAATATAAGAGTGTTTAGATCCCTATTTTAGTGATCTAAACGCTCTTATATTAGTTTACAGA<br>GAGAGTATTAAGTAGACTACTCAATAAAGAAATCACTGGTCTGTGTTAACTCTCTACTACTTTGCATCTCCTCACTGTTTTCGGGAACTAAGACTAGAA<br>CTGGGTTATGCTGATTTCGTTCCGTTTAATCGACTCAAGATTGGAGAGTCACTAAATTCAGTACAGCACAAACTTAATTTGTCTCCCTAGGAAAATTCA<br>GTCCATTCTTTGGAAAAATCTGTCGCGAGCTTTGACTCTTCCTCTTGACCTGCTTCGTGTGCAAGGGATCATGCCTTTCCGTTTTGGGCCTAGGGGAG<br>AGGAAGCTTCCGATGTAGTAGTAAAATGCTTCACTTAACTTTATCTGACTTCTCCTCTGATTTTTCTGAGTGTCCAGTTCAAATCAGACATATAGAGGA<br>AAAGCTCGAATTCTGATGCTACTTTTGGCTACATCCACGTGCTTTTCTTCAAAGTTATTGACTGTCCTGTTTTGGATGTTCAGCCTTCTTTTCTGTAATA<br>AGCGAAACTAAAGGAAGAAAATACATAGTTAGTCCGACCTAACTTGTCCATGATGAACCTATTTTCTGTTCAATGTTAGGCAGACAAGATAAATGATAA<br>AGGGACAGCAACCTATTTATTATTCTAAACCGTGATCGAATCATTTCTGAAACTCTGCACCATTGTATGATGATGATGATCAGGGACGAATTCCAAGTA<br>TGCTACTAGGAATGGGGCGGCCTTGAGCAGCTCCAGCAGCTATGCCTCCGCGGCGTCAGTGCCACGGAGCGAGGGTGAGATTCTGGAGTCAGCCA<br>ATGTCAAGGCCTTCTCTTTCAATGAGCTGAGGACCGCCACGAGAAACTTCCGTCCGGACAGTGTGCTAGGCGAGGGAGGGTTCGGGTCAGTCTTCA<br>AGGGGTGGATCGATGAGAAGACCCTCACCCCAACTAAGCCAGGCACCGGGATGGTCATTGCTGTAAAGAAGCTTAACCAGGAAAGCTATCAGGGCC<br>ATAGGGAATGGCTGGTTAGTGACAATTTTGCCTGCTGGAAATGGGATTTCTTGTTTATTTCAGTTCTGCATTGTGTCTGACATGCTCTTTCTTTTGGGC<br>GCAGGCTGAAGTGAATTACCTTGGACAACTATCGCACCCGAATCTTGTAAAGCTCGTTGGGTACTGTGTCGAAGACGAACAGCGGCTTCTCGTCTAC<br>GAGTTCATGCCCCGTGGGAGTTTAGAGAATCATCTATTCAGGAGTAAGCCCCTGGCCTTTTACTTTTCTTATTCGCTGGGTGTTATTCTCCAGTTTTGA<br>AGGAATGATGCTAAAGTGTTCCAACATTCAGGGAGTACACATTTCCAGCCGCTCTCCTGGAACCTTCGGATGAAAATTGCCCATGGAGCAGCAAAAG<br>GGCTCGCGTTTCTCCACAGTGACAAGGCCAAAGTCATCTACCGCGATTTCAAAACCTCTAATATCCTCCTAGATGCGGTATATATATCCACAGCCTTG<br>AAGGATCTTTTCCTTTGCGTCCGCAAAATATCTCTATCGGTCGATCTGACAGTCACGCAATTTCTTCTTCAGAACTATGACGCAAAGCTCTCAGATTTC<br>GGCCTGGCGAAGGACGGACCGACGGGTGACAAGAGCCATGTGTCCACAAGGGTGATGGGGACATATGGGTATGCTGCACCAGAATACCTTGCAAC<br>AGGTCGGTTGATCATTCCACTTTCAGAATCCTCAGCTGCGCAAATATAAGATATATTGCTGAAAATCTGACCACGCCTACCTGAATCGTGATTGCGTT<br>GTCACTCTGGTTGTGTCATCGACCAAGATGCCGAACATAACCAATTTTAGGCTACAACCTTTCAATCATCATCTGCACAAATATCTTGCCCGAAAATCT<br>AACCACACCTACCTGAATCATGATTGCGTTCTCACTCTGGTTGCGTCATCGACCAAGATGCCAAACTTAACTAATTTTTCGGCTAGAACCTTTCAGTCC<br>TCATCTGCACAAATATCTTGCTGAAAATCTAAACACACCTACCTGAATCGCGAGTGCATTGTCACCCTGGTTGCGTCATCAACCATCATGCCGAACTT<br>AAACTAATTTTCCTGCTGCAATATTTCCATGATCAGGCCACCTGACCACGAAGAGCGACGTGTACAGCTTCGGCGTGGTCCTCCTGGAGATGCTCTC<br>GGGGCGTCGCGCGGTGGACAAGAACCGGCCGACCGGCGAGCACAACCTGGTGGAGTGGGCGCGGCCGTACCTGACAAGCAAGCGGCGCATCTT<br>CCGCGTCCTGGACCCCCGTCTGGGGGGGCAGTACTCCCTCGCCAAGGCCCAGAAGGCGGCGTCGCTGGCGCTGCAGTGCCTCTCGGTGGACTCG<br>AGGAACAGGCCGAGCATGGAGCAGGTCGTCGTGGTGCTGGAGCAGCTCCACGACGCCAAGGAGGGAGGGAACAGCCCTCGCCCGCAGCTGCAGA<br>GAAAGCCGAGCAGCAACCGGGGCGTGAACGGCTCGAGATCGTCGTCGACCAAGGGGAACAACAAGAAGCCCGCCTCACCGAGACCGGTTTGACC<br>GTGCGAGTGGGATCACATAGCAGAATCTACTAGAGAGATGCGTCAAGGTGTAATGTATGAGTGGTGATCTGCGAAGAGGCAGCGGATTTGTGAATG<br>TTTTGTGCCCGTGTTGTAGGGATGTATCTTTGCAGCTTCTAGTGTTGGTATGTACAGCTTGTATCTATCCGGTTGTAGCTAGTCTGTATGTAGTCCTTT<br>TGTGTATGCCTGATTGCTTTGGTTCTGACTTAAGGTCCAGAGGTTTTGATCTGATTTAGATGCATGCACCCTGTTAAACCAAGACCTTAAAATATGAAG<br>ATGAACAGTGTAAAGTACATATTTGTCACTTCATTTATCAAATGTGAATGAACAATCATATTGGTGTTTTAGCAGAGCAGGCCATGACTTCCATGGGTC<br>AACTGTATCTTTTCCCTTAGGGATGTTGACCATTTTGTTCATATCATACAGTACTAGTAGTATATGTTTCATTTTTTTTATGAAAAAAGTAGTATATGTTA<br>CAGATAATGTTGGGAAAATCACCTTCTGTATTTTTAATTTCAAACAGTTGGCCACAATGATCTTTTTATTTACTTGGTGGGTTCAGCCAAATTACCATTG<br>TTTTTTTCAGGGGTTTCAGCCAAATTATTATTATCTGGGCAAGCGTACGGCGGCGGCCCAAGGCAGAGCACGCAGCCCAGCCGCCAAAACAGAGCT<br>CGCCCTCGCTCCCCTCCGGCCCAAGTGCCGCTCCTCCTCCTCCTCGGTGGACGCCGGCGCCGGTGGATGGCTCCGCCGCGCCAAATCGAGCCCC<br>TCACGCCGCGAGCCTCTCCTCCTCCTCCTCAGCCTGCAATCCCCGCCGAGCTCCGATCCCCGCCGCCGAGCTCCGATCCGCGGGCGATCGCCGG<br>GGCGCCGCCAAGATCAGCTCCGGCCCCTCCCGTTCCTTTAGGTGCGCGTTTCTATTCTTCAGCAAAATAGTTTTCTGGCATCCGACCAGGTTAATAC<br>CCACCGTAACAAACGGACAGGCTATCGCGAATGTTTTGATGAACGATACTAATTGC |
| SEQ ID NO: 7__<br>Traes-<br>CS1B01G041300 | atggcagctctaaccagccttgcctcaaacccgaatccaaacaagtcattcgaggtccttcctaatccgggtgactccctctcaagcctcagttttagcccgaaaagtaatcttcttgtggc<br>aacttcctgggataaccaggtgaggtgttgggagataggtaatggtaacagtcagccaaaggcatccatatcacatgatcagccagtgctctgctcagcctggaaagatgatgggactactg<br>tcttctctggagggtgtgataaacaggtcaaaatgtggcctctgctgtctggtgggcaggctcagacggttgcaatgcatgatgcacctgtcaaggaggtcgcatggatttctcagatgaat |

-continued

SEQUENCES OF THE PRESENT DISCLOSURE

| Sequence number | Sequence |
|---|---|
| (TaRAE1-like)<br>CDS | cttcttgtatccggaagctgggacaagacactaaggtattgggacacaagacagccgaatccagcccatgttcagcaacttcctgatcgttgctacgcacttgctgtgaattatccccttat<br>gattgtgggaacagctgatcgcaatattgtgatcttcaacttgcagaatcctcagactgagtttaagcgtattcaatcacctctgaaataccagacacggtgcgttgctgcctttccagatc<br>aacaaggattcctggtgggttccatagaaggaagagttggtgtgcatcatattgatgattcacagcaaagcaaaaacttcacattcaagtgtcacagggaaggaaatgatattttctctgtc<br>aattcgctcaactttcaccctgttcatcacacgtttgccacagctggatctgatggtgctttcaacttttgggataaagatagcaagcagagacttaaggctttcagtcggtgtcctcaacc<br>cattccttgcagtagcttcaataatgatggttcaatatttgcttatggggtgtgctatgactggagccgtggcgctgagaaccataatcctgcaaatgcaaagacatccatctatctccaca<br>gtccccaggaagccgaggtgaaagggaagccaagaatcgcaacggggcggaagtga |
| SEQ ID NO: 8_<br>Traes-<br>CS1B01G041300<br>(TaRAE1-like) | maaltslasnpnpnksfevlpnpgdslsslsfspksnllvatswdnqvrcweigngnsqpkasishdqpvlcsawkddgttvfsggcdkqvkmwpllsggqaqtvamhdapvkevawisqmn<br>llvsgswdktlrywdtrqpnpahvqqlpdrcyalavnyplmivgtadrnivifnlqnpqtefkriqsplkyqtrcvaafpdqqgflvgsiegrvgvhhiddsqqsknftfkchregndifsv<br>nslnfhpvhhtfatagsdgafnfwdkdskqrlkafsrcpqpipcssfnndgsifaygvcydwsrgaenhnpanaktsiylhspqeaevkgkpriatgrk |
| SEQ ID NO: 9_<br>Traes-<br>CS1B01G041300<br>(TaRAE1-like)<br>genomic | ggtgaggttatggtatgtacaattttggcgcacaatgacggcgacttccctgatccttcgtcatcgtctccaccgtgttggttttggtgctggcgtgaggcctgaggtatgtctcttggatc<br>taatgctcgtctagcgttggtggtttctccttcagagcgatggcccggtaagacgtggccttaatcactccccgcccgtgatgaacatcaggctggcttcgatgatggagaagcatgtgttg<br>gctcggcatgttctagaggatgaagaaggatgacccaggaattttgatgtaactttattaatatttcttcctataatttgtacttccttttcttagaaaaaaactattttgtactgctag<br>tttgattaatattcgtggcttcacatgcgctggtttggttatataagagggagcatatgggtgttgtctttttatataagaaaaaaaagagcaaaataagccacgcgccgatcaagcctgcg<br>aactgagagtatacccggccatgggcaacccagactgacccgacccgtcccgactcgaccttgcccacgggccgggcccaggcctagatttgagcccgatggctgggccgacatgttgtat<br>ttgcgatttaaggaagaggcccggcccaagggccgaggcccgacgggtttttgactgatgggccggggttgggccaaattgttaggcccaacggccgggctcggcctaagccttttgctt<br>gcgttcaggctttgataggctcagcccgaagtccacatccacatcaaccaccccgcgtgccgatgaagccatttttggaaggaccttcgcgtgcatccgacgcgacgcgctacaccgaag<br>cctatactactacatctcgtctcatcgccctcctcccacacgacgactcgagaatcctcggctgaggctccactccgcactcgcaagtcgcacccgcagccgccgccgaccgctccccgtcc<br>ggcaggtaagcccccgagcccctcctcgccgctccgctcgcgcggactcctagctagctagggttcccggcaccgattccgcggcgctgcactccggcgcaatgctcgcggccgcggacgg<br>gcccgccgcttcgggggaagctctgatctggtggccggcgctcgctcgctcgctcgcggtctccggagcaaatcggccgcatcgagtggccggagcaagcttaggatagttcgattatttcc<br>cccatccccgttggtcaggccgagagggccagtttgggcgacctcctggtgattccgctgccgtggtggggattgggtggtcgtggcccgggtgtaggcgtttgtaggtcgagtgagtgttt<br>ccttccaggttctatgctcacccagcttgtgttatcactgggatccgggcgttcggcaggctaacattcaccggattttggacctgcattgttgcggcgcgtgccggggatagcgtttatg<br>ctggctttggcgcggtgattttgtgcgtgcgtgcaaacttttggggctgccttctggtgatctcgctgtcgggtggtgcgagttcatcaagcggtcagggtgtaggcatttgtagtcgagcg<br>accccagctttcatgcccaccagctcgtattattcggtcgttaaccacgtttaccgaatttggaccgacgtcgttgcggcacgtaccaggggacagcgtttatgctggtttcggtgtggag<br>attttgtggtttaaacttggggcgcgcttggtttgcgaggctacctcctggtgatttcaccgtcgggtggtgggaatcggatggtcggggtgtaggcatttatagtggagcggaccccttgt<br>tttatgaccagacatttagccgaaatttggacctacactatcgtggcgtaccaggggatatcatttatgcgggttttggcgcgacactttctttgtcggattttgtggtgcaaacttaaat<br>aatgacttccctaatgttaaacactcgttctggcatcgtggactgttggaatcgttctttttcgtagtctgagctactttaagttgttacttatgctctcgtgtgcgtgggagactccacgt<br>gctgatttctcttacttgcttctcatggtcactggactgatatttcttttccagattttgaaggttcacagaaggagagatggcagctctaaccagccttgcctcaaacccgaatccaaaca<br>agtcattcgaggtgtgatacttttgtggccatgtctgtcctgctttttatttttttgcgtcttgtcattctgtatatgctacatgttctctgcaatggttgctttcaaatgcaggtccttcc<br>gtaatccggtgactccctctcaagcctcagttttagcccgaaaagtaatcttcttgtggcaacttcctgggataaccaggtaattttgtttctgctgtaattttcagtgagcttccattatt<br>gtgatgtatcttactaggaatgtcttttgagttttgtgcaggtgaggtgttgggagataggtaatggtaacagtcagccaaaggcatccatatcacatgatcagccagtacgttctcataca<br>tgtttctcctgaaagtagtttcatcttacacattagagtggttccttacctgtttacttggtatgatgattgatttgtttccttccatcaggtgctctgctcagcctggaaagatgatggga<br>ctactgtcttctctggagggtgtgataaacaggtcaaaatgtggcctctgctgtctggtgggcaggctcagacggttgcaatgcatgatgcacctgtcaaggaggtcgcatggatttctcag<br>atgaatcttcttgtatccggaagctgggacaagacactaaggtgcaagaacaatattcctctccaccctcagtattctttttacatggaaattcagcgcatatcacccatatctgatcccaa<br>attgttatttatggctgttttgcttttgggaattcgtgttgtttgtggtatcctttctgtacttcatgtgttctgcattaatgttcacacattggctaaccaaatattgtagaagttctatc<br>tcatcctctttatatttgcactcattttgtatgccttctttgatcctgaagagttttctactacttgttgaatcatactgccctattcttatcaaaggttgtgcactttctgggtatcatct<br>gtactatttatggctgtagtgaattttcttatggcagaagtttttatagaagtaactgttgatgcagacagttactatattaaatgtacattatgtgattagtgttagaaatgttcgtttc<br>gagttttagcatcatctttatgaagattatttatgaaacatcaagttagggtctggctgtcagtttaaacatgagcacagattgagcataggcgataatcatggttggtaggaggccaggga<br>ccgggatccttgtgggacctgccggcgtacccgtgatagcagaaggggtgcaagggacagggcactggaactaaggcaggcagaaacagagaaataaagattggggattagactttgtagcc<br>aattcataaaaaaattggttgcatcattttgtagaggttggccttaacatatgactaaaaaacaaaaacaaaccaagactcttccctaaactgaataccgcagatactcaagacaccatata<br>gggccacgggctcaggctgaagtcatctaggtctcagacatgccaaaacagactgggacaaggacaagctgaaactgactagtactaggtttcccgggtcaactaccgttcagctggaggtc<br>tgaatgcgtggtgccttctctgatacatggatctcatgtggcacttctgttgtgtatttgtcccagtctgcttattttcctttgtctgtatcatgctgagactaatacatttgggtcgtgca<br>tttgatcttcttctcattacaactttagctctgatcctgatgacttgtttctagtctgcatcaatgcttatcatcatactattgtaggtattgggacacaagacagccgaatcctgcccat<br>gttcagcaacttcctgatcgttgctacgcacttgctgtgaattatccccttatgattgtgggaacagctgatcgcaatattgtgatcttcaacttgcagaatcctcaggtaattttgcttcc<br>taaccgactatgcattttcaattcttgtggtggtggtgctcatgcttttactgccattgacttatatttgaactgcctgacttaaattcatccctgatgtgattttagactgagtttaagc<br>gtattcaatcacctctgaaataccagacacggtgcgttgctgcctttccagatcaacaaggattcctggtaatgccatattttcttgtgtcttttactctcagcattacgacaccaaccaaa |

-continued

SEQUENCES OF THE PRESENT DISCLOSURE

| Sequence number | Sequence |
|---|---|
| | acttccgttgtttgaatacataacttgttgttactatgctttgaagtttaatcatatgttcttctctacctatccatcataattatttatgttgcccaattatgttgtttttacctagcttg<br>agttttcgaccttaaacattgttacaaccttactcgaattagctttagatgttggcctgccatcatttgcagtgtaatgggcgttgttcctttagtgatctcatttcaaacttcctacccct<br>ctattataggataaataaggtatattgattgtgaaatcaaactttactgactataaatactatactatgtgatttatgtgacataaagttgatatcattggatttgttttcaaaagtacttt<br>gttacgattttgataaaatatgagaagaaatttatggccaaagattgaactcgagcagtcaaaatatgccttgtatatctggatagagtgtgtattactaggaatgttaatccaatataaat<br>gtcattaattgacatctctctagttagcacaaaagctgcataaaagaagaggatgcagttttccttaatgttttgaccaactccagctgtgttgcaaacagtttccttcaccagaactgtag<br>aacggatcttagcctatagcagttaaagctaatctgaacatgaaatccggctgaagtacaaatagtaaaaccatccaaggcttcaagcaattgtttttgaactacagatctttagatgtcta<br>tttctgcattttcctattcttcacctgcttgtgggtgttcttatagtgggtcgtcgtttcatcatgggctttgaccaatcaatttttgctgttacacaatgatctttttctacatcaatgaa<br>ctgcctatattggataaagctggtcgatacctggcaatagttcttgttttaattattttcttgttgtttccatattacttgggcaaaacatttttttacatgcgactgacacctgattttgtt<br>tgaaggtgggttccatagaaggaagagttggtgtgcatcatattgatgattcacagcaaagcaaaaacttcacattcaagtgtcacagggaaggaaatgatattttctctgtcaattcgctc<br>aactttcaccctgtaagatctctatcttgttctctcttgactccatatttatctatgtgccatactgccattcttatatttcattagtccacttctgctattatggaaaatgctaatggcga<br>cttctgttgagctttagtcactatgtctccatcatgatttgtaaaatactgaaagctcagttcgttgtcttccacaagatgtgttgagctttattcgatacagatacctaccacacttcgcc<br>taatataataaccactatgcttgaaggcatacatatgttagtaaactactccaaattgatcaagcaatattttgcagaaataaaaatcccaacagattagcttcagtttaattgagcaactc<br>gaaatcgtacctatttgttacagacacatcgaagagaagcgtttctgcttcttctgttgctaactttggcatcttattcattggattggtatatgcttgggtgatgatactatacatccatt<br>tagttgagtgtgcttgttggctatatatttcactggaaaatgcaactgactggtgataattgtgaagtatggaaattcagttagtctagttacttatgggatttcatgttatctaccacttg<br>gcacaggttcatcacacgtttgccacagctggatctgatggtgctttcaacttttgggataaagatagcaagcagagacttaaggtttgtctattccccttttttttttctattttcccctc<br>ttgttggtttatgttttcttgattggaattcaatgatttcaagatggctctactttgttgtgatctgtggacactgatgatctgcatataaattctttgttgatgcgcatacatagcctgaa<br>atcatcccgagctcaagctaataaactcactatcctggccatgagcagaaaaaaaaaatattagttcataaatgttatcaccaattctgatttcccagctgccttgtcatcctgctgctttt<br>ggcgtttagtatgcacttctttttattcttgataaaagcatattacatatttattactcaaccgcatggagcctctgcagtaaggtatatgtgtaatttgtcaacagataaccttttagctt<br>ttaggcatatcatacacagtgttgcattctgacagttgcttacttgcttagcatagagggctatctgtgtgtgcccaagtttattgcttcagttccctcatttgtcatacaccttctggtat<br>gttgcacataacacattcttacatttcccctacactgcttctatacaggctttcagtcggtgtcctcaacccattccttgcagtagcttcaataatgatggttcaatatttgcttatggggt<br>aagtcaagtgatgcttttgagagtgtcttgttatcaccatgtttttcagtccggtcagagtttagatatgttacatgcctgtcatttttcctgcaccttatttaatatacggaagaaatcag<br>ctcgacaaataattcatgttccttttgaactgctatcttgtcgtgtcctctgaatccaagttctgaatgcaaccgtaattatcattgctggggagcaggtgtgctatgactggagccgtggc<br>gctgagaaccataatcctgcaaatgcaaagacatccatctatctccacagtccccaggtagtttccgagtgctgatatcgccataaaaagaattcttgtattttcgacatcatttgagatcc<br>attcctgtttttataaattgttattatgttatcttttggcactcaacttgcatcattctggacaggaagccgaggtgaaagggaagccaagaatcgcaacggggcggaagtgatggtggcat<br>cctgcctgccgaaaagtcgatagttgtgcaagagatgatgtatattcaagggccttgtttcgctcgggccttgccttgacgtgtcctctggatgttcttacttggttcggccgcctggtaga<br>tgaaacgcctactcccagcaaccagtgataggttacttagccgtaggtcgtagcacatagccgtttatgtaatgcatagttgtccgaaggaatgtttccccgtgttcttgtgttgtgatata<br>gtcaggtcagcgcgtagtcttttgaaaaggagaaagccttcggtgtcttgtaagtggtgtagatctttggaaatatgggcatgatattcggtggagttattctgaaaaagatatcccggttt<br>cggtttcagcgaatgcaagctagatttatggggaaggttgtagttagcaccatgctgcaaatgcatgcggcattcggaggatttacagtttgaatcttcctgtttatccaagtctaggattc<br>ccaccttcctagtaccattgagcacgttagtttgaatttttttttgtttattatggttcagaacttccgattcaaaaaaatctgatttattttacgcgaatatatggatgtttaatcaatata<br>cggttttgtatgtgagatataaagaagggccaaagacatgcaaacaatgggcatttctttgtgctggatcttttgtgttcttatctgcactgcaccatcaaacgaaaattaccaggtgcgtg<br>cagaacgacgtgtaaagaaaacacccaacttttccgaaacttccaaatgccattttcgagctgttcaacatagtgtgcttcgaaaatccgttcttcagtacagtaccagccacgtagcaatg<br>gctccacagaagcctcattgcttacgagctttatgccgtgaacttgcatagattcagttcgacaacccaattgcataagcttgcgatctttttatgccgttaacttcaaaatagattcggcg<br>caacacgactcaatagccacgacacgggcaaagactagggcatcatcaaacctaacgcaatatagcattggtgtcggtacttaatttacagggttttattgcatgaccaaatcacaggtgcg<br>gcataaaattacagtcgcggagagaaagcgaacccagtttcacagcaagagagtagcagactagttaacaaacgtaagagaacccagcttcaagaatctaaacacaggtaaagaccacattg<br>tttcagcaccaagttcccgtccttccttccacgtgagaacccgacccggtcctagtcacagctccttcagacatcgaacacatcatcatacatgtcggcgtcccagtccgcgtcgtcgatat<br>aatcctccatgtcatcaaactcggcatcctcgtcgtcgtcggtgaccacgtccagcagatcatcgtacatgtcgacctcgatgtcggaaccgccggggtagtcatcactgccagcgaggtaa<br>gcccggtacttgaagtcggagatggggtccccggggagcctgaggttcccgatcctggcgcacttggatctcagggcatcgtccatctggaggttgcagcagcggcgcacgtcgagggactc<br>gaggcgggggcagtggtcgaggatcgccgccagcccggcgttggtcaggttgttgccgatcagctggaggtcccggagctcgggcatgctgctcgcgatccctagcacacccgtgtcatcat<br>ccatgccctcaaagactgcaaacccccctttggaggaccgtccagcgctcgttcagccgaaaggatttcaggtgtgggcaggctctgccgactgactcgcacacgttgctgttcagtgagcag<br>aatgtgatctccagctcctcaagctgaggaaagcccttgactgcatctgccagcgcctcattggatacttcatcacacaggcttagttgaaggctcttcagcgagggtgccctgcattgaga<br>catggcaagttcttatctaacacaagcatttaagctaatgccaaacccaatcatgctttccaagctcaggacaagaaataacactagaacaacagaattgattgaaataaccatgtgaaagt<br>aaaacattccatgctgttagattcaccatagtcttcaaataagtctaactccagtcacatgcaaatgaacttcagcacgcagttctaaacaaaatacgacatgacttgatactgtgtctgaa<br>ctccacatatcacatctagtcaaaccattagaagaagacgacaacgagccaggtgttaggtggtcaagaagacaagaagtgggatcaatttatttcaatgcaccaaaagatcaacacaacga<br>taagaaaatagcaactctgactagcactacgcttaccaagcaaacaaatggccacaagaatatggagttatgggcagcttaggggttttgcttcagtgagggggatataacagttgcaatac<br>cataaaagaaagtagctagtaatagttttacatatttatcgtttcactgcatagttgttgatttgattgttaatactatgcgatacagatatacaccagtggtaattggatgcacattcagt<br>aaggcccttaatttttttgtatgcaaggaaatgttgtagtggtggctccaacagtataatccataagaaccaattcgagtaaatgatgatttgaacccaggtagtgggcccacccaacatgt<br>aagttaactacatgaagagtgcaggcacactaaaacattcatcctgaagtacatgagttattttggaaacattctgatggattgttggataaaagcgtgaaagtttccaaggttgcaagttt<br>ctgtatgatctaaatgcacgagaggactgtgtacaagtgaaaggtactggaagatgcatgaaccaaaaacagttacaggaaggttaacagagaagtctgcagctaccaaaggcaggattgtc |

-continued

SEQUENCES OF THE PRESENT DISCLOSURE

| Sequence number | Sequence |
|---|---|
| | agaaatgccgaattgcatcatgcatcaatcttgcagtgaaactgcctacatctttatcagaaaaaaatggtactgaaccatcgaagtgatcatttggttttctacagacctttacagcaagt aatttgctggaaaccaacaaaaaagttcagatggccctccccctgtaaagtctccatgctgagactcacctatccttgtatgttttagggattggtcggtgccaatgttatatccaagagc acaatgatgcccccattctgactattagtgggaacaggccaattccctccaggaaaacaaaccttcagtcagtgtgctactctatatacattttccgggttgctccacatacattatgtccc aacgctacggagtagatagaacttagcaaggcacattgagtcacacaaagacatagcactggagactcatgtgatctgttccaacttgcaagcattttactgttgagtagtaccattttacc ccatccaatttcgttaggttatgaaaatgtgtgtttttttcaacctgtcaaatcaaacgtcagaaaggtccatttccaacttcagaatacagacttattttaagttaaagaccttccccatg aattttaatttaccagcagcgccagcaaccgttcgtttaactgaatgaataaactaagcgccgcatccacaaattggggaaaaaaaacccccactgtatgccagaaatgggcatgtgaaa caggaaggggagagccgtcgcgaacaacctgccggagatgtagctgaggagggcgtcggtgacgaaggtgtcggcgcagaaggactggagcgtgccggcggcgcggtcgacggcggcgcggg ccatggcctcggcctcctcggtctcgaggatgtccccgtggtgggtcatgtcgaggcggcgccacagcgcggggtcgccgtcggcgaggcggcgccaggcgcggcacgcccgcccggccccc gtcaggatg |
| SEQ ID NO: 10_ TaPK-like promoter region | ttgtcccgccgatgataagctcggttggcgactggtccatgcccctccggactccacacagccaggcgaattggtgagtctgcaactgctgagctggacacaagtaagtcataaatgcgacg caacaaaaaatgacgccacgaaagttgggacgttttctcaattatcccggaatattataatagcatgttgtacgcgtacctcatgtagccggaaaacatctacagccgggcaccccaaactc tatcatacgccccgacggacggccaagttagtgaccggtcacgaaagactgacctagacgggtaacttaaacgggtctcaagcgctcaggctaaccggcgcccctcatatccagtcccaaat gtagggcggataagggggcgcccaggagcatcgaggcgcgtccatcacgtcggtcctggcccacgatggcccacccgcctccatatatattcttctgcatccgctgcctgggccaaacacta tccacttcactcccctacgccacccaaactcctatccgacgatcacgagccttctccggtttgacgtgtagcagattcgacgacgaccagtacagatctgtcgactggggtgtcaacccgtg cggtttggagaaggaaatggccatccgcattgcactttgccatttccggaggacaacgcccttccgacgacaggatctcccagcgcgagtccattgcgtcggtgcatcgggcgctcagatcc tctggtgctggatcatcgtggtcctctaggcagccttccaatctcccttccccatcactggtccgtcggagtacgagtcctatcgagggtcagtgtgcccgccgtgggaagaagaggatgag ggcggctgaggtcagcgccttgctgccgacatggcggcggcggaggcggctgatacaatggcacgggcggccgcagaggaggaaggcatccgcgtccgcattgtaaagaagcggcagcggag gaacacgcgcgtccctcgtccgagagcataatcggcgatccgtgccattgccggactgccttccaaggaggagaaggaggacaacgatgggtcagatagctctggcgatgagcagacttgac tcgattcgtactgcctctttgatcggtacttgcgcgagaagaacgacaagggcaccaagaagggcaaagacagacatggattgatcttcttcatagctagcatgtacgtaggttaaacatgc ccaatttttgatagtccgatgtcatgtcctgatgtcgtagtaggaagatgtgtgtaatgcatcgtttatgtagttgcatgagtttgtatggatttgagataaggtaattaagatgttcgatt gtgagaagggaaatttaaggcgtgaccaacccgtgttcacggatgcgcctggacgcatcgctgaccggatcgtgtcgacgcgcgcgagcaaaggcggccggcgaggccaaccccaaccacca ctccgcccgcgccgcccctccctttctcccgccttttcggccccccatcaatggctccctccacctccttctagaagccgcctgccccaccacccgtgctagcggtagtgtatcgggttcccc ttccttccttcctctcccctccctgcctgcactgtcccatcgctcgctttctcgcccgctccgtggcggtggtggtggtgcgtggtgggggagaaagttggaggcgggggaaaggagacgca aagcggccacccaaaaaggcacatatactttctttctttccaccgccgccctcctcctcctggtcctggaggagttccgatccccccccccccccccctctctcttctttctctctctttc ttgctctgctctggaagcaggggagggagggggttccgatttgggcggggaggcactgttcgcggtgactcggttcggctgatttgggaggtcttctcgtttgatccgggctcgctgattga ttgattggttggttggttcgtctccggcggctcgatttgagggtcggtcggtccggcgagtgagtcgccatg |
| SEQ ID NO: 11_ TaRAE1-like promoter region | gacggctcaatggtgtatttttcccgtcgtgcgtcttcatcggtgaggttatggtatgtacaattttggcgcacaatgacggcgacttccctgatccttcgtcatcgtctccaccgtgttga ttttggtgctggcgtgaggcctgaggtatgtctcttggatctaatgctcgtctagcgttggtggtttctccttcagagcgatggcccggtaagacgtggccttaatcactccccgcccgtga tgaacatcaggctggcttcgatgatggagaagcatgtgttggctcggcatgttctagaggatgaagaaggatgacccagggattttgatgtaactttattaatattttcttcctataatttg tacttccttttcttagaaaaaaactatttttgtactgctagtttgattaatactcgtggcttcacatgcgctggtttggttatataagagggagcatatgggtgttgtctttttatataagaa aaaaaagagcaaaataagccacgcgccgatcaagcctgcgaactgagtgtatacccggccatgggcaacccagactgacccgacccatcccgaaaaagctcgacccgtcccgactcgacctt gcccacgggccgggcccaggcctagattttgagcccgatggctgggccgacatgttgtatttgcgatttaaggaagaggcccggcccaagggccgaggcccgacgggtttttttgactgatgg gccggggttgggccagattattaggcccaacggccgggccgggccgggctcgggcctaagccttttgcttgcgttcaggctttgataggctcagcccgaagtccacatccacatcaaccacc cccgcgtgccgatgaagccatttctttggaaggacctgcgcgtgcatccgacgcgacgcgctacaccgaagcctatactactacatctcgtctcatcgccctcctcccagacgacgcctcga gaatcctcggctgaggctccactccgcactcgcaagtcgcacccgcagccgcgccgtccccagcagccgccgccgaccgctccccgtccggcaggtaagcccccgagcccctcctcgccgc tccgctcgcgcggactcctagctagctagggttcccggcaccgattccgcggcgctgcactccggcgcaatgctcgcggccgcggacgggcccgccgcttcggggggaagctctgatctggtg gccggcgctcgctcgctcgctcgcggtctccggagcaaatcggccgcatcgagtggccggagcaagcttaggatagttcgattatttcccccatccccgttggtcaggccgagagggccagt ttgggcgacctcctggtgattccgctgccgtggtggggattgggtggtcgtggcccgggtgtaggcgtttgcaggtggagtgagtgtttccttccaggttctatgctcacgcagctcgtgtt attgctgggatccgggcgttcggcaggctaacattcaccggattttggacctgcattgttgcggcgcgtgccaggggatggcgtttatgctggctttggcgtggtgattttgtggagttgag tggtcaggttgtaggcatttgtagttgagtgatcccagctttcatgcccaccagcttgtattattactcgagttggtcgttaaccgtgtttaccgaattttggaccgccgttgttgtggcac gtaccaggggacagcgtttatgctggtttgcgaggctacctcctggtgatttcactctcgggtggtgggaatcgagtggtcggggtgtaggcatatttgtagtggagcgatcccaggtttta tgaccagacatttagccgaaatttggacctacactattgtggcacgtaccaggggatagcatttatgcaggttttggcgcgacacttcttttgtcgggatttttgtggtgcaaacttaaataa tgacttccctaatgttgaacaatggttctggtatcgtggactgccgaaaccgttctttttggtagtctgagctactttaagttgttacttatgctctcgtgtgcgtgggagactccacgtgc tggtttctcttacttgcttctcatggtcatcactggactgtgatatttcttttccagattttgaaggttcacagaaggagagatg |

-continued

SEQUENCES OF THE PRESENT DISCLOSURE

| Sequence number | Sequence |
|---|---|
| SEQ ID NO: 12_ | ttgtcccgccgatgataagctcggttggcgactggtccatgcccctccggactccacacagccaggcgaattggtgagtctgcaactgctgagctggacacaagtaagtcataaatgcgacg |
| pTaPK- | caacaaaaaatgacgccacgaaagttgggacgttttctcaattatcccggaatattataatagcatgttgtacgcgtacctcatgtagccggaaaacatctacagccgggcaccccaaactc |
| like: RFL29a | tatcatacgccccgacggacggccaagttagtgaccggtcacgaaagactgacctagacgggtaacttaaacgggtctcaagcgctcaggctaaccggcgcccctcatatccagtcccaaat |
| chimeric gene | gtagggcggataagggggcgcccaggagcatcgaggcgcgtccatcacgtcggtcctggcccacgatggcccacccgcctccatatatattcttctgcatccgctgcctgggccaaacacta |
| cassette | tccacttcactcccctacgccacccaaactcctatccgacgatcacgagccttctccggtttgacgtgtagcagattcgacgacgaccagtacagatctgtcgactggggtgtcaacccgtg |
| | cggtttggagaaggaaatggccatccgcattgcactttgccatttccggaggacaacgcccttccgacgacaggatctcccagcgcgagtccattgcgtcggtgcatcgggcgctcagatcc |
| | tctggtgctggatcatcgtggtcctctaggcagccttccaatctcccttccccatcactggtccgtcggagtacgagtcctatcgagggtcagtgtgcccgccgtgggaagaagaggatgag |
| | ggcggctgaggtcagcgccttgctgccgacatggcggcggcggaggcggctgatacaatggcacgggcggccgcagaggaggaaggcatccgcgtccgcattgtaaagaagcggcagcggag |
| | gaacacgcgcgtccctcgtccgagagcataatcggcgatccgtgccattgccggactgccttccaaggaggagaaggaggacaacgatgggtcagatagctctggcgatgagcagacttgac |
| | tcgattcgtactgcctctttgatcggtacttgcgcgagaagaacgacaagggcaccaagaagggcaaagacagacatggattgatcttcttcatagctagcatgtacgtaggttaaacatgc |
| | caattttgatagtccgatgtcatgtcctgatgtcgtagtaggaagatgtgtgtaatgcatcgtttatgtagttgcatgagtttgtatggatttgagataaggtaattaagatgttcgattg |
| | tgagaagggaaatttaaggcgtgaccaacccgtgttcacggatgcgcctggacgcatccgctgaccggatcgtgtcgacgcgcgcgagcaaaggcggccggcgaggccaaccccaaccacca |
| | ctccgcccgcgccgcccctccctttctcccgccttttcggccccccatcaatggctccctccacctccttctagaagccgcctgccccaccacccgtgctagcggtagtgtatcgggttcccc |
| | ttccttccttcctctcccctccctgcctgcactgtcccatcgctcgctttctcgcccgctccgtggcggtggtggtggtgcgtggtgggggagaaagttggaggcgggggaaaggagacgca |
| | aagcggccacccaaaaaggcacatatactttctttctttccaccgccgccctcctcctcctggtcctggaggagttccgatcccccccccccccccccctctctcttctttctctctctttc |
| | ttgctctgctctggaagcaggggagggaggggggttccgatttgggcggggaggcactgttcgcggtgactcggttcggctgatttgggaggtcttctcgtttgatccgggctcgctgattga |
| | ttgattggttggttggttcgtctccggcggctcgatttgagggtcggtcggtccggcgagtgagtcgccatgccccgcttctcctccaccacgccaatgtcgccaccccgcctccgcctccg |
| | actctgcgcccgccactcctcctccacctctcatccctcacgcatctgggatccccacgccgccttcgccgccgcggcacagcgggcgagctctggcacgctcactacggaggacgcacacc |
| | acctgtttgacgaattgctgcggcggggcaatcctgtccaggagcgtcccttgaataaatttctggctgccctcgcccgcgcgcccgcgtccgcatcctgctgcgatggccccgccctggca |
| | gtcgccctcttcggccgtttgtcccgagacgtcggacgacgggtggcgcagccaaatgtcttcacctatggcgtcctcatggactgctgctgccgcgcttgccgcacagatctggtgctcgc |
| | cttctttggccgtctcctcaagacgggcctggaggcaaaccaagtcgtcttcaacaccctcctcaagggcctttgccacacaaagcgggcggatgaggctctggacgtgctgcttcacagga |
| | tgcctgagctgggctgcactcctaatgtggtggcgtataacaccgttatccatggcttctttaaggaaggccatgtaagcaaggcctgcaatctgttccatgaaatggcgcagcagggcgtt |
| | aagcctaatgtggtgacatataactcagttatcgatgcgctgtgcaaggccagagccatggacaaggcagaggtggtccttcgtcagatgattgatgatggtgttggacctgataatgtgac |
| | gtatagtagcctcatccatggatattcctcttcaggccactggaaggaggcagttagggtattcaaagagatgacaagtcggagggttacagcagatgtgcatacttacaacatgtttatga |
| | cctttctttgcaaacatggaagaagcaaagaagctgcaggaatttttgataccatggctatcaagggcctgaaacctgacaacgtttcatatgctattctccttcatgggtatgccgccgaa |
| | ggatgcttagttgatatgattaatctcttcaattcaatggaaagagattgtattctacctgactgtcgtatcttcaacatactgattaatgcatatgctaaatctgggaagcttgataaggc |
| | tatgcttatcttcaatgaaatgcagaaacaaggagtgagtccaaatgcagtcacatattcaaccgtaatacatgcattttgcaagaagggtaggttggatgatgctgtgataaagtttaatc |
| | agatgattgatacaggagtacgaccggacgcatctgtttatcgtcccctaatccagggtttttgtacacatggcgatttggtgaaagcaaaggaatatgttactgaaatgatgaagaaaggt |
| | atgcctcctcctgatattatgttcttcagttcaatcatgcagaacctatgcacagaaggaagggtaacagaagcacgggatatccttgacttgatagtgcacattggtatgaggcctaatgt |
| | tatcatatttaatttgctgatcggtggatactgcctagtccgcaagatggcagatgcattgaaagtatttgatgatatggtgtcatatggtttagaaccttgtaactttacgtatggtatac |
| | ttattaatggctattgcaaaaatagaaggattgatgacgggcttattctgttcaaagagatgctgcacaagggacttaaacctacaacttttaattataacgtcatactggatggattattt |
| | ctggctggacaaactgttgctgcaaaagagaagtttgatgagatggttgaatctggagtaagtgtgtgcattgatacatactctataattcttggtggactttgtagaaatagctgcagtag |
| | cgaagcgatcaccccttttccggaaattaagcgcaatgaatgtgaaatttgatattacaattgtcaatatcattattggtgccttatacagggtcgagagaaaccaagaggctaaggatttgt |
| | ttgctgctatgccagccaatggcttggttcctaatgctgttacctacaccgtaatgatgacaaatcttataaaagaaggttcagtggaagaagctgacaatcttttcttatccatggagaag |
| | agcggctgtactgccaactcttgcctgttaaatcatatcatcagaaggttactggaaaaaggagagatagtcaaggctggaaattatatgtctaaagttgatgcaaagagctactcacttga |
| | agctaaaactgtttcgctgctgatctctctgttttcaaggaaagggaaatatagagaacacatcaaattgcttcctacaaagtatcagtttctggaagaagcagccacagttgaatagttgg |
| | tacatgatatctgaaatttaatttgcatcgcttgccatgggtccgtctgcttgtacaagaaatgcattttctatttgtaaataggaagtcagtttagaacaagccatcaggatgacgcaaag |
| | agtacaattcagttgcaccaccaataaaaaggcagaactagggctgccaaaacaacactgaatcaaaactcaaacagaaggagcagcaaactttttttttttttgaagctggacagtctgcta |
| | gccaaacaactacaggagactgtcagggggggcatgtagtggctggcgtctaagcgcctttgcttcttccaccatccatggcttagcctcacacggaatcgagtcaaccaattcccgtcggtt |
| | ttgggggctcccttgaagatgcaattgttttcagcggccagatacgcatggtcagattaatcagcgagtgtgccccttctgtctggttcgagaaagaatttgaagagctgagcttgtccctg |
| | ctggaaccagtttgaggttagttaatcataacagggtactagagaggtgttttattgactgttgatgtgtaatatgttatatgccatcctcttgatgattacggtgatctgtgaagaggcag |
| | catgcaaaagtctgaatcacatatgcttatgtaattgtgttattatttgtgcagcttctagaccttttgccttgtagatggctacatggatctagttgtagcaatctgtaactgttagtgtt |
| | ttgtatatgctggcattgatgattagggtgacttgtgaagcatgcagaagtctgaatcgtacatgcttgtctag |
| SEQ ID NO: 13_ | gtggccctgctcatccctggatgttgacggctcaatggtgtatttttcccgtcgtgcgtcttcatcggtgaggttatggtatgtacaattttggcgcacaatgacggcgacttccctgatcc |
| pTaRAE1- | ttcgtcatcgtctccaccgtgttgattttggtgctggcgtgaggcctgaggtatgtctcttggatctaatgctcgtctagcgttggtggtttctccttcagagcgatggcccggtaagacgt |
| like::RFL29a | ggccttaatcactccccgcccgtgatgaacatcaggctggcttcgatgatggagaagcatgtgttggctcggcatgttctagaggatgaagaaggatgacccagggattttgatgtaacttt |
| chimeric gene | attaatattttcttcctataatttgtacttccttttcttagaaaaaaactattttgtactgctagtttgattaatactcgtggcttcacatgcgctggtttggttatataagagggagcata |

-continued

SEQUENCES OF THE PRESENT DISCLOSURE

| Sequence number | Sequence |
|---|---|
| cassette | tgggtgttgtctttttatataagaaaaaaaagagcaaaataagccacgcgccgatcaagcctgcgaactgagtgtatacccggccatgggcaacccagactgacccgacccatcccgaaaaa<br>gctcgacccgtcccgactcgaccttgcccacgggccgggcccaggcctagattttgagcccgatggctgggccgacatgttgtatttgcgatttaaggaagaggcccggcccaagggccgag<br>gcccgacgggtttttgactgatggccggggttgggccagattattaggcccaacggccgggccgggccgggctcgggcctaagccttttgcttgcgttcaggctttgataggctcagccc<br>gaagtccacatccacatcaaccacccccgcgtgccgatgaagccatttctttggaaggacctgcgcgtgcatccgacgcgacgcgctacaccgaagcctatactactacatctcgtctcatc<br>gccctcctcccagacgacgcctcgagaatcctcggctgaggctccactccgcactcgcaagtcgcacccgcagccgcgccgtccccagcagccgccgccgaccgctccccgtccggcaggta<br>agccccccgagcccctcctcgccgctccgctcgcgcggactcctagctagctagggttcccggcaccgattccgcggcgctgcactccggcgcaatgctcgcggccgcggacgggcccgccg<br>cttcgggggaagctctgatctggtggccggcgctcgctcgctcgctcgcggtctccggagcaaatcggccgcatcgagtggccggagcaagcttaggatagttcgattatttccccccatccc<br>cgttggtcaggccgagagggccagtttgggcgacctcctggtgattccgctgccgtggtggggattgggtggtcgtggcccgggtgtaggcgtttgcaggtggagtgagtgtttccttccag<br>gttctatgctcacgcagctcgtgttattgctgggatccgggcgttcggcaggctaacattcaccggattttggacctgcattgttgcggcgcgtgccaggggatggcgtttatgctggcttt<br>ggcgtggtgatttgtggagttgagtggtcaggttgtaggcatttgtagttgagtgatcccagctttcatgcccaccagcttgtattattactcgagttggtcgttaaccgtgtttaccgaa<br>ttttggaccgccgttgttgtggcacgtaccaggggacagcgtttatgctggtttgcgaggctacctcctggtgatttcactctcgggggggggaatcgagtggtcggggtgtaggcatatttg<br>tagtggagcgatcccaggttttatgaccagacatttagccgaaatttggacctacactattgtggcacgtaccaggggatagcatttatgcaggttttggcgcgacacttcttttgtcggga<br>ttttgtggtgcaaacttaaataatgacttccctaatgttgaacaatggttctggtatcgtggactgccgaaaccgttctttttggtagtctgagctactttaagttgttacttatgctctcg<br>tgtgcgtgggagactccacgtgctggtttctcttacttgcttctcatggtcatcactggactgtgatatttcttttccagattttgaaggttcacagaaggagagatgccccgcttctcctc<br>caccacgccaatgtcgccaccccgcctccgcctccgactctgcgcccgccactcctcctccacctctcatccctcacgcatctgggatccccacgccgccttcgccgccgcggcacagcggg<br>cgagctctggcacgctcactacggaggacgcacaccacctgtttgacgaattgctgcggcggggcaatcctgtccaggagcgtcccttgaataaatttctggctgccctcgcccgcgcgccc<br>gcgtccgcatcctgctgcgatggccccgccctggcagtcgccctcttcggccgtttgtcccgagacgtcggacgacgggggcgcagccaaatgtcttcacctatggcgtcctcatggactgc<br>tgctgccgcgcttgccgcacagatctggtgctcgccttctttggccgtctcctcaagacgggcctggaggcaaaccaagtcgtcttcaacaccctcctcaagggcctttgccacacaaagcg<br>ggcggatgaggctctggacgtgctgcttcacaggatgcctgagctgggctgcactcctaatgtggtggcgtataacaccgttatccatggcttctttaaggaaggccatgtaagcaaggcct<br>gcaatctgttccatgaaatggcgcagcagggcgttaagcctaatgtggtgacatataactcagttatcgatgcgctgtgcaaggccagagccatggacaaggcagaggtggtccttcgtcag<br>atgattgatgatggtgttggacctgataatgtgacgtatagtagcctcatccatggatattcctcttcaggccactggaaggaggcagttagggtattcaaagagatgacaagtcggagggt<br>tacagcagatgtgcatacttacaacatgtttatgacctttctttgcaaacatggaagaagcaaagaagctgcaggaattttgataccatggctatcaagggcctgaaacctgacaacgttt<br>catatgctattctccttcatgggtatgccgccgaaggatgcttagttgatatgattaatctcttcaattcaatggaaagagattgtattctacctgactgtcgtatcttcaacatactgatt<br>aatgcatatgctaaatctgggaagcttgataaggctatgcttatcttcaatgaaatgcagaaacaaggagtgagtccaaatgcagtcacatattcaaccgtaatacatgcattttgcaagaa<br>gggtaggttggatgatgctgtgataaagtttaatcagatgattgatacaggagtacgaccggacgcatctgtttatcgtcccctaatccagggtttttgtacacatggcgatttggtgaaag<br>caaaggaatatgttactgaaatgatgaagaaaggtatgcctcctcctgatattatgttcttcagttcaatcatgcagaacctatgcacagaaggaagggtaacagaagcacgggatatcctt<br>gacttgatagtgcacattggtatgaggcctaatgttatcatatttaatttgctgatcggtggatactgcctagtccgcaagatggcagatgcattgaaagtatttgatgatatggtgtcata<br>tggtttagaaccttgtaactttacgtatggtatacttattaatggctattgcaaaaatagaaggattgatgacgggcttattctgttcaaagagatgctgcacaagggacttaaacctacaa<br>cttttaattataacgtcatactggatggattatttctggctggacaaactgttgctgcaaaagagaagtttgatgagatggttgaatctggagtaagtgtgtgcattgatacatactctata<br>attcttggtggactttgtagaaatagctgcagtagcgaagcgatcaccccttttccggaaattaagcgcaatgaatgtgaaatttgatattacaattgtcaatatcattattggtgccttata<br>cagggtcgagagaaaccaagaggctaaggatttgtttgctgctatgccagccaatggcttggttcctaatgctgttacctacaccgtaatgatgacaaatcttataaaagaaggttcagtgg<br>aagaagctgacaatcttttcttatccatggagaagagcggctgtactgccaactcttgcctgttaaatcatatcatcagaaggttactggaaaaaggagagatagtcaaggctggaaattat<br>atgtctaaagttgatgcaaagagctactcacttgaagctaaaactgtttcgctgctgatctctctgttttcaaggaaagggaaatatagagaacacatcaaattgcttcctacaaagtatca<br>gtttctggaagaagcagccacagttgaatagttggtacatgatatctgaaatttaatttgcatcgcttgccatgggtccgtctgcttgtacaagaaatgcattttctatttgtaaataggaa<br>gtcagtttagaacaagccatcaggatgacgcaaagagtacaattcagttgcaccaccaataaaaaggcagaactagggctgccaaaacaacactgaatcaaaactcaaacagaaggagcagc<br>aaactttttttttttttgaagctggacagtctgctagccaaacaactacaggagactgtcagggggggcatgtagtggctggcgtctaagcgcctttgcttcttccaccatccatggcttagcc<br>tcacacggaatcgagtcaaccaattcccgtcggttttgggtggctcccttgaagatgcaattgttttcagcggccagatacgcatggtcagattaatcagcgagtgtgccccttctgtctgg<br>ttcgagaaagaatttgaagagctgagcttgtccctgctggaaccagtttgaggttagttaatcataacagggtactagagaggtgttttattgactgttgatgtgtaatatgttatatgcca<br>tcctcttgatgattacggtgatctgtgaagaggcagcatgcaaaagtctgaatcacatatgcttatgtaattgtgttattatttgtgcagcttctagaccttttgccttgtagatggctaca<br>tggatctagttgtagcaatctgtaactgttagtgttttgtatatgctggcattgatgattagggtgacttgtgaagcatgcagaagtctgaatcgtacatgcttgtctag |
| SEQ ID NO: 14_ RFL29a CDS | atgccccgcttctcctccaccacgccaatgtcgccaccccgcctccgcctccgactctgcgcccgccactcctcctccacctctcatccctcacgcatctgggatccccacgccgccttcgc<br>cgccgcggcacagcgggcgagctctggcacgctcactacggaggacgcacaccacctgtttgacgaattgctgcggcggggcaatcctgtccaggagcgtcccttgaataaatttctggctg<br>ccctcgcccgcgcgcccgcgtccgcatcctgctgcgatggccccgccctggcagtcgccctcttcggccgtttgtcccgagacgtcggacgacgggggcgcagccaaatgtcttcacctatg<br>gcgtcctcatggactgctgctgccgcgcttgccgcacagatctggtgctcgccttctttggccgtctcctcaagacgggcctggaggcaaaccaagtcgtcttcaacaccctcctcaagggc<br>ctttgccacacaaagcgggcggatgaggctctggacgtgctgcttcacaggatgcctgagctgggctgcactcctaatgtggtggcgtataacaccgttatccatggcttctttaaggaagg<br>ccatgtaagcaaggcctgcaatctgttccatgaaatggcgcagcagggcgttaagcctaatgtggtgacatataactcagttatcgatgcgctgtgcaaggccagagccatggacaaggcag<br>aggtggtccttcgtcagatgattgatgatggtgttggacctgataatgtgacgtatagtagcctcatccatggatattcctcttcaggccactggaaggaggcagttagggtattcaaagag |

-continued

SEQUENCES OF THE PRESENT DISCLOSURE

| Sequence number | Sequence |
|---|---|
| | atgacaagtcggagggttacagcagatgtgcatacttacaacatgtttatgacctttctttgcaaacatggaagaagcaaagaagctgcaggaatttttgataccatggctatcaagggcct<br>gaaacctgacaacgtttcatatgctattctccttcatgggtatgccgccgaaggatgcttagttgatatgattaatctcttcaattcaatggaaagagattgtattctacctgactgtcgta<br>tcttcaacatactgattaatgcatatgctaaatctgggaagcttgataaggctatgcttatcttcaatgaaatgcagaaacaaggagtgagtccaaatgcagtcacatattcaaccgtaata<br>catgcattttgcaagaagggtaggttggatgatgctgtgataaagtttaatcagatgattgatacaggagtacgaccggacgcatctgtttatcgtcccctaatccagggtttttgtacaca<br>tggcgatttggtgaaagcaaaggaatatgttactgaaatgatgaagaaaggtatgcctcctcctgatattatgttcttcagttcaatcatgcagaacctatgcacagaaggaagggtaacag<br>aagcacgggatatccttgacttgatagtgcacattggtatgaggcctaatgttatcatatttaatttgctgatcggtggatactgcctagtccgcaagatggcagatgcattgaaagtattt<br>gatgatatggtgtcatatggtttagaaccttgtaactttacgtatggtatacttattaatggctattgcaaaaatagaaggattgatgacgggcttattctgttcaaagagatgctgcacaa<br>gggacttaaacctacaacttttaattataacgtcatactggatggattatttctggctggacaaactgttgctgcaaaagagaagtttgatgagatggttgaatctggagtaagtgtgtgca<br>ttgatacatactctataattcttggtggactttgtagaaatagctgcagtagcgaagcgatcacccttttccggaaattaagcgcaatgaatgtgaaatttgatattacaattgtcaatatc<br>attattggtgccttatacagggtcgagagaaaccaagaggctaaggatttgtttgctgctatgccagccaatggcttggttcctaatgctgttacctacaccgtaatgatgacaaatcttat<br>aaaagaaggttcagtggaagaagctgacaatcttttcttatccatggagaagagcggctgtactgccaactcttgcctgttaaatcatatcatcagaaggttactggaaaaaggagagatag<br>tcaaggctggaaattatatgtctaaagttgatgcaaagagctactcacttgaagctaaaactgtttcgctgctgatctctctgttttcaaggaaagggaaatatagagaacacatcaaattg<br>cttcctacaaagtatcagtttctggaagaagcagccacagttgaatag |
| SEQ ID NO: 15_<br>RFL29a | mprfssttpmspprlrlrlcarhssstshpsriwdphaafaaaaqrassgtlttedahhlfdellrrgnpvqerpinkflaalarapasasccdgpalavalfgrlsrdvgrrvaqpnvfty<br>gvlmdcccracrtdlvlaffgrilktgleanqvvfntllkglchtkradealdvllhrmpelgctpnvvayntvihgffkeghvskacnlfhemaqqgvkpnvvtynsvidalckaramdka<br>evvlrqmiddgvgpdnvtysslihgysssghwkeavrvfkemtsrrvtadvhtynmfmtflckhgrskeaagifdtmaikglkpdnvsyaillhgyaaegclvdminlfnsmerdcilpdcr<br>ifnilinayaksgkldkamlifnemqkqgvspnavtystvihafckkgrlddavikfnqmidtgvrpdasvyrpliqgfcthgdlvkakeyvtemmkkgmpppdimffssimqnlctegrvt<br>eardildlivhigmrpnviifnlliggyclvrkmadalkvfddmvsyglepcnftygilingycknrriddglilfkemlhkglkpttfnynvildglflagqtvaakekfdemvesgvsvc<br>idtysiilgglcrnscsseaitlfrklsamnvkfditivniiigalyrvernqeakdlfaampanglvpnavtytvmmtnlikegsveeadnlflsmeksgctanscllnhiirrllekgei<br>vkagnymskvdaksysleaktvsllislfsrkgkyrehikllptkyqfleeaatve |
| SEQ ID NO: 16_<br>RFL29a genomic | tcggatccagctcgtctctcgtcttactcagggtcggtcatcccggtgaccttgcctctggcagcgagggggtgtgcgtgctctatggtgggccttgtgaggcgatggcgcggttgctgcgc<br>aggggtgtgcatgccagcgattgcgcgggccagcttgtgtcggctgcgtgagggtgttggttgagtctgctccaagcgcaagcttgcccggctatggccggccggtgctggcggcgcctatg<br>ggcgtcgtttcccttgttgaaggcgttgttgtggagttcttcgacctactacaatctcgaatctggttcttcgggcgaaaacctcgccccatctaggtcgggcaacgacgtcgtctgtacgg<br>tgtttccccctttggggcgttgctttgaagaccggttatcctttcccgtgctacctttgggctggtcgtgcatggtgtcatggttggctggtgctcaaccggtgatgcgagtggttagcgt<br>tgcgactcgtgcggtgacgaagatggtgatgcgcggagctgggtcgcggcttgtccttctgatatcggcggttcggttccccctttgggtgcgtctgtgcttgtttctcactgtgacagagaa<br>gttgaagctacatgcggcgggggccctgcggcaatgatgactccatgagggggcttcggcggacgatgctctccgcaggttgcactggactagcttggtgtgaggcttgcaactttctcctg<br>tgatgctcatcaacaaaatcggagatgtcggtcctcgacgcctgcggccgatcgtttggcttggctgtcgaggtcctcgggtgccgtttgttcggaggggtcttgatgggtcgtcagcgagg<br>aaatcggagttgcctgctcgtggagaggcgatgacgatgacattgcttgcagcctcgacggtgtcctctcgtcagcagtatgtgtgtgatcttgtcagtgccaggtcggccggagtgctcta<br>ttcgatgggcgtgttttaattaaccgggcaactctcttcttcttaatcaatgaaaatggcaagtcttttacctcgtttcaaaaagagttaaatgcactggaggtcctaaaggtttcgtcggg<br>gtgtcactttagtcctatttcttccaaaatgcacctttaggtcctaattctttattaattggttcacccgaggtccttttccacgagcgctagctgaccagcacacgtgccgcattgaccca<br>cgccacatcgatagagggtctaaccgccaggcgagaagcttcgcaaagagacccccccccctcttagtggcaccctctctcctctttcacggtactttggcgacattggaggcgagcgacag<br>aggcaaccggaggtgatctggaggtaatttgtgtgggtgcccgtgaagatgccccttctacgacggccagtgagcaatcctcctccatgttaccgtaagaaccctaatcttgtcgacgatct<br>tctcctgtagctcttctaatatgtcataactttgccataatcaatagttgtagtccttgatttactttgatttgcataacggtgctacggacatggcaaaaaggacacaccaccagcggcaa<br>catacccgccgaagttggagcttgcttcgccgcaccggcggcggtgctgaggatgttgccatgctcctcatcttagttgtttccttgccgaggagcttgaagttccggccatggataggttt<br>agggaacgcgcgcgccgagagagagagcagatttggggaagaaataaagccagggactggggaatgagaagataatgtttataaggggttttctgtaaaaagaaagagcaacctacgcggcc<br>cttctgtcgatttggcatgggtcaacgcaccacacgagcaggtcaacgagcgctcgtgagaaaaaggacctagggtaaaccacttactaaagaattaggacctaaaggtgcattttggacga<br>aataagactaaagtgacaccctgacgaatttttaggaccttgagtgcatttaactctttcaaaaaataaagatgctaaaaaaactaaatgcttaaaaatacatttttctatgggaatactt<br>aaaaatactagtataatttgatggcttcctagtatatttctagcgcttacaactaaatttatattcttggtctaaataaaattataatctgataaattatgtgatatgtatatagccatatg<br>agaccataatttaattttacctgcaaaaagtaagtaatagtaatagtagtactacatactccctccgtccgaaaatacttgtcgaagaatttgatgaaaatggatgcatctagaacaagaat<br>acatctagatacatcaatctccccgacaagtatttccgaacggagggagtactagataataagataactatccaaaaaaaaaaagataactgaaggttgccacctagcacattcacattggt<br>acaacttggaaaagcacagccccgtcgtcctgctcccagttgagttcgcgacctacacaccggccatgccccgcttctcctccaccacgccaatgtcgccaccccgcctccgcctccgactc<br>tgcgcccgccactcctcctccacctctcatccctcacgcatctgggatccccacgccgccttcgccgccgcggcacagcgggcgagctctggcacgctcactacggaggacgcacaccacct<br>gtttgacgaattgctgcggcggggcaatcctgtccaggagcgtcccttgaataaatttctggctgccctcgcccgcgcgcccgcgtccgcatcctgctgcgatggccccgccctggcagtcg<br>ccctcttcggccgtttgtcccgagacgtcggacgacgggggcgcagccaaatgtcttcacctatggcgtcctcatggactgctgctgccgcgcttgccgcacagatctggtgctcgccttct<br>ttggccgtctcctcaagacgggcctggaggcaaaccaagtcgtcttcaacaccctcctcaagggcctttgccacacaaagcgggcggatgaggctctggacgtgctgcttcacaggatgcct<br>gagctgggctgcactcctaatgtggtggcgtataacaccgttatccatggcttctttaaggaaggccatgtaagcaaggcctgcaatctgttccatgaaatggcgcagcagggcgttaagcc |

-continued

SEQUENCES OF THE PRESENT DISCLOSURE

| Sequence number | Sequence |
| --- | --- |
| | taatgtggtgacatataactcagttatcgatgcgctgtgcaaggccagagccatggacaaggcagaggtggtccttcgtcagatgattgatgatggtgttggacctgataatgtgacgtata<br>gtagcctcatccatggatattcctcttcaggccactggaaggaggcagttagggtattcaaagagatgacaagtcggagggttacagcagatgtgcatacttacaacatgtttatgaccttt<br>ctttgcaaacatggaagaagcaaagaagctgcaggaattttgataccatggctatcaagggcctgaaacctgacaacgtttcatatgctattctccttcatgggtatgccgccgaaggatg<br>cttagttgatatgattaatctcttcaattcaatggaaagagattgtattctacctgactgtcgtatcttcaacatactgattaatgcatatgctaaatctgggaagcttgataaggctatgc<br>ttatcttcaatgaaatgcagaaacaaggagtgagtccaaatgcagtcacatattcaaccgtaatacatgcattttgcaagaagggtaggttggatgatgctgtgataaagtttaatcagatg<br>attgatacaggagtacgaccggacgcatctgtttatcgtcccctaatccagggttttgtacacatggcgatttggtgaaagcaaaggaatatgttactgaaatgatgaagaaaggtatgcc<br>tcctcctgatattatgttcttcagttcaatcatgcagaacctatgcacagaaggaagggtaacagaagcacgggatatccttgacttgatagtgcacattggtatgaggcctaatgttatca<br>tatttaatttgctgatcggtggatactgcctagtccgcaagatggcagatgcattgaaagtatttgatgatatggtgtcatatggtttagaaccttgtaactttacgtatggtatacttatt<br>aatggctattgcaaaaatagaaggattgatgacgggcttattctgttcaaagagatgctgcacaagggacttaaacctacaacttttaattataacgtcatactggatggattatttctggc<br>tggacaaactgttgctgcaaaagagaagtttgatgagatggttgaatctggagtaagtgtgtgcattgatacatactctataattcttggtggactttgtagaaatagctgcagtagcgaag<br>cgatcacccttttccggaaattaagcgcaatgaatgtgaaatttgatattacaattgtcaatatcattattggtgccttatacagggtcgagagaaaccaagaggctaaggatttgtttgct<br>gctatgccagccaatggcttggttcctaatgctgttacctacaccgtaatgatgacaaatcttataaaagaaggttcagtggaagaagctgacaatcttttcttatccatggagaagagcgg<br>ctgtactgccaactcttgcctgttaaatcatatcatcagaaggttactggaaaaaggagagatagtcaaggctggaaattatatgtctaaagttgatgcaaagagctactcacttgaagcta<br>caaactgtttcgctgctgatctctctgttttcaaggaaagggaaatatagagaacacatcaaattgcttcctacaaagtatcagtttctggaagaagcagccacagttgaatagttggtaca<br>tgatatctgaaatttaatttgcatcgcttgccatgggtccgtctgcttgtacaagaaatgcattttctatttgtaaataggaagtcagtttagaacaagccatcaggatgacgcaaagagta<br>caattcagttgcaccaccaataaaaaggcagaactagggctgccaaaacaacactgaatcaaaactcaaacagaaggagcagcaaactttttttttttgaagctggacagtctgctagcca<br>aacaactacaggagactgtcagggggggcatgtagtggctggcgtctaagcgctttgcttcttccaccatccatggcttagcctcacacggaatcgagtcaaccaattcccgtcggttttggg<br>ggctcccttgaagatgcaattgttttcagcggccagatacgcatggtcagattaatcagcgagtgtgccccttctgtctggttcgagaaagaatttgaagagctgagcttgtccctgctgga<br>accagtttgaggttagttaatcataacagggtactagagaggtgttttattgactgttgatgtgtaatatgttatatgccatcctcttgatgattacggtgatctgtgaagaggcagcatgc<br>aaaagtctgaatcacatatgcttatgtaattgtgttattatttgtgcagcttctagaccttttgccttgtagatggctacatggatctagttgtagcaatctgtaactgttagtgttttgta<br>tatgctggcattgatgattagggtgacttgtgaagcatgcagaagtctgaatcatacatgcttgtctagttatttttggagctctctctttgccatgtacatgttttatggatgcagttgta<br>gtctgtatgtgctggcatttaatatgagggctggtctgcaatttttctgttttgatcgatacagcgccatgttgagtttaaccctgtaacttggcttaactagatcatgctggtgttatctc<br>taggaatcccaatatcaatactctctgttgttgcacaaactgacgcagatcaatgtccagaggtaatatggttctgcctgtaattttcatcgactgtcagcatgttcctttttttatttagta<br>ctctgtatatcacggcggtatgactataataaggatatacggctggtgcattttgagcttctctgtttcttgggataaagctgataaatttctattcttgttggctttggtagtatgaacag<br>aaagcaggcagtaata |
| SEQ ID NO: 17_<br>TaPK-like CDS | atggggaactgctggggcgccaagatcagctccgacacctcctcctcctccccttcagggacgaattccaagtatgctagtaggaatggggcggccttgagcagctccagcagctatgcctc<br>cgcggcgtcagtgccgcggagcgagggtgagattctggagtcagcaaatgtcaaggcctttaccttcaatgagctgaggaccgccacgagaaacttcaggccggacagtgtgctaggcgagg<br>gagggtttgggtcagtcttcaaggggtggatcgatgagaagaccctcaccccaaccaagccaggcaccgggatggtcattgctgtaaagaagcttaaccaggaaagctatcagggccatagg<br>gaatggctggctgaagtgaattaccttggacaactatcgcacccgaatcttgtaaagctcgttgggtactgtgttgaagacgaacagcggcttctcgtctacgagttcatgcctcgtgggag<br>tttggagaatcatctcttcaggaggagtacacatttccagccgctctcctggaaccttcggatgaaaattgcccatggagcagcaaaagggctcgcatttctccacagtgacaaggccaaag<br>tcatctaccgcgatttcaaaacctctaatatcctcctagatgcgaactatgacgcaaagctctcagatttcggcctggcgaaggacggaccgacgggtgacaagagccatgtgtccacaagg<br>gtgatggggacatatgggtatgctgcaccagaataccttgcaacaggccaccttaccacgaagagcgacgtgtacagcttcggcgtggtcctcctggagatgctctcggggcgtcgcgctgt<br>ggacaagaaccggccgaccggcgagcacaacctggtggagtgggcgcggccgtacctgacaagcaagcggcgcatcttccgcgtcctggatccccgtctagggggcagtactccctcgccaa<br>ggcccagaaggcggcgtcgctggcgctgcagtgcctctcgatggactcgaggaacaggccgagcatggagcaggtcgtcgtggcgctggagcagctccacgacgccaaggagggagggaaca<br>gccctcgcccgcagctgcagagaaagccgagcagcaaccggggcgtgaacggctcgagatcgtcgtcgaccaaggggaacaccaagaagcccgcctcaccgagaccggtttga |
| SEQ ID NO: 18_<br>TaPK-like | mgncwgakissdtssspsgtnskyasrngaalsssssyasaasvprsegeilesanvkaftfnelrtatrnfrpdsvlgeggfgsvfkgwidektltptkpgtgmviavkklnqesyqghr<br>ewlaevnylgqlshpnlvklvgycvedeqrllvyefmprgslenhlfrrsthfqplswnlrmkiahgaakglaflhsdkakviyrdfktsnilldanydaklsdfglakdgptgdkshvstr<br>vmgtygyaapeylatghlttksdvysfgvvllemlsgrravdknrptgehnlvewarpyltskrrifrvldprlggqyslakaqkaaslalqclsmdsrnrpsmeqvvvaleqlhdakeggn<br>sprpqlqrkpssnrgvngsrssstkgntkkpasprpv* |
| SEQ ID NO: 19_<br>TaPK-like<br>genomic | ctgtcgtactcgtgacggccatctacacgtataatactcccacttgcacatacgtactatgcacatgtacaacacatgataataaagtttggcaaacattgatcgttgcggggcgagctgca<br>ggtccatgttcacattgtattttctcagccaagcagaacaatactagaggacatacgccattgacttgacaatttggttaccacccacaaactgtattgaccagatatatacaatatatgta<br>ataaatgttataaaaagaaatggaaaataataatttcggtgcatgaatcgtgcctcgtccacgaatggtgatactagacgttttcccggctagctagtaaaaaagtaggcgatcggtgtacg<br>ggtatcgccgtaaccactaatattgtcgcacctacgtatacgcatgtaccggccatattataaacaaaacacacgaagaagaaacggaggcgttgtacggacggcgatcgtgactgcacgat<br>gtgaggagccgtcccacactctatcgttttcctaccctagccgccgccgtcaccaagtgagtagggcgaggcgactcttttccttcgatctccaccggccggtgcgctggcccccctctccct<br>tcggccgctgctccggcggcaggagggagggggaccccgttcctctgttctgtagttaggttttggatttgtaggtcgtgatgcgtcgtttgggtggtgggagcggcgtccggacgaataaa |

-continued

SEQUENCES OF THE PRESENT DISCLOSURE

| Sequence number | Sequence |
|---|---|
| | tctgcctcaaccccactcccacaccggcggtgtctttcatggaggtgtctcggagttggtggcatcgtgtgtatgtcgatccctcagatcgacagcgttagggttcatggatggtgttggcg |
| | aggcggcggcggcgacgccatcaggtgtttctctccttctgctcggtccccgttgctgtggtgttgtctccgacgtcatggtggagcagggaggttttgtcgttcaggagtatgcgcaggcg |
| | gttgtctacgcaagtgacatctggaagatggagtatcttgtgttgggtccgtggtcgaaggcgggcagttctggtttccttctccgacgtcgtcgtcatgcgagggcgtcagttctgaagtt |
| | cgatggcgtgtccggggacatgttgccccggtctgattctttcaacggctatgattttgcttttggcaaactactttggagatccgtaaagctgctgatcagcgatggagccgcgtcgagct |
| | tgggcgaagatgtgatctgtcttcttaccctttggtcaccgcttcggtggtgtcgaaggaaagggacatgcgctggtattttgcatagaattttcctatttttccgtcatgtatggtcggt |
| | gcttacgtgccttgtaacttgatctttattctatataaatgagacacgtattatcatgaaaaaagaaaacggacggcgatctggcgtggcaatcacgggcagacgaaattgaccgtttggat |
| | ttgaatattcgcttttatatacgtcgaacgactctcgatgctgtaccatcaaatgtactgtataatcggagtagaaaatatactggcacacgagcaactagacataatttttattcgcactt |
| | gttttatactgatatatgttgtggcgatcagttttgtttaatcttttatcccgctgatgataagctcgattggcgactggtccatgcccctccgggctccacacagccaggcgaattcgtgc |
| | tatcatgcaggcagcccgaacaaagaacatgttctcagtctgcaactgctcagccggacccaagtaagtcataaatgcgacgcaacaaaaaatggcgccgcaaaagttgggacgttttctca |
| | gttatcctgaaatattataataacatgcatgttgtatgcgtacctcatgtagcggggaaacatatgcagccgggcaccccaaaccccgtcatacgcccggaccgacgcccaaattagtgacc |
| | ggtcacgaaagactgacccagacgcgtgcctcgaatgggtcttaaacgctcaggctaaccgccacccctcatatctagtcccaaatctaagacggataagggcgcgccgcccaggagcgtcg |
| | gggcgcgtccatcacgttggtcctggctcacgatggcccacccgactccacatccgctgcctgggccaaacactatccacttcacttccctccgccgcccaagctcctatccgccgatcacg |
| | agccttcttcggcttgacgtgtagcgaatccgacgacgaccagtacagatccgttgactagggtgtcaacccgtgcggtttggagaaggaaatggccatccgcattgcacttcgccactccc |
| | gggaggacaacgcccttccgaggggggatctacccaacgcgagtccattgcgtcggtgcatcgggcgctcagattctccggcgctggatcatcgtggtcctctcgggagccttccaatctcc |
| | ctttccccatcatggtccgtcggagtacgattcctatcgggtatcagtgtgcccgccgtgggaagaagaggatgagggcgtctgaggtccgcctcgctgccgacattgcggcagcggaggcg |
| | gctgatgcgatggcaggggcggtcgcaggggaggaagtcatctgcgtccgcattgtaaagaagcggcagcgaacgaacacgcgcgcccctcatccgagagcagaatcggcgggccgtgccat |
| | ggccggactgccctccaaggaggagaaggaggacaacgatgggtcagacagctccgacgatgagcagatttgagtattttcgtagtgcaaaatgtcatagacctgtttaaatacgagtatct |
| | tcctagtgcaaaatgtcgtagacctgtttaaatacgagtatcttcgtagtgcaaaatgtcgtaggaaatagaaatagtatcctacgggtatgtagttgcatttcttactagagtagatcgta |
| | ggctcaactgaaagcactactagtacgtggtggtgataacctaatacgtgactttgaacatgtctctgcccctccctttctctcgccttttcggccccatcaatggctccctcccccctcctt |
| | ctagagactagaagcaggccccgcctccacaggtgctagcggtagtgtatcccgctcggtggcggtggtggtgcgtggtgggggagaaagttggaggccggccagcgcacggggaaaaggag |
| | acgcaaagcggccacccaaaaaggcgcacatactttctttttttctttccaccgccgccctccggaggagttccgattcccccctctctttctctctcttctttctctctctctctttcttgct |
| | ctgctctggaagcaggggaaggagggaggggcttccgatttgggcgcggaagcactgtccgccgtgattcgattcggctgatttgggaggtctgctcgtttgatttgggttcgctgatttat |
| | tggttgatttgttggttcgtgtccggcggctcgatttgagggccggacggtcctcgccatggggaactgctggggcgccaagatcagctccgacacctcctcctcctccccttcaggtgcgc |
| | gcgtcttcctcgtctcctgctgctatttacaaatgtttttactagtactactatactagcagtactgatctgtgcccataactcgactagtagtactgatctgtgcccacagggccgattg |
| | ctatttctttgcccctcaatttttcacaactcacaagcagccgaataaataagttctgaatgagaaacaagtgttcaaccaaccatttctctcactccaatctgctcatttcgtgctctg |
| | catctcttctctccttcccgaaaccattcttaggttatgctgatttcggcgacaggtttggtcaaagtcaatttcgttctgtttaattggcttatgatagttgagtcactaaattcagtccc |
| | tccttttggaaaaatctgtcgcgagcttggactcttcctcttgacctgcttcatgtgcaaggccaaggaatcatgcctttccgtttatggcctaggggagaggaagcttccgatgtagtaaa |
| | atgcttcacttaactttatctgacttctcctctgatttttctgagtgtccagttcaaatcagacatatagaggaaaagctcgaattctgatgctacttttggctacatccacgtgcttttct |
| | tcaaagttattgactgtcctgttttggatgttcagtcttcttttctgtaataagcgaaactaaaggaagaaaatacatagttagtccgacctaacttgtccatgatggacctattttctgtt |
| | caatgttaggcagacaagataaatgattaagggacatcaacttatttatgctaaaatgtgactgaataatctctgaaagtctgcaccattttatgatgatgatcagggacgaattccaagta |
| | tgctagtaggaatggggcggccttgagcagctccagcagctatgcctccgcggcgtcagtgccgcggagcgagggtgagattctggagtcagcaaatgtcaaggcctttaccttcaatgagc |
| | tgaggaccgccacgagaaacttcaggccggacagtgtgctaggcgagggagggtttgggtcagtcttcaagggggggatcgatgagaagaccctcaccccaaccaagccaggcaccgggatgg |
| | tcattgctgtaaagaagcttaaccaggaaagctatcagggccatagggaatggctggttagtgacaattttgcctgctggaaatgggatttcttgtttatttcagttctgcattgtgtctga |
| | catgctctttcttttgggcgcaggctgaagtgaattaccttggacaactatcgcacccgaatcttgtaaagctcgttgggtactgtgttgaagacgaacagcggcttctcgtctacgagttc |
| | atgcctcgtgggagtttggagaatcatctcttcaggagtaagtgcctggacttttacttttcttattattcgctgggtgttattctccatttttttaaggaatgatgctaaagtgttccaaca |
| | ttcagggagtacacatttccagccgctctcctggaaccttcggatgaaaattgcccatggagcagcaaaagggctcgcatttctccacagtgacaaggccaaagtcatctaccgcgatttca |
| | aaacctctaatatcctcctagatgcggtatatatgtccacagcctggaaggatcttttccttcgtgtccgcaaaatatctctatcggttggtctgacagtcacgcaatttcttcttcagaac |
| | tatgacgcaaagctctcagatttcggcctggcgaaggacggaccgacgggtgacaagagccatgtgtccacaagggtgatggggacatatgggtatgctgcaccagaataccttgcaacagg |
| | tcggttgatcattccactttcagaatcctcagctgcgcaaatatcagatatattgccgaaaatctgaccacacctacctgaatcgtgattgcgttgtcactctggttgtgtcatcgaccaag |
| | atgccaaacataaccaatttaggctacaacctttcaatcctcatctgcacaaatatcttgcccgaaaatctaaccacacctacctgaatcatgattgcgttctcactctggttgcgtcatc |
| | gaccaagatgccaaactcaactaatttttcggctagaacctttcaatcatcatctgcacaaatatcttgctgaaaatccaaacacacctacctgaatcgcgagtgcattgtcaccctggttg |
| | cgtcatcaaccatcatgccgaacctaaactaattttcctgctgcaatatttccatgatcaggccaccttaccacgaagagcgacgtgtacagcttcggcgtggtcctcctggagatgctctc |
| | ggggcgtcgcgctgtggacaagaaccggccgaccggcgagcacaacctggtggagtgggcgcggccgtacctgacaagcaagcggcgcatcttccgcgtcctggatccccgtctaggcgggc |
| | agtactccctcgccaaggcccagaaggcggcgtcgctggcgctgcagtgcctctcgatggactcgaggaacaggccgagcatggagcaggtcgtcgtggcgctggagcagctccacgacgcc |
| | aaggagggagggaacagccctcgcccgcagctgcagagaaagccgagcagcaaccggggcgtgaacggctcgagatcgtcgtcgaccaaggggaacaccaagaagcccgcctcaccgagacc |
| | ggtttgaccgtgtgagtgggatcacatagcagaatctagtagagagatgcgtcaaggtgtaatgtatgtatggtataatagggttttagagtggtgatctgcgaagaggcagcggatttgtg |
| | aatgttttgtgcccgtgttgtagggatgtatctttgcagcttctagtgttggtatgtacagcttgtatctatccggttgtagctagtctgtatgtagtccttttgtgtatgcctgattgctt |
| | tggttctgacttaaggtccagaggttttgatctgatttagatgcatgcaccctgttaaaccaagaccttaaaatatgaagatgaacagtgtaaagtacatatttgtcacttcatttatcaaa |

-continued

SEQUENCES OF THE PRESENT DISCLOSURE

| Sequence number | Sequence |
|---|---|
| | tgtgaatgaacaatcatgttggtgttttagcagagcaggccatgacttccatgggtcaactgtatcttttcccttagggatgttgaccattttgttcatatcatacagtactagtagtatat |
| | gtttcatttttttaatgaaaaaagtagtatatgttacagataatgttgggaaaatcaccttctgtattttttaatttcaaacagttggccacaatgatctttttatttacttggtgggttcag |
| | ccaaattaccattgtttttttcaggggtttcagccaaattattattatctgggcaagcgtacggcggcggcccaaggcagagcacgcagcccagccgccaaaacagagctcgccctcgctcc |
| | cctccggcccaagtgccgctcctcctcctcctcggtggacgccggcgccggtggatggctccgccgcgccaaatcgagcccctcacgccgcgagccgctcctcctcctcctcagcctgcaat |
| | ccccgccgagctccgatccccgccgccgagctccgatccgcgggcgatcgccggggcgccgccaagatcagctccggcccctcccgttcc |
| SEQ ID NO: 20_ | atggcagctctaaccagccttgcctcaaacccgaatccaaacaagtcattcgaggtccttcctaatccgggtgactccctctcaagcctcagttttagcccgaaaagtaatcttcttgtggc |
| TaRAE1-like CDS | aacttcctgggataaccaggtgaggtgttgggagataggtaatggtaacagtcagccaaaggcatccatatcacatgatcagccagtgctctgctcagcctggaaagatgatgggactactg |
| | tcttctctggagggtgtgataaacaggtcaaaatgtggcctctgctgtctggtgggcaggctcagacggttgcaatgcatgatgcacctgtcaaggaggtcgcatggatttctcagatgaat |
| | cttcttgtatccggaagctgggacaagacactaaggtattgggacacaagacagccgaatcctgcccatgttcagcaacttcctgatcgttgctacgcacttgctgtgaattatccccttat |
| | gattgtgggaacagctgatcgcaatattgtgatcttcaacttgcagaatcctcagactgagtttaagcgtattcaatcacctctgaaataccagacacggtgcgttgctgcctttccagatc |
| | aacaaggattcctggtgggttccatagaaggaagagttggtgtgcatcatattgatgattcacagcaaagcaaaaacttcacattcaagtgtcacagggaaggaaatgatattttctctgtc |
| | aattcgctcaactttcaccctgttcatcacacgtttgccacagctggatctgatggtgctttcaacttttgggataaagatagcaagcagagacttaaggctttcagtcggtgtcctcaacc |
| | cattccttgcagtagcttcaataatgatggttcaatatttgcttatggggtgtgctatgactggagccatggcgctgagaaccataatcctgcaaatgcaaagacatccatctatctccaca |
| | gtccccaggaagccgaggtgaaagggaagccaagaatcgcaacagggcggaagtga |
| SEQ ID NO: 21_ | maaltslasnpnpnksfevlpnpgdslsslsfspksnllvatswdnqvrcweigngnsqpkasishdqpvlcsawkddgttvfsggcdkqvkmwpllsggqaqtvamhdapvkevawisqmn |
| TaRAE1-like | llvsgswdktlrywdtrqpnpahvqqlpdrcyalavnyplmivgtadrnivifnlqnpqtefkriqsplkyqtrcvaafpdqqgflvgsiegrvgvhhiddsqqsknftfkchregndifsv |
| | nslnfhpvhhtfatagsdgafnfwdkdskqrlkafsrcpqpipcssfnndgsifaygvcydwshgaenhnpanaktsiylhspqeaevkgkpriatgrk* |
| SEQ ID NO: 22_ | tttgtaaaaggctatggggacatttgttttcctctggcgcacagaaatcaagaggtgtcattaattctgaatgaagaagacaatgctatgggctccgcaatacctcgctaacgaaggtgtcg |
| TaRAE1-like | agggggccgagctatcatcagccggatacaggagacgggaggaactcgcccctcaatccgaagacttcaagaagcacagagctaatggaaattatcgacctcgctgttggaggctagttcgg |
| genomic | aggctaatgagggtgtcttggactaaggggtcctcgggctgccgacctatttctcatgggccgtactagtggactgtttgttgttcgtcaggggaagaccggacttcggacgaccccgtgct |
| | ccaaaaggaaaccttcggagacttgacgtatcctccaagtctggcttagtgtgacttgtgtgtttatcccctgttggtaaccgacatatgtaaccctagggacccctggtgtctatataaac |
| | agagggtttagtctgtagaggctagaaccatcatcctactcctatagggtttagttcatctgatctcgtggtagatcaactctgtaatcatcacacaaacacaccaagacaatcaagcagaa |
| | tgtagggttttacctcttcgagagggctcgaacctgggtaaatactatctctaccttccctgttacccatgcatccaagatctacaactcaggacccccctaccgagatctgccggttttgac |
| | accaacacacataaaattgagggtgaccaatcacgtaaagctcttaatagcgatattaatatacgtacacatagcaattgtcgatgaaattgttggnnnnnnnnnnnnnnnnnnnnnnnnnn |
| | nnnnnnnnnnnnnnnnnnnnnnnnnnnnnnnnnnnnnnnnnnnnnnnncctgctcatccctggatgttgacggctcaatggtgtatttttcccgtcgtgcgtcttcatcggtgaggttatgg |
| | tatgtacaattttggcgcacaatgacggcgacttccctgatccttcgtcatcgtctccaccgtgttgattttggtgctggcgtgaggcctgaggtatgtctcttggatctaatgctcgtcta |
| | gcgttggtggtttctccttcagagcgatggcccggtaagacgtggccttaatcactccccgcccgtgatgaacatcaggctggcttcgatgatggagaagcatgtgttggctcggcatgttc |
| | tagaggatgaagaaggatgacccagggattttgatgtaactttattaatatttcttcctataatttgtacttccttttcttagaaaaaaactatttggcttcacatgcgctggtttggtta |
| | tataagagggagcatatgggtgttgtctttttatataagaaaaaaaagagcaaaataagccacgcgccgatcaagcctgcgaactgagtgtatacccggccatgggcaacccagactgaccc |
| | gacccatcccgaaaaagctcgacccgtcccgactcgaccttgcccacgggccgggcccaggcctagattttgagcccgatggctgggccgacatgttgtatttgcgatttaaggaagaggcc |
| | cggcccaagggccgaggcccgacgggtttttttgactgatgggccggggttgggccagattattaggcccaacggccgggccgggccgggctcggggcctaagccttttgcttgcgttcaggct |
| | ttgataggctcagcccgaagtccacatccacatcaaccacccccgcgtgccgatgaagccatttctttggaaggacctgcgcgtgcatccgacgcgacgcgctacaccgaagcctatactac |
| | tacatctcgtctcatcgccctcctcccagacgacgcctcgagaatcctcggctgaggctccactccgcactcgcaagtcgcacccgcagccgcgccgtccccagcagccgccgccgaccgct |
| | ccccgtccggcaggtaagcccccgagcccctcctcgccgctccgctcgcgcggactcctagctagctagggttcccggcaccgattccgcggcgctgcactccggcgcaatgctcgcggcc |
| | gcggacgggcccgccgcttcgggggaagctctgatctggtggccggcgctcgctcgctcgctcgcggtctccggagcaaatcggccgcatcgagtggccggagcaagcttaggatagttcga |
| | ttatttcccccatccccgttggtcaggccgagagggccagtttgggcgacctcctggtgattccgctgccgtggtggggattgggtggtcgtggcccgggtgtaggcgtttgtaggtcgagt |
| | gagtgtttccttccaggttctatgctcacccagcttgtgttatcactgggatccgggcgttcggcaggctaacattcactggattttggacctgcattgttgcggcgcgtgccgggggatag |
| | cgtttatgctggctttggcgcggtgattttgtgcgtgcgtgcaaacttttggggctgccttctggtgatctcgctgtcgggtggtgcgagttcatcaagcggtcagggtgtaggcatttgta |
| | gtcgagcgaccccagctttcatgcccaccagctcgtattattcggtcgttaaccacgtttaccgaattttggaccgacgtcgttgcggcacgtaccaggggacagcgtttatgctggtttcg |
| | gtgtggagattttgtggtttaaacttggggcgcgcttggtttgcgaggctacctcctggtgatttcaccgtcgggtggtgggaatcggatggtcggggtgtaggcatttatagtggagcgga |
| | ccccttgttttatgaccagacatttagccgaaatttggacctacactatcgtggcacgtaccaggggatatcatttatgcgggttttggcgcgacactttctttgtcgggattttgtggtgc |
| | aaacttaaataatgacttccctaatgttaaacactcgttctggcatcgtggactgttggaatcgttctttttcgtagtctgagctactttaaggtgttacttatgctctcgtgtgcgtggga |
| | gactccacgtgctgatttctcttacttgcttctcatggtcactggactgatatttcttttccagattttgaaggttcacagaaggagagatggcagctctaaccagccttgcctcaaacccg |
| | aatccaaacaagtcattcgaggtgtgatactttttgtggccatgtctgtcctgcttttattttttttgcgtcttgtcattctgtatatgctacatgttctctgcaatggttgctttcaaatgc |
| | aggtccttcctaatccgggtgactccctctcaagcctcagttttagcccgaaaagtaatcttcttgtggcaacttcctgggataaccaggtaattttgtttctgctgtaattttcagtgagc |

-continued

SEQUENCES OF THE PRESENT DISCLOSURE

| Sequence number | Sequence |
|---|---|
| | ttccattattgtgatgtatcttactaggaatgtcttttgagttttgtgcaggtgaggtgttgggagataggtaatggtaacagtcagccaaaggcatccatatcacatgatcagccagtacg |
| | ttctcatacatgtttctcctgaaagtagtttcatcttacacattagagtggttccttacctgtttacttggtatgatgattgatttgtttccttccatcaggtgctctgctcagcctggaaa |
| | gatgatgggactactgtcttctctggagggtgtgataaacaggtcaaaatgtggcctctgctgtctggtgggcaggctcagacggttgcaatgcatgatgcacctgtcaaggaggtcgcatg |
| | gatttctcagatgaatcttcttgtatccggaagctgggacaagacactaaggtgcaagaacaatattcctctccaccctcagtattctttttacatggaaattcagcgcatatcacccatat |
| | ctgatcccaaattgttatttatggctgttttgcttttgggaattcgtgttgtttgtggtatcctttctgtacttcatgtgttctgcattaatgttcacacattggctaaccaaatattgtag |
| | aagttctatctcatcctctttatatttgcactcattttgtatgccttctttgatcctgaagagttttctactacttgttgaatcatactgccctattcttatcaaaggttgtgcactttctg |
| | ggtatcatctgtactatttatggctgtagtgaatttttcttatggcagaagtttttatagaagtaactgttgatgcagacagttactatattaaatgtacattatgtgattagtgttagaaa |
| | tgttcgtttcgagttttagcatcatctttatgaagattatttatgaaacatcaagttagggtctggctgtcagtttaaacatgagcacagattgagcataggcgataatcatggttggtagg |
| | aggccagggaccgggatccttgtgggacctgccggcgtacccgtgatagcagaaggggtgcaagggacagggcactggaactaaggcaggcagaaacagagaaataaagattggggattaga |
| | ctttgtagccaattcataaaaaaattggttgcatcatttgtagaggttggccttaacatatgactaaaaaacaaaaacaaaccaagactcttccctaaactgaataccgcagatactcaag |
| | acaccatatagggccacgggctcaggctgaagtcatctaggtctcagacatgccaaaacagactgggacaaggacaagctgaaactgactagtactaggtttcccggggcaactaccgttca |
| | gctggaggtctgaatgcgtggtgccttctctgatacatggatctcatgtggcacttctgttgtgtatttgtcccagtctgcttattttcctttgtctgtatcatgctgagactaatacattt |
| | gggtcgtgcattgatcttcttctcattacaacttttagctctgatcccgatgacttgtttctagtctgctatcaatgcttatcatcatactattgtaggtattgggacacaagacagccgaa |
| | tcctgcccatgttcagcaacttcctgatcgttgctacgcacttgctgtgaattatccccttatgattgtgggaacagctgatcgcaatattgtgatcttcaacttgcagaatcctcaggtaa |
| | ttttgcttcctaaccgactatgcattttcaattcttgtggtggtggtgctcatgcttttactgccattgacttatattttgaactgcctgacttaaattcatccctgatgtgattttagact |
| | gagtttaagcgtattcaatcacctctgaaataccagacacggtgcgttgctgcctttccagatcaacaaggattcctggtaatgccatatttcttgtgtcttttactctcagcattacgac |
| | accaaccaaaacttccgttgtttgaatacataacttgttgttactatgctttgaagtttaatcatatgttcttctctacctatcccatcataattatttatgttgcccaattatgttgtttt |
| | tacctagcttgagttttcgaccttaaacattgttacaaccttactcgaattagctttagatgttggcctgccatcatttgcagtgtaatgggcgttgttcctttagtgatctcatttcaaac |
| | ttcctacccctctattataggataaataaggtatattgattgtgaaatcaaactttactgactataaatactatactatgtgatttatgtgacataaagttgatatcattggatttgttttc |
| | aagagtactttgttacgattttgataaaatatgagaagaaatttatggccaaagattgaactcgagcagtcaaaatatgccttgtatatctggatagagtgtgtattactaggaatgttaat |
| | ccaatataaatgtcactaattgacatctctctagttagcacaaaagctgcataaaagaagaggatgcagttttccttaatgttttgaccaactccagctgtgttgcaaacagtttccttcac |
| | cagaactgtagaacggatcttagcctatagcagttaaagctaatctgaacatgaaatccggctgaagtacaaatagtaaaaccatccaaggcttcaagcaattgtttttgaactacagatct |
| | ttatagatgtctatttctgcattttcctattcttcacctgcttgtgggtgttcttatagtgggtcgtcgtttcatcatgggctttgaccaatcaatttttgctgttacacaatgatcttttt |
| | ctacatcaatgaactgcctatattggataaagctggtcgatacctggcaatagttcttgttttaattattttcttgttgtttccatattacttgggcaaaacatttttttacatgcgactga |
| | cacctgattttgtttgaaggtgggttccatagaaggaagagttggtgtgcatcatattgatgattcacagcaaagcaaaaacttcacattcaagtgtcacagggaaggaaatgatattttct |
| | ctgtcaattcgctcaactttcaccctgtaagatctctatcttgttctctcttgactccatatttatctatgtgccatactgccattcttatatttcattagtccacttctgctattatggaa |
| | aatgctaatggcgacttctgttgagctttagtcactatgtctccatcatgatttgtaaaatactgaaagctcagttcgttgtcttccacaagatgtgttgagctttattcaatacagatacc |
| | taccacacttcgcctaatataataaccactatgcttgaaggcatacatatgttagtaaactactccaaattgatcaagcaatatttgcagaaataaaaatcccaacagattagcttcagtt |
| | taattgagcaactcgaaatcgtacctatttgttacagacacatcgaagagaagcgtttctgcttcttcttttgctaactttggcatcttattcattggattggtatatgcttgggtgatgat |
| | actatacatccatttagttgagtgtgcttgttggctatatatttcactggaaaatgcaactgactggtgataattgtgaagtatggaaattcagttagtctagttacttatgggatttcatg |
| | ttatctaccacttggcacaggttcatcacacgtttgccacagctggatctgatggtgctttcaacttttgggataaagatagcaagcagagacttaaggtttgtctattcccgttttttttt |
| | ctattttcccctcttgttggtttatgttttcttgattggaattcaatgatttcaagatggctctactttgttgtgatctgtggacactgatgatctgcatataaattctttgttgatgcgca |
| | tacatagcctgaaatcatcccgagctcaagctaataaactcactatcctggccatgagcagaaaaaaaaaatattagttcataaatgttatcaccaattctgattttcccagccgccttgtca |
| | tcctgctgcttttggcgtttagtatgcacttctttttattcttgataaaagcatattacatatttattactcaaccgcatggagcctctgcagtaaggtatatgtgtaatttgtcaacagat |
| | aacctttttagcttttaggcatatcatacacagtgttgcattctgacagttgcttacttgcttagcatagagggctatctgtgtgtgcccaagtttattgcttcagttccctcatttgtcatg |
| | caccttctggtatgttgcacataacacattcttacatttcccctacactgcttctatacaggctttcagtcggtgtcctcaacccattccttgcagtagcttcaataatgatggttcaatat |
| | ttgcttatggggtaagtcaagtgatgcttttgagagtgtcttgttatcaccatgtttttcagtccggtcagagtttagatatgttacatgcctgtcattttcctgcaccttatttaatata |
| | cggaagaaatcagctcgacaaataattcatgttccttttgaactgctatcttgtcgtgtcctctgaatccaagttctgaatgcaaccgtaattatcattgctggggagcaggtgtgctatga |
| | ctggagccatggcgctgagaaccataatcctgcaaatgcaaagacatccatctatctccacagtccccaggtagtttccgagtgctgatatcgccataaaaagaattcttgtattttcgaca |
| | tcatttgagatccattcctgtttttataaattgttattatgttatcttttggcactcaacttgcatcattctggacaggaagccgaggtgaaagggaagccaagaatcgcaacagggcggaa |
| | gtgatggtggcatcctgcctgccgaaaagtcgatagttgtgcaagagatgatgtatattcaagggccttgtttcgctcgggccttgccttgacgtgtcctctggatgttcttacttggttcg |
| | gccgcctggtagatgaaacgcctactcccagcaaccagtgataggttacttagccgtaggtcgtagcacatagccgtttatgtaatgcatagttgtccgaaggaatgtttccccgtgttctt |
| | gtgttgtgatatagtcaggtcagcgcgtagtcttttgaaaaggagaaagccttcggtgtcttgtaagtggtgtagatctttggaaatatgggcatgatattcggtggagttattctgaaaaa |
| | gatatcccggtttcggtttcagcgaatgcaagctagatttatggggaaggttgtagttagcaccatgctgcaaatgcatgcggcattcggaggatttacggtttgaatcttcctgtttatcc |
| | aagtctaggattcccaccttcctagtaccattgagcacgttagtttgaatttttttttttattatggttcaaaacttccgattcaaaaaaatctgatttattttacgcgaatatatggatgt |
| | ttcatcaatatacggttttgtatgtgagatataaagaagggccaaagacatgcaaacaatgggcatttctttgtgctggatcttttgtgttcttatctgcactgcaccatcaaatgaaaatt |

-continued

| SEQUENCES OF THE PRESENT DISCLOSURE | |
|---|---|
| Sequence number | Sequence |
| | accaggtgcgtgcagaacgacgtgtaaagaaaacacccagcttttccgaaacttccaaatgccattttcgagctgttcaacatagtgtgcttcgaaaatccgttcttcagtacagtaccagc<br>cacgtagcaatggctccacagaagcctcattgcttgcgagctttatgccgtgaacttgcatagattcagttcgacaacccaattgcataagcttgtgatctttttacgccgttaacttcaaa<br>atagattcggcgcaacacgactcaatagccacg<br>acacggg |
| SEQ ID NO: 23_ Target 983r | GCGGGGCATGGCCGGTGTGTAGG |
| SEQ ID NO: 24_ Target 991r | GAGGAGAAGCGGGGCATGGCCGG |
| SEQ ID NO: 25_ Target 972f | TGAGTTCGCGACCTACACACCGG |
| SEQ ID NO: 26_ Target 479r | TCCCCATGGCGAGGACCGTCCGG |
| SEQ ID NO: 27_ Target 488r | CCCAGCAGTTCCCCATGGCGAGG |
| SEQ ID NO: 28_ Target 478f | GCCGGACGGTCCTCGCCATGGGG |
| SEQ ID NO: 29_ Target 1145r | TTCTGTGAACCTTCAAAATCTGG |
| SEQ ID NO: 30_ Target 1147f | AGATTTTGAAGGTTCACAGAAGG |
| SEQ ID NO: 31_ Target 1155f | AAGGTTCACAGAAGGAGAGATGG |
| SEQ ID NO: 32_ Target 1151f | TTTGAAGGTTCACAGAAGGAGAGATGG |
| SEQ ID NO: 33_ TaU6 promoter | gaccaagcccgttattctgacagttctggtgctcaacacatttatatttatcaaggagcacattgttactcactgctaggagggaatcgaactaggaatattgatcagaggaactacgagag<br>agctgaagataactgccctctagctctcactgatctgggtcgcatagtgagatgcagcccacgtgagttcagcaacggtctagcgctgggcttttaggcccgcatgatcgggcttttgtcgg<br>gtggtcgacgtgttcacgattggggagagcaacgcagcagttcctcttagtttagtcccacctcgcctgtccagcagagttctgaccggtttataaactcgcttgctgcatcagactt |
| SEQ ID NO: 34_ gRNA_983r | GCGGGGCATGGCCGGTGTGTgttttagagctagaaatagcaagttaaaataaggctagtccgttatcaacttgaaaaagtggcaccgagtcggtgcttttttt |
| SEQ ID NO: 35_ gRNA_991r | GAGGAGAAGCGGGGCATGGCgttttagagctagaaatagcaagttaaaataaggctagtccgttatcaacttgaaaaagtggcaccgagtcggtgcttttttt |
| SEQ ID NO: 36_ gRNA_972f | TGAGTTCGCGACCTACACACgttttagagctagaaatagcaagttaaaataaggctagtccgttatcaacttgaaaaagtggcaccgagtcggtgcttttttt |

-continued

| SEQUENCES OF THE PRESENT DISCLOSURE | |
|---|---|
| Sequence number | Sequence |
| SEQ ID NO: 37_ gRNA_479r | TCCCCATGGCGAGGACCGTCgttttagagctagaaatagcaagttaaaataaggctagtccgttatcaacttgaaaaagtggcaccgagtcggtgcttttttt |
| SEQ ID NO: 38_ gRNA_488r | CCCAGCAGTTCCCCATGGCGgttttagagctagaaatagcaagttaaaataaggctagtccgttatcaacttgaaaaagtggcaccgagtcggtgcttttttt |
| SEQ ID NO: 39_ gRNA_478f | GCCGGACGGTCCTCGCCATGgttttagagctagaaatagcaagttaaaataaggctagtccgttatcaacttgaaaaagtggcaccgagtcggtgcttttttt |
| SEQ ID NO: 40_ gRNA_1145r | TTCTGTGAACCTTCAAAATCgttttagagctagaaatagcaagttaaaataaggctagtccgttatcaacttgaaaaagtggcaccgagtcggtgcttttttt |
| SEQ ID NO: 41_ gRNA_1147f | AGATTTTGAAGGTTCACAGAgttttagagctagaaatagcaagttaaaataaggctagtccgttatcaacttgaaaaagtggcaccgagtcggtgcttttttt |
| SEQ ID NO: 42_ gRNA_1155f | AAGGTTCACAGAAGGAGAGAgttttagagctagaaatagcaagttaaaataaggctagtccgttatcaacttgaaaaagtggcaccgagtcggtgcttttttt |
| SEQ ID NO: 43_ crRNA_1151f | taatttctactaagtgtagatAAGGTTCACAGAAGGAGAGATGGttttttt |
| SEQ ID NO: 44_ ZmUbiquitin promoter+ 5'UTR | gtgcagcgtgacccggtcgtgcccctctctagagataatgagcattgcatgtctaagttataaaaaattaccacatatttttttgtcacacttgtttgaagtgcagtttatctatctttat<br>acatatatttaaactttactctacgaataatataatctatagtactacaataatatcagtgttttagagaatcatataaatgaacagttagacatggtctaaaggacaattgagtattttga<br>caacaggactctacagttttatctttttagtgtgcatgtgttctcctttttttttgcaaatagcttcacctatataatacttcatccattttattagtacatccatttagggtttagggtta<br>atggtttttatagactaatttttttagtacatctattttattctattttagcctctaaattaagaaaactaaaactctattttagtttttttatttaataatttagatataaaatagaataa<br>aataaagtgactaaaaattaaacaaatacccttaagaaattaaaaaaactaaggaaacatttttcttgtttcgagtagataatgccagcctgttaaacgccgtcgacgagtctaacggaca<br>ccaaccagcgaaccagcagcgtcgcgtcgggccaagcgaagcagacggcacggcatctctgtcgctgcctctggacccctctcgagagttccgctccaccgttggacttgctccgctgtcgg<br>catccagaaattgcgtggcggagcggcagacgtgagccggcacggcaggcggcctcctcctcctctcacggcaccggcagctacgggggattcctttcccaccgctccttcgctttcccttc<br>ctcgcccgccgtaataaatagacaccccctccacaccctctttccccaacctcgtgttgttcggagcgcacacacacacaaccagatctcccccaaatccacccgtcggcacctccgcttca<br>aggtacgccgctcgtcctcccccccccccctctctaccttctctagatcggcgttccggtccatggttagggcccggtagttctacttctgttcatgtttgtgttagatccgtgtttgtgt<br>tagatccgtgctgctagcgttcgtacacggatgcgacctgtacgtcagacacgttctgattgctaacttgccagtgtttctctttggggaatcctgggatggctctagccgttccgcagacg<br>ggatcgatttcatgattttttttgtttcgttgcatagggtttggtttgcccttttcctttatttcaatatatgccgtgcacttgtttgtcgggtcatcttttcatgcttttttttgtcttgg<br>ttgtgatgatgtggtctggttgggcggtcgttctagatcggagtagaattaattctgtttcaaactacctggtggatttattaattttggatctgtatgtgtgtgccatacatattcatagt<br>tacgaattgaagatgatggatggaaatatcgatctaggataggtatacatgttgatgcgggttttactgatgcatatacagagatgcttttttgttcgcttggttgtgatgatgtggtgtggt<br>tgggcggtcgttcattcgttctagatcggagtagaatactgtttcaaactacctggtgtatttattaattttggaactgtatgtgtgtgtcatacatcttcatagttacgagtttaagatgg<br>atggaaatatcgatctaggataggtatacatgttgatgtgggttttactgatgcatatacatgatggcatatgcagcatctattcatatgctctaaccttgagtacctatctattataataa<br>acaagtatgttttataattattttgatcttgatatacttggatgatggcatatgcagcagctatatgtggatttttttagccctgccttcatacgctatttatttgcttggtactgtttctt<br>ttgtcgatgctcaccctgttgtttggtgttacttctgcag |
| SEQ ID NO: 45_ NLS-Cas9-NLS | atggctcctaagaagaagcgcaaggttgggatccacggggttccggcggctatggacaagaagtacagcatcgggctcgacatcgggacgaacagcgttgggggggtcatcacggacgagt<br>acaaggttccctccaagaagttcaaggtgctggggaacaccgaccgccactccatcaagaagaacctcatcggggccctcctgttcgacagcggggagaccgctgaggctacgaggctcaag<br>agaaccgcgaggcgcagatacacgagaaggaagaacaggatctgctacctccaagagatcttctccaacgagatggccaaggttgacgattcattcttccaccgcctggaggagtctttcct<br>cgtggaggaggacaagaagcacgagcggcatcccatcttcgggaacatcgtcgacgaggttgcctaccacgagaagtaccctacgatctaccatctgcggaagaagctcgtggacagcaccg<br>ataaggcggacctcagactgatctacctcgccctggcgcacatgatcaagttccgcgggcatttcctgatcgagggggatctcaacccagacaactccgatgttgacaagctgttcatccaa<br>ctcgtgcagacctacaaccaactcttcgaggagaacccgatcaacgcttcgggggtcgacgctaaggccatcctgtcagcccgcctctcgaagtcacgcaggctggagaacctgatcgcgca<br>gctcccaggggagaagaagaacgggctgttcgggaacctcatcgctctctctctggggctcacgccgaacttcaagtccaacttcgatctcgccgaggacgcgaagctgcaactcagcaagg<br>acacctacgacgatgacctcgataacctcctggcgcagatcggggatcaatacgctgacctgttcctcgccgcgaagaacctgtcggacgccatcctcctgtcagatatcctccgcgtgaac<br>accgagatcacgaaggccccactctctgcgtccatgatcaagcgctacgacgagcaccatcaggatctgaccctcctgaaggcgctggtccgccaacagctcccggagaagtacaaggagat |

-continued

SEQUENCES OF THE PRESENT DISCLOSURE

| Sequence number | Sequence |
|---|---|
| | cttcttcgatcagtcgaagaacgggtacgctgggtacatcgacggggggcgtcacaagaggagttctacaagttcatcaagccaatcctggagaagatggacgggacggaggagctcctgg<br>tgaagctcaacagggaggacctcctgcggaagcagagaaccttcgataacgggtccatcccccaccaaatccatctcggggagctgcacgccatcctgagaaggcaagaggacttctaccct<br>ttcctcaaggataaccgggagaagatcgagaagatcctgaccttcagaatcccatactacgtcggccgctcgctcggggaacagcagattcgcctggatgacccgcaagtcggaggagac<br>catcacgccgtggaacttcgaggaggtggtcgacaaggggcgagcgctcagtcgttcatcgagaggatgaccaacttcgacaagaacctgcccaacgagaaggtgctccctaagcactcgc<br>tcctgtacgagtacttcaccgtctacaacgagctcacgaaggtgaagtatgtgaccgaggggatgagaaagcctgccttcctgtccggggagcagaagaaggcgatcgtggacctcctgttc<br>aagaccaaccggaaggtcacggttaagcaactcaaggaggactacttcaagaagatcgagtgcttcgattcggtggagatctcaggggtcgaggacaggttcaacgcctccctcgggaccta<br>ccacgatctcctgaagatcatcaaggataaggacttcctggacaacgaggagaacgaggacatcctggaggacatcgtgctgaccctcacgctgttcgaggacagggagatgatcgaggagc<br>gcctgaagacgtacgcccatctcttcgatgacaaggtcatgaagcaactcaagagaagaagatacaccggggggggaggctgtcccgcaagctcatcaacgggatccgggacaagcagtcag<br>ggaagaccatcctcgacttcctgaagtctgatgggttcgccaacaggaacttcatgcaactgatccacgatgactcactcaccttcaaggaggatatccaaaaggctcaggtgagcgggcag<br>ggggactcgctgcacgagcatatcgctaacctcgctgggtcccctgcgatcaagaaggggatcctgcagaccgtgaaggttgtggacgagctcgtgaaggtcatggggcggcataagcctga<br>gaacatcgtcatcgagatggccagagagaaccaaaccacgcagaaggggcaaaagaactctagggagcgcatgaagcgcatcgaggaggggatcaaggagctggggtcccaaatcctcaagg<br>agcacccagttgagaacacccaactgcagaacgagaagctctacctgtactacctccagaacggggggatatgtatgtggaccaagagctggatatcaaccgcctcagcgattacgacgttg<br>atcatatcgtgccccagtctttcctgaaggatgactccatcgacaacaaggtcctcaccaggtcggacaagaaccgcgggaagtcagataacgttccatctgaggaggtcgttaagaagatg<br>aagaactactggaggcagctcctgaacgccaagctgatcacgcaaaggaagttcgacaacctcaccaaggctgagagagggggctctcagagctggacaaggctgggttcatcaagcggca<br>gctggtcgagaccagacaaatcacgaagcacgttgcgcaaatcctcgactctcggatgaacacgaagtacgatgagaacgacaagctgatcagggaggtgaaggtcatcaccctgaagtcta<br>agctcgtctccgacttccgcaaggacttccagttctacaaggttcgcgagatcaacaactaccaccatgcgcatgacgcttacctcaacgctgtggtcgggaccgccctgatcaagaagtac<br>ccgaagctggagagcgagttcgtgtacggggactacaaggtttacgatgtgcgcaagatgatcgccaagtcggagcaagagatcgggaaggccaccgccaagtacttcttctactcaaacat<br>catgaacttctttaagaccgagatcacgctggccaacggggagatccggaagagacccctcatcgagaccaacggggagacgggggagatcgtgtgggacaagggggagggatttcgcgaccg<br>tccgcaaggttctctccatgccccaggtgaacatcgtcaagaagaccgaggtccaaacgggggggttctcaaaggagtctatcctgcctaagcggaacagcgacaagctcatcgccagaaag<br>aaggactgggatccaaagaagtacggggggttcgacagccctaccgtcgcgtactcggttctggttgtggctaaggttgagaaggggaagtccaagaagctcaagagcgtgaaggagctcct<br>ggggatcaccatcatggagcgctccagcttcgagaagaacccaatcgacttcctggaggccaaggggtacaaggaggtgaagaaggacctgatcatcaagctcccgaagtactctctcttcg<br>agctggagaacgggaggaagcgcatgctggcttccgctggggagctccaaaaggggaacgagctcgccctgccatccaagtatgtgaacttcctctacctggcgtcccactacgagaagctc<br>aaggggagcccggaggacaacgagcaaaagcagctgttcgtcgagcagcacaagcattacctcgacgagatcatcgagcaaatctccgagttctccaagcgcgtgatcctcgcggacgctaa<br>cctggataaggtcctctccgcttacaacaagcaccgggacaagcccatcagagagcaggccgagaacatcatccatctcttcaccctgacgaacctcggggcccctgctgccttcaagtact<br>tcgacaccacgatcgatcggaagagatacaccagcacgaaggaggtcctggacgcgaccctcatccaccaatctatcacggggctgtacgagacgagaatcgacctgtcacaactgggggg<br>gacaagaggccggcggcaaccaagaaggcgggccaggccaagaagaagaagtga |
| SEQ ID NO: 46_<br>NLS-Cas12a-NLS | atggccccgaagaagaagaggaaagtgggcatccacggcgtgcctgcagcaatgtccaagctggagaagttcaccaactgctactccctgagcaagaccctccgcttcaaggccatccccgt<br>gggcaagacccaggagaacatcgacaacaagaggctcctggtggaggatgagaagagggcagaggactacaagggcgtcaagaagctgctcgacaggtactacctgtccttcatcaacgacg<br>tcctccacagcatcaagctgaagaacctcaacaactacatctccctcttcaggaagaagacccgcaccgagaaggagaacaaggagctggagaacctcgagatcaacctgcgcaaggagatc<br>gccaaggccttcaagggcaacgagggctacaagagcctcttcaagaaggacatcatcgagaccatcctgcctgagttcctcgacgacaaggatgaaatcgccctggtgaactccttcaacgg<br>cttcaccaccgccttcaccggcttcttcgacaacagggagaacatgttcagcgaggaagccaaatcaacctccatcgccttcaggtgcatcaacgagaacctcacccgctacatctccaaca<br>tggacatcttcgagaaggtcgacgccatcttcgacaagcacgaggtgcaggagatcaaggagaagatcctgaacagcgactacgacgtggaggacttcttcgagggcgagttcttcaacttc<br>gtcctcacccaagagggcatcgacgtgtacaacgccatcatcggcggcttcgtcaccgagtccggcgagaagatcaagggcctgaacgagtacatcaacctctacaaccagaagaccaagca<br>gaagctgccgaagttcaagccactgtacaagcaggtgctctccgacagggagtccctcagcttctacggcgagggctacaccagcgacgaggaagtgctggaggtgttccgcaacaccctca<br>acaagaacagcgagatcttctccagcatcaagaagctggagaagctgttcaagaacttcgacgagtactccagcgccggcatcttcgtgaagaacggcccggccatctccaccatcagcaag<br>gacatcttcggcgagtggaacgtcatccgcgacaagtggaacgccgagtacgacgacatccacctgaagaagaaggccgtggtcaccgagaagtacgaggacgacaggcgcaagtccttcaa<br>gaagatcggctccttcagcctggagcagctccaggagtacgccgacgccgacctgagcgtggtcgagaagctcaaggagatcatcatccagaaggtcgacgagatctacaaggtgtacggct<br>ccagcgagaagctgttcgacgccgacttcgtgctggagaagtccctcaagaagaacgacgccgtggtcgccatcatgaaagacctgctcgactccgtcaagagcttcgagaactacatcaag<br>gccttcttcggcgagggcaaggagaccaacagggacgagtccttctacggcgacttcgtcctggcctacgacatcctgctcaaggtggaccacatctacgacgccatcaggaactacgtgac<br>ccagaagccgtacagcaaggacaagttcaagctctacttccagaacccacagttcatgggcggctgggacaaggacaaggagaccgactacagggccaccatcctgcgctacggcagcaagt<br>actacctcgccatcatggacaagaagtacgccaagtgcctgcagaagatcgacaaggacgacgtgaacggcaactacgagaagatcaactacaagctgctcccgggcccaaacaagatgctc<br>cccaaggtcttcttctccaagaagtggatggcctactacaaccctagcgaggacatccagaagatctacaagaacggcaccttcaagaagggcgacatgttcaacctgaacgactgccacaa<br>gctcatcgacttcttcaaggactccatcagcaggtacccgaagtggtccaacgcctacgacttcaacttcagcgagaccgagaagtacaaggacatcgccggcttctaccgcgaggtcgagg<br>agcagggctacaaggtgtccttcgagtccgcctccaagaaggaagtggacaagctggtggaggaaggcaagctgtacatgttccagatctacaacaaggacttctccgacaagagccacggc<br>accccaaacctgcacaccatgtacttcaagctgctgttcgacgagaacaaccacggccagatcaggctctccggcggcgccgagctgttcatgcgtagagccagcctgaagaaagaggagct<br>ggtggtccacccagcaaacagccctatcgccaacaagaaccccgacaaccctaagaagaccaccaccctgtcctacgacgtgtacaaggacaagaggttcagcgaggaccagtacgagctcc |

-continued

SEQUENCES OF THE PRESENT DISCLOSURE

| Sequence number | Sequence |
|---|---|
| | acatccccatcgccatcaacaagtgccctaagaacatcttcaagatcaacaccgaggtccgcgtgctgctcaagcacgacgacaacccatacgtgatcggcatcgacaggggcgagcgcaac<br>ctgctctacatcgtggtcgtggacggcaagggcaacatcgtcgagcagtactccctcaacgagatcatcaacaacttcaacggcatcaggatcaagaccgactaccacagcctgctcgacaa<br>gaaggagaaggagaggttcgaggcccgccagaactggacctccatcgagaacatcaaggagctgaaggccggctacatcagccaggtcgtgcacaagatctgcgagctcgtcgagaagtacg<br>acgccgtgatcgccctggaggacctcaactccggcttcaagaacagccgcgtcaaggtggagaagcaggtgtaccagaagttcgagaagatgctgatcgacaagctcaactacatggtcgac<br>aagaagtccaacccctgcgcaaccggcggcgccctgaagggctaccagatcaccaacaagttcgagagcttcaagtccatgagcacccagaacggcttcatcttctacatcccggcctggct<br>cacctccaagatcgacccaagcaccggcttcgtgaacctgctcaagaccaagtacacctccatcgccgacagcaagaagttcatctccagcttcgacaggatcatgtatgtgcccgaggaag<br>acctgttcgagttcgccctcgactacaagaacttctcccgcaccgacgccgattacatcaagaagtggaagctgtacagctacggcaacaggatccgcatcttcaggaaccctaagaagaac<br>aacgtcttcgactgggaggaagtgtgcctgacctccgcctacaaggagctgttcaacaagtacggcatcaactaccagcagggcgacatcagggccctgctctgcgagcagagcgacaaggc<br>cttctactccagcttcatggccctgatgtccctgatgctccagatgaggaacagcatcaccggccgcaccgacgtcgacttcctcatctccccggtgaagaacagcgacggcatcttctacg<br>actccaggaactacgaggcccaggagaacgccatcctgccaaagaacgccgacgccaacggcgcctacaacatcgcaaggaaggtgctctgggcaatcggccagttcaagaaggccgaggac<br>gagaagctggacaaggtgaagatcgccatctccaacaaggagtggctcgagtacgcccagacctctgtcaagcacaagaggccagcagcaaccaagaaggcgggccaggccaagaagaagaa<br>gggcagctacccgtacgacgtcccagactacgcctacccctacgacgtgcctgactacgcttacccatacgatgtgccagactacgcctga |
| SEQ ID NO: 47_ Nopaline synthase polyadenylation sequence | gatcgttcaaacatttggcaataaagtttcttaagattgaatcctgttgccggtcttgcgatgattatcatataatttctgttgaattacgttaagcatgtaataattaacatgtaatgcat<br>gacgttatttatgagatgggtttttatgattagagtcccgcaattatacatttaatacgcgatagaaaacaaaatatagcgcgcaaactaggataaattatcgcgcgcggtgtcatctatgt<br>tactag |
| SEQ ID NO: 48_ Traes-CS1B02G037100 (TaAt5g02240-like) CDS | ATGGCCACGGCGGCGGCGGCGGCGGCGACGATGCGTCTGTCTTCCCCGTTCAGGGCCCCGCCTCTCCGTCCTCCCTGCCACCGCGTCGTCCCGT<br>CGATGCGGGGCCCCAGGCGGGCCGGGCTGGCCGTCTCGGCGGCCGCCGCCGGGTCGCCCCCCACCGTGCTCGTCACCGGCGCCGGAGGACGG<br>ACAGGCCAAATTGTGTACAAGAAGCTGAAGGAGAGGGCAGACCAGTTTGTGGCCAGAGGGCTGGTCAGGACGCCGGACAGCAAGGGTAAGATAGG<br>CGGCGGCGACGACGTGTTCATCGGCGACATCAGGGATCCTGGGAGCATTGCTCCGGCGATTGAGGGCATCGACGCGCTCATCATCCTCACCAGTG<br>GGGTCCCGAAGATGAAGCCCGGGTTCGATCCTAGCAAGGGTGGACGGCCGGAGTTTTACTTTGAGGAAGGGTCTGATCCTGAGCAGGTGGATTGG<br>ATAGGCCAAAAGAACCAAATTGATGCTGCCAAGAGCATTGGTGTAAAGCAGATAGTTTTGGTTGGATCCATGGGGGGAACAGATATCAACCATCCATT<br>AAACAAGCTTGGGAATGGGAATATACTGGTGTGGAAACGGAAGGCAGAGCAGTACCTAGCGGACTCTGGTCTACCATACACAATTATAAGGGCTGG<br>AGGACTACAAGACAAAGATGGTGGGGTGCGTGAGTTGATTGTTGGAAAGGATGACGAGATCTTGAAGACGGAAACAAAAACTATTGCCAGGGCAGA<br>TGTTGCAGAAGTTTGCATACAGGCCTTGCTATTTGAGGAAGCAAAGTTCAAGGCGTTTGATCTGGCTTCAAAACCTGAAGGTGAAGGAACACCGATG<br>ACAGATTTTAAGTCTGTTTTTGCACAAATTGCTACTCGCTTCTAA |
| SEQ ID NO: 49_ Traes-CS1B02G037100 (TaAt5g02240-like) | MATAAAAAATMRLSSPFRAPPLRPPCHRVVPSMRGPRRAGLAVSAAAAGSPPTVLVTGAGGRTGQIVYKKLKERADQFVARGLVRTPDSKGKIGGGDDVF<br>IGDIRDPGSIAPAIEGIDALIILTSGVPKMKPGFDPSKGGRPEFYFEEGSDPEQVDWIGQKNQIDAAKSIGVKQIVLVGSMGGTDINHPLNKLGNGNILVWKRK<br>AEQYLADSGLPYTIIRAGGLQDKDGGVRELIVGKDDEILKTETKTIARADVAEVCIQALLFEEAKFKAFDLASKPEGEGTPMTDFKSVFAQIATRF |
| SEQ ID NO: 50_ Traes-CS1B02G037100 (TaAt5g02240-like) genomic | CGCCTTAGATGCCGTCGCCTCCTAGCCATAAGCGTCAGAAGGCGGTATATAGGTTATCTCCGCCGGAAAAAGGGTAAGGTTTGCCTCGAGAATGTTT<br>TGTTTGACTATATCCTATGTGGAACCAAGGCTAGGTTTGCATGCAATGAAAAAATGTAATTGTAGGAGGAGAAGGGAGGGTGGTAGATGTGCGCGAC<br>AACAACACACACGCCATATATATATATAGTTGGAGGAGGTGGAAAACAAGGAGGCGATAAGAAAAAGGGGGGAATATGGAGAATGTTTGAAATAGCGT<br>CCAACCCGAGTTTCCATTATTAATTGTCGGCCAAAAAAAGAAGGCATGTTACTCATGATGGTAGTTTCAAGGGAAGTGGAGCCTCCCAGCTAGTTTGA<br>ACACTTAAAAAACAAGCTACAACAGAAAGTAGTTTCAAGGGGAGTGGAGCCTAAAACTTGCATTTAAAAAGGAAATGCGCACACTAAGCCGAAAGTGT<br>GAACACTTTGTGCCGACATTTCCGAGGAAGTAGGTTTTATGCGCATAACATTTTTTTTGAGACAATTTTATGCGCATAACTAGGGTTGACTGCTGTGG<br>GGAAGATGAAATTTGAACTGCCATTGTGACGCAAAGATTTGGTGATCCAAATTTGTATATGGACCATGCCTGTAGGTTGGGCTAAGTATACTTTTCGA<br>AGAAAATAGGCCCATGTTAACTTGGGAAGTGGGCCTAGGCCCACAAACCTGAAATCCCTGTGAAGCCCACATTCACACGCGGGCCCACCGTCGAAG<br>CGATAAGGAGAGTGACAGCCGCTCAGCCCGCCGGCACACCCGACAACAACTCTCGCTTCACTCGCCGGAGGGGGACGGAGCAAATATGGCCACG<br>GCGGCGGCGGCGGCGGCGACGATGCGTCTGTCTTCCCCGTTCAGGGCCCCGCCTCTCCGTCCTCCCTGCCACCGCGTCGTCCCGTCGATGCGGG<br>GCCCCAGGCGGGCCGGGCTGGCCGTCTCGGCGGCCGCCGCCGGGTCGCCCCCCACCGTGCTCGTCACCGGCGCCGGAGGACGGACAGGTAGAT<br>ACTACACATCCCGCTAGCTTCTTTACCTTCGCGTCCTGTAGCCGCACATTGTTGCACGATGCCGCCTTCTCTTGCTGTTCCAATGGGATTCAGTTTGC |

-continued

SEQUENCES OF THE PRESENT DISCLOSURE

| Sequence number | Sequence |
|---|---|
| | ATTTGTGGGAGAATTTACCGGCGGAGGCGGCGGTTTCTTGGAATCAAGATGCTTCACAACCTATGGAACCTCCTATTGATTTAAAATTTACACTGCCG<br>TTTACGTGCTGTGATCCGGCGTGCGCCTCTGACCCTTGCGCTGTGGTGACCCAGGCCAAATTGTGTACAAGAAGCTGAAGGAGAGGGCAGACCAGT<br>TTGTGGCCAGAGGGCTGGTCAGGACGCCGGACAGCAAGGGTAAGATAGGCGGCGGCGACGACGTGTTCATCGGCGACATCAGGGATCCTGGGAG<br>CATTGCTCCGGCGATTGAGGGCATCGACGCGCTCATCATCCTCACCAGTGGGGTCCCGAAGATGAAGCCCGGGTTCGATCCTAGCAAGGGTGGAC<br>GGCCGGAGTTTTACTTTGAGGAAGGGTCTGATCCTGAGCAGGTAACCGGCAAAAATCGCTTGGCAATGACATTAGTCACATTAGCAATGACAACTTA<br>TGCATTTCTTTTAGAGTTAATTAATGTCCTTTGCTGTTTTCCCTTGATTTAAGGTGGATTGGATAGGCCAAAAGAACCAAATTGATGCTGGTAAATCTTC<br>ACCTTCTTCTTGTTCTGTTAGAGCATTATACAATGTTTAGCATGTTCATTGAAACGATTGATTGGTGAAGCATCGATGTGTCATTTTCTCTCCGGTCGA<br>CCTTTTTCTTGTCTGCTCTCTAAGTTTCCCATCTTTAATTATCCATGCAGCCAAGAGCATTGGTGTAAAGCAGATAGTTTTGGTTGGATCCATGGGCGG<br>AACAGATATCAACCATCCATTAAACAAGCTTGGGAATGGGAATATACTGGTATATAGCATGCTCGACGATTTTTGTATATGTTCTAATTCCCTATACTTG<br>TGTGTGCATAAACATATAATATGTACCATTTTGAAACTTAGAATGGCCAATTGCTCTTCTAATTTGCAGGTGTGGAAACGGAAGGCAGAGCAGTACCTA<br>GCGGACTCTGGTCTACCATACACAATTATAAGGTTATAACACAGACTCATTCGGTAGTGCTATTCTTGCCATGTTCTGCAAAGATTTTTTTTTGTCACA<br>TTTGAGTTATGTAATAGGCTGACAGTCACTGTTTTCTCCAAAGATGCACAGTCATAGAAATAATTTTATATATGTGATGAATGAAGAAAACAACAAAACA<br>ACAGAAGTGCATTATGGAGTATGAAGCACCACAAAGAACATTAATTTTGTATAAGAAATAAAAAATTCCAATTTATTTCATAGGGACATTAATCGTTGGA<br>GTATTTTCCACCAACAATCGTGTGCTGATAAAATACCTTTCCCATATCCCATCTCTTTCCAGGGCTGGAGGACTACAAGACAAAGATGGTGGGGTGCG<br>TGAGTTGATTGTTGGAAAGGATGACGAGATCTTGAAGACGGAAACAAAAACTATTGCCAGGGCAGATGTTGCAGAAGTTTGCATACAGGTACCTTTAT<br>AGAACAAAACACATGTTTCTGTAGATAAACTACTGCTCAATATTTTTTTCATCATCTACCAAATATATTTCTTGCATCTATTTATGTCTTACTAGCTAGTG<br>GTCATACCACTGATCCATCTGTGCCTTTCCTGAGTAGGCCTTGCTATTTGAGGAAGCAAAGTTCAAGGCGTTTGATCTGGCTTCAAAACCTGAAGGTG<br>AAGGAACACCGATGACAGATTTTAAGTCTGTTTTTGCACAAATTGCTACTCGCTTCTAAGAGGACAAGATCATTCTGGCCAATGAAATGGGACAGTAT<br>CTTTAATTAGGCGATATGGAATTTGTACTGGGTCAGGTTAGTGTTCTGTTTATTAATTGAGGAAATGCAACATTTTATTCTACGCACTATTATTCCATAG<br>TAAATTTTGTGTTTATCTCTTTTCTTTGTGGTCAA |
| SEQ ID NO: 51_ TaAt5g02240-like CDS | ATGGCCACGGCGGCGGCGGCGGCGGCGACGATGCGTCTGTCTTCCCCGTTCAGGGCCCCGCCTCTCCGTCCTCCCTGCCACCGCGTCGTCCCGT<br>CGATGCGGGGCCCCAGGCGGGCCGGGCTGGCCGTCTCGGCGGCCGCCGCCGGGTCGCCCCCCACCGTGCTCGTCACCGGCGCCGGAGGACGG<br>ACAGGCCAAATTGTGTACAAGAAGCTGAAGGAGAGGGCAGACCAGTTTGTGGCCAGAGGGCTGGTCAGGACGCCGGACAGCAAGGGTAAGATAGG<br>CGGCGGCGACGACGTGTTCATCGGCGACATCAGGGATCCTGGGAGCATTGCTCCGGCGATTGAGGGCATCGACGCGCTCATCATCCTCACCAGTG<br>GGGTCCCGAAGATGAAGCCCGGGTTCGATCCTAGCAAGGGTGGACGGCCGGAGTTTTACTTTGAGGAAGGGTCTGATCCTGAGCAGGTGGATTGG<br>ATAGGCCAAAAGAACCAAATTGATGCTGCCAAGAGCATTGGTGTAAAGCAGATAGTTTTGGTTGGATCCATGGGCGGAACAGATATCAACCATCCATT<br>AAACAAGCTTGGGAATGGGAATATACTGGTGTGGAAACGGAAGGCAGAGCAGTACCTAGCGGACTCTGGGACATTAATCGTTGGAGTATTTTCCACC<br>AACAATCGTGTGCTGATAAAATACCTTTCCCATATCCCATCTCTTTCCAGGGCTGGAGGACTACAAGACAAAGATGGTGGGGTGCGTGAGTTGATTGT<br>TGGAAAGGATGACGAGATCTTGAAGACGGAAACAAAAACTATTGCCAGGGCAGATGTTGCAGAAGTTTGCATACAGGCCTTGCTATTTGAGGAAGCA<br>AAGTTCAAGGCGTTTGATCTGGCTTCAAAACCTGAAGGTGAAGGAACACCGATGACAGATTTTAAGTCTGTTTTTGCACAAATTGCTACTCGCTTCTAA |
| SEQ ID NO: 52_ TaAt5g02240-like | MATAAAAAATMRLSSPFRAPPLRPPCHRVVPSMRGPRRAGLAVSAAAAGSPPTVLVTGAGGRTGQIVYKKLKERADQFVARGLVRTPDSKGKIGGGDDVF<br>IGDIRDPGSIAPAIEGIDALIILTSGVPKMKPGFDPSKGGRPEFYFEEGSDPEQVDWIGQKNQIDAAKSIGVKQIVLVGSMGGTDINHPLNKLGNGNILVWKRK<br>AEQYLADSGTLIVGVFSTNNRVLIKYLSHIPSLSRAGGLQDKDGGVRELIVGKDDEILKTETKTIARADVAEVCIQALLFEEAKFKAFDLASKPEGEGTPMTDF<br>KSVFAQIATRF |
| SEQ ID NO: 53_ TaAt5g02240-like genomic | GGAGTCGTGTCTTATTTGGTGGCGTTTGTCGACTATCTCCTGTGTGGAGCCAATGCTTGGCTCGCACGCAAGTCGAAAAGAACTGCAATGGTAGGAG<br>GAGAAGGGAGAGGGTGTGGTAGATGCGCACGACAACAACAACACACGACAAATATATATAGTTGGAGTAAGTGGAAAACAAGGACGCGACAAGAAA<br>GGGGGAGAATGTTCGAAATAGCGTCCAACCTAAGTTCAGAGAATTAATTGTCAACCAAAAATTGGGCAAGGGCTCAGTATACCGGCCTAGAAGTGAA<br>AATTGCGATCAAAAGTTTGCACCGCCGAAGAAGAGAAAAGCAAAAACTTCTCATATTTTTCAAAGGATTGAACATTTTTTATTGTCATGTTATCCCGTA<br>GGCAGGATATTGACCTAGCAACTTTGGTGTAGCCTATTGTATTACTCATATTCATCGAGCAGTATATTATTGAAGGGGCTTTTATTGACTCTAAATGTA<br>GCATTGTTGTAATGCATTTGCATAATTAAGGGTGTGTTTGGTTGTGTGGCTAAGGATAGCCACTTTTTAAGTGGTTGCCATGTGTTTGATTTTAAAATTT<br>GTGTAGTTCAGGATAGCCATATCCAAGGAATATTCCATAAAATGTGGCACAGCGGAAGCGCCAAAAAGTGATGGGTAAGGTCAACCACCCTATGCTT<br>GCATGCTCACCTCACCATCTGAATCATTTACAACCTGTTCTGACCCCCTCCCCCAAAGGAATTTTATCAGGCTTTTGGTGAGGGCATTCGCATGTCTG<br>CACTTGTCATCCAATGAACTGTGACGAATACTAGGGTGTTAGAAAGGAAACGGCAACTCATGAAATATAACCGACAAACATATATATCTATAAATCATG<br>CAACAAAGAAACCGAAAGATTACAACAAAAACCATATATGGATCTGATCATAAAGGGGCAATTCATCACACGGAAACAAACACACCGAGAATTACATC<br>AGATGGAACACAATCATGTAGAGCAGCGCATGTGACCATTGATTGAAAAGCAAGGGAGAGAAGGAAAAGCAAGGGAGAGAAGATGCCAACTAGCTA |

-continued

SEQUENCES OF THE PRESENT DISCLOSURE

| Sequence number | Sequence |
| --- | --- |
| | CTGTTATGGACCCATAGTTCAAAGAGGACTATTCACACATGGTCATGGTGGCAACGAGGTTGCTGGAGATGCATCCGGCGATGATTTATCCCTCCAG<br>GAAAGTACCGGAAAAAGGTCTCCGGATTGGATCATCGCGAAACAAGTGGTGGCGACAGCAGAAAAATCCTTGATAAACAAATCACGTGAGAGAGCTC<br>CGAAATTAGGGAGCATACTGAATTTAAAGATACTAGATGATACCCCGCATGTTATTGTGAACTCTGGTCTACCATACACAATTATAAGGTTATAACACA<br>GACTCATTCGGTAGTGCTATTTGTGGTATGAGACTTATTCTTGCCATGTTCTGCAAAGAATTTTTTTGTCACATTTGAGTTATGTAATAGGCTGACAGT<br>CACTGTTTTCTCCAAAGACGCACAGTCATAAAAGTAATTTGAAAAAACTGTGCATTTTGAAAAAAATGTTCGCGGAATCAAAAAATGTTTGTGATTTTAC<br>AAAAAAATATTCACATATTCAGAAAATGTTGGCGTATTCAGAAAATGTTATGGAATTGAGAAATTTTCTGCAAAGTTTAAAATTTTTCATGTATTTTAAAA<br>AGGCTTCACAAAATTTAAAAAATGTCCATTCATTACAAAAATGATCCTCGATTCAAAAATGCTCATTCAAATAAAAAAATGTTCATGAATTACAAAATTAA<br>TTCCCCCAATTTTTAAAAGTGTTTCGCTGATTCAAAACAAATATTCACAGGCTTAAAAGATGTTCACAATTCCTAGAAATGTACACAAATTTGTAAAAAA<br>TCCTCGTCAATTTAAAAAATGTTCGTCAATTAAAAAAATGTAATGTAGTAGTAGTATGTTGAGTAGTCCAACCGAAGGATATTAATTCTCATCTCAGTCA<br>TCACTCCTCTTCCTCGGATCACCGGCGATGGCAATGGCATTGTCCCTCCCCACCACGGTCTTGCTCCTCCTCCTCCTCCTCCTCCCCGTCGCCT<br>TAGATGCCGTCGCCTCCTAGCCATAAGCGTCAGAAGGCGGTATATAGGTTATCTCCGCCGGAAAAAGGGTAAGGTTTGCCTCGAGAATGTTTTGTTT<br>GACTATATCCTATGTGGAACCAAGGCTAGGTTTGCATGCAATGAAAAAATGTAATTGTAGGAGGAGAAGGGAGGGTGGTAGATGTGCGCGACAACAA<br>CACACACGCCATATATATATATAGTTGGAGGAGGTGGAAAACAAGGAGGCGATAAGAAAAAGGGGGGGGGGGAATATGGAGAATGTTTGAAATAGCGT<br>CCAACCCGAGTTTCCATTATTAATTGTCGGCCAAAAAAAGAAGGCATGTTACTCATGATGGTAGTTTCAAGGGAAGTGGAGCCTCCCAGCTAGTTTGA<br>ACACTTAAAAAAACAAGCTACAACAGAAAGTAGTTTCAAGGGGAGTGGAGCCTAAAACTTGCATTTAAAAAGGAAATGCGCACACTAAGCCGAAAGTG<br>TGAACACTTTGTGCCGACATTTCCGAGGAAGTAGGTTTTATGCGCATAACATTTTTTTGAGACAATTTTATGCGCATAACTAGGGTTGACTGCTGTGG<br>GGAAGATGAAATTTGAACTGCCATTGTGACGCAAAGATTTGGTGATCCAAATTTGTATATGGACCATGCCTGTAGGTTGGGCTAAGTATACTTTTCGA<br>AGAAAATAGGCCCATGTTAACTTGGGAAGTGGGCCTAGGCCCACAAACCTGAAATCCCTGTGAAGCCCACATTCACACGCGGGCCCACCGTCGAAG<br>CGATAAGGAGAGTGACAGCCGCTCAGCCCGCCGGCACACCCGACAACAACTCTCGCTTCACTCGCCGGAGGGGGACGGAGCAAATATGGCCACG<br>GCGGCGGCGGCGGCGGCGACGATGCGTCTGTCTTCCCCGTTCAGGGCCCCGCCTCTCCGTCCTCCCTGCCACCGCGTCGTCCCGTCGATGCGGG<br>GCCCCAGGCGGGCCGGGCTGGCCGTCTCGGCGGCCGCCGCCGGGTCGCCCCCCACCGTGCTCGTCACCGGCGCCGGAGGACGGACAGGTAGAT<br>ACTACACATCCCGCTAGCTTCTTTACCTTCGCGTCCTGTAGCCGCACATTGTTGCACGATGCCGCCTTCTCTTGCTGTTCCAATGGGATTCAGTTTGC<br>ATTTGTGGGAGAATTTACCGGCGGAGGCGGCGGTTTCTTGGAATCAAGATGCTTCACAACCTATGGAACCTCCTATTGATTTAAAATTTACACTGCCG<br>TTTACGTGCTGTGATCCGGCGTGCGCCTCTGACCCTTGCGCTGTGGTGACCCAGGCCAAATTGTGTACAAGAAGCTGAAGGAGAGGGCAGACCAGT<br>TTGTGGCCAGAGGGCTGGTCAGGACGCCGGACAGCAAGGGTAAGATAGGGGGGGGCGACGACGTGTTCATCGGCGACATCAGGGATCCTGGGAG<br>CATTGCTCCGGCGATTGAGGGCATCGACGCGCTCATCATCCTCACCAGTGGGGTCCCGAAGATGAAGCCCGGGTTCGATCCTAGCAAGGGTGGAC<br>GGCCGGAGTTTTACTTTGAGGAAGGGTCTGATCCTGAGCAGGTAACCGGCAAAAATCGCTTGGCAATGACATTAGTCACATTAGCAATGACAACTTA<br>TGCATTTCTTTTAGAGTTAATTAATGTCCTTTGCTGTTTTCCCTTGATTTAAGGTGGATTGGATAGGCCAAAAGAACCAAATTGATGCTGGTAAATCTTC<br>ACCTTCTTCTTGTTCTGTTAGAGCATTATACAATGTTTAGCATGTTCATTGAAACGATTGATTGGTGAAGCATCGATGTGTCATTTTCTCTCCGGTCGA<br>CCTTTTTCTTGTCTGCTCTCTAAGTTTCCCATCTTTAATTATCCATGCAGCCAAGAGCATTGGTGTAAAGCAGATAGTTTTGGTTGGATCCATGGGGGG<br>AACAGATATCAACCATCCATTAAACAAGCTTGGGAATGGGAATATACTGGTATATAGCATGCTCGACGATTTTTGTATATGTTCTAATTCCCTATACTTG<br>TGTGTGCATAAACATATAATATGTACCATTTTGAAACTTAGAATGGCCAATTGCTCTTCTAATTTGCAGGTGTGGAAACGGAAGGCAGAGCAGTACCTA<br>GCGGACTCTGGTCTACCATACACAATTATAAGGTTATAACACAGACTCATTCGGTAGTGCTATTCTTGCCATGTTCTGCAAAGATTTTTTTTTGTCACA<br>TTTGAGTTATGTAATAGGCTGACAGTCACTGTTTTCTCCAAAGATGCACAGTCATAGAAATAATTTTATATATGTGATGAATGAAGAAAACAACAAAACA<br>ACAGAAGTGCATTATGGAGTATGAAGCACCACAAAGAACATTAATTTTGTATAAGAAATAAAAAATTCCAATTTATTTCATAGGGACATTAATCGTTGGA<br>GTATTTTCCACCAACAATCGTGTGCTGATAAAATACCTTTCCCATATCCCATCTCTTTCCAGGGCTGGAGGACTACAAGACAAAGATGGTGGGGTGCG<br>TGAGTTGATTGTTGGAAAGGATGACGAGATCTTGAAGACGGAAACAAAAACTATTGCCAGGGCAGATGTTGCAGAAGTTTGCATACAGGTACCTTTAT<br>AGAACAAAACACATGTTTCTGTAGATAAACTACTGCTCAATATTTTTATCATCATCTACCAAATATATTTCTTGCATCTATTTATGTCTTACTAGCTAGTG<br>GTCATACCACTGATCCATCTGTGCCTTTCCTGAGTAGGCCTTGCTATTTGAGGAAGCAAAGTTCAAGGCGTTTGATCTGGCTTCAAAACCTGAAGGTG<br>AAGGAACACCGATGACAGATTTTAAGTCTGTTTTTGCACAAATTGCTACTCGCTTCTAAGAGGACAAGATCATTCTGGCCAATGAAATGGGACAGTAT<br>CTTTAATTAGGCGATATGGAATTTGTACTGGGTCAGGTTAGTGTTCTGTTTATTAATTGAGGAAATGCAACATTTTATTCTACGCACTATTATTCCATAG<br>TAAATTTTGTGTTTATCTCTTTTCTTTGTGGTCAATGGATTCTGCATAAAATGTTTATGGCCCTTCTGTTACCTGGTTGATCTGTCCTAATTTGGATGTAC<br>ACACTTAGTATTTGCAGTTAGTTTATTTTGTAACTAAAGGTCGGACATGCTTGGGGTCATGCGGTCATGATGTTCTGGTTGATCTAGTTTTAAGTTAAT<br>CCATTTGCTAGTTTAAACAACGTTTAGGGTTATCCATGTTGCGTATTTATAGTCCCACCAAATCGTTGGTTAGTATAATCTGGATTGTAAATTTGTTAGG<br>GCTATAAACACCCAACTTCACATGCTCCTTCTGTAGCAAAAGTAGAAGTGGCATGTCCTCTCCTTCCAGATTGTCTCCGATGCTCTGCCAACAAAACA<br>ACAACAACAACAACAAC |

-continued

SEQUENCES OF THE PRESENT DISCLOSURE

| Sequence number | Sequence |
|---|---|
| SEQ ID NO: 54_ Target 70f | CTTCACTCGCCGGAGGGGGACGG |
| SEQ ID NO: 55_ Target 81f | GGAGGGGGACGGAGCAAATATGG |
| SEQ ID NO: 56_ gRNA_70f | CTTCACTCGCCGGAGGGGGAgttttagagctagaaatagcaagttaaaataaggctagtccgttatcaacttgaaaaagtggcaccgagtcggtgcttttttt |
| SEQ ID NO: 57_ gRNA_81f | GGAGGGGGACGGAGCAAATAgttttagagctagaaatagcaagttaaaataaggctagtccgttatcaacttgaaaaagtggcaccgagtcggtgcttttttt |
| SEQ ID NO: 58_ RFL79 gene | atgcctcgct tctcctccac cacgccaatg tcgccacccc gcctcctcct ccggctcggc gcccgccact cctcctccac ctctcatccc<br>tcacgcatct gggatcccca cgccgccttc gccgctgcga cgcagcgggc gcgctctggc acgctcacca cggaggacgc acaccacctg<br>tttgatgaat tgctgcggca gggcaatcct gtccaggagc gtcccttgac taactttctg gctgccctcg cccgcgcgcc cgcgtccgca<br>ttctgcagcg atggccctgc cctggccgtc gccctcttcg gccgtttgtc ccgaggcgcc ggacgacggg tggcgcagcc aaatgtcttc<br>acctatggcg tcctcatgga ctgctgctgc cgtgcgcgcc gcctggatct agcgatcgcc ttcttcgccc gtctcctcaa gacgggactg<br>gaggcaaacc aagtcatctt ctgcaccctc ctcaagggac tctgccacgc aaagcgctca gatgaggctt tggacgtggt gcttcacagg<br>atgcctgagc taggctgcac ccccaacgtg gtggcctata ccacggtcat ccacggcttc ttgaaggaag gccaagtagg caaggcatgc<br>aatctattcc atggaatggc gcagcagggc gttgcgcctg atgtggtgac atataactcg gttatcgatg cgttgtgcaa ggccagagca<br>atggacaagg cagagtattt ccttcgtgaa atggttgata atggtgtcgt acctaataat gtgacatata atagcctcat ccatggatat<br>tcctctttgg gccatcagaa ggaggctgtt agggtgctga aagaaatgac aagacagggt atcataccag atgtcattac ctgcacctca<br>ctcatgacct tcctttgcaa gaatggaaaa agcaaggaag ctgcagaaat ttttgattca atggccacga agggcctgaa acatgacgcc<br>gtttcatatg ctattctcct tcatgggtat gccactgaag gatgcttggt tgatatgatt aatctcttca attcgatgga cagagactgt<br>attctaccta actgtcatat cttcaacata ctgatttatg catatgctaa atctgggaag cttgataagg ctatgcttat atttagagat<br>atgcagaaac aaggagtgag tgatacagga gtacgacagg caaccttaat ttatggttct tgtaaaaagg gtcggttgga cgatgctatg<br>ataaagttta atcagatggt tgatacagga gtacgacagg gcacagctgt ttatggttct ctaatccagg gtttttgtac acacggcgat<br>ttggtgaaag gaaaggaatt ggttactgaa atgatgaaca aaggtatacc tcctcctgac attatgttct tccattcaat catgcagaac<br>ctatgcacag aaggaagggt agtagaagca cgggatatcc ttggcttgat agcacacata ggtatgaggc ctaatgtttg cacatttaat<br>atactgattg gtggatactg cctagtccgc aagatggagg atgcctcaaa aatatttcat gatatgatgt catatggttt agaaccttct<br>ggacttaaac ctacaacttt taattacaac atcatactgg atggattatt tctggctgga cgaactgttg ctgcaaagga aaagtttgat<br>gagatggttg aatctggagt aagtatgtgc atcagtactt actctatagt tcttcgtgga ctttgtagaa ataattgtag cggcgaagcc<br>atcacgctat tccagacatt aagcgcaatg gatgtgaaat tcaatattag aattgtcaat atcatgattg atgccttctt cagggttcag<br>cgaaagcaag aagctaagga tttgtttgct gcaataacag ccaatgggtt ggttgctaat gtttttacct acagcctaat gatgacaaat<br>cttataaaag aagggtcagt ggaagaggct gacacactct ttttatcgat ggagatgagc ggctgtactt cgaactcgtg gatgttaaat<br>cttattatca gagggttgct ggaaaaagga gagatagtca aggctggatg ttatatgtct aaagttgatg ccaagagcta ctcacttgaa<br>gctaaaactg tttcgttgct gatctatctc ttttcaggga aagggaaata cagagaacac ataagattgc tacctacaaa gtatcagttt<br>ctcgaagaag cagccacagt tgaatggtttgctatatag |
| SEQ ID NO: 59_ At5g02240-like promoter | GAGTCGTGTCTTATTTGGTGGCGTTTGTCGACTATCTCCTGTGTGGAGCCAATGCTTGGCTCGCACGCAAGTCGAAAAGAACTGCAATGGTAGGAGG<br>AGAAGGGAGAGGGTGTGGTAGATGCGCACGACAACAACAACACACGACAAATATATATAGTTGGAGTAAGTGGAAAACAAGGACGCGACAAGAAAG<br>GGGGAGAATGTTCGAAATAGCGTCCAACCTAAGTTCAGAGAATTAATTGTCAACCAAAAATTGGGCAAGGGCTCAGTATACCGGCCTAGAAGTGAAA<br>ATTGCGATCAAAAGTTTGCACCGCCGAAGAAGAGAAAAGCAAAAACTTCTCATATTTTTCAAAGGATTGAACATTTTTTATTGTCATGTTATCCCGTAG<br>GCAGGATATTGACCTAGCAACTTTGGTGTAGCCTATTGTATTACTCATATTCATCGAGCAGTATATTATTGAAGGGGCTTTTATTGACTCTAAATGTAG<br>CATTGTTGTAATGCATTTGCATAATTAAGGGTGTGTTTGGTTGTGTGGCTAAGGATAGCCACTTTTTAAGTGGTTGCCATGTGTTTGATTTTAAAATTTG<br>TGTAGTTCAGGATAGCCATATCCAAGGAATATTCCATAAAATGTGGCACAGCGGAAGCGCCAAAAAGTGATGGGTAAGGTCAACCACCCTATGCTTG<br>CATGCTCACCTCACCATCTGAATCATTTACAACCTGTTCTGACCCCCTCCCCCAAAGGAATTTTATCAGGCTTTTGGTGAGGGCATTCGCATGTCTGC<br>ACTTGTCATCCAATGAACTGTGACGAATACTAGGGTGTTAGAAAGGAAACGGCAACTCATGAAATATAACCGACAAACATATATATCTATAAATCATGC |

-continued

| SEQUENCES OF THE PRESENT DISCLOSURE | |
|---|---|
| Sequence number | Sequence |
| | AACAAAGAAACCGAAAGATTACAACAAAAACCATATATGGATCTGATCATAAAGGGGCAATTCATCACACGGAAACAAACACACCGAGAATTACATCA<br>GATGGAACACAATCATGTAGAGCAGCGCATGTGACCATTGATTGAAAAGCAAGGGAGAGAAGGAAAAGCAAGGGAGAGAAGATGCCAACTAGCTAC<br>TGTTATGGACCCATAGTTCAAAGAGGACTATTCACACATGGTCATGGTGGCAACGAGGTTGCTGGAGATGCATCCGGCGATGATTTATCCCTCCAGG<br>AAAGTACCGGAAAAAGGTCTCCGGATTGGATCATCGCGAAACAAGTGGTGGCGACAGCAGAAAAATCCTTGATAAACAAATCACGTGAGAGAGCTCC<br>GAAATTAGGGAGCATACTGAATTTAAAGATACTAGATGATACCCCGCATGTTATTGTGAACTCTGGTCTACCATACACAATTATAAGGTTATAACACAG<br>ACTCATTCGGTAGTGCTATTTGTGGTATGAGACTTATTCTTGCCATGTTCTGCAAAGAATTTTTTTTGTCACATTTGAGTTATGTAATAGGCTGACAGTC<br>ACTGTTTTCTCCAAAGACGCACAGTCATAAAAGTAATTTGAAAAAACTGTGCATTTTGAAAAAAATGTTCGCGGAATCAAAAAATGTTTGTGATTTTACA<br>AAAAAATATTCACATATTCAGAAAATGTTGGCGTATTCAGAAAATGTTATGGAATTGAGAAATTTTCTGCAAAGTTTAAAATTTTTCATGTATTTTAAAAA<br>GGCTTCACAAAATTTAAAAAATGTCCATTCATTACAAAAATGATCCTCGATTCAAAAATGCTCATTCAAATAAAAAAATGTTCATGAATTACAAAATTAAT<br>TCCCCCAATTTTTAAAAGTGTTTCGCTGATTCAAAACAAATATTCACAGGCTTAAAAGATGTTCACAATTCCTAGAAATGTACACAAATTTGTAAAAAAT<br>CCTCGTCAATTTAAAAAATGTTCGTCAATTAAAAAAATGTAATGTAGTAGTAGTATGTTGAGTAGTCCAACCGAAGGATATTAATTCTCATCTCAGTCAT<br>CACTCCTCTTCCTCGGATCACCGGCGATGGCAATGGCATTGTCCCTCCCCACCACGGTCTTGCTCCTCCTCCTCCTCCTCCTCCTCCCCGTCGCCTT<br>AGATGCCGTCGCCTCCTAGCCATAAGCGTCAGAAGGCGGTATATAGGTTATCTCCGCCGGAAAAAGGGTAAGGTTTGCCTCGAGAATGTTTTGTTTG<br>ACTATATCCTATGTGGAACCAAGGCTAGGTTTGCATGCAATGAAAAAATGTAATTGTAGGAGGAGAAGGGAGGGTGGTAGATGTGCGCGACAACAAC<br>ACACACGCCATATATATATATAGTTGGAGGAGGTGGAAAACAAGGAGGCGATAAGAAAAAGGGGGGGGGGGAATATGGAGAATGTTTGAAATAGCGTC<br>CAACCCGAGTTTCCATTATTAATTGTCGGCCAAAAAAAGAAGGCATGTTACTCATGATGGTAGTTTCAAGGGAAGTGGAGCCTCCCAGCTAGTTTGAA<br>CACTTAAAAAAACAAGCTACAACAGAAAGTAGTTTCAAGGGGAGTGGAGCCTAAAACTTGCATTTAAAAAGGAAATGCGCACACTAAGCCGAAAGTGT<br>GAACACTTTGTGCCGACATTTCCGAGGAAGTAGGTTTTATGCGCATAACATTTTTTTGAGACAATTTTATGCGCATAACTAGGGTTGACTGCTGTGGG<br>GAAGATGAAATTTGAACTGCCATTGTGACGCAAAGATTTGGTGATCCAAATTTGTATATGGACCATGCCTGTAGGTTGGGCTAAGTATACTTTTCGAA<br>GAAAATAGGCCCATGTTAACTTGGGAAGTGGGCCTAGGCCCACAAACCTGAAATCCCTGTGAAGCCCACATTCACACGCGGGCCCACCGTCGAAGC<br>GATAAGGAGAGTGACAGCCGCTCAGCCCGCCGGC |

BIBLIOGRAPHY

1 Bohra A, Jha U C, Adhimoolam P, et al (2016) Cytoplasmic male sterility (CMS) in hybrid breeding in field crops. Plant Cell Rep 35:967-993. doi: 10.1007/s00299-016-1949-3

2 A chalcone synthase-like gene is highly expressed in the tapetum of both wheat (*Triticum aestivum* L.) and triticale (xTriticosecale Wittmack). Wu S, O'Leary S J B, Gleddie S, Eudes F, André Laroche A and Robert L S (2008). Plant Cell Rep 27:1441-9.

3 CRISPR/Cas9-Mediated Deletion of Large Genomic Fragments in Soybean. Yupeng Cai, Li Chen, Shi Sun, Cunxiang Wu, Weiwei Yao, Bingjun Jiang, Tianfu Han and Wensheng Hou. Int. J. Mol. Sci. 2018, 19, 3835.

4 Highly efficient heritable targeted deletions of gene clusters and non-coding regulatory regions in *Arabidopsis* using CRISPR/Cas9; Julius Durr1, Ranjith Papareddy, Keiji Nakajima & Jose Gutierrez-Marcos. Scientific Reports (2018) 8:4443.

5 Generation of megabase-scale deletions, inversions and duplications involving the contactin-6 gene in mice by CRISPR/Cas9 Technology. Alexei N. Korablev, Irina A. Serova and Oleg L. Serov. BMC Genetics 2017, 18(Suppl 1):112.

6 Generation of chromosomal deletions in dicotyledonous plants employing a user-friendly genome editing toolkit. Jana Ordon, Johannes Gantner, Jan Kemna, Lennart Schwalgun, Maik Reschke, Jana Streubel, Jens Boch and Johannes Stuttmann. The Plant Journal (2017) 89, 155-168.

7 Efficient inversions and duplications of mammalian regulatory DNA elements and gene clusters by CRISPR/Cas9. Jinhuan Li, JiaShou, YaGuo, Yuanxiao Tang, YonghuWu, Zhilian Jia, Yanan Zhai, Zhifeng Chen, Quan Xu, and Qiang Wu. Journal of Molecular Cell Biology (2015), 7(4), 284-298.

8 Multiple wheat genomes reveal global variation in modern breeding. Nature. 2020 December; 588(7837):277-283. Walkowiak et al. doi: 10.1038/s41586-020-2961-x. Epub 2020 Nov. 25.

9 The genetic basis of cytoplasmic male sterility and fertility restoration in wheat. Melonek J, Duarte J, Martin J, Beuf L, Murigneux A, Varenne P, Comadran J, Specel S, Levadoux S, Bernath-Levin K, Torney F, Pichon J-P, Perez P and Small I (2021). Nature Communications.

The Examples below are given for illustration purposes only.

EXAMPLES

Example 1: Identification of Promoter Candidates to Improve Fertility Restoration The *T. timopheevii* CMS restorer gene RF3 has been identified as a PPR protein on Chr1B referred to as RFL29 (TraesCS1B01G038500) (WO2019086510). This gene is present in most wheat lines such as Chinese Spring though its level of expression is low as measured by RNAseq data (FIG. 2).

There are at least 3 RFL29 variants in wheat; RFL29a, RFL29b, RFL29c. RFL29b, present in Chinese Spring is a less effective restorer than the RFL29a allele found in lines such as Spelt (WO2019086510, Walkowiak et al. 2020).

To determine if RFL29-mediated fertility restoration can be improved, RFL29a and RFL29b were placed under the control of the strong ZmUbiquitin promoter and transformed into a wheat line containing *T. timopheevii* CMS. Full male fertility was observed in single copy T-DNA transformants (Melonek et al. 2021). This indicates that an increase in RFL29 expression would be sufficient to create a single locus restorer.

Figure 1:
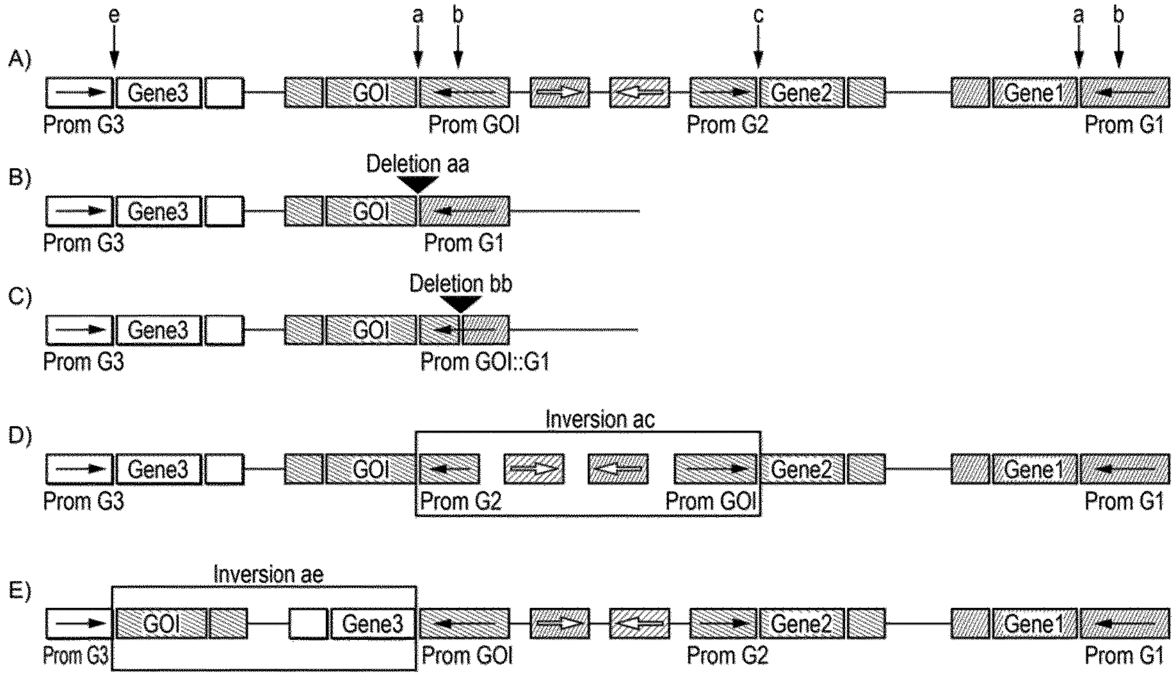

In this example, inventors search to identify a strong promoter in a gene upstream of RFL29 and perform a genomic deletion such that the strong promoter is brought in front of RFL29 (FIG. 1). A further alternative approach is the generation of a genomic inversion so as to again bring a strong promoter in front of RFL29 (FIG. 1).

RNAseq data from the wheat Chinese Spring was used to identify candidate promoters that could be brought in front of the RFL29 promoter. RFL29 should be expressed in the anther to give restoration, thus candidate promoters should therefore have good expression levels in RNAseq samples from the floral spike. In particular, overexpression of RFL29b from the tapetum-specific ZmMac2 promoter was sufficient to restore fertility to CMS wheat (Melonek et al. 2021). The expression of the wheat tapetum-specific gene TaCHSL1 (Wu et al., 2008) was detected in RNAseq floral spike samples Z32 and most strongly in Z39 with no expression at stage Z65 (FIG. 2D). This indicated that candidate promoters to drive RFL29 should be expressed in Z32 and Z39 spikes. Two candidate genes in the same orientation as RFL29 were identified with good spike expression in Chinese Spring at these stages; TraesCS1B01G041300 (2172 kb upstream of RFL29) and TraesCS1B01 G038800 (304 kb upstream of RFL29).

The predicted protein encoded by TraesCS1B01 G041300 shows 99% identity to a protein from *Aegilops tauschii* subsp. *Tauschii* annotated as RAE1-like (accession XP_020173482.1). RAE1 proteins are required for export of mRNA from the nucleus. TraesCS1B01G041300 was thus named RAE1-like. This protein is represented by SEQ ID NO:8.

TraesCS1B01 G038800 shows 98% identity to a protein annotated as probable serine/threonine-protein kinase PBL11 from *Aegilops tauschii* subsp. *Tauschii* (accession XP_020157135.1) and was named TaPK-like. This protein is represented by SEQ ID NO:5.

The TaPK-like gene is about 7-fold more expressed than RFL29 in Z39 spikes and RAE1-like about 44 fold more expressed (FIG. 2E).

To confirm that the promoter regions of TaPK-like and TaRAE1-like are sufficient to restore fertility when used to drive RFL29 expression, the putative promoter regions of TaPK-like and TaRAE1-like were amplified from the wheat variety Fielder and linked to the coding region of RFL29a (represented by SEQ ID NO:14).

The chimeric pTaPK-like::RFL29a (SEQ ID NO:12) and pTaRAE1-like::RFL29a (SEQ ID NO:13) gene cassettes were cloned into a plant binary vector containing a plant transformation selectable marker forming plasmids pBIOS12569 and pBIOS12526 respectively.

These binary vectors were transformed into agrobacteria, forming strains T11861 and T11844, which were transformed into a Fielder CMS line, a wheat line bearing a CMS sterility trait, by agrobacterial-mediated transformation and the fertility of the transformants scored.

The scoring method is outlined in FIG. 3. A fertility score is calculated as the number of seeds divided by the number of spikelets. Maximum fertility potential corresponds to spikelet number multiplied by 3 flowers. Since each spikelet has 3 flowers that maximum score=3. In the greenhouse, Fielder has a fertility score of between 2.1 to 2.3 whereas the CMS Fielder line is completely sterile.

The transformed TO plants that had the level of fertility of Fielder were classified as fully fertile. Both the pTaPK-like::RFL29a and pTaRAE1-like::RFL29a constructs gave fully fertile plants however the level of restoration was greater for pTaRAE1-like::RFL29a with 92% of TO plants being fully fertile as opposed to 61% for pTaPK-like::RFL29a (Table 1).

TABLE 1

Fertility restoration of pTaPK-like::RFL29a and pTaRAE1-like::RFL29a transformants

| Construct | Promoter | RFL | Terminator | Transformed plants | Fully Fertile Plants | Fully Sterile plants | Partial Fertility | Restoration efficiency |
|---|---|---|---|---|---|---|---|---|
| T11842 | TaRAE1-like | TaRFL29a | RFL29a | 26 | 24 | 2 | 0 | 92% |
| T11861 | TaPK-like | TaRFL29a | RFL29a | 32 | 19 (+4*) | 7 | 2 | 60% (71*)% |

Fertility restoration of pTaPK-like::RFL29a and pTaRAE1-like::RFL29a transformants. TO plants were phenotyped for fertility as described in FIG. 3.

Plants with the fertility of Wild-type Fielder were classified as fully fertile. All plants are single-copy for the transgene apart for 4 plants from construct pTaPK-like::RFL29a (indicated as *).

Example 2: Creation of Genomic Deletions to Bring the PK-Like and RAE1-Like Promoters in Front of RFL29

As described in example 1, the promoters of TaPK-like and TaRAE1-like are candidate promoters to boost or replace the natural RFL29 promoter. The wheat line 'Spelt' has the favourable RFL29 allele (RFL29a) therefore it is desirable to engineer a strong RFL29 restorer in this or other lines that possess RFL29a. This strong restorer can then be introgressed into any wheat line to create a male line for hybrid seed production.

The deletion could replace a part of the RFL29a promoter by bringing enhancer elements of TaPK-like or TaRAE1-like (FIG. 1C) or alternatively the entire RFL29 promoter and the majority of the 5'UTR region could be replaced (FIG. 1B). In this example the second strategy is adopted such that double strand DNA breaks (DSBs) are created just in front of the initiating Methionine ATG of the coding sequences of RFL29a and TaPK-like or TaRAE1-like.

The Spelt RFL29a (SEQ ID NO: 16), TaPK-like (SEQ ID NO: 19) and TaRAE1-like (SEQ ID NO: 22) genomic sequences were identified by BLASTN analysis of the Spelt genome sequence. The regions in the coding sequences were analysed for sites that could be cleaved using CRISPR Cas9 or Cas12a guide RNAs (gRNAs). FIG. 4 shows the positions of candidate gRNAs and Table 2 suggests combinations to create the desired deletions.

TABLE 2

Pairs of gRNA targets for generation of genomic deletions in the RFL29 region

| Gene | Target (5' to 3') | Guide | CRISPR | gRNA combinations: RFL29 del PK-like | | | | gRNA combinations: RFL29 del RAE1-like | | | | | |
|---|---|---|---|---|---|---|---|---|---|---|---|---|---|
| RFL29 | GCGGGGCATGGCCGGTGTGT**AGG** | 983r | Cas9 | | | | Y | | | | | Y | Y |
| RFL29 | GAGGAGAAGCGGGGCATGGC**CGG** | 991r | Cas9 | Y | Y | | | Y | Y | | | | |
| RFL29 | TGAGTTCGCGACCTACACAC**CGG** | 972f | Cas9 | | | Y | | | | Y | Y | | |
| PK-like | TCCCCATGGCGAGGACCGTC**CGG** | 479r | Cas9 | | | Y | Y | | | | | | |
| PK-like | CCCAGCAGTTCCCCATGGCG**AGG** | 488r | Cas9 | | Y | | | | | | | | |
| PK-like | GCCGGACGGTCCTCGCCATG**GGG** | 478f | Cas9 | Y | | | | | | | | | |
| RAE-like | TTCTGTGAACCTTCAAAATC**TGG** | 1145r | Cas9 | | | | | | | | Y | | Y |
| RAE-like | AGATTTTGAAGGTTCACAGA**AGG** | 1147f | Cas9 | | | | | | | Y | | Y | |
| RAE-like | AAGGTTCACAGAAGGAGAGA**TGG** | 1155f | Cas9 | | | | | Y | | | | | |
| RAE-like | **TTTG**AAGGTTCACAGAAGGAGAGATGG | 1151f | Cas12a | | | | | | Y | | | | |

In Table 2, the combinations of gRNAs are read vertically. Such combinations are designed to maintain the Kozak translational initiation sequences of either TaRFL29a (such as combinations with targets 972f or 983r) or that of TaPK-like (478f or 488r) or of TaRAE1-like (1155f or 1151f).

The selected pairs of gRNAs are constructed such that they are expressed from the wheat U6 promoter (SEQ ID NO: 33) and the gRNA cassettes cloned into a plant binary transformation vector containing a ZmUbiquitin promoter::Cas9 gene cassette. In the case of use of target 1151f, the plant binary vector also contains a Cas12a gene cassette.

These binary vectors are then transformed into the wheat variety Spelt using *agrobacterium*-mediated transformation. Primary transformants are then screened for the desired deletion using a PCR screen with primers in the coding region of RFL29a combined with primers in the TaPK-like or TaRAE1-like promoters. PCR bands obtained of approximately the expect size for the deletion are sequenced to confirm the junction sequence. The junction sequence should maintain the functions of the TaPK-like or TaRAE1-like promoter and allow the translation of RFL29a. Junctions that lack a Kozak sequence or that remove the ATG of RFL29 or introduce a novel ATG sequence or alter an intron splice junction are less desirable.

Plants with a desirable junction sequence between the TaPK-like promoter and the RFL29a CDS or with the TaRAE1-like promoter and the RFL29a CDS are used as males in crosses to the Fielder CMS line. F1 progeny of these crosses are sown and scored for male fertility.

Example 3: Creation of Genomic Inversions to Bring the TaAt5g02240-Like Promoter in Front of RFL29

RNAseq data from wheat Chinese Spring spikes were used to identify candidate promoters that could be brought in front of the RFL29 coding region via a genomic inversion. A gene with an opposing orientation to RFL29 was identified with good spike expression in Chinese Spring (FIG. 5).

The predicted protein of this gene (TraesCS1B02G037100) shows 97% identity to a protein from *Aegilops tauschii* subsp. *Tauschii* annotated as At5g02240-like (accession XP_020198298.1). TraesCS1B02G037100 was thus named TaAt5g02240-like. This protein is represented by SEQ ID NO:49.

The TaAt5g02240-like gene is about 80-fold more expressed than RFL29 in Z39 spikes.

In this example double strand DNA breaks (DSBs) are created just in front of the initiating Methionine ATG of the coding sequences of RFL29a and TaAt5g02240-like. The Spelt RFL29a (SEQ ID NO:16) and TaAt5g02240-like (SEQ ID NO:50) genomic sequences were identified by BLASTN analysis of the Spelt genome sequence. The regions in from of the coding sequences were analyzed for sites that could be cleaved using CRISPR Cas9 guide RNAs (gRNAs). FIG. 6 shows the positions of candidate gRNAs and Table 3 suggested combinations to create the desired deletions.

TABLE 3

Pairs of gRNA targets for generation of genomic inversions in the RFL29 region

| Gene | Target (5' to 3') | Guide | CRISPR | gRNA combination | | |
|---|---|---|---|---|---|---|
| RFL29 | GCGGGGCATGGCCGGTGTGT**AGG** | 983r | Cas9 | | | Y |
| RFL29 | GAGGAGAAGCGGGGCATGGC**CGG** | 991r | Cas9 | Y | | |
| RFL29 | TGAGTTCGCGACCTACACAC**CGG** | 972f | Cas9 | | Y | |
| At5g02240-like | CTTCACTCGCCGGAGGGGGA**CGG** | 70f | Cas9 | | Y | Y |
| At5g02240-like | GGAGGGGGACGGAGCAAATA**TGG** | 81f | Cas9 | Y | | |

The combinations of gRNAs are read vertically.

Such combinations are designed to maintain the Kozak translational initiation sequences of either RFL29a (combinations with targets 972f or 983r) or that of TaAt5g02240-like (81f)).

The selected pairs of gRNAs are constructed such that they are expressed from the wheat U6 promoter (SEQ ID NO: 33) and the gRNA cassettes cloned into a plant binary transformation vector containing a ZmUbiquitin promoter::Cas9 gene cassette.

These binary vectors are then transformed into the wheat variety Spelt using *agrobacterium*-mediated transformation. Primary transformants are then screened for the desired inversion using a PCR screen with primers in the coding region of RFL29a combined with primers in the TaAt5g02240-like promoter or 5'UTR region. PCR bands obtained of approximately the expect size for the deletion are sequenced to confirm the junction sequence. The junction sequence should maintain the functions of the TaAt5g02240-like promoter and allow the translation of RFL29a. Junctions that lack a Kozak sequence or that remove the ATG of RFL29 or introduce a novel ATG sequence or alter an intron splice junction are less desirable.

Plants with a desirable junction sequence between the TaAt5g02240-like promoter and the RFL29a CDS are used as males in crosses to the Fielder CMS line. F1 progeny of these crosses are sown and scored for male fertility.

The invention claimed is:

1. A method to modify the expression of a gene of interest in a plant, the method comprising the steps of:

a) introducing into the plant at least one gene-editing system;

b) allowing the gene-editing system to perform the desired editing at a target genomic site;

and wherein the gene-editing system is designed so that, after the desired editing, the gene of interest is operably linked to an endogenous promoter, or part of an endogenous promoter, the endogenous promoter being distal from a naturally occurring promoter of the gene of interest in the genome of a non-modified plant, wherein said desired editing is a deletion or an inversion of a size from 10 kb to 10 Mb.

2. The method to modify the expression of a gene of interest according claim 1, wherein the performance of the desired editing as recited in step b) comprises two or more DNA breaks within the target genomic site.

3. The method to modify the expression of a gene of interest according to claim 1, wherein:

the deletion is a deletion of a genomic region comprising the full naturally occurring promoter, or is a deletion of a genomic region comprising only a part of the naturally occurring promoter, or the inversion is an inversion of a genomic region resulting in the replacement of the naturally occurring promoter by the endogenous promoter, or is an inversion of a genomic region resulting in the replacement of a part of the naturally occurring promoter by a part of the endogenous promoter.

4. The method to modify the expression of a gene of interest according to claim 1, wherein the gene of interest is fertility-restorer gene RFL29 or

RFL79.

5. The method to modify the expression of a gene of interest according to claim 1, wherein the endogenous promoter drives a higher expression of the gene of interest, changes the pattern of expression of the gene of interest during the development cycle of a plant, changes the spatial pattern of expression of the gene of interest or is a promoter which is activated by biotic or abiotic stress.

6. The method to modify the expression of a gene of interest according to claim 1, wherein the modification of the expression is an enhancement, the endogenous promoter being a strong promoter.

7. The method to modify the expression of a gene of interest in a plant according to claim 1, wherein the break occurs in a promoter, in an untranslated region, in gene-gene junction region, in exon or in intron.

8. The method to modify the expression of a gene of interest according to claim 1, wherein the editing system is chosen among a zinc finger nuclease (ZFN) gene editing system, a transcription activator-like effector nucleases (TALEN) gene editing system, a clustered regularly interspaced short palindromic repeats (CRISPR) gene editing system, or a meganuclease gene editing system.

9. The method to modify the expression of a gene of interest according to claim 1, wherein the gene-editing system comprises a meganuclease, zinc-finger nuclease, transcription-activator like effector nuclease, CRISPR-nickase or a CRISPR-nuclease.

10. The method to modify the expression of a gene of interest in a plant according to claim 1, the method comprising the steps of:

a) identifying an endogenous promoter, distal from a naturally occurring promoter of the gene of interest in a non-modified plant, which is capable of modifying the expression of the gene of interest;

b) identifying the deletion or insertion of a genomic region to be performed in order to operably link the endogenous promoter, or part of an endogenous promoter, to the gene of interest;

c) introducing into the plant at least one gene-editing system designed to perform the deletion or insertion identified in step b);

d) allowing the gene-editing system to perform the desired editing at the target genomic site;

e) optionally selecting a plant with the desired editing.

11. A method to enhance the expression of a fertility-restorer gene of interest, in a plant, the method comprising the steps of:

a) introducing into the plant, at least one gene-editing system;

b) allowing the gene-editing system to perform a desired editing at a target genomic site;

and wherein the gene-editing system is designed so that, after the desired editing, the fertility-restorer gene of interest is operably linked to an endogenous promoter, or part of an endogenous promoter, the endogenous promoter being distal from a naturally occurring promoter of the fertility-restorer gene of interest in the genome of a non-modified plant, wherein said desired editing is a deletion or an inversion of a size from 10 kb to 10 Mb.

12. The method to enhance the expression of a fertility-restorer gene according to claim 11, wherein the plant is a wheat plant.

13. The method to enhance the expression of a fertility-restorer gene according to claim 11, wherein the fertility-restorer gene is RFL29 or RFL79.

14. A plant, or plant part, comprising a gene-editing system designed to perform a desired editing at a target genomic site, so that after the desired editing, a gene of interest in the plant is operably linked to an endogenous promoter, the endogenous promoter being distal from a naturally occurring promoter of the gene of interest in the genome of a non-modified plant, wherein said desired editing is a deletion or an inversion of a size from 10 kb to 10 Mb.

15. The plant as obtained according to the method according to claim 11, wherein the plant comprises the desired editing.

16. A method comprising:

performing PCR on the plant according to claim 15 after the desired editing was performed, determining the expression level of the gene of interest, and determining the level of the expressed protein encoded by the gene of interest.

17. A method to restore fertility in wheat, comprising a step of crossing a sterile wheat plant with the plant of claim 15 wherein the expression of the fertility-restorer gene has been enhanced.

18. The method to modify the expression of a gene of interest according to claim 1, wherein the plant is a wheat plant, the gene of interest is the fertility-restorer gene RFL29 and said endogenous promoter is a TaPK-like promoter represented by SEQ ID NO: 10; aTaRAE1-like promoter represented by SEQ ID NO: 11; or a TaAt5g02240-like promoter represented by SEQ ID NO:59.

19. The method to modify the expression of a gene of interest according to claim 18, wherein the RFL29 gene is represented by SEQ ID NO:14.

20. The method to enhance the expression of a fertility-restorer gene of interest according to claim 11, wherein the plant is a wheat plant, wherein the fertility-restorer gene of interest is RFL29 gene and wherein said endogenous promoter a TaPK-like promoter represented by SEQ ID NO:10; aTaRAE1-like promoter represented by SEQ ID NO:11; or a TaAt5g02240-like promoter represented by SEQ ID NO:59.

21. The method to enhance the expression of a fertility-restorer gene of interest according to claim 20, wherein the RFL29 gene is represented by SEQ ID NO: 14.

22. The plant, or plant part, according to claim 14, wherein the plant is a wheat plant, the gene of interest is the fertility-restorer gene RFL29 and said endogenous promoter is a TaPK-like promoter represented by SEQ ID NO: 10; aTaRAE1-like promoter represented by SEQ ID NO: 11; or a TaAt5g02240-like promoter represented by SEQ ID NO:59.

23. The plant, or plant part, according to claim 22, wherein the RFL29 gene is represented by SEQ ID NO:14.

* * * * *

SEQUENCE LISTING

<160> NUMBER OF SEQ ID NOS: 63

<210> SEQ ID NO 1
<211> LENGTH: 2373
<212> TYPE: DNA

<213> ORGANISM: Triticum aestivum (var. Chinese Spring)

<400> SEQUENCE: 1
atgccccgct tctcctccac cacgccaatg tcgccacccc gcctccgcct ccgcctccga 60
ctctgcgccc gccactcctc ctccacctct catccctcac gcatctggga tccccacgcc 120
gccttcgccg ccgcggcaca gcgggcgagc tctggcacgc tcactacgga ggacgcacac 180
cacctgtttg acgaattgct gcggcggggc aatcctgtcc aggagcgtcc cttgaataaa 240
tttctggctg ccctcgcccg cgcgcccgcg tccgcatcct gctgcgatgg ccccgccctg 300
gcagtcaccc tcttcggccg tttgtcccga gacgtcggac gacgggtggc gcagccaaat 360
gtcttcacct atggcgtcct catggactgc tgctgccgcg cttgccgcac agatctggtg 420
ctcgccttct ttggccgtct cctcaagacg ggcctggagg caaaccaagt cgtcttcaac 480
accctcctca agggcctttg ccacacaaag cgggcggatg aggctctgga cgtgctgctt 540
cacaggatgc ctgagctggg ctgcactcct aatgtggtgg cgtataacac cgttatccat 600
ggcttcttta aggaaggcca tgtaagcaag gcctgcaatc tgttccatga aatggcgcag 660
cagggcgtta agcctaatgt ggtgacatat aactcagtta ttgatgcgct gtgcaaggcc 720
agagccatgg acaaggcaga ggtggtcctt cgtcagatga ttgatgatgg tgttggacct 780
gataatgtga cgtatagtag cctcatccat ggatattcct cttcaggcca ctggaaggag 840
gcagttaggg tattcaaaga gatgacaagt cggagggtta cagcagatgt gcatacttac 900
aacatgttta tgacctttct ttgcaaacat ggaagaagca aagaagctgc aggaattttt 960
gataccatgg ctatcaaggg cctgaaacct gacaacgttt catatgctat tcgccttcat 1020
gggtatgcca ccgaaggatg cctagttgac atgatcaatc tcttcaattc catggcaaca 1080
cactgcattc tacctaactg tcatatattc aacatactga ttaatgcata tgctaaatct 1140
gggaagcttg ataaggctat gcttatcttc aatgaaatgc agaaacaagg agtgagtcca 1200
aatgcagtca catattcaac cgtaatacat gcattttgca agaagggtag gttggatgat 1260
gctgtgataa agtttaatca gatgattgat acaggagtac gaccggacgc atctgtttat 1320
cgtcccctaa tccagggttt ttgtacacat ggcgatttgg tgaaagcaaa ggaatatgtt 1380
actgaaatga tgaagaaagg tatgcctcct cctgatatta tgttcttcag ttcaatcatg 1440
cagaacctat gcacagaagg aagggtaaca gaagcacggg atatccttga cttgatagtg 1500
cacattggta tgaggcctaa tgttatcata tttaatttgc tgatcggtgg atactgccta 1560
gtccgcaaga tggcagatgc attgaaagta tttgatgata tggtgtcata tggtttagaa 1620
ccttgtaact ttacgtatgg tatacttatt aatggctatt gcaaaaatag aaggattgat 1680
gacgggctta ttctgttcaa agagatgctg cacaagggac ttaaacctac aacttttaat 1740
tataacgtca tactggatgg attatttctg gctggacaaa ctgttgctgc aaaagagaag 1800
tttgatgaga tggttgaatc tggagtaagt gtgtgcattg atacatactc tataattctt 1860
ggtggacttt gtagaaatag ctgcagtagc gaagcgatca ccctttttcg gaaattaagc 1920
gcaatgaatg tgaaatttga tattacaatt gtcaatatca ttattggtgc cttatacagg 1980
gtcgagagaa accaagaggc taaggatttg tttgctgcta tgccagccaa tggcttggtt 2040
cctaatgctg ttacctacac cgtaatgatg acaaatctta taaaagaagg ttcagtggaa 2100
gaagctgaca atcttttctt atccatggag aagagcggct gtactgccaa ctcttgcctg 2160
ttaaatcata tcatcagaag gttactggaa aaaggagaga tagtcaaggc tggaaattat 2220
atgtctaaag ttgatgcaaa gagctactca cttgaagcta aaactgtttc gctgctgatc 2280

```
tctctgtttt caaggaaagg gaaatataga gaacacatca aattgcttcc tacaaagtat   2340

cagtttctgg aagaagcagc cacagttgaa tag                                2373


<210> SEQ ID NO 2
<211> LENGTH: 790
<212> TYPE: PRT
<213> ORGANISM: Triticum aestivum (var. Chinese Spring)

<400> SEQUENCE: 2

Met Pro Arg Phe Ser Ser Thr Thr Pro Met Ser Pro Pro Arg Leu Arg
1               5                   10                  15

Leu Arg Leu Arg Leu Cys Ala Arg His Ser Ser Ser Thr Ser His Pro
            20                  25                  30

Ser Arg Ile Trp Asp Pro His Ala Ala Phe Ala Ala Ala Ala Gln Arg
        35                  40                  45

Ala Ser Ser Gly Thr Leu Thr Thr Glu Asp Ala His His Leu Phe Asp
    50                  55                  60

Glu Leu Leu Arg Arg Gly Asn Pro Val Gln Glu Arg Pro Leu Asn Lys
65                  70                  75                  80

Phe Leu Ala Ala Leu Ala Arg Ala Pro Ala Ser Ala Ser Cys Cys Asp
                85                  90                  95

Gly Pro Ala Leu Ala Val Thr Leu Phe Gly Arg Leu Ser Arg Asp Val
            100                 105                 110

Gly Arg Arg Val Ala Gln Pro Asn Val Phe Thr Tyr Gly Val Leu Met
        115                 120                 125

Asp Cys Cys Cys Arg Ala Cys Arg Thr Asp Leu Val Leu Ala Phe Phe
    130                 135                 140

Gly Arg Leu Leu Lys Thr Gly Leu Glu Ala Asn Gln Val Val Phe Asn
145                 150                 155                 160

Thr Leu Leu Lys Gly Leu Cys His Thr Lys Arg Ala Asp Glu Ala Leu
                165                 170                 175

Asp Val Leu Leu His Arg Met Pro Glu Leu Gly Cys Thr Pro Asn Val
            180                 185                 190

Val Ala Tyr Asn Thr Val Ile His Gly Phe Phe Lys Glu Gly His Val
        195                 200                 205

Ser Lys Ala Cys Asn Leu Phe His Glu Met Ala Gln Gln Gly Val Lys
    210                 215                 220

Pro Asn Val Val Thr Tyr Asn Ser Val Ile Asp Ala Leu Cys Lys Ala
225                 230                 235                 240

Arg Ala Met Asp Lys Ala Glu Val Val Leu Arg Gln Met Ile Asp Asp
                245                 250                 255

Gly Val Gly Pro Asp Asn Val Thr Tyr Ser Ser Leu Ile His Gly Tyr
            260                 265                 270

Ser Ser Ser Gly His Trp Lys Glu Ala Val Arg Val Phe Lys Glu Met
        275                 280                 285

Thr Ser Arg Arg Val Thr Ala Asp Val His Thr Tyr Asn Met Phe Met
    290                 295                 300

Thr Phe Leu Cys Lys His Gly Arg Ser Lys Glu Ala Ala Gly Ile Phe
305                 310                 315                 320

Asp Thr Met Ala Ile Lys Gly Leu Lys Pro Asp Asn Val Ser Tyr Ala
                325                 330                 335

Ile Arg Leu His Gly Tyr Ala Thr Glu Gly Cys Leu Val Asp Met Ile
            340                 345                 350
```

```
Asn Leu Phe Asn Ser Met Ala Thr His Cys Ile Leu Pro Asn Cys His
        355                 360                 365

Ile Phe Asn Ile Leu Ile Asn Ala Tyr Ala Lys Ser Gly Lys Leu Asp
    370                 375                 380

Lys Ala Met Leu Ile Phe Asn Glu Met Gln Lys Gln Gly Val Ser Pro
385                 390                 395                 400

Asn Ala Val Thr Tyr Ser Thr Val Ile His Ala Phe Cys Lys Lys Gly
                405                 410                 415

Arg Leu Asp Asp Ala Val Ile Lys Phe Asn Gln Met Ile Asp Thr Gly
            420                 425                 430

Val Arg Pro Asp Ala Ser Val Tyr Arg Pro Leu Ile Gln Gly Phe Cys
        435                 440                 445

Thr His Gly Asp Leu Val Lys Ala Lys Glu Tyr Val Thr Glu Met Met
    450                 455                 460

Lys Lys Gly Met Pro Pro Pro Asp Ile Met Phe Phe Ser Ser Ile Met
465                 470                 475                 480

Gln Asn Leu Cys Thr Glu Gly Arg Val Thr Glu Ala Arg Asp Ile Leu
                485                 490                 495

Asp Leu Ile Val His Ile Gly Met Arg Pro Asn Val Ile Ile Phe Asn
            500                 505                 510

Leu Leu Ile Gly Gly Tyr Cys Leu Val Arg Lys Met Ala Asp Ala Leu
        515                 520                 525

Lys Val Phe Asp Asp Met Val Ser Tyr Gly Leu Glu Pro Cys Asn Phe
    530                 535                 540

Thr Tyr Gly Ile Leu Ile Asn Gly Tyr Cys Lys Asn Arg Arg Ile Asp
545                 550                 555                 560

Asp Gly Leu Ile Leu Phe Lys Glu Met Leu His Lys Gly Leu Lys Pro
                565                 570                 575

Thr Thr Phe Asn Tyr Asn Val Ile Leu Asp Gly Leu Phe Leu Ala Gly
            580                 585                 590

Gln Thr Val Ala Ala Lys Glu Lys Phe Asp Glu Met Val Glu Ser Gly
        595                 600                 605

Val Ser Val Cys Ile Asp Thr Tyr Ser Ile Ile Leu Gly Gly Leu Cys
    610                 615                 620

Arg Asn Ser Cys Ser Ser Glu Ala Ile Thr Leu Phe Arg Lys Leu Ser
625                 630                 635                 640

Ala Met Asn Val Lys Phe Asp Ile Thr Ile Val Asn Ile Ile Ile Gly
                645                 650                 655

Ala Leu Tyr Arg Val Glu Arg Asn Gln Glu Ala Lys Asp Leu Phe Ala
            660                 665                 670

Ala Met Pro Ala Asn Gly Leu Val Pro Asn Ala Val Thr Tyr Thr Val
        675                 680                 685

Met Met Thr Asn Leu Ile Lys Glu Gly Ser Val Glu Glu Ala Asp Asn
    690                 695                 700

Leu Phe Leu Ser Met Glu Lys Ser Gly Cys Thr Ala Asn Ser Cys Leu
705                 710                 715                 720

Leu Asn His Ile Ile Arg Arg Leu Leu Glu Lys Gly Glu Ile Val Lys
                725                 730                 735

Ala Gly Asn Tyr Met Ser Lys Val Asp Ala Lys Ser Tyr Ser Leu Glu
            740                 745                 750

Ala Lys Thr Val Ser Leu Leu Ile Ser Leu Phe Ser Arg Lys Gly Lys
        755                 760                 765

Tyr Arg Glu His Ile Lys Leu Leu Pro Thr Lys Tyr Gln Phe Leu Glu
```

770 775 780

Glu Ala Ala Thr Val Glu
785 790

<210> SEQ ID NO 3
<211> LENGTH: 7650
<212> TYPE: DNA
<213> ORGANISM: Triticum aestivum (var. Chinese Spring)

<400> SEQUENCE: 3
gcacctttag gtcctaattc tttattaatt ggttcacccg aggtcctttt ccacgagcgc 60
tcgctgacca gcacacgtgc cgcattgacc catgccacat cgatagaggg tctaaccgcc 120
aggcgagaag cttcgcaaag agaccccccc ccctcttagt ggcaccctct ctcctctttc 180
acggtacttt ggcgacattg gaggcgagcg acagaggcaa ccggaggtga tctggaggta 240
atttgtgtgg gtgcccgtga agatgcccct tctatgacgg ccagtgagca atcctcctcc 300
atgttaccgt aagaacccta atcttgtcga tgatcttctc ctgtagctct tctaatatgt 360
cataactttg tcataatcaa tagttgtagt ccttgattta ctttgatttg cataacggtg 420
atacggacac ggcaaaaagg acacaccacc agcggcaaca tacccgccga agttggagct 480
tgcttcgccg cgccggcggc ggtgctgagg atgttgccat gctcctcatc ttagttgttt 540
ccttgccgag gagcttgaag ttccggccat ggataggttt aggggacgcg cgcgccgaga 600
gagagagcag atttggggaa gaaataaagc cagggactgg ggaatgagaa gataatgttt 660
ataaggggtt ttctgtaaaa agaaagagca acctacgcag cccttctgtc gatttggcat 720
gggtcaacgc accacacgag caggtcaacg agcgctcgtg agaaaaagga cctagggtaa 780
accacttact aaagaattag gacctaaagg tgcattttgg acgaaataag actaaagtga 840
caccctgacg aattttttag gaccttgagt gcatttaact ctttcaaaaa ataaagatgc 900
taaaaaaact aaatgcttaa aaatacattt ttctatggga atacttaaaa atactagtat 960
aatttgatgg cttcctagta tatttctagg gcttacaact aaatttatat tcttggtcta 1020
aataaaatta taatctgata aattatgtga tatgaatata gccatatgag accataattt 1080
aattttacct gcaaaaagta agtaatagta gtagtagtac tacatactcc ctccgtccgg 1140
aaatacttgt cgaagaattt gatgaaaatg gatgcatcta gaacaagaat acatctagat 1200
acatcaatct ccctgacaag tatttccgag cggagggagt actagataat actccctccg 1260
ttcctaaata attgtctttc tagctatctc aaataaacta caacatacgg atgtatgtag 1320
acatgtttta gagtgtagat tcactcattt tgttccgtat gtagtcattt gttgaaatct 1380
ctagagagac aattatttag gaacggaggg agtaagataa ctaccctaaa aaaaaagata 1440
actgaaggtt gccacctagc acattcacat tggtacaact tggaaaagca cagccccgtc 1500
gtcctgctcc cagttgagtt cgcgacctac acaccggcca tgccccgctt ctcctccacc 1560
acgccaatgt cgccaccccg cctccgcctc cgcctccgac tctgcgcccg ccactcctcc 1620
tccacctctc atccctcacg catctgggat ccccacgccg ccttcgccgc cgcggcacag 1680
cgggcgagct ctggcacgct cactacggag gacgcacacc acctgtttga cgaattgctg 1740
cggcggggca atcctgtcca ggagcgtccc ttgaataaat ttctggctgc cctcgcccgc 1800
gcgcccgcgt ccgcatcctg ctgcgatggc cccgccctgg cagtcaccct cttcggccgt 1860
ttgtcccgag acgtcggacg acgggtggcg cagccaaatg tcttcaccta tggcgtcctc 1920
atggactgct gctgccgcgc ttgccgcaca gatctggtgc tcgccttctt tggccgtctc 1980

-continued

```
ctcaagacgg gcctggaggc aaaccaagtc gtcttcaaca ccctcctcaa gggcctttgc   2040
cacacaaagc gggcggatga ggctctggac gtgctgcttc acaggatgcc tgagctgggc   2100
tgcactccta atgtggtggc gtataacacc gttatccatg gcttctttaa ggaaggccat   2160
gtaagcaagg cctgcaatct gttccatgaa atggcgcagc agggcgttaa gcctaatgtg   2220
gtgacatata actcagttat tgatgcgctg tgcaaggcca gagccatgga caaggcagag   2280
gtggtccttc gtcagatgat tgatgatggt gttggacctg ataatgtgac gtatagtagc   2340
ctcatccatg gatattcctc ttcaggccac tggaaggagg cagttagggt attcaaagag   2400
atgacaagtc ggagggttac agcagatgtg catacttaca acatgtttat gacctttctt   2460
tgcaaacatg gaagaagcaa agaagctgca ggaatttttg ataccatggc tatcaagggc   2520
ctgaaacctg acaacgtttc atatgctatt cgccttcatg ggtatgccac cgaaggatgc   2580
ctagttgaca tgatcaatct cttcaattcc atggcaacac actgcattct acctaactgt   2640
catatattca acatactgat taatgcatat gctaaatctg ggaagcttga taaggctatg   2700
cttatcttca atgaaatgca gaaacaagga gtgagtccaa atgcagtcac atattcaacc   2760
gtaatacatg cattttgcaa gaagggtagg ttggatgatg ctgtgataaa gtttaatcag   2820
atgattgata caggagtacg accggacgca tctgtttatc gtcccctaat ccagggtttt   2880
tgtacacatg gcgatttggt gaaagcaaag gaatatgtta ctgaaatgat gaagaaaggt   2940
atgcctcctc ctgatattat gttcttcagt tcaatcatgc agaacctatg cacagaagga   3000
agggtaacag aagcacggga tatccttgac ttgatagtgc acattggtat gaggcctaat   3060
gttatcatat ttaatttgct gatcggtgga tactgcctag tccgcaagat ggcagatgca   3120
ttgaaagtat ttgatgatat ggtgtcatat ggtttagaac cttgtaactt tacgtatggt   3180
atacttatta atggctattg caaaaataga aggattgatg acgggcttat tctgttcaaa   3240
gagatgctgc acaagggact taaacctaca acttttaatt ataacgtcat actggatgga   3300
ttatttctgg ctggacaaac tgttgctgca aaagagaagt ttgatgagat ggttgaatct   3360
ggagtaagtg tgtgcattga tacatactct ataattcttg gtggactttg tagaaatagc   3420
tgcagtagcg aagcgatcac ccttttccgg aaattaagcg caatgaatgt gaaatttgat   3480
attacaattg tcaatatcat tattggtgcc ttatacaggg tcgagagaaa ccaagaggct   3540
aaggatttgt ttgctgctat gccagccaat ggcttggttc ctaatgctgt tacctacacc   3600
gtaatgatga caaatcttat aaaagaaggt tcagtggaag aagctgacaa tcttttctta   3660
tccatggaga agagcggctg tactgccaac tcttgcctgt taaatcatat catcagaagg   3720
ttactggaaa aaggagagat agtcaaggct ggaaattata tgtctaaagt tgatgcaaag   3780
agctactcac ttgaagctaa aactgtttcg ctgctgatct ctctgttttc aaggaaaggg   3840
aaatatagag aacacatcaa attgcttcct acaaagtatc agtttctgga agaagcagcc   3900
acagttgaat agttggtaca tgatatctga aatttaattt gcatcgcttg ccatgggtcc   3960
gtctgcttgt acaagaaatg cattttctat ttgtaaatag gaagtcagtt tagaacaagc   4020
catcaggatg acgcaaagag tacaattcag ttgcaccacc aataaaaagg cagaactagg   4080
gctgccaaaa caacactgaa tcaaaactca aacagaagga gcagcaaact tttttttttg   4140
aagctggaca gtctgctagc caaacaacta caggagactg tcaggcgggg catgtagtgg   4200
ctggcgtcta agcgcctttg cttcttccac catccatggc ttagcctcac acggaatcga   4260
gtcaaccaat tcccgtcggt tttgggtggc tcccttgaag atgcaattgt tttcagcggc   4320
cagatacgca tggtcagatt aatcagcgag tgtgcccctt ctgtctggtt cgagaaagaa   4380
```

-continued

```
tttgaagagc tgagcttgtc ccagctggaa ccagtttgag gttagttaat cataacaggg   4440
tactagagag gtgttttatt gactgttgat gtgtaatatg ttatatgcca tcctcttgat   4500
gattacggtg atctgtgaag aggcagcatg caaaagtctg aatcacatat gcttatgtaa   4560
ttgtgttatt atttgtgcag cttctagacc ttttgccttg tagatggcta catggatcta   4620
gttgtagcaa tctgtaactg ttagtgtttt gtatatgctg gcattgatga ttagggtgac   4680
ttgtgaagca tgcagaagtc tgaatcatac atgcttgtct agttattttt ggggctctct   4740
ctttgccatg tacatgtttt atggatgcag ttgtagtctg tatgtgctgg catttaatat   4800
gagggctggt ctgcaatttt tctgttttga tcgatacagc gccatgttga gtttaaccct   4860
gtaacttggc ttaactagat catgctggtg ttatctctag gaatcacaat atcaatactc   4920
tctgttgttg cacaaactga cgcagatcaa tgtccagagg taatatggtt ctgcccgtaa   4980
ttttcatcga ctgtcagcat gttccttttt tatttagtac tctgtatatc acggcggtat   5040
gactataata aggatatacg gctggtgcat tttgagcttc tctgtttctt gggataaagc   5100
tgataaattt ctattcttgt tggctttggt agtatgaaca gaaagcaggc agtaataaac   5160
tgatatgtgg tactattttg ttagtgaaac agggtccttt ttattatcta ttttatccag   5220
caatagtgtt ccataaaatt atagatcggt tcattcatct catatggatt tcggtgagct   5280
tcgcccgtcc ttggtacatt ttgttactat agaacaattg gtgtgcgctt tttttctttt   5340
ggctgtacgt tatagaacaa caaaacctgt ttatttcatt aattcattgt ctaatttatt   5400
ttcttacgag agctcagaag ttcagcattt tattttatct tgttccttcc gcgtaatttt   5460
tcatttactc actgagtagt acaggtcttg gacctgaaat tcttgtacta atttagtaga   5520
accattcttc gagaaacact ccaaaaatgg tttgtcttgg gtctgaatca tattgtctct   5580
gaacaaacag gtgtgactca tgcatggaaa gatccccaag aaacattgca catttggtag   5640
atatgtctat gcatgaatac tattttttga aaaagaattt agtaaatatt ttggtagcat   5700
tttttatacg tatgatgctt tttcttcttc ccgaaataag ggttttgatt tttgaatttt   5760
tgtaaagcaa catggtttgt agtacgtacg aaagaacgct agtgtgtttt cgcgatcgta   5820
agaatgttat aaactgtttt cctgggtcat gtaggtgtaa gctatagaag gaattcaata   5880
tcgtcctaaa catccttggc agtggccagt gaaagtcttg gacctgaaat cataccagta   5940
ctatttttct gaaagagaac ccattcttgt attccataag ttggctggtg cctgggcata   6000
attgtctaat catatagtac tatttgcatc tcataattcc attcagtttt gcactatagc   6060
tgaactgaag gagtacctag cacaaaatat gtatgactgt atttcagatc ttgcaatcgc   6120
agctgtaatg gagtagcaca ccctgtagca gcatatggat gtactctgaa tgttgggact   6180
ctttgaaatg ataaattggt ctattctggg agcagatttt ttccggcttt cggagattca   6240
ttgatctttt tttttcagaa agtacagttg taagttataa tcaaacatcc cgaacaaacc   6300
tcacttgtac atgtaagaat gcactatgaa tcagtggaaa gtagatttgt ggtgaaccaa   6360
aatagccaag gaataggttc actttcctcc ctccttatgt ctaaagttga tgcaaagagc   6420
tactcacttg aagctaaaac tgtttcgctg ctgatctctc tcttttcagg gaaagggaaa   6480
tacagagaac agataagatt gctccccgca aagtatcagt ttcgcggaga atgagctaca   6540
gttgaatggt tttacatgat atctgaactt aactcctcag aaggtaaggt tgaattattg   6600
tttgccatga gtttatctgc ttgtacaaca agtgcaattt ccatatgtaa ataggaaggc   6660
agttgagaac aagccatcag gatgacgcaa agagtacaat tcaactgtag gaccagcaat   6720
```

tgttttgaag ttgtatgtct gctagtagaa cacctacggg agagattcag gcggccgggc 6780
atgtagtggc acctgtgtaa gtcccttttc tgctgccagc atccatggct tggcctcaca 6840
gggaatggag tcaaccaatt tctcggcgta gctgttgcaa atgttttctc agccaccaga 6900
tacaccaaag tttcagagta atcagcgagc gtgtctcttt tgtctggttc gagaaagaat 6960
ttgaaaacgc tgagcagcaa caggtgcttg accagcttgt ccctgccgaa gccagtttga 7020
ggttagttaa tcataacagg gtactagaca ggtgttttgt tgactgttga tgggtaatac 7080
tcctatgtta tatgccagcc acttgatgaa tagggtgatc tgtgaatcac atatgcttat 7140
gtaattgtgt tattatttgt gcagcttcta gaccttctgc cttgtatggc tacatggatc 7200
acgttgtagc agtctgtgac tgtgactgtt agtgttttgt atatgctggc attgattaat 7260
ttagggccgg gctccaaatt atttgttttg atcgattcag caccatgttg agtttaaccc 7320
tgtaacttgg cttaaccaga tcaatatcag gggcctcggc atttttaaac gttgaattaa 7380
acatactctg tggcatatca atgttcagag gtaatatggt tctgtccata atttcatcga 7440
ctgtcagcat gttcctttgt tattcaatac tctgtatatc atgccggtat gactataata 7500
aggatatagt atgtttgatg cattttgaac ttctctattc cgtccgatag aggtgataaa 7560
ttctctattc tttttggctt tggtagtatg aacagtaagc aggcagtata tattaaactg 7620
atatgtggta ctattttgtt aatgaaacag 7650

<210> SEQ ID NO 4
<211> LENGTH: 1215
<212> TYPE: DNA
<213> ORGANISM: Triticum aestivum (var. Chinese Spring)

<400> SEQUENCE: 4
atggggaact gctggggcgc caagatcagc tccgacacct cctcctcctc ctccccttca 60
gggacgaatt ccaagtatgc tactaggaat ggggcggcct tgagcagctc cagcagctat 120
gcctccgcgg cgtcagtgcc acggagcgag ggtgagattc tggagtcagc caatgtcaag 180
gccttctctt tcaatgagct gaggaccgcc acgagaaact tccgtccgga cagtgtgcta 240
ggcgagggag ggttcgggtc agtcttcaag gggtggatcg atgagaagac cctcacccca 300
actaagccag gcaccgggat ggtcattgct gtaaagaagc ttaaccagga aagctatcag 360
ggccataggg aatggctggc tgaagtgaat taccttggac aactatcgca cccgaatctt 420
gtaaagctcg ttgggtactg tgtcgaagac gaacagcggc ttctcgtcta cgagttcatg 480
ccccgtggga gtttagagaa tcatctattc aggaggagta cacatttcca gccgctctcc 540
tggaaccttc ggatgaaaat tgcccatgga gcagcaaaag ggctcgcgtt tctccacagt 600
gacaaggcca aagtcatcta ccgcgatttc aaaacctcta atatcctcct agatgcgaac 660
tatgacgcaa agctctcaga tttcggcctg gcgaaggacg gaccgacggg tgacaagagc 720
catgtgtcca caagggtgat ggggacatat gggtatgctg caccagaata ccttgcaaca 780
ggccacctga ccacgaagag cgacgtgtac agcttcggcg tggtcctcct ggagatgctc 840
tcggggcgtc gcgcggtgga caagaaccgg ccgaccggcg agcacaacct ggtggagtgg 900
gcgcggccgt acctgacaag caagcggcgc atcttccgcg tcctggaccc ccgtctgggc 960
gggcagtact ccctcgccaa ggcccagaag gcggcgtcgc tggcgctgca gtgcctctcg 1020
gtggactcga ggaacaggcc gagcatggag caggtcgtcg tggtgctgga gcagctccac 1080
gacgccaagg agggagggaa cagccctcgc ccgcagctgc agagaaagcc gagcagcaac 1140
cggggcgtga acggctcgag atcgtcgtcg accaagggga acaacaagaa gcccgcctca 1200
ccgagaccgg tttga 1215

<210> SEQ ID NO 5
<211> LENGTH: 404
<212> TYPE: PRT
<213> ORGANISM: Triticum aestivum (var. Chinese Spring)

<400> SEQUENCE: 5

Met Gly Asn Cys Trp Gly Ala Lys Ile Ser Ser Asp Thr Ser Ser Ser
1 5 10 15

Ser Ser Pro Ser Gly Thr Asn Ser Lys Tyr Ala Thr Arg Asn Gly Ala
20 25 30

Ala Leu Ser Ser Ser Ser Ser Tyr Ala Ser Ala Ala Ser Val Pro Arg
35 40 45

Ser Glu Gly Glu Ile Leu Glu Ser Ala Asn Val Lys Ala Phe Ser Phe
50 55 60

Asn Glu Leu Arg Thr Ala Thr Arg Asn Phe Arg Pro Asp Ser Val Leu
65 70 75 80

Gly Glu Gly Gly Phe Gly Ser Val Phe Lys Gly Trp Ile Asp Glu Lys
85 90 95

Thr Leu Thr Pro Thr Lys Pro Gly Thr Gly Met Val Ile Ala Val Lys
100 105 110

Lys Leu Asn Gln Glu Ser Tyr Gln Gly His Arg Glu Trp Leu Ala Glu
115 120 125

Val Asn Tyr Leu Gly Gln Leu Ser His Pro Asn Leu Val Lys Leu Val
130 135 140

Gly Tyr Cys Val Glu Asp Glu Gln Arg Leu Leu Val Tyr Glu Phe Met
145 150 155 160

Pro Arg Gly Ser Leu Glu Asn His Leu Phe Arg Arg Ser Thr His Phe
165 170 175

Gln Pro Leu Ser Trp Asn Leu Arg Met Lys Ile Ala His Gly Ala Ala
180 185 190

Lys Gly Leu Ala Phe Leu His Ser Asp Lys Ala Lys Val Ile Tyr Arg
195 200 205

Asp Phe Lys Thr Ser Asn Ile Leu Leu Asp Ala Asn Tyr Asp Ala Lys
210 215 220

Leu Ser Asp Phe Gly Leu Ala Lys Asp Gly Pro Thr Gly Asp Lys Ser
225 230 235 240

His Val Ser Thr Arg Val Met Gly Thr Tyr Gly Tyr Ala Ala Pro Glu
245 250 255

Tyr Leu Ala Thr Gly His Leu Thr Thr Lys Ser Asp Val Tyr Ser Phe
260 265 270

Gly Val Val Leu Leu Glu Met Leu Ser Gly Arg Arg Ala Val Asp Lys
275 280 285

Asn Arg Pro Thr Gly Glu His Asn Leu Val Glu Trp Ala Arg Pro Tyr
290 295 300

Leu Thr Ser Lys Arg Arg Ile Phe Arg Val Leu Asp Pro Arg Leu Gly
305 310 315 320

Gly Gln Tyr Ser Leu Ala Lys Ala Gln Lys Ala Ala Ser Leu Ala Leu
325 330 335

Gln Cys Leu Ser Val Asp Ser Arg Asn Arg Pro Ser Met Glu Gln Val
340 345 350

Val Val Val Leu Glu Gln Leu His Asp Ala Lys Glu Gly Gly Asn Ser
355 360 365

```
Pro Arg Pro Gln Leu Gln Arg Lys Pro Ser Ser Asn Arg Gly Val Asn
    370                 375                 380

Gly Ser Arg Ser Ser Ser Thr Lys Gly Asn Asn Lys Lys Pro Ala Ser
385                 390                 395                 400

Pro Arg Pro Val


<210> SEQ ID NO 6
<211> LENGTH: 6090
<212> TYPE: DNA
<213> ORGANISM: Triticum aestivum (var. Chinese Spring)
<220> FEATURE:
<221> NAME/KEY: misc_feature
<222> LOCATION: (1389)..(1669)
<223> OTHER INFORMATION: n is a, c, g, or t

<400> SEQUENCE: 6

cacggagtga caaatcccag tctcgatccg cataaaacaa tagatacttt cggagatacc     60

tgtagtgcac ctttatagtc acccaattac gttgtgacgt ttgatacacc caaagcactc    120

ctacggtatc caggagttac acgctctcat ggtcaaagga agagatactt gacattggca    180

aaactctagc aaatgaacta cacgatcttt tgtgctagtc ttaggattgg gtcttgtcca    240

tcacatcatt ctcctaatga tgtgatcccg ttatcaacga catccaatgt ccatagccag    300

gaaaccatga ctatctgttg atcacaacga gctagtcaac tagaggctca ctagggacat    360

attgtggtct atgtattcac acatgtatta ctatttccgg ataatacagt tatagcatga    420

ataaaagaca attatcatga acaaggaaat ataataataa tacttttatt atttcctcta    480

gggcatattt ccaacaaaag tgtcgcagga aatagaaagt agtatcctac ggtatgtatt    540

gcatttatta gttgtaggct caactaaaag cactactgcg tggtgacaac ctaagactag    600

ccacagtgag agtaacttta gtagtaacat cgagtccaac tcagcaaatt tgcttatgtg    660

gcaatgagtt aatgaggaga gatgtaatac aagtaactta gctaattact gtaacactac    720

atctcccaat gcattatgag ggggtgtttg gttcagaagt cctaggactt tttctagtcc    780

cagggactaa taaaaaaaaa ctctctacta gagtcttttt ctagtccatg cataaaaagt    840

cccttccgtt tggttcatag gaacttttta gggacctttt ctagtctctg agactaaaaa    900

atctctgaac caaacacccc ctgagtctat aacctaataa atgaatcttt gtatgttacc    960

atacttatgt tactacccat agcctagaaa cgtgtgtatg ttactctcca tagtggttag   1020

tctaatacgt gactttaaac atctctctgc ccaagtagct gccacataag cagatgggcg   1080

tcttaatata ataatataga aatgtatcgg ggtaatataa tactgtggcg ataggcttgg   1140

gttaatttct ttagtcccgc cgataagctc gattggtcag tgctggtgcc cctctcgact   1200

ccacacacac acacacagag ggcgaaaaat aagggcacac gaggccacgt cacgtggggc   1260

ccccatgacc cacacgcggg cccgcgcgcc atcgtgtcga cgcgccgcga gcagagacgg   1320

ccggcgaggc caacccgaac caccactccg cgcgagccgc ccctcccttt ctctcgcctt   1380

ttcggcccnn nnnnnnnnnn nnnnnnnnnn nnnnnnnnnn nnnnnnnnnn nnnnnnnnnn   1440

nnnnnnnnnn nnnnnnnnnn nnnnnnnnnn nnnnnnnnnn nnnnnnnnnn nnnnnnnnnn   1500

nnnnnnnnnn nnnnnnnnnn nnnnnnnnnn nnnnnnnnnn nnnnnnnnnn nnnnnnnnnn   1560

nnnnnnnnnn nnnnnnnnnn nnnnnnnnnn nnnnnnnnnn nnnnnnnnnn nnnnnnnnnn   1620

nnnnnnnnnn nnnnnnnnnn nnnnnnnnnn nnnnnnnnnn nnnnnnnnnt agcggtagtg   1680

tatcgggttc gcctccctcc ccctccccct gcctgcactg tcccatcgct cgctcgctcg   1740
```

-continued

```
ctttctcgcc cgctcggtgg cggtcgtggg ggagaaagtt gccggccggc cagcgcacgg   1800
ggaaaaggcg cacatacttt ctttctttct ttccaccgcc gccctcctcc tcctcccgga   1860
ggagttccga ttccccctct ctttctctct cttctttctc tctctctttc ttgctctgct   1920
ctggaagcag gggtcctga tttgggcgcg ggcgccgtcc gccgtgattc ggttcggctg   1980
atttgggagg tctgctcgtt tgatccgggt tcgctgattg gttgattgat tgattggttg   2040
gttcatctcc ggcggctcga tttgagggcc ggtcggcttg gtcgccatgg ggaactgctg   2100
gggcgccaag atcagctccg acacctcctc ctcctcctcc ccttcaggtg cgtgcgtcgt   2160
cctccctccc tctcctcatg ctactatttt gcaaagattt ttaatactac gtaccagcgg   2220
tacgactagt tcataactaa tctgtgccca gagggtcgaa taaatcctga atgaaaaatc   2280
tggtggtttt tggtttgcgg cgacttcgtg ctctgcatcc cttctctcct tcccgaaacc   2340
agtcctcggt catgctgatt cgatttcggt ccaatccaac tgcttcaaca tagggcaaac   2400
actaggttag gttcactact gtagaaactt aatctggttc ctaccaaata gtactccctc   2460
cgtaaactaa tataagagtg tttagatccc tattttagtg atctaaacgc tcttatatta   2520
gtttacagag agagtattaa gtagactact caataaagaa atcactggtc tgtgttaact   2580
ctctactact ttgcatctcc tcactgtttt cgggaactaa gactagaact gggttatgct   2640
gatttcgttc cgtttaatcg actcaagatt ggagagtcac taaattcagt acagcacaaa   2700
cttaatttgt ctccctagga aaattcagtc cattctttgg aaaaatctgt cgcgagcttt   2760
gactcttcct cttgacctgc ttcgtgtgca agggatcatg cctttccgtt ttgggcctag   2820
gggagaggaa gcttccgatg tagtagtaaa atgcttcact taactttatc tgacttctcc   2880
tctgattttt ctgagtgtcc agttcaaatc agacatatag aggaaaagct cgaattctga   2940
tgctactttt ggctacatcc acgtgctttt cttcaaagtt attgactgtc ctgttttgga   3000
tgttcagcct tcttttctgt aataagcgaa actaaaggaa gaaaatacat agttagtccg   3060
acctaacttg tccatgatga acctattttc tgttcaatgt taggcagaca agataaatga   3120
taaagggaca gcaacctatt tattattcta aaccgtgatc gaatcatttc tgaaactctg   3180
caccattgta tgatgatgat gatcagggac gaattccaag tatgctacta ggaatggggc   3240
ggccttgagc agctccagca gctatgcctc cgcggcgtca gtgccacgga gcgagggtga   3300
gattctggag tcagccaatg tcaaggcctt ctctttcaat gagctgagga ccgccacgag   3360
aaacttccgt ccggacagtg tgctaggcga gggagggttc gggtcagtct tcaaggggtg   3420
gatcgatgag aagaccctca ccccaactaa gccaggcacc gggatggtca ttgctgtaaa   3480
gaagcttaac caggaaagct atcagggcca tagggaatgg ctggttagtg acaattttgc   3540
ctgctggaaa tgggatttct tgtttatttc agttctgcat tgtgtctgac atgctctttc   3600
ttttgggcgc aggctgaagt gaattacctt ggacaactat cgcacccgaa tcttgtaaag   3660
ctcgttgggt actgtgtcga agacgaacag cggcttctcg tctacgagtt catgccccgt   3720
gggagtttag agaatcatct attcaggagt aagcccctgg ccttttactt ttcttattcg   3780
ctgggtgtta ttctccagtt ttgaaggaat gatgctaaag tgttccaaca ttcagggagt   3840
acacatttcc agccgctctc ctggaacctt cggatgaaaa ttgcccatgg agcagcaaaa   3900
gggctcgcgt ttctccacag tgacaaggcc aaagtcatct accgcgattt caaaacctct   3960
aatatcctcc tagatgcggt atatatatcc acagccttga aggatctttt cctttgcgtc   4020
cgcaaaatat ctctatcggt cgatctgaca gtcacgcaat ttcttcttca gaactatgac   4080
gcaaagctct cagatttcgg cctggcgaag gacggaccga cgggtgacaa gagccatgtg   4140
```

tccacaaggg tgatggggac atatgggtat gctgcaccag aataccttgc aacaggtcgg 4200
ttgatcattc cactttcaga atcctcagct gcgcaaatat aagatatatt gctgaaaatc 4260
tgaccacgcc tacctgaatc gtgattgcgt tgtcactctg gttgtgtcat cgaccaagat 4320
gccgaacata accaatttta ggctacaacc tttcaatcat catctgcaca aatatcttgc 4380
ccgaaaatct aaccacacct acctgaatca tgattgcgtt ctcactctgg ttgcgtcatc 4440
gaccaagatg ccaaacttaa ctaatttttc ggctagaacc tttcagtcct catctgcaca 4500
aatatcttgc tgaaaatcta aacacaccta cctgaatcgc gagtgcattg tcaccctggt 4560
tgcgtcatca accatcatgc cgaacttaaa ctaattttcc tgctgcaata tttccatgat 4620
caggccacct gaccacgaag agcgacgtgt acagcttcgg cgtggtcctc ctggagatgc 4680
tctcggggcg tcgcgcggtg gacaagaacc ggccgaccgg cgagcacaac ctggtggagt 4740
gggcgcggcc gtacctgaca agcaagcggc gcatcttccg cgtcctggac cccgtctgg 4800
gcgggcagta ctccctcgcc aaggcccaga aggcggcgtc gctggcgctg cagtgcctct 4860
cggtggactc gaggaacagg ccgagcatgg agcaggtcgt cgtggtgctg gagcagctcc 4920
acgacgccaa ggagggaggg aacagccctc gcccgcagct gcagagaaag ccgagcagca 4980
accggggcgt gaacggctcg agatcgtcgt cgaccaaggg gaacaacaag aagcccgcct 5040
caccgagacc ggtttgaccg tgcgagtggg atcacatagc agaatctact agagagatgc 5100
gtcaaggtgt aatgtatgag tggtgatctg cgaagaggca gcggatttgt gaatgttttg 5160
tgcccgtgtt gtagggatgt atctttgcag cttctagtgt tggtatgtac agcttgtatc 5220
tatccggttg tagctagtct gtatgtagtc cttttgtgta tgcctgattg ctttggttct 5280
gacttaaggt ccagaggttt tgatctgatt tagatgcatg caccctgtta aaccaagacc 5340
ttaaaatatg aagatgaaca gtgtaaagta catatttgtc acttcattta tcaaatgtga 5400
atgaacaatc atattggtgt tttagcagag caggccatga cttccatggg tcaactgtat 5460
cttttccctt agggatgttg accattttgt tcatatcata cagtactagt agtatatgtt 5520
tcattttttt tatgaaaaaa gtagtatatg ttacagataa tgttgggaaa atcaccttct 5580
gtatttttaa tttcaaacag ttggccacaa tgatcttttt atttacttgg tgggttcagc 5640
caaattacca ttgttttttt caggggtttc agccaaatta ttattatctg ggcaagcgta 5700
cggcggcggc ccaaggcaga gcacgcagcc cagccgccaa aacagagctc gccctcgctc 5760
ccctccggcc caagtgccgc tcctcctcct cctcggtgga cgccggcgcc ggtggatggc 5820
tccgccgcgc caaatcgagc ccctcacgcc gcgagcctct cctcctcctc ctcagcctgc 5880
aatccccgcc gagctccgat ccccgccgcc gagctccgat ccgcgggcga tcgccggggc 5940
gccgccaaga tcagctccgg cccctcccgt tcctttaggt gcgcgtttct attcttcagc 6000
aaaatagttt tctggcatcc gaccaggtta atacccaccg taacaaacgg acaggctatc 6060
gcgaatgttt tgatgaacga tactaattgc 6090

<210> SEQ ID NO 7
<211> LENGTH: 1032
<212> TYPE: DNA
<213> ORGANISM: Triticum aestivum (var. Chinese Spring)

<400> SEQUENCE: 7
atggcagctc taaccagcct tgcctcaaac ccgaatccaa acaagtcatt cgaggtcctt 60
cctaatccgg gtgactccct ctcaagcctc agttttagcc cgaaaagtaa tcttcttgtg 120

```
gcaacttcct gggataacca ggtgaggtgt tgggagatag gtaatggtaa cagtcagcca    180

aaggcatcca tatcacatga tcagccagtg ctctgctcag cctggaaaga tgatgggact    240

actgtcttct ctggagggtg tgataaacag gtcaaaatgt ggcctctgct gtctggtggg    300

caggctcaga cggttgcaat gcatgatgca cctgtcaagg aggtcgcatg gatttctcag    360

atgaatcttc ttgtatccgg aagctgggac aagacactaa ggtattggga cacaagacag    420

ccgaatccag cccatgttca gcaacttcct gatcgttgct acgcacttgc tgtgaattat    480

cccttatga ttgtgggaac agctgatcgc aatattgtga tcttcaactt gcagaatcct    540

cagactgagt ttaagcgtat tcaatcacct ctgaaatacc agacacggtg cgttgctgcc    600

tttccagatc aacaaggatt cctggtgggt tccatagaag gaagagttgg tgtgcatcat    660

attgatgatt cacagcaaag caaaaacttc acattcaagt gtcacaggga aggaaatgat    720

attttctctg tcaattcgct caactttcac cctgttcatc acacgtttgc cacagctgga    780

tctgatggtg ctttcaactt ttgggataaa gatagcaagc agagacttaa ggctttcagt    840

cggtgtcctc aacccattcc ttgcagtagc ttcaataatg atggttcaat atttgcttat    900

ggggtgtgct atgactggag ccgtggcgct gagaaccata atcctgcaaa tgcaaagaca    960

tccatctatc tccacagtcc ccaggaagcc gaggtgaaag ggaagccaag aatcgcaacg   1020

gggcggaagt ga                                                         1032
```

```
<210> SEQ ID NO 8
<211> LENGTH: 343
<212> TYPE: PRT
<213> ORGANISM: Triticum aestivum (var. Chinese Spring)

<400> SEQUENCE: 8

Met Ala Ala Leu Thr Ser Leu Ala Ser Asn Pro Asn Pro Asn Lys Ser
1               5                   10                  15

Phe Glu Val Leu Pro Asn Pro Gly Asp Ser Leu Ser Ser Leu Ser Phe
            20                  25                  30

Ser Pro Lys Ser Asn Leu Leu Val Ala Thr Ser Trp Asp Asn Gln Val
        35                  40                  45

Arg Cys Trp Glu Ile Gly Asn Gly Asn Ser Gln Pro Lys Ala Ser Ile
    50                  55                  60

Ser His Asp Gln Pro Val Leu Cys Ser Ala Trp Lys Asp Asp Gly Thr
65                  70                  75                  80

Thr Val Phe Ser Gly Gly Cys Asp Lys Gln Val Lys Met Trp Pro Leu
                85                  90                  95

Leu Ser Gly Gly Gln Ala Gln Thr Val Ala Met His Asp Ala Pro Val
            100                 105                 110

Lys Glu Val Ala Trp Ile Ser Gln Met Asn Leu Leu Val Ser Gly Ser
        115                 120                 125

Trp Asp Lys Thr Leu Arg Tyr Trp Asp Thr Arg Gln Pro Asn Pro Ala
    130                 135                 140

His Val Gln Gln Leu Pro Asp Arg Cys Tyr Ala Leu Ala Val Asn Tyr
145                 150                 155                 160

Pro Leu Met Ile Val Gly Thr Ala Asp Arg Asn Ile Val Ile Phe Asn
                165                 170                 175

Leu Gln Asn Pro Gln Thr Glu Phe Lys Arg Ile Gln Ser Pro Leu Lys
            180                 185                 190

Tyr Gln Thr Arg Cys Val Ala Ala Phe Pro Asp Gln Gln Gly Phe Leu
        195                 200                 205
```

```
Val Gly Ser Ile Glu Gly Arg Val Gly Val His His Ile Asp Asp Ser
    210                 215                 220

Gln Gln Ser Lys Asn Phe Thr Phe Lys Cys His Arg Glu Gly Asn Asp
225                 230                 235                 240

Ile Phe Ser Val Asn Ser Leu Asn Phe His Pro Val His His Thr Phe
                245                 250                 255

Ala Thr Ala Gly Ser Asp Gly Ala Phe Asn Phe Trp Asp Lys Asp Ser
            260                 265                 270

Lys Gln Arg Leu Lys Ala Phe Ser Arg Cys Pro Gln Pro Ile Pro Cys
        275                 280                 285

Ser Ser Phe Asn Asn Asp Gly Ser Ile Phe Ala Tyr Gly Val Cys Tyr
    290                 295                 300

Asp Trp Ser Arg Gly Ala Glu Asn His Asn Pro Ala Asn Ala Lys Thr
305                 310                 315                 320

Ser Ile Tyr Leu His Ser Pro Gln Glu Ala Glu Val Lys Gly Lys Pro
                325                 330                 335

Arg Ile Ala Thr Gly Arg Lys
            340


<210> SEQ ID NO 9
<211> LENGTH: 11234
<212> TYPE: DNA
<213> ORGANISM: Triticum aestivum (var. Chinese Spring)

<400> SEQUENCE: 9

ggtgaggtta tggtatgtac aattttggcg cacaatgacg gcgacttccc tgatccttcg     60

tcatcgtctc caccgtgttg gttttggtgc tggcgtgagg cctgaggtat gtctcttgga    120

tctaatgctc gtctagcgtt ggtggtttct ccttcagagc gatggcccgg taagacgtgg    180

ccttaatcac tccccgcccg tgatgaacat caggctggct tcgatgatgg agaagcatgt    240

gttggctcgg catgttctag aggatgaaga aggatgaccc aggaattttg atgtaacttt    300

attaatattt tcttcctata atttgtactt ccttttctta gaaaaaaaac tattttgtac    360

tgctagtttg attaatattc gtggcttcac atgcgctggt ttggttatat aagagggagc    420

atatgggtgt tgtcttttta tataagaaaa aaaagagcaa aataagccac gcgccgatca    480

agcctgcgaa ctgagagtat acccggccat gggcaaccca gactgacccg acccgtcccg    540

actcgacctt gcccacgggc cgggcccagg cctagatttt gagcccgatg gctgggccga    600

catgttgtat ttgcgattta aggaagaggc ccggcccaag ggccgaggcc cgacgggttt    660

tttgactgat gggccggggt tgggccaaat tgttaggccc aacggccggg ctcgggccta    720

agccttttgc ttgcgttcag gctttgatag gctcagcccg aagtccacat ccacatcaac    780

cacccccgcg tgccgatgaa gccatttctt tggaaggacc ttcgcgtgca tccgacgcga    840

cgcgctacac cgaagcctat actactacat ctcgtctcat cgccctcctc ccacacgacg    900

actcgagaat cctcggctga ggctccactc cgcactcgca agtcgcaccc gcagccgccg    960

ccgaccgctc cccgtccggc aggtaagccc cccgagcccc tcctcgccgc tccgctcgcg   1020

cggactccta gctagctagg gttcccggca ccgattccgc ggcgctgcac tccggcgcaa   1080

tgctcgcggc cgcggacggg cccgccgctt cgggggaagc tctgatctgg tggccggcgc   1140

tcgctcgctc gctcgcggtc tccggagcaa atcggccgca tcgagtggcc ggagcaagct   1200

taggatagtt cgattatttc ccccatcccc gttggtcagg ccgagagggc cagtttgggc   1260

gacctcctgg tgattccgct gccgtggtgg ggattgggtg gtcgtggccc gggtgtaggc   1320
```

gtttgtaggt cgagtgagtg tttccttcca ggttctatgc tcacccagct tgtgttatca 1380
ctgggatccg ggcgttcggc aggctaacat tcaccggatt ttggacctgc attgttgcgg 1440
cgcgtgccgg gggatagcgt ttatgctggc tttggcgcgg tgattttgtg cgtgcgtgca 1500
aacttttggg gctgccttct ggtgatctcg ctgtcgggtg gtgcgagttc atcaagcggt 1560
cagggtgtag gcatttgtag tcgagcgacc ccagctttca tgcccaccag ctcgtattat 1620
tcggtcgtta accacgttta ccgaattttg gaccgacgtc gttgcggcac gtaccagggg 1680
acagcgttta tgctggtttc ggtgtggaga ttttgtggtt taaacttggg gcgcgcttgg 1740
tttgcgaggc tacctcctgg tgatttcacc gtcgggtggt gggaatcgga tggtcggggt 1800
gtaggcattt atagtggagc ggaccccttg ttttatgacc agacatttag ccgaaatttg 1860
gacctacact atcgtggcgt accaggggat atcatttatg cgggttttgg cgcgacactt 1920
tctttgtcgg gattttgtgg tgcaaactta aataatgact tccctaatgt taaacactcg 1980
ttctggcatc gtggactgtt ggaatcgttc tttttcgtag tctgagctac tttaagttgt 2040
tacttatgct ctcgtgtgcg tgggagactc cacgtgctga tttctcttac ttgcttctca 2100
tggtcactgg actgatattt cttttccaga ttttgaaggt tcacagaagg agagatggca 2160
gctctaacca gccttgcctc aaacccgaat ccaaacaagt cattcgaggt gtgatacttt 2220
ttgtggccat gtctgtcctg cttttatttt tttgcgtctt gtcattctgt atatgctaca 2280
tgttctctgc aatggttgct ttcaaatgca ggtccttcct aatccgggtg actccctctc 2340
aagcctcagt tttagcccga aaagtaatct tcttgtggca acttcctggg ataaccaggt 2400
aattttgttt ctgctgtaat tttcagtgag cttccattat tgtgatgtat cttactagga 2460
atgtcttttg agttttgtgc aggtgaggtg ttgggagata ggtaatggta acagtcagcc 2520
aaaggcatcc atatcacatg atcagccagt acgttctcat acatgtttct cctgaaagta 2580
gtttcatctt acacattaga gtggttcctt acctgtttac ttggtatgat gattgatttg 2640
tttccttcca tcaggtgctc tgctcagcct ggaaagatga tgggactact gtcttctctg 2700
gagggtgtga taaacaggtc aaaatgtggc ctctgctgtc tggtgggcag gctcagacgg 2760
ttgcaatgca tgatgcacct gtcaaggagg tcgcatggat ttctcagatg aatcttcttg 2820
tatccggaag ctgggacaag acactaaggt gcaagaacaa tattcctctc caccctcagt 2880
attcttttta catggaaatt cagcgcatat cacccatatc tgatcccaaa ttgttattta 2940
tggctgtttt gcttttggga attcgtgttg tttgtggtat cctttctgta cttcatgtgt 3000
tctgcattaa tgttcacaca ttggctaacc aaatattgta gaagttctat ctcatcctct 3060
ttatatttgc actcattttg tatgccttct ttgatcctga agagttttct actacttgtt 3120
gaatcatact gccctattct tatcaaaggt tgtgcacttt ctgggtatca tctgtactat 3180
ttatggctgt agtgaatttt tcttatggca gaagttttta tagaagtaac tgttgatgca 3240
gacagttact atattaaatg tacattatgt gattagtgtt agaaatgttc gtttcgagtt 3300
ttagcatcat ctttatgaag attatttatg aaacatcaag ttagggtctg gctgtcagtt 3360
taaacatgag cacagattga gcataggcga taatcatggt tggtaggagg ccagggaccg 3420
ggatccttgt gggacctgcc ggcgtacccg tgatagcaga aggggtgcaa gggacagggc 3480
actggaacta aggcaggcag aaacagagaa ataaagattg gggattagac tttgtagcca 3540
attcataaaa aaattggttg catcattttg tagaggttgg ccttaacata tgactaaaaa 3600
acaaaaacaa accaagactc ttccctaaac tgaataccgc agatactcaa gacaccatat 3660
agggccacgg gctcaggctg aagtcatcta ggtctcagac atgccaaaac agactgggac 3720

```
aaggacaagc tgaaactgac tagtactagg tttcccgggt caactaccgt tcagctggag   3780
gtctgaatgc gtggtgcctt ctctgataca tggatctcat gtggcacttc tgttgtgtat   3840
ttgtcccagt ctgcttattt tcctttgtct gtatcatgct gagactaata catttgggtc   3900
gtgcattgat cttcttctca ttacaacttt tagctctgat cctgatgact tgtttctagt   3960
ctgctatcaa tgcttatcat catactattg taggtattgg gacacaagac agccgaatcc   4020
tgcccatgtt cagcaacttc ctgatcgttg ctacgcactt gctgtgaatt atccccttat   4080
gattgtggga acagctgatc gcaatattgt gatcttcaac ttgcagaatc ctcaggtaat   4140
tttgcttcct aaccgactat gcattttcaa ttcttgtggt ggtggtgctc atgcttttac   4200
tgccattgac ttatattttg aactgcctga cttaaattca tccctgatgt gattttagac   4260
tgagtttaag cgtattcaat cacctctgaa ataccagaca cggtgcgttg ctgcctttcc   4320
agatcaacaa ggattcctgg taatgccata ttttcttgtg tcttttactc tcagcattac   4380
gacaccaacc aaaacttccg ttgtttgaat acataacttg ttgttactat gctttgaagt   4440
ttaatcatat gttcttctct acctatccat cataattatt tatgttgccc aattatgttg   4500
tttttaccta gcttgagttt tcgaccttaa acattgttac aaccttactc gaattagctt   4560
tagatgttgg cctgccatca tttgcagtgt aatgggcgtt gttcctttag tgatctcatt   4620
tcaaacttcc taccccctcta ttataggata aataaggtat attgattgtg aaatcaaact   4680
ttactgacta taaatactat actatgtgat ttatgtgaca taaagttgat atcattggat   4740
ttgttttcaa aagtactttg ttacgatttt gataaaatat gagaagaaat ttatggccaa   4800
agattgaact cgagcagtca aaatatgcct tgtatatctg gatagagtgt gtattactag   4860
gaatgttaat ccaatataaa tgtcattaat tgacatctct ctagttagca caaaagctgc   4920
ataaaagaag aggatgcagt tttccttaat gttttgacca actccagctg tgttgcaaac   4980
agtttccttc accagaactg tagaacggat cttagcctat agcagttaaa gctaatctga   5040
acatgaaatc cggctgaagt acaaatagta aaaccatcca aggcttcaag caattgtttt   5100
tgaactacag atctttagat gtctatttct gcattttcct attcttcacc tgcttgtggg   5160
tgttcttata gtgggtcgtc gtttcatcat gggctttgac caatcaattt ttgctgttac   5220
acaatgatct tttctacat caatgaactg cctatattgg ataaagctgg tcgatacctg   5280
gcaatagttc ttgttttaat tattttcttg ttgtttccat attacttggg caaaacattt   5340
tttacatgcg actgacacct gattttgttt gaaggtgggt tccatagaag gaagagttgg   5400
tgtgcatcat attgatgatt cacagcaaag caaaaacttc acattcaagt gtcacaggga   5460
aggaaatgat attttctctg tcaattcgct caactttcac cctgtaagat ctctatcttg   5520
ttctctcttg actccatatt tatctatgtg ccatactgcc attcttatat ttcattagtc   5580
cacttctgct attatggaaa atgctaatgg cgacttctgt tgagctttag tcactatgtc   5640
tccatcatga tttgtaaaat actgaaagct cagttcgttg tcttccacaa gatgtgttga   5700
gctttattcg atacagatac ctaccacact tcgcctaata taataaccac tatgcttgaa   5760
ggcatacata tgttagtaaa ctactccaaa ttgatcaagc aatattttgc agaaataaaa   5820
atcccaacag attagcttca gtttaattga gcaactcgaa atcgtaccta tttgttacag   5880
acacatcgaa gagaagcgtt tctgcttctt ctgttgctaa ctttggcatc ttattcattg   5940
gattggtata tgcttgggtg atgatactat acatccattt agttgagtgt gcttgttggc   6000
tatatatttc actggaaaat gcaactgact ggtgataatt gtgaagtatg gaaattcagt   6060
```

-continued

```
tagtctagtt acttatggga tttcatgtta tctaccactt ggcacaggtt catcacacgt   6120
ttgccacagc tggatctgat ggtgctttca acttttggga taaagatagc aagcagagac   6180
ttaaggtttg tctattcccc ttttttttt ctattttccc ctcttgttgg tttatgtttt   6240
cttgattgga attcaatgat ttcaagatgg ctctactttg ttgtgatctg tggacactga   6300
tgatctgcat ataaattctt tgttgatgcg catacatagc ctgaaatcat cccgagctca   6360
agctaataaa ctcactatcc tggccatgag cagaaaaaaa aatattagtt cataaatgtt   6420
atcaccaatt ctgattttcc cagctgcctt gtcatcctgc tgcttttggc gtttagtatg   6480
cacttctttt tattcttgat aaaagcatat tacatattta ttactcaacc gcatggagcc   6540
tctgcagtaa ggtatatgtg taatttgtca acagataacc ttttagcttt taggcatatc   6600
atacacagtg ttgcattctg acagttgctt acttgcttag catagagggc tatctgtgtg   6660
tgcccaagtt tattgcttca gttccctcat ttgtcataca ccttctggta tgttgcacat   6720
aacacattct tacatttccc ctacactgct tctatacagg ctttcagtcg gtgtcctcaa   6780
cccattcctt gcagtagctt caataatgat ggttcaatat ttgcttatgg ggtaagtcaa   6840
gtgatgcttt tgagagtgtc ttgttatcac catgtttttc agtccggtca gagtttagat   6900
atgttacatg cctgtcattt ttcctgcacc ttatttaata tacggaagaa atcagctcga   6960
caaataattc atgttccttt tgaactgcta tcttgtcgtg tcctctgaat ccaagttctg   7020
aatgcaaccg taattatcat tgctggggag caggtgtgct atgactggag ccgtggcgct   7080
gagaaccata atcctgcaaa tgcaaagaca tccatctatc tccacagtcc ccaggtagtt   7140
tccgagtgct gatatcgcca taaaaagaat tcttgtattt tcgacatcat ttgagatcca   7200
ttcctgtttt tataaattgt tattatgtta tcttttggca ctcaacttgc atcattctgg   7260
acaggaagcc gaggtgaaag ggaagccaag aatcgcaacg gggcggaagt gatggtggca   7320
tcctgcctgc cgaaaagtcg atagttgtgc aagagatgat gtatattcaa gggccttgtt   7380
tcgctcgggc cttgccttga cgtgtcctct ggatgttctt acttggttcg gccgcctggt   7440
agatgaaacg cctactccca gcaaccagtg ataggttact tagccgtagg tcgtagcaca   7500
tagccgttta tgtaatgcat agttgtccga aggaatgttt ccccgtgttc ttgtgttgtg   7560
atatagtcag gtcagcgcgt agtcttttga aaaggagaaa gccttcggtg tcttgtaagt   7620
ggtgtagatc tttggaaata tgggcatgat attcggtgga gttattctga aaaagatatc   7680
ccggtttcgg tttcagcgaa tgcaagctag atttatgggg aaggttgtag ttagcaccat   7740
gctgcaaatg catgcggcat tcggaggatt tacagtttga atcttcctgt ttatccaagt   7800
ctaggattcc caccttccta gtaccattga gcacgttagt ttgaattttt tttgtttatt   7860
atggttcaga acttccgatt caaaaaaatc tgatttattt tacgcgaata tatggatgtt   7920
taatcaatat acggttttgt atgtgagata taaagaaggg ccaaagacat gcaaacaatg   7980
ggcatttctt tgtgctggat cttttgtgtt cttatctgca ctgcaccatc aaacgaaaat   8040
taccaggtgc gtgcagaacg acgtgtaaag aaaacaccca acttttccga aacttccaaa   8100
tgccattttc gagctgttca acatagtgtg cttcgaaaat ccgttcttca gtacagtacc   8160
agccacgtag caatggctcc acagaagcct cattgcttac gagctttatg ccgtgaactt   8220
gcatagattc agttcgacaa cccaattgca taagcttgcg atctttttat gccgttaact   8280
tcaaaataga ttcggcgcaa cacgactcaa tagccacgac acgggcaaag actagggcat   8340
catcaaacct aacgcaatat agcattggtg tcggtactta atttacaggg ttttattgca   8400
tgaccaaatc acaggtgcgg cataaaatta cagtcgcgga gagaaagcga acccagtttc   8460
```

acagcaagag agtagcagac tagttaacaa acgtaagaga acccagcttc aagaatctaa 8520
acacaggtaa agaccacatt gtttcagcac caagttcccg tccttccttc cacgtgagaa 8580
cccgacccgg tcctagtcac agctccttca gacatcgaac acatcatcat acatgtcggc 8640
gtcccagtcc gcgtcgtcga tataatcctc catgtcatca aactcggcat cctcgtcgtc 8700
gtcggtgacc acgtccagca gatcatcgta catgtcgacc tcgatgtcgg aaccgccggg 8760
gtagtcatca ctgccagcga ggtaagcccg gtacttgaag tcggagatgg ggtccccggg 8820
gagcctgagg ttcccgatcc tggcgcactt ggatctcagg gcatcgtcca tctggaggtt 8880
gcagcagcgg cgcacgtcga gggactcgag gcgggggcag tggtcgagga tcgccgccag 8940
cccggcgttg gtcaggttgt tgccgatcag ctggaggtcc cggagctcgg gcatgctgct 9000
cgcgatccct agcacacccg tgtcatcatc catgccctca aagactgcaa accccctttg 9060
gaggaccgtc cagcgctcgt tcagccgaaa ggatttcagg tgtgggcagg ctctgccgac 9120
tgactcgcac acgttgctgt tcagtgagca gaatgtgatc tccagctcct caagctgagg 9180
aaagcccttg actgcatctg ccagcgcctc attggatact tcatcacaca ggcttagttg 9240
aaggctcttc agcgagggtg ccctgcattg agacatggca agttcttatc taacacaagc 9300
atttaagcta atgccaaacc caatcatgct ttccaagctc aggacaagaa ataacactag 9360
aacaacagaa ttgattgaaa taaccatgtg aaagtaaaac attccatgct gttagattca 9420
ccatagtctt caaataagtc taactccagt cacatgcaaa tgaacttcag cacgcagttc 9480
taaacaaaat acgacatgac ttgatactgt gtctgaactc cacatatcac atctagtcaa 9540
accattagaa gaagacgaca acgagccagg tgttaggtgg tcaagaagac aagaagtggg 9600
atcaatttat ttcaatgcac caaaagatca acacaacgat aagaaaatag caactctgac 9660
tagcactacg cttaccaagc aaacaaatgg ccacaagaat atggagttat gggcagctta 9720
ggggttttgc ttcagtgagg gggatataac agttgcaata ccataaaaga aagtagctag 9780
taatagtttt acatatttat cgtttcactg catagttgtt gatttgattg ttaatactat 9840
gcgatacaga tatacaccag tggtaattgg atgcacattc agtaaggccc ttaatttttt 9900
tgtatgcaag gaaatgttgt agtggtggct ccaacagtat aatccataag aaccaattcg 9960
agtaaatgat gatttgaacc caggtagtgg gcccacccaa catgtaagtt aactacatga 10020
agagtgcagg cacactaaaa cattcatcct gaagtacatg agttattttg gaaacattct 10080
gatggattgt tggataaaag cgtgaaagtt tccaaggttg caagtttctg tatgatctaa 10140
atgcacgaga ggactgtgta caagtgaaag gtactggaag atgcatgaac caaaaacagt 10200
tacaggaagg ttaacagaga agtctgcagc taccaaaggc aggattgtca gaaatgccga 10260
attgcatcat gcatcaatct tgcagtgaaa ctgcctacat ctttatcaga aaaaaatggt 10320
actgaaccat cgaagtgatc atttggtttt ctacagacct ttacagcaag taatttgctg 10380
gaaaccaaca aaaaagttca gatggccctc ccccctgtaa agtctccatg ctgagactca 10440
cctatccttg tatgttttag ggattggtcg gtgccaatgt tatatccaag agcacaatga 10500
tgcccccatt ctgactatta gtgggaacag gccaattccc tccaggaaaa caaaccttca 10560
gtcagtgtgc tactctatat acattttccg ggttgctcca catacattat gtcccaacgc 10620
tacggagtag atagaactta gcaaggcaca ttgagtcaca caaagacata gcactggaga 10680
ctcatgtgat ctgttccaac ttgcaagcat tttactgttg agtagtacca ttttacccca 10740
tccaatttcg ttaggttatg aaaatgtgtg tttttttcaa cctgtcaaat caaacgtcag 10800

```
aaaggtccat ttccaacttc agaatacaga cttattttaa gttaaagacc ttccccatga  10860

attttaattt accagcagcg ccagcaaccg ttcgtttaac tgaatgaata aactaagcgc  10920

cgcatccaca aattggggga aaaaaaaccc cccactgtat gccagaaatg ggcatgtgaa  10980

acaggaaggg gagagccgtc gcgaacaacc tgccggagat gtagctgagg agggcgtcgg  11040

tgacgaaggt gtcggcgcag aaggactgga gcgtgccggc ggcgcggtcg acggcggcgc  11100

gggccatggc ctcggcctcc tcggtctcga ggatgtcccc gtggtgggtc atgtcgaggc  11160

ggcgccacag cgcggggtcg ccgtcggcga ggcggcgcca ggcgcggcac gcccgcccgg  11220

cccccgtcag gatg                                                    11234
```

<210> SEQ ID NO 10
<211> LENGTH: 2024
<212> TYPE: DNA
<213> ORGANISM: Triticum aestivum (var. Fielder)

<400> SEQUENCE: 10

```
ttgtcccgcc gatgataagc tcggttggcg actggtccat gcccctccgg actccacaca     60

gccaggcgaa ttggtgagtc tgcaactgct gagctggaca caagtaagtc ataaatgcga    120

cgcaacaaaa aatgacgcca cgaaagttgg gacgttttct caattatccc ggaatattat    180

aatagcatgt tgtacgcgta cctcatgtag ccggaaaaca tctacagccg ggcaccccaa    240

actctatcat acgccccgac ggacggccaa gttagtgacc ggtcacgaaa gactgaccta    300

gacgggtaac ttaaacgggt ctcaagcgct caggctaacc ggcgcccctc atatccagtc    360

ccaaatgtag ggcggataag gggcgcccca ggagcatcga ggcgcgtcca tcacgtcggt    420

cctggcccac gatggcccac ccgcctccat atatattctt ctgcatccgc tgcctgggcc    480

aaacactatc cacttcactc ccctacgcca cccaaactcc tatccgacga tcacgagcct    540

tctccggttt gacgtgtagc agattcgacg acgaccagta cagatctgtc gactggggtg    600

tcaacccgtg cggtttggag aaggaaatgg ccatccgcat tgcactttgc catttccgga    660

ggacaacgcc cttccgacga caggatctcc cagcgcgagt ccattgcgtc ggtgcatcgg    720

gcgctcagat cctctggtgc tggatcatcg tggtcctcta ggcagccttc caatctccct    780

tccccatcac tggtccgtcg gagtacgagt cctatcgagg gtcagtgtgc ccgccgtggg    840

aagaagagga tgagggcggc tgaggtcagc gccttgctgc cgacatggcg gcggcggagg    900

cggctgatac aatggcacgg gcggccgcag aggaggaagg catccgcgtc cgcattgtaa    960

agaagcggca gcggaggaac acgcgcgtcc ctcgtccgag agcataatcg gcgatccgtg   1020

ccattgccgg actgccttcc aaggaggaga aggaggacaa cgatgggtca gatagctctg   1080

gcgatgagca gacttgactc gattcgtact gcctctttga tcggtacttg cgcgagaaga   1140

acgacaaggg caccaagaag ggcaaagaca gacatggatt gatcttcttc atagctagca   1200

tgtacgtagg ttaaacatgc caatttttga tagtccgatg tcatgtcctg atgtcgtagt   1260

aggaagatgt gtgtaatgca tcgtttatgt agttgcatga gtttgtatgg atttgagata   1320

aggtaattaa gatgttcgat tgtgagaagg gaaatttaag gcgtgaccaa cccgtgttca   1380

cggatgcgcc tggacgcatc cgctgaccgg atcgtgtcga cgcgcgcgag caaaggcggc   1440

cggcgaggcc aaccccaacc accactccgc ccgcgccgcc cctccctttc tcccgccttt   1500

tcggccccca tcaatggctc cctccacctc cttctagaag ccgcctgccc caccacccgt   1560

gctagcggta gtgtatcggg ttccccttcc ttccttcctc tcccctccct gcctgcactg   1620

tcccatcgct cgctttctcg cccgctccgt ggcggtggtg gtggtgcgtg gtgggggaga   1680
```

aagttggagg cgggggaaag gagacgcaaa gcggccaccc aaaaaggcac atatactttc 1740
tttctttcca ccgccgccct cctcctcctg gtcctggagg agttccgatc cccccccccc 1800
cccccccctct ctcttctttc tctctctttc ttgctctgct ctggaagcag gggagggagg 1860
gggttccgat ttgggcgggg aggcactgtt cgcggtgact cggttcggct gatttgggag 1920
gtcttctcgt ttgatccggg ctcgctgatt gattgattgg ttggttggtt cgtctccggc 1980
ggctcgattt gagggtcggt cggtccggcg agtgagtcgc catg 2024

<210> SEQ ID NO 11
<211> LENGTH: 2159
<212> TYPE: DNA
<213> ORGANISM: Triticum aestivum (var. Fielder)

<400> SEQUENCE: 11
gacggctcaa tggtgtattt ttcccgtcgt gcgtcttcat cggtgaggtt atggtatgta 60
caattttggc gcacaatgac ggcgacttcc ctgatccttc gtcatcgtct ccaccgtgtt 120
gattttggtg ctggcgtgag gcctgaggta tgtctcttgg atctaatgct cgtctagcgt 180
tggtggtttc tccttcagag cgatggcccg gtaagacgtg gccttaatca ctccccgccc 240
gtgatgaaca tcaggctggc ttcgatgatg gagaagcatg tgttggctcg gcatgttcta 300
gaggatgaag aaggatgacc cagggatttt gatgtaactt tattaatatt ttcttcctat 360
aatttgtact tccttttctt agaaaaaaac tattttgtac tgctagtttg attaatactc 420
gtggcttcac atgcgctggt ttggttatat aagagggagc atatgggtgt tgtcttttta 480
tataagaaaa aaaagagcaa aataagccac gcgccgatca agcctgcgaa ctgagtgtat 540
acccggccat gggcaaccca gactgacccg acccatcccg aaaaagctcg acccgtcccg 600
actcgacctt gcccacgggc cggcccagg cctagatttt gagcccgatg gctgggccga 660
catgttgtat ttgcgattta aggaagaggc ccggcccaag ggccgaggcc cgacgggttt 720
tttgactgat gggccggggt tgggccagat tattaggccc aacggccggg ccgggccggg 780
ctcgggccta agccttttgc ttgcgttcag gctttgatag gctcagcccg aagtccacat 840
ccacatcaac cacccccgcg tgccgatgaa gccatttctt tggaaggacc tgcgcgtgca 900
tccgacgcga cgcgctacac cgaagcctat actactacat ctcgtctcat cgccctcctc 960
ccagacgacg cctcgagaat cctcggctga ggctccactc cgcactcgca agtcgcaccc 1020
gcagccgcgc cgtccccagc agccgccgcc gaccgctccc cgtccggcag gtaagccccc 1080
cgagcccctc ctcgccgctc cgctcgcgcg gactcctagc tagctagggt tcccggcacc 1140
gattccgcgg cgctgcactc cggcgcaatg ctcgcggccg cggacgggcc cgccgcttcg 1200
ggggaagctc tgatctggtg gccggcgctc gctcgctcgc tcgcggtctc cggagcaaat 1260
cggccgcatc gagtggccgg agcaagctta ggatagttcg attatttccc ccatccccgt 1320
tggtcaggcc gagagggcca gtttgggcga cctcctggtg attccgctgc cgtggtgggg 1380
attgggtggt cgtggcccgg gtgtaggcgt ttgcaggtgg agtgagtgtt tccttccagg 1440
ttctatgctc acgcagctcg tgttattgct gggatccggg cgttcggcag gctaacattc 1500
accggatttt ggacctgcat tgttgcggcg cgtgccaggg gatggcgttt atgctggctt 1560
tggcgtggtg attttgtgga gttgagtggt caggttgtag gcatttgtag ttgagtgatc 1620
ccagctttca tgcccaccag cttgtattat tactcgagtt ggtcgttaac cgtgtttacc 1680
gaattttgga ccgccgttgt tgtggcacgt accaggggac agcgtttatg ctggtttgcg 1740
aggctacctc ctggtgattt cactctcggg tggtgggaat cgagtggtcg gggtgtaggc 1800
atatttgtag tggagcgatc ccaggtttta tgaccagaca tttagccgaa atttggacct 1860
acactattgt ggcacgtacc aggggatagc atttatgcag gttttggcgc gacacttctt 1920
ttgtcgggat tttgtggtgc aaacttaaat aatgacttcc ctaatgttga acaatggttc 1980
tggtatcgtg gactgccgaa accgttcttt ttggtagtct gagctacttt aagttgttac 2040
ttatgctctc gtgtgcgtgg gagactccac gtgctggttt ctcttacttg cttctcatgg 2100
tcatcactgg actgtgatat ttcttttcca gattttgaag gttcacagaa ggagagatg 2159

<210> SEQ ID NO 12
<211> LENGTH: 5200
<212> TYPE: DNA
<213> ORGANISM: Artificial sequence
<220> FEATURE:
<223> OTHER INFORMATION: pTaPK-like::RFL29a chimeric gene cassette

<400> SEQUENCE: 12
ttgtcccgcc gatgataagc tcggttggcg actggtccat gcccctccgg actccacaca 60
gccaggcgaa ttggtgagtc tgcaactgct gagctggaca caagtaagtc ataaatgcga 120
cgcaacaaaa aatgacgcca cgaaagttgg gacgttttct caattatccc ggaatattat 180
aatagcatgt tgtacgcgta cctcatgtag ccggaaaaca tctacagccg ggcaccccaa 240
actctatcat acgccccgac ggacggccaa gttagtgacc ggtcacgaaa gactgaccta 300
gacgggtaac ttaaacgggt ctcaagcgct caggctaacc ggcgcccctc atatccagtc 360
ccaaatgtag ggcggataag ggggcgccca ggagcatcga ggcgcgtcca tcacgtcggt 420
cctggcccac gatggcccac ccgcctccat atatattctt ctgcatccgc tgcctgggcc 480
aaacactatc cacttcactc ccctacgcca cccaaactcc tatccgacga tcacgagcct 540
tctccggttt gacgtgtagc agattcgacg acgaccagta cagatctgtc gactggggtg 600
tcaacccgtg cggtttggag aaggaaatgg ccatccgcat tgcactttgc catttccgga 660
ggacaacgcc cttccgacga caggatctcc cagcgcgagt ccattgcgtc ggtgcatcgg 720
gcgctcagat cctctggtgc tggatcatcg tggtcctcta ggcagccttc caatctccct 780
tccccatcac tggtccgtcg gagtacgagt cctatcgagg gtcagtgtgc ccgccgtggg 840
aagaagagga tgagggcggc tgaggtcagc gccttgctgc cgacatggcg gcggcggagg 900
cggctgatac aatggcacgg gcggccgcag aggaggaagg catccgcgtc cgcattgtaa 960
agaagcggca gcggaggaac acgcgcgtcc ctcgtccgag agcataatcg gcgatccgtg 1020
ccattgccgg actgccttcc aaggaggaga aggaggacaa cgatgggtca gatagctctg 1080
gcgatgagca gacttgactc gattcgtact gcctctttga tcggtacttg cgcgagaaga 1140
acgacaaggg caccaagaag ggcaaagaca gacatggatt gatcttcttc atagctagca 1200
tgtacgtagg ttaaacatgc caatttttga tagtccgatg tcatgtcctg atgtcgtagt 1260
aggaagatgt gtgtaatgca tcgtttatgt agttgcatga gtttgtatgg atttgagata 1320
aggtaattaa gatgttcgat tgtgagaagg gaaatttaag gcgtgaccaa cccgtgttca 1380
cggatgcgcc tggacgcatc cgctgaccgg atcgtgtcga cgcgcgcgag caaaggcggc 1440
cggcgaggcc aaccccaacc accactccgc ccgcgccgcc cctccctttc tcccgccttt 1500
tcggccccca tcaatggctc cctccacctc cttctagaag ccgcctgccc caccacccgt 1560
gctagcggta gtgtatcggg ttccccttcc ttccttcctc tcccctccct gcctgcactg 1620
tcccatcgct cgctttctcg cccgctccgt ggcggtggtg gtggtgcgtg gtgggggaga 1680
aagttggagg cgggggaaag gagacgcaaa gcggccaccc aaaaaggcac atatactttc 1740
tttctttcca ccgccgccct cctcctcctg gtcctggagg agttccgatc cccccccccc 1800
ccccccctct ctcttctttc tctctctttc ttgctctgct ctggaagcag gggagggagg 1860
gggttccgat ttgggcgggg aggcactgtt cgcggtgact cggttcggct gatttgggag 1920
gtcttctcgt ttgatccggg ctcgctgatt gattgattgg ttggttggtt cgtctccggc 1980
ggctcgattt gagggtcggt cggtccggcg agtgagtcgc catgccccgc ttctcctcca 2040
ccacgccaat gtcgccaccc cgcctccgcc tccgactctg cgcccgccac tcctcctcca 2100
cctctcatcc ctcacgcatc tgggatcccc acgccgcctt cgccgccgcg gcacagcggg 2160
cgagctctgg cacgctcact acggaggacg cacaccacct gtttgacgaa ttgctgcggc 2220
ggggcaatcc tgtccaggag cgtcccttga ataaatttct ggctgccctc gcccgcgcgc 2280
ccgcgtccgc atcctgctgc gatggccccg ccctggcagt cgccctcttc ggccgtttgt 2340
cccgagacgt cggacgacgg gtggcgcagc caaatgtctt cacctatggc gtcctcatgg 2400
actgctgctg ccgcgcttgc cgcacagatc tggtgctcgc cttctttggc cgtctcctca 2460
agacgggcct ggaggcaaac caagtcgtct tcaacaccct cctcaagggc ctttgccaca 2520
caaagcgggc ggatgaggct ctggacgtgc tgcttcacag gatgcctgag ctgggctgca 2580
ctcctaatgt ggtggcgtat aacaccgtta tccatggctt ctttaaggaa ggccatgtaa 2640
gcaaggcctg caatctgttc catgaaatgg cgcagcaggg cgttaagcct aatgtggtga 2700
catataactc agttatcgat gcgctgtgca aggccagagc catggacaag gcagaggtgg 2760
tccttcgtca gatgattgat gatggtgttg gacctgataa tgtgacgtat agtagcctca 2820
tccatggata ttcctcttca ggccactgga aggaggcagt tagggtattc aaagagatga 2880
caagtcggag ggttacagca gatgtgcata cttacaacat gtttatgacc tttctttgca 2940
aacatggaag aagcaaagaa gctgcaggaa tttttgatac catggctatc aagggcctga 3000
aacctgacaa cgtttcatat gctattctcc ttcatgggta tgccgccgaa ggatgcttag 3060
ttgatatgat taatctcttc aattcaatgg aaagagattg tattctacct gactgtcgta 3120
tcttcaacat actgattaat gcatatgcta aatctgggaa gcttgataag gctatgctta 3180
tcttcaatga aatgcagaaa caaggagtga gtccaaatgc agtcacatat tcaaccgtaa 3240
tacatgcatt ttgcaagaag ggtaggttgg atgatgctgt gataaagttt aatcagatga 3300
ttgatacagg agtacgaccg gacgcatctg tttatcgtcc cctaatccag ggtttttgta 3360
cacatggcga tttggtgaaa gcaaaggaat atgttactga aatgatgaag aaaggtatgc 3420
ctcctcctga tattatgttc ttcagttcaa tcatgcagaa cctatgcaca gaaggaaggg 3480
taacagaagc acgggatatc cttgacttga tagtgcacat tggtatgagg cctaatgtta 3540
tcatatttaa tttgctgatc ggtggatact gcctagtccg caagatggca gatgcattga 3600
aagtatttga tgatatggtg tcatatggtt tagaaccttg taactttacg tatggtatac 3660
ttattaatgg ctattgcaaa aatagaagga ttgatgacgg gcttattctg ttcaaagaga 3720
tgctgcacaa gggacttaaa cctacaactt ttaattataa cgtcatactg gatggattat 3780
ttctggctgg acaaactgtt gctgcaaaag agaagtttga tgagatggtt gaatctggag 3840
taagtgtgtg cattgataca tactctataa ttcttggtgg actttgtaga aatagctgca 3900
gtagcgaagc gatcaccctt ttccggaaat taagcgcaat gaatgtgaaa tttgatatta 3960
caattgtcaa tatcattatt ggtgccttat acagggtcga gagaaaccaa gaggctaagg 4020
atttgtttgc tgctatgcca gccaatggct tggttcctaa tgctgttacc tacaccgtaa 4080
tgatgacaaa tcttataaaa gaaggttcag tggaagaagc tgacaatctt ttcttatcca 4140
tggagaagag cggctgtact gccaactctt gcctgttaaa tcatatcatc agaaggttac 4200
tggaaaaagg agagatagtc aaggctggaa attatatgtc taaagttgat gcaaagagct 4260
actcacttga agctaaaact gtttcgctgc tgatctctct gttttcaagg aaagggaaat 4320
atagagaaca catcaaattg cttcctacaa agtatcagtt tctggaagaa gcagccacag 4380
ttgaatagtt ggtacatgat atctgaaatt taatttgcat cgcttgccat gggtccgtct 4440
gcttgtacaa gaaatgcatt ttctatttgt aaataggaag tcagtttaga acaagccatc 4500
aggatgacgc aaagagtaca attcagttgc accaccaata aaaaggcaga actagggctg 4560
ccaaaacaac actgaatcaa aactcaaaca gaaggagcag caaacttttt ttttttgaa 4620 gctggacagt ctgctagcca aacaactaca ggagactgtc aggcggggca tgtagtggct 4680
ggcgtctaag cgcctttgct tcttccacca tccatggctt agcctcacac ggaatcgagt 4740
caaccaattc ccgtcggttt tgggtggctc ccttgaagat gcaattgttt tcagcggcca 4800
gatacgcatg gtcagattaa tcagcgagtg tgccccttct gtctggttcg agaaagaatt 4860
tgaagagctg agcttgtccc tgctggaacc agtttgaggt tagttaatca taacagggta 4920
ctagagaggt gttttattga ctgttgatgt gtaatatgtt atatgccatc ctcttgatga 4980
ttacggtgat ctgtgaagag gcagcatgca aaagtctgaa tcacatatgc ttatgtaatt 5040
gtgttattat ttgtgcagct tctagacctt ttgccttgta gatggctaca tggatctagt 5100
tgtagcaatc tgtaactgtt agtgttttgt atatgctggc attgatgatt agggtgactt 5160
gtgaagcatg cagaagtctg aatcgtacat gcttgtctag 5200

<210> SEQ ID NO 13
<211> LENGTH: 5360
<212> TYPE: DNA
<213> ORGANISM: Artificial sequence
<220> FEATURE:
<223> OTHER INFORMATION: pTaRAE1-like::RFL29a chimeric gene cassette

<400> SEQUENCE: 13
gtggccctgc tcatccctgg atgttgacgg ctcaatggtg tatttttccc gtcgtgcgtc 60
ttcatcggtg aggttatggt atgtacaatt ttggcgcaca atgacggcga cttccctgat 120
ccttcgtcat cgtctccacc gtgttgattt tggtgctggc gtgaggcctg aggtatgtct 180
cttggatcta atgctcgtct agcgttggtg gtttctcctt cagagcgatg gcccggtaag 240
acgtggcctt aatcactccc cgcccgtgat gaacatcagg ctggcttcga tgatggagaa 300
gcatgtgttg gctcggcatg ttctagagga tgaagaagga tgacccaggg attttgatgt 360
aactttatta atattttctt cctataattt gtacttcctt ttcttagaaa aaaactattt 420
tgtactgcta gtttgattaa tactcgtggc ttcacatgcg ctggtttggt tatataagag 480
ggagcatatg ggtgttgtct ttttatataa gaaaaaaaag agcaaaataa gccacgcgcc 540
gatcaagcct gcgaactgag tgtatacccg gccatgggca acccagactg acccgaccca 600
tcccgaaaaa gctcgacccg tcccgactcg accttgccca cgggccgggc ccaggcctag 660
attttgagcc cgatggctgg gccgacatgt tgtatttgcg atttaaggaa gaggcccggc 720
ccaagggccg aggcccgacg ggttttttga ctgatgggcc ggggttgggc cagattatta 780
ggcccaacgg ccgggccggg ccgggctcgg gcctaagcct tttgcttgcg ttcaggcttt 840
gataggctca gcccgaagtc cacatccaca tcaaccaccc ccgcgtgccg atgaagccat 900

```
ttctttggaa ggacctgcgc gtgcatccga cgcgacgcgc tacaccgaag cctatactac    960
tacatctcgt ctcatcgccc tcctcccaga cgacgcctcg agaatcctcg gctgaggctc   1020
cactccgcac tcgcaagtcg cacccgcagc cgcgccgtcc ccagcagccg ccgccgaccg   1080
ctccccgtcc ggcaggtaag ccccccgagc ccctcctcgc cgctccgctc gcgcggactc   1140
ctagctagct agggttcccg gcaccgattc cgcggcgctg cactccggcg caatgctcgc   1200
ggccgcggac gggcccgccg cttcggggga agctctgatc tggtggccgg cgctcgctcg   1260
ctcgctcgcg gtctccggag caaatcggcc gcatcgagtg gccggagcaa gcttaggata   1320
gttcgattat ttcccccatc cccgttggtc aggccgagag ggccagtttg ggcgacctcc   1380
tggtgattcc gctgccgtgg tggggattgg gtggtcgtgg cccgggtgta ggcgtttgca   1440
ggtggagtga gtgtttcctt ccaggttcta tgctcacgca gctcgtgtta ttgctgggat   1500
ccgggcgttc ggcaggctaa cattcaccgg attttggacc tgcattgttg cggcgcgtgc   1560
caggggatgg cgtttatgct ggctttggcg tggtgatttt gtggagttga gtggtcaggt   1620
tgtaggcatt tgtagttgag tgatcccagc tttcatgccc accagcttgt attattactc   1680
gagttggtcg ttaaccgtgt ttaccgaatt ttggaccgcc gttgttgtgg cacgtaccag   1740
gggacagcgt ttatgctggt ttgcgaggct acctcctggt gatttcactc tcgggtggtg   1800
ggaatcgagt ggtcggggtg taggcatatt tgtagtggag cgatcccagg ttttatgacc   1860
agacatttag ccgaaatttg gacctacact attgtggcac gtaccagggg atagcattta   1920
tgcaggtttt ggcgcgacac ttcttttgtc gggattttgt ggtgcaaact taaataatga   1980
cttccctaat gttgaacaat ggttctggta tcgtggactg ccgaaaccgt tctttttggt   2040
agtctgagct actttaagtt gttacttatg ctctcgtgtg cgtgggagac tccacgtgct   2100
ggtttctctt acttgcttct catggtcatc actggactgt gatatttctt ttccagattt   2160
tgaaggttca cagaaggaga gatgccccgc ttctcctcca ccacgccaat gtcgccaccc   2220
cgcctccgcc tccgactctg cgcccgccac tcctcctcca cctctcatcc ctcacgcatc   2280
tgggatcccc acgccgcctt cgccgccgcg gcacagcggg cgagctctgg cacgctcact   2340
acggaggacg cacaccacct gtttgacgaa ttgctgcggc ggggcaatcc tgtccaggag   2400
cgtcccttga ataaatttct ggctgccctc gcccgcgcgc ccgcgtccgc atcctgctgc   2460
gatggccccg ccctggcagt cgccctcttc ggccgtttgt cccgagacgt cggacgacgg   2520
gtggcgcagc caaatgtctt cacctatggc gtcctcatgg actgctgctg ccgcgcttgc   2580
cgcacagatc tggtgctcgc cttctttggc cgtctcctca agacgggcct ggaggcaaac   2640
caagtcgtct tcaacaccct cctcaagggc ctttgccaca caaagcgggc ggatgaggct   2700
ctggacgtgc tgcttcacag gatgcctgag ctgggctgca ctcctaatgt ggtggcgtat   2760
aacaccgtta tccatggctt ctttaaggaa ggccatgtaa gcaaggcctg caatctgttc   2820
catgaaatgg cgcagcaggg cgttaagcct aatgtggtga catataactc agttatcgat   2880
gcgctgtgca aggccagagc catggacaag gcagaggtgg tccttcgtca gatgattgat   2940
gatggtgttg gacctgataa tgtgacgtat agtagcctca tccatggata ttcctcttca   3000
ggccactgga aggaggcagt tagggtattc aaagagatga caagtcggag ggttacagca   3060
gatgtgcata cttacaacat gtttatgacc tttctttgca aacatggaag aagcaaagaa   3120
gctgcaggaa tttttgatac catggctatc aagggcctga aacctgacaa cgtttcatat   3180
gctattctcc ttcatgggta tgccgccgaa ggatgcttag ttgatatgat taatctcttc   3240
```

```
aattcaatgg aaagagattg tattctacct gactgtcgta tcttcaacat actgattaat   3300
gcatatgcta aatctgggaa gcttgataag gctatgctta tcttcaatga aatgcagaaa   3360
caaggagtga gtccaaatgc agtcacatat tcaaccgtaa tacatgcatt ttgcaagaag   3420
ggtaggttgg atgatgctgt gataaagttt aatcagatga ttgatacagg agtacgaccg   3480
gacgcatctg tttatcgtcc cctaatccag ggtttttgta cacatggcga tttggtgaaa   3540
gcaaaggaat atgttactga aatgatgaag aaaggtatgc ctcctcctga tattatgttc   3600
ttcagttcaa tcatgcagaa cctatgcaca gaaggaaggg taacagaagc acgggatatc   3660
cttgacttga tagtgcacat tggtatgagg cctaatgtta tcatatttaa tttgctgatc   3720
ggtggatact gcctagtccg caagatggca gatgcattga aagtatttga tgatatggtg   3780
tcatatggtt tagaaccttg taactttacg tatggtatac ttattaatgg ctattgcaaa   3840
aatagaagga ttgatgacgg gcttattctg ttcaaagaga tgctgcacaa gggacttaaa   3900
cctacaactt ttaattataa cgtcatactg gatggattat ttctggctgg acaaactgtt   3960
gctgcaaaag agaagtttga tgagatggtt gaatctggag taagtgtgtg cattgataca   4020
tactctataa ttcttggtgg actttgtaga aatagctgca gtagcgaagc gatcacccctt   4080
ttccggaaat taagcgcaat gaatgtgaaa tttgatatta caattgtcaa tatcattatt   4140
ggtgccttat acagggtcga gagaaaccaa gaggctaagg atttgtttgc tgctatgcca   4200
gccaatggct tggttcctaa tgctgttacc tacaccgtaa tgatgacaaa tcttataaaa   4260
gaaggttcag tggaagaagc tgacaatctt ttcttatcca tggagaagag cggctgtact   4320
gccaactctt gcctgttaaa tcatatcatc agaaggttac tggaaaaagg agagatagtc   4380
aaggctggaa attatatgtc taaagttgat gcaaagagct actcacttga agctaaaact   4440
gtttcgctgc tgatctctct gttttcaagg aaagggaaat atagagaaca catcaaattg   4500
cttcctacaa agtatcagtt tctggaagaa gcagccacag ttgaatagtt ggtacatgat   4560
atctgaaatt taatttgcat cgcttgccat gggtccgtct gcttgtacaa gaaatgcatt   4620
ttctatttgt aaataggaag tcagtttaga acaagccatc aggatgacgc aaagagtaca   4680
attcagttgc accaccaata aaaaggcaga actagggctg ccaaaacaac actgaatcaa   4740
aactcaaaca gaaggagcag caaacttttt ttttttgaa gctggacagt ctgctagcca   4800
aacaactaca ggagactgtc aggcggggca tgtagtggct ggcgtctaag cgcctttgct   4860
tcttccacca tccatggctt agcctcacac ggaatcgagt caaccaattc ccgtcggttt   4920
tgggtggctc ccttgaagat gcaattgttt tcagcggcca gatacgcatg gtcagattaa   4980
tcagcgagtg tgccccttct gtctggttcg agaaagaatt tgaagagctg agcttgtccc   5040
tgctggaacc agtttgaggt tagttaatca taacagggta ctagagaggt gttttattga   5100
ctgttgatgt gtaatatgtt atatgccatc ctcttgatga ttacggtgat ctgtgaagag   5160
gcagcatgca aaagtctgaa tcacatatgc ttatgtaatt gtgttattat ttgtgcagct   5220
tctagacctt ttgccttgta gatggctaca tggatctagt tgtagcaatc tgtaactgtt   5280
agtgttttgt atatgctggc attgatgatt agggtgactt gtgaagcatg cagaagtctg   5340
aatcgtacat gcttgtctag                                               5360
```

<210> SEQ ID NO 14
<211> LENGTH: 2367
<212> TYPE: DNA
<213> ORGANISM: Triticum aestivum (var. Spelt)

<400> SEQUENCE: 14

```
atgccccgct tctcctccac cacgccaatg tcgccacccc gcctccgcct ccgactctgc     60
gcccgccact cctcctccac ctctcatccc tcacgcatct gggatcccca cgccgccttc    120
gccgccgcgg cacagcgggc gagctctggc acgctcacta cggaggacgc acaccacctg    180
tttgacgaat tgctgcggcg gggcaatcct gtccaggagc gtcccttgaa taaatttctg    240
gctgccctcg cccgcgcgcc cgcgtccgca tcctgctgcg atggccccgc cctggcagtc    300
gccctcttcg gccgtttgtc ccgagacgtc ggacgacggg tggcgcagcc aaatgtcttc    360
acctatggcg tcctcatgga ctgctgctgc cgcgcttgcc gcacagatct ggtgctcgcc    420
ttctttggcc gtctcctcaa gacgggcctg gaggcaaacc aagtcgtctt caacaccctc    480
ctcaagggcc tttgccacac aaagcgggcg gatgaggctc tggacgtgct gcttcacagg    540
atgcctgagc tgggctgcac tcctaatgtg gtggcgtata acaccgttat ccatggcttc    600
tttaaggaag gccatgtaag caaggcctgc aatctgttcc atgaaatggc gcagcagggc    660
gttaagccta atgtggtgac atataactca gttatcgatg cgctgtgcaa ggccagagcc    720
atggacaagg cagaggtggt ccttcgtcag atgattgatg atggtgttgg acctgataat    780
gtgacgtata gtagcctcat ccatggatat tcctcttcag gccactggaa ggaggcagtt    840
agggtattca aagagatgac aagtcggagg gttacagcag atgtgcatac ttacaacatg    900
tttatgacct ttctttgcaa acatggaaga agcaaagaag ctgcaggaat tttgatacc     960
atggctatca agggcctgaa acctgacaac gtttcatatg ctattctcct tcatgggtat   1020
gccgccgaag gatgcttagt tgatatgatt aatctcttca attcaatgga aagagattgt   1080
attctacctg actgtcgtat cttcaacata ctgattaatg catatgctaa atctgggaag   1140
cttgataagg ctatgcttat cttcaatgaa atgcagaaac aaggagtgag tccaaatgca   1200
gtcacatatt caaccgtaat acatgcattt tgcaagaagg gtaggttgga tgatgctgtg   1260
ataaagttta atcagatgat tgatacagga gtacgaccgg acgcatctgt ttatcgtccc   1320
ctaatccagg gtttttgtac acatggcgat ttggtgaaag caaaggaata tgttactgaa   1380
atgatgaaga aggtatgcc tcctcctgat attatgttct tcagttcaat catgcagaac    1440
ctatgcacag aaggaagggt aacagaagca cgggatatcc ttgacttgat agtgcacatt   1500
ggtatgaggc ctaatgttat catatttaat ttgctgatcg gtggatactg cctagtccgc   1560
aagatggcag atgcattgaa agtatttgat gatatggtgt catatggttt agaaccttgt   1620
aactttacgt atggtatact tattaatggc tattgcaaaa atagaaggat tgatgacggg   1680
cttattctgt tcaaagagat gctgcacaag ggacttaaac ctacaacttt taattataac   1740
gtcatactgg atggattatt tctggctgga caaactgttg ctgcaaaaga gaagtttgat   1800
gagatggttg aatctggagt aagtgtgtgc attgatacat actctataat tcttggtgga   1860
ctttgtagaa atagctgcag tagcgaagcg atcacccttt tccggaaatt aagcgcaatg   1920
aatgtgaaat ttgatattac aattgtcaat atcattattg gtgccttata cagggtcgag   1980
agaaaccaag aggctaagga tttgtttgct gctatgccag ccaatggctt ggttcctaat   2040
gctgttacct acaccgtaat gatgacaaat cttataaaag aaggttcagt ggaagaagct   2100
gacaatcttt tcttatccat ggagaagagc ggctgtactg ccaactcttg cctgttaaat   2160
catatcatca gaaggttact ggaaaaagga gagatagtca aggctggaaa ttatatgtct   2220
aaagttgatg caaagagcta ctcacttgaa gctaaaactg tttcgctgct gatctctctg   2280
ttttcaagga aagggaaata tagagaacac atcaaattgc ttcctacaaa gtatcagttt   2340
```

ctggaagaag cagccacagt tgaatag 2367

<210> SEQ ID NO 15
<211> LENGTH: 788
<212> TYPE: PRT
<213> ORGANISM: Triticum aestivum (var. Spelt)

<400> SEQUENCE: 15

```
Met Pro Arg Phe Ser Ser Thr Thr Pro Met Ser Pro Pro Arg Leu Arg
1               5                   10                  15

Leu Arg Leu Cys Ala Arg His Ser Ser Ser Thr Ser His Pro Ser Arg
            20                  25                  30

Ile Trp Asp Pro His Ala Ala Phe Ala Ala Ala Ala Gln Arg Ala Ser
        35                  40                  45

Ser Gly Thr Leu Thr Thr Glu Asp Ala His His Leu Phe Asp Glu Leu
    50                  55                  60

Leu Arg Arg Gly Asn Pro Val Gln Glu Arg Pro Leu Asn Lys Phe Leu
65                  70                  75                  80

Ala Ala Leu Ala Arg Ala Pro Ala Ser Ala Ser Cys Cys Asp Gly Pro
                85                  90                  95

Ala Leu Ala Val Ala Leu Phe Gly Arg Leu Ser Arg Asp Val Gly Arg
            100                 105                 110

Arg Val Ala Gln Pro Asn Val Phe Thr Tyr Gly Val Leu Met Asp Cys
        115                 120                 125

Cys Cys Arg Ala Cys Arg Thr Asp Leu Val Leu Ala Phe Phe Gly Arg
    130                 135                 140

Leu Leu Lys Thr Gly Leu Glu Ala Asn Gln Val Val Phe Asn Thr Leu
145                 150                 155                 160

Leu Lys Gly Leu Cys His Thr Lys Arg Ala Asp Glu Ala Leu Asp Val
                165                 170                 175

Leu Leu His Arg Met Pro Glu Leu Gly Cys Thr Pro Asn Val Val Ala
            180                 185                 190

Tyr Asn Thr Val Ile His Gly Phe Phe Lys Glu Gly His Val Ser Lys
        195                 200                 205

Ala Cys Asn Leu Phe His Glu Met Ala Gln Gln Gly Val Lys Pro Asn
    210                 215                 220

Val Val Thr Tyr Asn Ser Val Ile Asp Ala Leu Cys Lys Ala Arg Ala
225                 230                 235                 240

Met Asp Lys Ala Glu Val Val Leu Arg Gln Met Ile Asp Asp Gly Val
                245                 250                 255

Gly Pro Asp Asn Val Thr Tyr Ser Ser Leu Ile His Gly Tyr Ser Ser
            260                 265                 270

Ser Gly His Trp Lys Glu Ala Val Arg Val Phe Lys Glu Met Thr Ser
        275                 280                 285

Arg Arg Val Thr Ala Asp Val His Thr Tyr Asn Met Phe Met Thr Phe
    290                 295                 300

Leu Cys Lys His Gly Arg Ser Lys Glu Ala Ala Gly Ile Phe Asp Thr
305                 310                 315                 320

Met Ala Ile Lys Gly Leu Lys Pro Asp Asn Val Ser Tyr Ala Ile Leu
                325                 330                 335

Leu His Gly Tyr Ala Ala Glu Gly Cys Leu Val Asp Met Ile Asn Leu
            340                 345                 350

Phe Asn Ser Met Glu Arg Asp Cys Ile Leu Pro Asp Cys Arg Ile Phe
        355                 360                 365
```

```
Asn Ile Leu Ile Asn Ala Tyr Ala Lys Ser Gly Lys Leu Asp Lys Ala
    370                 375                 380

Met Leu Ile Phe Asn Glu Met Gln Lys Gln Gly Val Ser Pro Asn Ala
385                 390                 395                 400

Val Thr Tyr Ser Thr Val Ile His Ala Phe Cys Lys Lys Gly Arg Leu
                405                 410                 415

Asp Asp Ala Val Ile Lys Phe Asn Gln Met Ile Asp Thr Gly Val Arg
            420                 425                 430

Pro Asp Ala Ser Val Tyr Arg Pro Leu Ile Gln Gly Phe Cys Thr His
        435                 440                 445

Gly Asp Leu Val Lys Ala Lys Glu Tyr Val Thr Glu Met Met Lys Lys
    450                 455                 460

Gly Met Pro Pro Pro Asp Ile Met Phe Phe Ser Ser Ile Met Gln Asn
465                 470                 475                 480

Leu Cys Thr Glu Gly Arg Val Thr Glu Ala Arg Asp Ile Leu Asp Leu
                485                 490                 495

Ile Val His Ile Gly Met Arg Pro Asn Val Ile Ile Phe Asn Leu Leu
            500                 505                 510

Ile Gly Gly Tyr Cys Leu Val Arg Lys Met Ala Asp Ala Leu Lys Val
        515                 520                 525

Phe Asp Asp Met Val Ser Tyr Gly Leu Glu Pro Cys Asn Phe Thr Tyr
    530                 535                 540

Gly Ile Leu Ile Asn Gly Tyr Cys Lys Asn Arg Arg Ile Asp Asp Gly
545                 550                 555                 560

Leu Ile Leu Phe Lys Glu Met Leu His Lys Gly Leu Lys Pro Thr Thr
                565                 570                 575

Phe Asn Tyr Asn Val Ile Leu Asp Gly Leu Phe Leu Ala Gly Gln Thr
            580                 585                 590

Val Ala Ala Lys Glu Lys Phe Asp Glu Met Val Glu Ser Gly Val Ser
        595                 600                 605

Val Cys Ile Asp Thr Tyr Ser Ile Ile Leu Gly Gly Leu Cys Arg Asn
    610                 615                 620

Ser Cys Ser Ser Glu Ala Ile Thr Leu Phe Arg Lys Leu Ser Ala Met
625                 630                 635                 640

Asn Val Lys Phe Asp Ile Thr Ile Val Asn Ile Ile Ile Gly Ala Leu
                645                 650                 655

Tyr Arg Val Glu Arg Asn Gln Glu Ala Lys Asp Leu Phe Ala Ala Met
            660                 665                 670

Pro Ala Asn Gly Leu Val Pro Asn Ala Val Thr Tyr Thr Val Met Met
        675                 680                 685

Thr Asn Leu Ile Lys Glu Gly Ser Val Glu Glu Ala Asp Asn Leu Phe
    690                 695                 700

Leu Ser Met Glu Lys Ser Gly Cys Thr Ala Asn Ser Cys Leu Leu Asn
705                 710                 715                 720

His Ile Ile Arg Arg Leu Leu Glu Lys Gly Glu Ile Val Lys Ala Gly
                725                 730                 735

Asn Tyr Met Ser Lys Val Asp Ala Lys Ser Tyr Ser Leu Glu Ala Lys
            740                 745                 750

Thr Val Ser Leu Leu Ile Ser Leu Phe Ser Arg Lys Gly Lys Tyr Arg
        755                 760                 765

Glu His Ile Lys Leu Leu Pro Thr Lys Tyr Gln Phe Leu Glu Glu Ala
    770                 775                 780

Ala Thr Val Glu
```

785

<210> SEQ ID NO 16
<211> LENGTH: 6120
<212> TYPE: DNA
<213> ORGANISM: Triticum aestivum (var. Spelt)

<400> SEQUENCE: 16

```
tcggatccag ctcgtctctc gtcttactca gggtcggtca tcccggtgac cttgcctctg     60
gcagcgaggg ggtgtgcgtg ctctatggtg ggccttgtga ggcgatggcg cggttgctgc    120
gcaggggtgt gcatgccagc gattgcgcgg gccagcttgt gtcggctgcg tgagggtgtt    180
ggttgagtct gctccaagcg caagcttgcc cggctatggc cggccggtgc tggcggcgcc    240
tatgggcgtc gtttcccttg ttgaaggcgt tgttgtggag ttcttcgacc tactacaatc    300
tcgaatctgg ttcttcgggc gaaaacctcg ccccatctag gtcgggcaac gacgtcgtct    360
gtacggtgtt ttcccccttt ggggcgttgc tttgaagacc ggttatcctt tcccgtgcta    420
cctttgggct ggtcgtgcat ggtgtcatgg ttggctggtg ctcaaccggt gatgcgagtg    480
gttagcgttg cgactcgtgc ggtgacgaag atggtgatgc gcggagctgg gtcgcggctt    540
gtccttctga tatcggcggt tcggttcccc tttgggtgcg tctgtgcttg tttctcactg    600
tgacagagaa gttgaagcta catgcggcgg gggccctgcg gcaatgatga ctccatgagg    660
gtggcttcgg cggacgatgc tctccgcagg ttgcactgga ctagcttggt gtgaggcttg    720
caactttctc ctgtgatgct catcaacaaa atcggagatg tcggtcctcg acgcctgcgg    780
ccgatcgttt ggcttggctg tcgaggtcct cgggtgccgt ttgttcggag ggtcttgat     840
gggtcgtcag cgaggaaatc ggagttgcct gctcgtggag aggcgatgac gatgacattg    900
cttgcagcct cgacggtgtc ctctcgtcag cagtatgtgt gtgatcttgt cagtgccagg    960
tcggccggag tgctctattc gatgggcgtg ttttaattaa ccgggcaact ctcttcttct   1020
taatcaatga aaatggcaag tcttttacct cgtttcaaaa agagttaaat gcactggagg   1080
tcctaaaggt ttcgtcgggg tgtcacttta gtcctatttc ttccaaaatg cacctttagg   1140
tcctaattct ttattaattg gttcacccga ggtccttttc cacgagcgct agctgaccag   1200
cacacgtgcc gcattgaccc acgccacatc gatagagggt ctaaccgcca ggcgagaagc   1260
ttcgcaaaga gacccccccc cctcttagtg gcaccctctc tcctctttca cggtactttg   1320
gcgacattgg aggcgagcga cagaggcaac cggaggtgat ctggaggtaa tttgtgtggg   1380
tgcccgtgaa gatgcccctt ctacgacggc cagtgagcaa tcctcctcca tgttaccgta   1440
agaaccctaa tcttgtcgac gatcttctcc tgtagctctt ctaatatgtc ataactttgc   1500
cataatcaat agttgtagtc cttgatttac tttgatttgc ataacggtgc tacggacatg   1560
gcaaaaagga cacaccacca gcggcaacat acccgccgaa gttggagctt gcttcgccgc   1620
accggcggcg gtgctgagga tgttgccatg ctcctcatct tagttgtttc cttgccgagg   1680
agcttgaagt tccggccatg gataggttta gggaacgcgc gcgccgagag agagagcaga   1740
tttggggaag aaataaagcc agggactggg gaatgagaag ataatgttta taaggggttt   1800
tctgtaaaaa gaaagagcaa cctacgcggc ccttctgtcg atttggcatg ggtcaacgca   1860
ccacacgagc aggtcaacga gcgctcgtga gaaaaaggac ctagggtaaa ccacttacta   1920
aagaattagg acctaaaggt gcattttgga cgaaataaga ctaaagtgac accctgacga   1980
atttttttagg accttgagtg catttaactc tttcaaaaaa taaagatgct aaaaaaacta   2040
aatgcttaaa aatacatttt tctatgggaa tacttaaaaa tactagtata atttgatggc   2100
```

ttcctagtat atttctagcg cttacaacta aatttatatt cttggtctaa ataaaattat 2160
aatctgataa attatgtgat atgtatatag ccatatgaga ccataattta attttacctg 2220
caaaaagtaa gtaatagtaa tagtagtact acatactccc tccgtccgaa aatacttgtc 2280
gaagaatttg atgaaaatgg atgcatctag aacaagaata catctagata catcaatctc 2340
cccgacaagt atttccgaac ggagggagta ctagataata agataactat ccaaaaaaaa 2400
aaagataact gaaggttgcc acctagcaca ttcacattgg tacaacttgg aaaagcacag 2460
ccccgtcgtc ctgctcccag ttgagttcgc gacctacaca ccggccatgc cccgcttctc 2520
ctccaccacg ccaatgtcgc caccccgcct ccgcctccga ctctgcgccc gccactcctc 2580
ctccacctct catccctcac gcatctggga tccccacgcc gccttcgccg ccgcggcaca 2640
gcgggcgagc tctggcacgc tcactacgga ggacgcacac cacctgtttg acgaattgct 2700
gcggcggggc aatcctgtcc aggagcgtcc cttgaataaa tttctggctg ccctcgcccg 2760
cgcgcccgcg tccgcatcct gctgcgatgg ccccgccctg gcagtcgccc tcttcggccg 2820
tttgtcccga gacgtcggac gacgggtggc gcagccaaat gtcttcacct atggcgtcct 2880
catggactgc tgctgccgcg cttgccgcac agatctggtg ctcgccttct ttggccgtct 2940
cctcaagacg ggcctggagg caaaccaagt cgtcttcaac accctcctca agggcctttg 3000
ccacacaaag cgggcggatg aggctctgga cgtgctgctt cacaggatgc ctgagctggg 3060
ctgcactcct aatgtggtgg cgtataacac cgttatccat ggcttcttta aggaaggcca 3120
tgtaagcaag gcctgcaatc tgttccatga aatggcgcag cagggcgtta agcctaatgt 3180
ggtgacatat aactcagtta tcgatgcgct gtgcaaggcc agagccatgg acaaggcaga 3240
ggtggtcctt cgtcagatga ttgatgatgg tgttggacct gataatgtga cgtatagtag 3300
cctcatccat ggatattcct cttcaggcca ctggaaggag gcagttaggg tattcaaaga 3360
gatgacaagt cggagggtta cagcagatgt gcatacttac aacatgttta tgacctttct 3420
ttgcaaacat ggaagaagca aagaagctgc aggaattttt gataccatgg ctatcaaggg 3480
cctgaaacct gacaacgttt catatgctat tctccttcat gggtatgccg ccgaaggatg 3540
cttagttgat atgattaatc tcttcaattc aatggaaaga gattgtattc tacctgactg 3600
tcgtatcttc aacatactga ttaatgcata tgctaaatct gggaagcttg ataaggctat 3660
gcttatcttc aatgaaatgc agaaacaagg agtgagtcca aatgcagtca catattcaac 3720
cgtaatacat gcattttgca agaagggtag gttggatgat gctgtgataa agtttaatca 3780
gatgattgat acaggagtac gaccggacgc atctgtttat cgtcccctaa tccagggttt 3840
ttgtacacat ggcgatttgg tgaaagcaaa ggaatatgtt actgaaatga tgaagaaagg 3900
tatgcctcct cctgatatta tgttcttcag ttcaatcatg cagaacctat gcacagaagg 3960
aagggtaaca gaagcacggg atatccttga cttgatagtg cacattggta tgaggcctaa 4020
tgttatcata tttaatttgc tgatcggtgg atactgccta gtccgcaaga tggcagatgc 4080
attgaaagta tttgatgata tggtgtcata tggtttagaa ccttgtaact ttacgtatgg 4140
tatacttatt aatggctatt gcaaaaatag aaggattgat gacgggctta ttctgttcaa 4200
agagatgctg cacaagggac ttaaacctac aacttttaat tataacgtca tactggatgg 4260
attatttctg gctggacaaa ctgttgctgc aaaagagaag tttgatgaga tggttgaatc 4320
tggagtaagt gtgtgcattg atacatactc tataattctt ggtggacttt gtagaaatag 4380
ctgcagtagc gaagcgatca cccttttccg gaaattaagc gcaatgaatg tgaaatttga 4440

```
tattacaatt gtcaatatca ttattggtgc cttatacagg gtcgagagaa accaagaggc   4500
taaggatttg tttgctgcta tgccagccaa tggcttggtt cctaatgctg ttacctacac   4560
cgtaatgatg acaaatctta taaaagaagg ttcagtggaa gaagctgaca atcttttctt   4620
atccatggag aagagcggct gtactgccaa ctcttgcctg ttaaatcata tcatcagaag   4680
gttactggaa aaaggagaga tagtcaaggc tggaaattat atgtctaaag ttgatgcaaa   4740
gagctactca cttgaagcta aaactgtttc gctgctgatc tctctgtttt caaggaaagg   4800
gaaatataga gaacacatca aattgcttcc tacaaagtat cagtttctgg aagaagcagc   4860
cacagttgaa tagttggtac atgatatctg aaatttaatt tgcatcgctt gccatgggtc   4920
cgtctgcttg tacaagaaat gcattttcta tttgtaaata ggaagtcagt ttagaacaag   4980
ccatcaggat gacgcaaaga gtacaattca gttgcaccac caataaaaag gcagaactag   5040
ggctgccaaa acaacactga atcaaaactc aaacagaagg agcagcaaac ttttttttt    5100
ttgaagctgg acagtctgct agccaaacaa ctacaggaga ctgtcaggcg gggcatgtag   5160
tggctggcgt ctaagcgcct ttgcttcttc caccatccat ggcttagcct cacacggaat   5220
cgagtcaacc aattcccgtc ggttttgggt ggctcccttg aagatgcaat tgttttcagc   5280
ggccagatac gcatggtcag attaatcagc gagtgtgccc cttctgtctg gttcgagaaa   5340
gaatttgaag agctgagctt gtccctgctg gaaccagttt gaggttagtt aatcataaca   5400
gggtactaga gaggtgtttt attgactgtt gatgtgtaat atgttatatg ccatcctctt   5460
gatgattacg gtgatctgtg aagaggcagc atgcaaaagt ctgaatcaca tatgcttatg   5520
taattgtgtt attatttgtg cagcttctag accttttgcc ttgtagatgg ctacatggat   5580
ctagttgtag caatctgtaa ctgttagtgt tttgtatatg ctggcattga tgattagggt   5640
gacttgtgaa gcatgcagaa gtctgaatca tacatgcttg tctagttatt tttggagctc   5700
tctctttgcc atgtacatgt tttatggatg cagttgtagt ctgtatgtgc tggcatttaa   5760
tatgagggct ggtctgcaat ttttctgttt tgatcgatac agcgccatgt tgagtttaac   5820
cctgtaactt ggcttaacta gatcatgctg gtgttatctc taggaatccc aatatcaata   5880
ctctctgttg ttgcacaaac tgacgcagat caatgtccag aggtaatatg gttctgcctg   5940
taattttcat cgactgtcag catgttcctt ttttatttag tactctgtat atcacggcgg   6000
tatgactata ataaggatat acggctggtg catttgagc  ttctctgttt cttgggataa   6060
agctgataaa tttctattct tgttggcttt ggtagtatga acagaaagca ggcagtaata   6120
```

<210> SEQ ID NO 17
<211> LENGTH: 1212
<212> TYPE: DNA
<213> ORGANISM: Triticum aestivum (var. Spelt)

<400> SEQUENCE: 17

```
atggggaact gctggggcgc caagatcagc tccgacacct cctcctcctc cccttcaggg     60
acgaattcca agtatgctag taggaatggg gcggccttga gcagctccag cagctatgcc    120
tccgcggcgt cagtgccgcg gagcgagggt gagattctgg agtcagcaaa tgtcaaggcc    180
tttaccttca atgagctgag gaccgccacg agaaacttca ggccggacag tgtgctaggc    240
gagggagggt ttgggtcagt cttcaagggg tggatcgatg agaagaccct caccccaacc    300
aagccaggca ccgggatggt cattgctgta aagaagctta accaggaaag ctatcagggc    360
catagggaat ggctggctga agtgaattac cttggacaac tatcgcaccc gaatcttgta    420
aagctcgttg ggtactgtgt tgaagacgaa cagcggcttc tcgtctacga gttcatgcct    480
```

```
cgtgggagtt tggagaatca tctcttcagg aggagtacac atttccagcc gctctcctgg    540

aaccttcgga tgaaaattgc ccatggagca gcaaaagggc tcgcatttct ccacagtgac    600

aaggccaaag tcatctaccg cgatttcaaa acctctaata tcctcctaga tgcgaactat    660

gacgcaaagc tctcagattt cggcctggcg aaggacggac cgacgggtga caagagccat    720

gtgtccacaa gggtgatggg gacatatggg tatgctgcac cagaatacct tgcaacaggc    780

caccttacca cgaagagcga cgtgtacagc ttcggcgtgg tcctcctgga gatgctctcg    840

gggcgtcgcg ctgtggacaa gaaccggccg accggcgagc acaacctggt ggagtgggcg    900

cggccgtacc tgacaagcaa gcggcgcatc ttccgcgtcc tggatccccg tctaggcggg    960

cagtactccc tcgccaaggc ccagaaggcg gcgtcgctgg cgctgcagtg cctctcgatg   1020

gactcgagga acaggccgag catggagcag gtcgtcgtgg cgctggagca gctccacgac   1080

gccaaggagg gagggaacag ccctcgcccg cagctgcaga gaaagccgag cagcaaccgg   1140

ggcgtgaacg gctcgagatc gtcgtcgacc aaggggaaca ccaagaagcc cgcctcaccg   1200

agaccggttt ga                                                       1212
```

<210> SEQ ID NO 18
<211> LENGTH: 403
<212> TYPE: PRT
<213> ORGANISM: Triticum aestivum (var. Spelt)

<400> SEQUENCE: 18

```
Met Gly Asn Cys Trp Gly Ala Lys Ile Ser Ser Asp Thr Ser Ser Ser
1               5                   10                  15

Ser Pro Ser Gly Thr Asn Ser Lys Tyr Ala Ser Arg Asn Gly Ala Ala
            20                  25                  30

Leu Ser Ser Ser Ser Ser Tyr Ala Ser Ala Ala Ser Val Pro Arg Ser
        35                  40                  45

Glu Gly Glu Ile Leu Glu Ser Ala Asn Val Lys Ala Phe Thr Phe Asn
    50                  55                  60

Glu Leu Arg Thr Ala Thr Arg Asn Phe Arg Pro Asp Ser Val Leu Gly
65                  70                  75                  80

Glu Gly Gly Phe Gly Ser Val Phe Lys Gly Trp Ile Asp Glu Lys Thr
                85                  90                  95

Leu Thr Pro Thr Lys Pro Gly Thr Gly Met Val Ile Ala Val Lys Lys
            100                 105                 110

Leu Asn Gln Glu Ser Tyr Gln Gly His Arg Glu Trp Leu Ala Glu Val
        115                 120                 125

Asn Tyr Leu Gly Gln Leu Ser His Pro Asn Leu Val Lys Leu Val Gly
    130                 135                 140

Tyr Cys Val Glu Asp Glu Gln Arg Leu Leu Val Tyr Glu Phe Met Pro
145                 150                 155                 160

Arg Gly Ser Leu Glu Asn His Leu Phe Arg Arg Ser Thr His Phe Gln
                165                 170                 175

Pro Leu Ser Trp Asn Leu Arg Met Lys Ile Ala His Gly Ala Ala Lys
            180                 185                 190

Gly Leu Ala Phe Leu His Ser Asp Lys Ala Lys Val Ile Tyr Arg Asp
        195                 200                 205

Phe Lys Thr Ser Asn Ile Leu Leu Asp Ala Asn Tyr Asp Ala Lys Leu
    210                 215                 220

Ser Asp Phe Gly Leu Ala Lys Asp Gly Pro Thr Gly Asp Lys Ser His
225                 230                 235                 240
```

```
Val Ser Thr Arg Val Met Gly Thr Tyr Gly Tyr Ala Ala Pro Glu Tyr
                245                 250                 255

Leu Ala Thr Gly His Leu Thr Thr Lys Ser Asp Val Tyr Ser Phe Gly
            260                 265                 270

Val Val Leu Leu Glu Met Leu Ser Gly Arg Arg Ala Val Asp Lys Asn
        275                 280                 285

Arg Pro Thr Gly Glu His Asn Leu Val Glu Trp Ala Arg Pro Tyr Leu
    290                 295                 300

Thr Ser Lys Arg Arg Ile Phe Arg Val Leu Asp Pro Arg Leu Gly Gly
305                 310                 315                 320

Gln Tyr Ser Leu Ala Lys Ala Gln Lys Ala Ala Ser Leu Ala Leu Gln
                325                 330                 335

Cys Leu Ser Met Asp Ser Arg Asn Arg Pro Ser Met Glu Gln Val Val
            340                 345                 350

Val Ala Leu Glu Gln Leu His Asp Ala Lys Glu Gly Gly Asn Ser Pro
        355                 360                 365

Arg Pro Gln Leu Gln Arg Lys Pro Ser Ser Asn Arg Gly Val Asn Gly
    370                 375                 380

Ser Arg Ser Ser Ser Thr Lys Gly Asn Thr Lys Lys Pro Ala Ser Pro
385                 390                 395                 400

Arg Pro Val
```

<210> SEQ ID NO 19
<211> LENGTH: 7170
<212> TYPE: DNA
<213> ORGANISM: Triticum aestivum (var. Spelt)

<400> SEQUENCE: 19

```
ctgtcgtact cgtgacggcc atctacacgt ataatactcc cacttgcaca tacgtactat     60

gcacatgtac aacacatgat aataaagttt ggcaaacatt gatcgttgcg gggcgagctg    120

caggtccatg ttcacattgt attttctcag ccaagcagaa caatactaga ggacatacgc    180

cattgacttg acaatttggt taccacccac aaactgtatt gaccagatat atacaatata    240

tgtaataaat gttataaaaa gaaatggaaa ataataattt cggtgcatga atcgtgcctc    300

gtccacgaat ggtgatacta gacgttttcc cggctagcta gtaaaaaagt aggcgatcgg    360

tgtacgggta tcgccgtaac cactaatatt gtcgcaccta cgtatacgca tgtaccggcc    420

atattataaa caaaacacac gaagaagaaa cggaggcgtt gtacggacgg cgatcgtgac    480

tgcacgatgt gaggagccgt cccacactct atcgttttcc taccctagcc gccgccgtca    540

ccaagtgagt agggcgaggc gactcttttc cttcgatctc caccggccgg tgcgctggcc    600

ccctctccct tcggccgctg ctccggcggc aggagggagg gggaccccgt tcctctgttc    660

tgtagttagg ttttggattt gtaggtcgtg atgcgtcgtt tgggtggtgg gagcggcgtc    720

cggacgaata aatctgcctc aaccccactc ccacaccggc ggtgtctttc atggaggtgt    780

ctcggagttg gtggcatcgt gtgtatgtcg atccctcaga tcgacagcgt tagggttcat    840

ggatggtgtt ggcgaggcgg cggcggcgac gccatcaggt gtttctctcc ttctgctcgg    900

tccccgttgc tgtggtgttg tctccgacgt catggtggag cagggaggtt ttgtcgttca    960

ggagtatgcg caggcggttg tctacgcaag tgacatctgg aagatggagt atcttgtgtt   1020

gggtccgtgg tcgaaggcgg gcagttctgg tttccttctc cgacgtcgtc gtcatgcgag   1080

ggcgtcagtt ctgaagttcg atggcgtgtc cggggacatg ttgccccggt ctgattcttt   1140
```

-continued

```
caacggctat gattttgctt ttggcaaact actttggaga tccgtaaagc tgctgatcag   1200
cgatggagcc gcgtcgagct tgggcgaaga tgtgatctgt cttcttaccc tttggtcacc   1260
gcttcggtgg tgtcgaagga aagggacatg cgctggtatt ttgcatagaa ttttcctatt   1320
ttttccgtca tgtatggtcg gtgcttacgt gccttgtaac ttgatcttta ttctatataa   1380
atgagacacg tattatcatg aaaaaagaaa acggacggcg atctggcgtg gcaatcacgg   1440
gcagacgaaa ttgaccgttt ggatttgaat attcgctttt atatacgtcg aacgactctc   1500
gatgctgtac catcaaatgt actgtataat cggagtagaa aatatactgg cacacgagca   1560
actagacata atttttattc gcacttgttt tatactgata tatgttgtgg cgatcagttt   1620
tgtttaatct tttatcccgc tgatgataag ctcgattggc gactggtcca tgcccctccg   1680
ggctccacac agccaggcga attcgtgcta tcatgcaggc agcccgaaca aagaacatgt   1740
tctcagtctg caactgctca gccggaccca agtaagtcat aaatgcgacg caacaaaaaa   1800
tggcgccgca aaagttggga cgttttctca gttatcctga aatattataa taacatgcat   1860
gttgtatgcg tacctcatgt agcggggaaa catatgcagc cggcacccc aaaccccgtc   1920
atacgcccgg accgacgccc aaattagtga ccggtcacga aagactgacc cagacgcgtg   1980
cctcgaatgg gtcttaaacg ctcaggctaa ccgccacccc tcatatctag tcccaaatct   2040
aagacggata agggcgcgcc gcccaggagc gtcggggcgc gtccatcacg ttggtcctgg   2100
ctcacgatgg cccacccgac tccacatccg ctgcctgggc caaacactat ccacttcact   2160
tccctccgcc gcccaagctc ctatccgccg atcacgagcc ttcttcggct tgacgtgtag   2220
cgaatccgac gacgaccagt acagatccgt tgactagggt gtcaacccgt gcggtttgga   2280
gaaggaaatg gccatccgca ttgcacttcg ccactcccgg gaggacaacg cccttccgag   2340
ggcgggatct acccaacgcg agtccattgc gtcggtgcat cgggcgctca gattctccgg   2400
cgctggatca tcgtggtcct ctcgggagcc ttccaatctc cctttcccca tcatggtccg   2460
tcggagtacg attcctatcg ggtatcagtg tgcccgccgt gggaagaaga ggatgagggc   2520
gtctgaggtc cgcctcgctg ccgacattgc ggcagcggag gcggctgatg cgatggcagg   2580
ggcggtcgca ggggaggaag tcatctgcgt ccgcattgta aagaagcggc agcgaacgaa   2640
cacgcgcgcc cctcatccga gagcagaatc ggcgggccgt gccatggccg gactgccctc   2700
caaggaggag aaggaggaca acgatgggtc agacagctcc gacgatgagc agatttgagt   2760
attttcgtag tgcaaaatgt catagacctg tttaaatacg agtatcttcc tagtgcaaaa   2820
tgtcgtagac ctgtttaaat acgagtatct tcgtagtgca aaatgtcgta ggaaatagaa   2880
atagtatcct acgggtatgt agttgcattt cttactagag tagatcgtag gctcaactga   2940
aagcactact agtacgtggt ggtgataacc taatacgtga ctttgaacat gtctctgccc   3000
ctccctttct ctcgcctttt cggccccatc aatggctccc tccccctcct tctagagact   3060
agaagcaggc cccgcctcca caggtgctag cggtagtgta tcccgctcgg tggcggtggt   3120
ggtgcgtggt gggggagaaa gttggaggcc ggccagcgca cggggaaaag gagacgcaaa   3180
gcggccaccc aaaaaggcgc acatactttc tttctttctt tccaccgccg ccctccggag   3240
gagttccgat tccccctctc tttctctctc ttctttctct ctctctcttt cttgctctgc   3300
tctggaagca ggggaaggag ggaggggctt ccgatttggg cgcggaagca ctgtccgccg   3360
tgattcgatt cggctgattt gggaggtctg ctcgtttgat ttgggttcgc tgatttattg   3420
gttgatttgt tggttcgtgt ccggcggctc gatttgaggg ccggacggtc ctcgccatgg   3480
ggaactgctg gggcgccaag atcagctccg acacctcctc ctcctcccct tcaggtgcgc   3540
```

```
gcgtcttcct cgtctcctgc tgctatttta caaatgtttt tactagtact actatactag   3600
cagtactgat ctgtgcccat aactcgacta gtagtactga tctgtgccca cagggccgat   3660
tgctattttc tttgcccctc aatttctttc acaactcaca agcagccgaa taaataagtt   3720
ctgaatgaga aacaagtgtt caaccaacca tttctctcac tccaatctgc tcatttcgtg   3780
ctctgcatct cttctctcct tcccgaaacc attcttaggt tatgctgatt tcggcgacag   3840
gtttggtcaa agtcaatttc gttctgttta attggcttat gatagttgag tcactaaatt   3900
cagtccctcc ttttggaaaa atctgtcgcg agcttggact cttcctcttg acctgcttca   3960
tgtgcaaggc caaggaatca tgcctttccg tttatggcct aggggagagg aagcttccga   4020
tgtagtaaaa tgcttcactt aactttatct gacttctcct ctgatttttc tgagtgtcca   4080
gttcaaatca gacatataga ggaaaagctc gaattctgat gctacttttg gctacatcca   4140
cgtgcttttc ttcaaagtta ttgactgtcc tgttttggat gttcagtctt cttttctgta   4200
ataagcgaaa ctaaaggaag aaaatacata gttagtccga cctaacttgt ccatgatgga   4260
cctattttct gttcaatgtt aggcagacaa gataaatgat taagggacat caacttattt   4320
atgctaaaat gtgactgaat aatctctgaa agtctgcacc attttatgat gatgatcagg   4380
gacgaattcc aagtatgcta gtaggaatgg ggcggccttg agcagctcca gcagctatgc   4440
ctccgcggcg tcagtgccgc ggagcgaggg tgagattctg gagtcagcaa atgtcaaggc   4500
ctttaccttc aatgagctga ggaccgccac gagaaacttc aggccggaca gtgtgctagg   4560
cgagggaggg tttgggtcag tcttcaaggg gtggatcgat gagaagaccc tcaccccaac   4620
caagccaggc accgggatgg tcattgctgt aaagaagctt aaccaggaaa gctatcaggg   4680
ccatagggaa tggctggtta gtgacaattt tgcctgctgg aaatgggatt tcttgtttat   4740
ttcagttctg cattgtgtct gacatgctct ttcttttggg cgcaggctga agtgaattac   4800
cttggacaac tatcgcaccc gaatcttgta aagctcgttg ggtactgtgt tgaagacgaa   4860
cagcggcttc tcgtctacga gttcatgcct cgtgggagtt tggagaatca tctcttcagg   4920
agtaagtgcc tggactttta cttttcttat tattcgctgg gtgttattct ccatttttta   4980
aggaatgatg ctaaagtgtt ccaacattca gggagtacac atttccagcc gctctcctgg   5040
aaccttcgga tgaaaattgc ccatggagca gcaaaagggc tcgcatttct ccacagtgac   5100
aaggccaaag tcatctaccg cgatttcaaa acctctaata tcctcctaga tgcggtatat   5160
atgtccacag cctggaagga tcttttcctt cgtgtccgca aaatatctct atcggttggt   5220
ctgacagtca cgcaatttct tcttcagaac tatgacgcaa agctctcaga tttcggcctg   5280
gcgaaggacg gaccgacggg tgacaagagc catgtgtcca caagggtgat ggggacatat   5340
gggtatgctg caccagaata ccttgcaaca ggtcggttga tcattccact ttcagaatcc   5400
tcagctgcgc aaatatcaga tatattgccg aaaatctgac cacacctacc tgaatcgtga   5460
ttgcgttgtc actctggttg tgtcatcgac caagatgcca aacataacca attttaggct   5520
acaacctttc aatcctcatc tgcacaaata tcttgcccga aaatctaacc acacctacct   5580
gaatcatgat tgcgttctca ctctggttgc gtcatcgacc aagatgccaa actcaactaa   5640
tttttcggct agaacctttc aatcatcatc tgcacaaata tcttgctgaa aatccaaaca   5700
cacctacctg aatcgcgagt gcattgtcac cctggttgcg tcatcaacca tcatgccgaa   5760
cctaaactaa ttttcctgct gcaatatttc catgatcagg ccaccttacc acgaagagcg   5820
acgtgtacag cttcggcgtg gtcctcctgg agatgctctc ggggcgtcgc gctgtggaca   5880
```

agaaccggcc gaccggcgag cacaacctgg tggagtgggc gcggccgtac ctgacaagca 5940
agcggcgcat cttccgcgtc ctggatcccc gtctaggcgg gcagtactcc ctcgccaagg 6000
cccagaaggc ggcgtcgctg gcgctgcagt gcctctcgat ggactcgagg aacaggccga 6060
gcatggagca ggtcgtcgtg gcgctggagc agctccacga cgccaaggag ggagggaaca 6120
gccctcgccc gcagctgcag agaaagccga gcagcaaccg gggcgtgaac ggctcgagat 6180
cgtcgtcgac caaggggaac accaagaagc ccgcctcacc gagaccggtt tgaccgtgtg 6240
agtgggatca catagcagaa tctagtagag agatgcgtca aggtgtaatg tatgtatggt 6300
ataatagggt tttagagtgg tgatctgcga agaggcagcg gatttgtgaa tgttttgtgc 6360
ccgtgttgta gggatgtatc tttgcagctt ctagtgttgg tatgtacagc ttgtatctat 6420
ccggttgtag ctagtctgta tgtagtcctt ttgtgtatgc ctgattgctt tggttctgac 6480
ttaaggtcca gaggttttga tctgatttag atgcatgcac cctgttaaac caagacctta 6540
aaatatgaag atgaacagtg taaagtacat atttgtcact tcatttatca aatgtgaatg 6600
aacaatcatg ttggtgtttt agcagagcag gccatgactt ccatgggtca actgtatctt 6660
ttcccttagg gatgttgacc attttgttca tatcatacag tactagtagt atatgtttca 6720 ttttttaat gaaaaaagta gtatatgtta cagataatgt tgggaaaatc accttctgta 6780
tttttaattt caaacagttg gccacaatga tctttttatt tacttggtgg gttcagccaa 6840
attaccattg tttttttcag gggtttcagc caaattatta ttatctgggc aagcgtacgg 6900
cggcggccca aggcagagca cgcagcccag ccgccaaaac agagctcgcc ctcgctcccc 6960
tccggcccaa gtgccgctcc tcctcctcct cggtggacgc cggcgccggt ggatggctcc 7020
gccgcgccaa atcgagcccc tcacgccgcg agccgctcct cctcctcctc agcctgcaat 7080
ccccgccgag ctccgatccc cgccgccgag ctccgatccg cgggcgatcg ccggggcgcc 7140
gccaagatca gctccggccc ctcccgttcc 7170

<210> SEQ ID NO 20
<211> LENGTH: 1032
<212> TYPE: DNA
<213> ORGANISM: Triticum aestivum (var. Spelt)

<400> SEQUENCE: 20
atggcagctc taaccagcct tgcctcaaac ccgaatccaa acaagtcatt cgaggtcctt 60
cctaatccgg gtgactccct ctcaagcctc agttttagcc cgaaaagtaa tcttcttgtg 120
gcaacttcct gggataacca ggtgaggtgt tgggagatag gtaatggtaa cagtcagcca 180
aaggcatcca tatcacatga tcagccagtg ctctgctcag cctggaaaga tgatgggact 240
actgtcttct ctggagggtg tgataaacag gtcaaaatgt ggcctctgct gtctggtggg 300
caggctcaga cggttgcaat gcatgatgca cctgtcaagg aggtcgcatg gatttctcag 360
atgaatcttc ttgtatccgg aagctgggac aagacactaa ggtattggga cacaagacag 420
ccgaatcctg cccatgttca gcaacttcct gatcgttgct acgcacttgc tgtgaattat 480
ccccttatga ttgtgggaac agctgatcgc aatattgtga tcttcaactt gcagaatcct 540
cagactgagt ttaagcgtat tcaatcacct ctgaaatacc agacacggtg cgttgctgcc 600
tttccagatc aacaaggatt cctggtgggt tccatagaag gaagagttgg tgtgcatcat 660
attgatgatt cacagcaaag caaaaacttc acattcaagt gtcacaggga aggaaatgat 720
attttctctg tcaattcgct caactttcac cctgttcatc acacgtttgc cacagctgga 780
tctgatggtg ctttcaactt ttgggataaa gatagcaagc agagacttaa ggctttcagt 840

```
cggtgtcctc aacccattcc ttgcagtagc ttcaataatg atggttcaat atttgcttat    900

ggggtgtgct atgactggag ccatggcgct gagaaccata atcctgcaaa tgcaaagaca    960

tccatctatc tccacagtcc ccaggaagcc gaggtgaaag ggaagccaag aatcgcaaca   1020

gggcggaagt ga                                                      1032


<210> SEQ ID NO 21
<211> LENGTH: 343
<212> TYPE: PRT
<213> ORGANISM: Triticum aestivum (var. Spelt)

<400> SEQUENCE: 21

Met Ala Ala Leu Thr Ser Leu Ala Ser Asn Pro Asn Pro Asn Lys Ser
1               5                   10                  15

Phe Glu Val Leu Pro Asn Pro Gly Asp Ser Leu Ser Ser Leu Ser Phe
            20                  25                  30

Ser Pro Lys Ser Asn Leu Leu Val Ala Thr Ser Trp Asp Asn Gln Val
        35                  40                  45

Arg Cys Trp Glu Ile Gly Asn Gly Asn Ser Gln Pro Lys Ala Ser Ile
    50                  55                  60

Ser His Asp Gln Pro Val Leu Cys Ser Ala Trp Lys Asp Asp Gly Thr
65                  70                  75                  80

Thr Val Phe Ser Gly Gly Cys Asp Lys Gln Val Lys Met Trp Pro Leu
                85                  90                  95

Leu Ser Gly Gly Gln Ala Gln Thr Val Ala Met His Asp Ala Pro Val
            100                 105                 110

Lys Glu Val Ala Trp Ile Ser Gln Met Asn Leu Leu Val Ser Gly Ser
        115                 120                 125

Trp Asp Lys Thr Leu Arg Tyr Trp Asp Thr Arg Gln Pro Asn Pro Ala
    130                 135                 140

His Val Gln Gln Leu Pro Asp Arg Cys Tyr Ala Leu Ala Val Asn Tyr
145                 150                 155                 160

Pro Leu Met Ile Val Gly Thr Ala Asp Arg Asn Ile Val Ile Phe Asn
                165                 170                 175

Leu Gln Asn Pro Gln Thr Glu Phe Lys Arg Ile Gln Ser Pro Leu Lys
            180                 185                 190

Tyr Gln Thr Arg Cys Val Ala Ala Phe Pro Asp Gln Gln Gly Phe Leu
        195                 200                 205

Val Gly Ser Ile Glu Gly Arg Val Gly Val His His Ile Asp Asp Ser
    210                 215                 220

Gln Gln Ser Lys Asn Phe Thr Phe Lys Cys His Arg Glu Gly Asn Asp
225                 230                 235                 240

Ile Phe Ser Val Asn Ser Leu Asn Phe His Pro Val His His Thr Phe
                245                 250                 255

Ala Thr Ala Gly Ser Asp Gly Ala Phe Asn Phe Trp Asp Lys Asp Ser
            260                 265                 270

Lys Gln Arg Leu Lys Ala Phe Ser Arg Cys Pro Gln Pro Ile Pro Cys
        275                 280                 285

Ser Ser Phe Asn Asn Asp Gly Ser Ile Phe Ala Tyr Gly Val Cys Tyr
    290                 295                 300

Asp Trp Ser His Gly Ala Glu Asn His Asn Pro Ala Asn Ala Lys Thr
305                 310                 315                 320

Ser Ile Tyr Leu His Ser Pro Gln Glu Ala Glu Val Lys Gly Lys Pro
                325                 330                 335
```

Arg Ile Ala Thr Gly Arg Lys
340

<210> SEQ ID NO 22
<211> LENGTH: 9314
<212> TYPE: DNA
<213> ORGANISM: Triticum aestivum (var. Spelt)
<220> FEATURE:
<221> NAME/KEY: misc_feature
<222> LOCATION: (830)..(903)
<223> OTHER INFORMATION: n is a, c, g, or t

<400> SEQUENCE: 22
tttgtaaaag gctatgggga catttgtttt cctctggcgc acagaaatca agaggtgtca 60
ttaattctga atgaagaaga caatgctatg ggctccgcaa tacctcgcta acgaaggtgt 120
cgagggtggc cgagctatca tcagccggat acaggagacg ggaggaactc gcccctcaat 180
ccgaagactt caagaagcac agagctaatg gaaattatcg acctcgctgt tggaggctag 240
ttcggaggct aatgagggtg tcttggacta aggggtcctc gggctgccga cctatttctc 300
atgggccgta ctagtggact gtttgttgtt cgtcagggga agaccggact tcggacgacc 360
ccgtgctcca aaaggaaacc ttcggagact tgacgtatcc tccaagtctg gcttagtgtg 420
acttgtgtgt ttatcccctg ttggtaaccg acatatgtaa ccctagggac ccctggtgtc 480
tatataaaca gagggtttag tctgtagagg ctagaaccat catcctactc ctatagggtt 540
tagttcatct gatctcgtgg tagatcaact ctgtaatcat cacacaaaca caccaagaca 600
atcaagcaga atgtagggtt ttacctcttc gagagggctc gaacctgggt aaatactatc 660
tctaccttcc ctgttaccca tgcatccaag atctacaact caggaccccc taccgagatc 720
tgccggtttt gacaccaaca cacataaaat tgagggtgac caatcacgta aagctcttaa 780
tagcgatatt aatatacgta cacatagcaa ttgtcgatga aattgttggn nnnnnnnnnn 840
nnnnnnnnnn nnnnnnnnnn nnnnnnnnnn nnnnnnnnnn nnnnnnnnnn nnnnnnnnnn 900
nnncctgctc atccctggat gttgacggct caatggtgta tttttcccgt cgtgcgtctt 960
catcggtgag gttatggtat gtacaatttt ggcgcacaat gacggcgact tccctgatcc 1020
ttcgtcatcg tctccaccgt gttgattttg gtgctggcgt gaggcctgag gtatgtctct 1080
tggatctaat gctcgtctag cgttggtggt ttctccttca gagcgatggc ccggtaagac 1140
gtggccttaa tcactccccg cccgtgatga acatcaggct ggcttcgatg atggagaagc 1200
atgtgttggc tcggcatgtt ctagaggatg aagaaggatg acccagggat tttgatgtaa 1260
ctttattaat attttcttcc tataatttgt acttcctttt cttagaaaaa aactatttgg 1320
cttcacatgc gctggtttgg ttatataaga gggagcatat gggtgttgtc tttttatata 1380
agaaaaaaaa gagcaaaata agccacgcgc cgatcaagcc tgcgaactga gtgtataccc 1440
ggccatgggc aacccagact gacccgaccc atcccgaaaa agctcgaccc gtcccgactc 1500
gaccttgccc acgggccggg cccaggccta gattttgagc ccgatggctg ggccgacatg 1560
ttgtatttgc gatttaagga agaggcccgg ccccaagggcc gaggcccgac gggtttttttg 1620 actgatgggc cggggttggg ccagattatt aggcccaacg gccgggccgg gccgggctcg 1680
ggcctaagcc ttttgcttgc gttcaggctt tgataggctc agcccgaagt ccacatccac 1740
atcaaccacc cccgcgtgcc gatgaagcca tttctttgga aggacctgcg cgtgcatccg 1800
acgcgacgcg ctacaccgaa gcctatacta ctacatctcg tctcatcgcc ctcctcccag 1860
acgacgcctc gagaatcctc ggctgaggct ccactccgca ctcgcaagtc gcacccgcag 1920
ccgcgccgtc cccagcagcc gccgccgacc gctccccgtc cggcaggtaa gccccccgag 1980
cccctcctcg ccgctccgct cgcgcggact cctagctagc tagggttccc ggcaccgatt 2040
ccgcggcgct gcactccggc gcaatgctcg cggccgcgga cgggcccgcc gcttcggggg 2100
aagctctgat ctggtggccg gcgctcgctc gctcgctcgc ggtctccgga gcaaatcggc 2160
cgcatcgagt ggccggagca agcttaggat agttcgatta tttcccccat ccccgttggt 2220
caggccgaga gggccagttt gggcgacctc ctggtgattc cgctgccgtg gtggggattg 2280
ggtggtcgtg gcccgggtgt aggcgtttgt aggtcgagtg agtgtttcct tccaggttct 2340
atgctcaccc agcttgtgtt atcactggga tccgggcgtt cggcaggcta acattcactg 2400
gattttggac ctgcattgtt gcggcgcgtg ccgggggata gcgtttatgc tggctttggc 2460
gcggtgattt tgtgcgtgcg tgcaaacttt tggggctgcc ttctggtgat ctcgctgtcg 2520
ggtggtgcga gttcatcaag cggtcagggt gtaggcattt gtagtcgagc gaccccagct 2580
ttcatgccca ccagctcgta ttattcggtc gttaaccacg tttaccgaat tttggaccga 2640
cgtcgttgcg gcacgtacca ggggacagcg tttatgctgg tttcggtgtg gagattttgt 2700
ggtttaaact tggggcgcgc ttggtttgcg aggctacctc ctggtgattt caccgtcggg 2760
tggtgggaat cggatggtcg gggtgtaggc atttatagtg gagcggaccc cttgttttat 2820
gaccagacat ttagccgaaa tttggaccta cactatcgtg gcacgtacca ggggatatca 2880
tttatgcggg ttttggcgcg acactttctt tgtcgggatt ttgtggtgca aacttaaata 2940
atgacttccc taatgttaaa cactcgttct ggcatcgtgg actgttggaa tcgttctttt 3000
tcgtagtctg agctacttta aggtgttact tatgctctcg tgtgcgtggg agactccacg 3060
tgctgatttc tcttacttgc ttctcatggt cactggactg atatttcttt tccagatttt 3120
gaaggttcac agaaggagag atggcagctc taaccagcct tgcctcaaac ccgaatccaa 3180
acaagtcatt cgaggtgtga tactttttgt ggccatgtct gtcctgcttt tatttttttg 3240
cgtcttgtca ttctgtatat gctacatgtt ctctgcaatg gttgctttca aatgcaggtc 3300
cttcctaatc cgggtgactc cctctcaagc ctcagtttta gcccgaaaag taatcttctt 3360
gtggcaactt cctgggataa ccaggtaatt ttgtttctgc tgtaattttc agtgagcttc 3420
cattattgtg atgtatctta ctaggaatgt cttttgagtt ttgtgcaggt gaggtgttgg 3480
gagataggta atggtaacag tcagccaaag gcatccatat cacatgatca gccagtacgt 3540
tctcatacat gtttctcctg aaagtagttt catcttacac attagagtgg ttccttacct 3600
gtttacttgg tatgatgatt gatttgtttc cttccatcag gtgctctgct cagcctggaa 3660
agatgatggg actactgtct tctctggagg gtgtgataaa caggtcaaaa tgtggcctct 3720
gctgtctggt gggcaggctc agacggttgc aatgcatgat gcacctgtca aggaggtcgc 3780
atggatttct cagatgaatc ttcttgtatc cggaagctgg gacaagacac taaggtgcaa 3840
gaacaatatt cctctccacc ctcagtattc tttttacatg gaaattcagc gcatatcacc 3900
catatctgat cccaaattgt tatttatggc tgttttgctt ttgggaattc gtgttgtttg 3960
tggtatcctt tctgtacttc atgtgttctg cattaatgtt cacacattgg ctaaccaaat 4020
attgtagaag ttctatctca tcctctttat atttgcactc attttgtatg ccttctttga 4080
tcctgaagag ttttctacta cttgttgaat catactgccc tattcttatc aaaggttgtg 4140
cactttctgg gtatcatctg tactatttat ggctgtagtg aatttttctt atggcagaag 4200
tttttataga agtaactgtt gatgcagaca gttactatat taaatgtaca ttatgtgatt 4260

-continued agtgttagaa atgttcgttt cgagttttag catcatcttt atgaagatta tttatgaaac 4320
atcaagttag ggtctggctg tcagtttaaa catgagcaca gattgagcat aggcgataat 4380
catggttggt aggaggccag ggaccgggat ccttgtggga cctgccggcg tacccgtgat 4440
agcagaaggg gtgcaaggga cagggcactg gaactaaggc aggcagaaac agagaaataa 4500
agattgggga ttagactttg tagccaattc ataaaaaaat tggttgcatc attttgtaga 4560
ggttggcctt aacatatgac taaaaaacaa aaacaaacca agactcttcc ctaaactgaa 4620
taccgcagat actcaagaca ccatataggg ccacgggctc aggctgaagt catctaggtc 4680
tcagacatgc caaaacagac tgggacaagg acaagctgaa actgactagt actaggtttc 4740
ccggggcaac taccgttcag ctggaggtct gaatgcgtgg tgccttctct gatacatgga 4800
tctcatgtgg cacttctgtt gtgtatttgt cccagtctgc ttattttcct ttgtctgtat 4860
catgctgaga ctaatacatt tgggtcgtgc attgatcttc ttctcattac aacttttagc 4920
tctgatcccg atgacttgtt tctagtctgc tatcaatgct tatcatcata ctattgtagg 4980
tattgggaca caagacagcc gaatcctgcc catgttcagc aacttcctga tcgttgctac 5040
gcacttgctg tgaattatcc ccttatgatt gtgggaacag ctgatcgcaa tattgtgatc 5100
ttcaacttgc agaatcctca ggtaattttg cttcctaacc gactatgcat tttcaattct 5160
tgtggtggtg gtgctcatgc ttttactgcc attgacttat attttgaact gcctgactta 5220
aattcatccc tgatgtgatt ttagactgag tttaagcgta ttcaatcacc tctgaaatac 5280
cagacacggt gcgttgctgc ctttccagat caacaaggat tcctggtaat gccatatttt 5340
cttgtgtctt ttactctcag cattacgaca ccaaccaaaa cttccgttgt ttgaatacat 5400
aacttgttgt tactatgctt tgaagtttaa tcatatgttc ttctctacct atcccatcat 5460
aattatttat gttgcccaat tatgttgttt ttacctagct tgagttttcg accttaaaca 5520
ttgttacaac cttactcgaa ttagctttag atgttggcct gccatcattt gcagtgtaat 5580
gggcgttgtt cctttagtga tctcatttca aacttcctac ccctctatta taggataaat 5640
aaggtatatt gattgtgaaa tcaaacttta ctgactataa atactatact atgtgattta 5700
tgtgacataa agttgatatc attggatttg ttttcaagag tactttgtta cgattttgat 5760
aaaatatgag aagaaattta tggccaaaga ttgaactcga gcagtcaaaa tatgccttgt 5820
atatctggat agagtgtgta ttactaggaa tgttaatcca atataaatgt cactaattga 5880
catctctcta gttagcacaa aagctgcata aaagaagagg atgcagtttt ccttaatgtt 5940
ttgaccaact ccagctgtgt tgcaaacagt ttccttcacc agaactgtag aacggatctt 6000
agcctatagc agttaaagct aatctgaaca tgaaatccgg ctgaagtaca aatagtaaaa 6060
ccatccaagg cttcaagcaa ttgtttttga actacagatc tttatagatg tctatttctg 6120
cattttccta ttcttcacct gcttgtgggt gttcttatag tgggtcgtcg tttcatcatg 6180
ggctttgacc aatcaatttt tgctgttaca caatgatctt tttctacatc aatgaactgc 6240
ctatattgga taaagctggt cgatacctgg caatagttct tgttttaatt attttcttgt 6300
tgtttccata ttacttgggc aaaacatttt tttacatgcg actgacacct gattttgttt 6360
gaaggtgggt tccatagaag gaagagttgg tgtgcatcat attgatgatt cacagcaaag 6420
caaaaacttc acattcaagt gtcacaggga aggaaatgat attttctctg tcaattcgct 6480
caactttcac cctgtaagat ctctatcttg ttctctcttg actccatatt tatctatgtg 6540
ccatactgcc attcttatat ttcattagtc cacttctgct attatggaaa atgctaatgg 6600
cgacttctgt tgagctttag tcactatgtc tccatcatga tttgtaaaat actgaaagct 6660
cagttcgttg tcttccacaa gatgtgttga gctttattca atacagatac ctaccacact 6720
tcgcctaata taataaccac tatgcttgaa ggcatacata tgttagtaaa ctactccaaa 6780
ttgatcaagc aatattttgc agaaataaaa atcccaacag attagcttca gtttaattga 6840
gcaactcgaa atcgtaccta tttgttacag acacatcgaa gagaagcgtt tctgcttctt 6900
cttttgctaa ctttggcatc ttattcattg gattggtata tgcttgggtg atgatactat 6960
acatccattt agttgagtgt gcttgttggc tatatatttc actggaaaat gcaactgact 7020
ggtgataatt gtgaagtatg gaaattcagt tagtctagtt acttatggga tttcatgtta 7080
tctaccactt ggcacaggtt catcacacgt ttgccacagc tggatctgat ggtgctttca 7140
acttttggga taaagatagc aagcagagac ttaaggtttg tctattcccg tttttttttc 7200
tattttcccc tcttgttggt ttatgttttc ttgattggaa ttcaatgatt tcaagatggc 7260
tctactttgt tgtgatctgt ggacactgat gatctgcata taaattcttt gttgatgcgc 7320
atacatagcc tgaaatcatc ccgagctcaa gctaataaac tcactatcct ggccatgagc 7380
agaaaaaaaa atattagttc ataaatgtta tcaccaattc tgattttccc agccgccttg 7440
tcatcctgct gcttttggcg tttagtatgc acttcttttt attcttgata aaagcatatt 7500
acatatttat tactcaaccg catggagcct ctgcagtaag gtatatgtgt aatttgtcaa 7560
cagataacct tttagctttt aggcatatca tacacagtgt tgcattctga cagttgctta 7620
cttgcttagc atagagggct atctgtgtgt gcccaagttt attgcttcag ttccctcatt 7680
tgtcatgcac cttctggtat gttgcacata acacattctt acatttcccc tacactgctt 7740
ctatacaggc tttcagtcgg tgtcctcaac ccattccttg cagtagcttc aataatgatg 7800
gttcaatatt tgcttatggg gtaagtcaag tgatgctttt gagagtgtct tgttatcacc 7860
atgtttttca gtccggtcag agtttagata tgttacatgc ctgtcatttt tcctgcacct 7920
tatttaatat acggaagaaa tcagctcgac aaataattca tgttcctttt gaactgctat 7980
cttgtcgtgt cctctgaatc caagttctga atgcaaccgt aattatcatt gctggggagc 8040
aggtgtgcta tgactggagc catggcgctg agaaccataa tcctgcaaat gcaaagacat 8100
ccatctatct ccacagtccc caggtagttt ccgagtgctg atatcgccat aaaaagaatt 8160
cttgtatttt cgacatcatt tgagatccat tcctgttttt ataaattgtt attatgttat 8220
cttttggcac tcaacttgca tcattctgga caggaagccg aggtgaaagg gaagccaaga 8280
atcgcaacag ggcggaagtg atggtggcat cctgcctgcc gaaaagtcga tagttgtgca 8340
agagatgatg tatattcaag ggccttgttt cgctcgggcc ttgccttgac gtgtcctctg 8400
gatgttctta cttggttcgg ccgcctggta gatgaaacgc ctactcccag caaccagtga 8460
taggttactt agccgtaggt cgtagcacat agccgtttat gtaatgcata gttgtccgaa 8520
ggaatgtttc cccgtgttct tgtgttgtga tatagtcagg tcagcgcgta gtcttttgaa 8580
aaggagaaag ccttcggtgt cttgtaagtg gtgtagatct ttggaaatat gggcatgata 8640
ttcggtggag ttattctgaa aaagatatcc cggtttcggt ttcagcgaat gcaagctaga 8700
tttatgggga aggttgtagt tagcaccatg ctgcaaatgc atgcggcatt cggaggattt 8760
acggtttgaa tcttcctgtt tatccaagtc taggattccc accttcctag taccattgag 8820
cacgttagtt tgaatttttt ttgtttatta tggttcaaaa cttccgattc aaaaaaatct 8880
gatttatttt acgcgaatat atggatgttt catcaatata cggttttgta tgtgagatat 8940
aaagaagggc caaagacatg caaacaatgg gcatttcttt gtgctggatc ttttgtgttc 9000
ttatctgcac tgcaccatca aatgaaaatt accaggtgcg tgcagaacga cgtgtaaaga 9060
aaacacccag cttttccgaa acttccaaat gccattttcg agctgttcaa catagtgtgc 9120
ttcgaaaatc cgttcttcag tacagtacca gccacgtagc aatggctcca cagaagcctc 9180
attgcttgcg agctttatgc cgtgaacttg catagattca gttcgacaac ccaattgcat 9240
aagcttgtga tctttttacg ccgttaactt caaaatagat tcggcgcaac acgactcaat 9300
agccacgaca cggg 9314

<210> SEQ ID NO 23
<211> LENGTH: 23
<212> TYPE: DNA
<213> ORGANISM: Triticum aestivum (var. Spelt)

<400> SEQUENCE: 23
gcggggcatg gccggtgtgt agg 23

<210> SEQ ID NO 24
<211> LENGTH: 23
<212> TYPE: DNA
<213> ORGANISM: Triticum aestivum (var. Spelt)

<400> SEQUENCE: 24
gaggagaagc ggggcatggc cgg 23

<210> SEQ ID NO 25
<211> LENGTH: 23
<212> TYPE: DNA
<213> ORGANISM: Triticum aestivum (var. Spelt)

<400> SEQUENCE: 25
tgagttcgcg acctacacac cgg 23

<210> SEQ ID NO 26
<211> LENGTH: 23
<212> TYPE: DNA
<213> ORGANISM: Triticum aestivum (var. Spelt)

<400> SEQUENCE: 26
tccccatggc gaggaccgtc cgg 23

<210> SEQ ID NO 27
<211> LENGTH: 23
<212> TYPE: DNA
<213> ORGANISM: Triticum aestivum (var. Spelt)

<400> SEQUENCE: 27
cccagcagtt ccccatggcg agg 23

<210> SEQ ID NO 28
<211> LENGTH: 23
<212> TYPE: DNA
<213> ORGANISM: Triticum aestivum (var. Spelt)

<400> SEQUENCE: 28
gccggacggt cctcgccatg ggg 23

<210> SEQ ID NO 29
<211> LENGTH: 23
<212> TYPE: DNA
<213> ORGANISM: Triticum aestivum (var. Spelt)

<400> SEQUENCE: 29
ttctgtgaac cttcaaaatc tgg 23

<210> SEQ ID NO 30
<211> LENGTH: 23
<212> TYPE: DNA
<213> ORGANISM: Triticum aestivum (var. Spelt)

<400> SEQUENCE: 30
agattttgaa ggttcacaga agg 23

<210> SEQ ID NO 31
<211> LENGTH: 23
<212> TYPE: DNA
<213> ORGANISM: Triticum aestivum (var. Spelt)

<400> SEQUENCE: 31
aaggttcaca gaaggagaga tgg 23

<210> SEQ ID NO 32
<211> LENGTH: 27
<212> TYPE: DNA
<213> ORGANISM: Triticum aestivum (var. Spelt)

<400> SEQUENCE: 32
tttgaaggtt cacagaagga gagatgg 27

<210> SEQ ID NO 33
<211> LENGTH: 362
<212> TYPE: DNA
<213> ORGANISM: Triticum aestivum

<400> SEQUENCE: 33
gaccaagccc gttattctga cagttctggt gctcaacaca tttatattta tcaaggagca 60
cattgttact cactgctagg agggaatcga actaggaata ttgatcagag gaactacgag 120
agagctgaag ataactgccc tctagctctc actgatctgg gtcgcatagt gagatgcagc 180
ccacgtgagt tcagcaacgg tctagcgctg ggcttttagg cccgcatgat cgggcttttg 240
tcgggtggtc gacgtgttca cgattgggga gagcaacgca gcagttcctc ttagtttagt 300
cccacctcgc ctgtccagca gagttctgac cggtttataa actcgcttgc tgcatcagac 360
tt 362

<210> SEQ ID NO 34
<211> LENGTH: 103
<212> TYPE: DNA
<213> ORGANISM: Artificial sequence
<220> FEATURE:
<223> OTHER INFORMATION: gRNA_983r

<400> SEQUENCE: 34
gcggggcatg gccggtgtgt gttttagagc tagaaatagc aagttaaaat aaggctagtc 60
cgttatcaac ttgaaaaagt ggcaccgagt cggtgctttt ttt 103

<210> SEQ ID NO 35
<211> LENGTH: 103
<212> TYPE: DNA
<213> ORGANISM: Artificial sequence
<220> FEATURE:
<223> OTHER INFORMATION: gRNA_991r

<400> SEQUENCE: 35
gaggagaagc ggggcatggc gttttagagc tagaaatagc aagttaaaat aaggctagtc 60
cgttatcaac ttgaaaaagt ggcaccgagt cggtgctttt ttt 103

<210> SEQ ID NO 36
<211> LENGTH: 103
<212> TYPE: DNA
<213> ORGANISM: Artificial sequence
<220> FEATURE:
<223> OTHER INFORMATION: gRNA_972f

<400> SEQUENCE: 36
tgagttcgcg acctacacac gttttagagc tagaaatagc aagttaaaat aaggctagtc 60
cgttatcaac ttgaaaaagt ggcaccgagt cggtgctttt ttt 103

<210> SEQ ID NO 37
<211> LENGTH: 103
<212> TYPE: DNA
<213> ORGANISM: Artificial sequence
<220> FEATURE:
<223> OTHER INFORMATION: gRNA_479r

<400> SEQUENCE: 37
tccccatggc gaggaccgtc gttttagagc tagaaatagc aagttaaaat aaggctagtc 60
cgttatcaac ttgaaaaagt ggcaccgagt cggtgctttt ttt 103

<210> SEQ ID NO 38
<211> LENGTH: 103
<212> TYPE: DNA
<213> ORGANISM: Artificial sequence
<220> FEATURE:
<223> OTHER INFORMATION: gRNA_488r

<400> SEQUENCE: 38
cccagcagtt ccccatggcg gttttagagc tagaaatagc aagttaaaat aaggctagtc 60
cgttatcaac ttgaaaaagt ggcaccgagt cggtgctttt ttt 103

<210> SEQ ID NO 39
<211> LENGTH: 103
<212> TYPE: DNA
<213> ORGANISM: Artificial sequence
<220> FEATURE:
<223> OTHER INFORMATION: gRNA_478f

<400> SEQUENCE: 39
gccggacggt cctcgccatg gttttagagc tagaaatagc aagttaaaat aaggctagtc 60
cgttatcaac ttgaaaaagt ggcaccgagt cggtgctttt ttt 103

<210> SEQ ID NO 40
<211> LENGTH: 103
<212> TYPE: DNA
<213> ORGANISM: Artificial sequence
<220> FEATURE:
<223> OTHER INFORMATION: gRNA_1145r

<400> SEQUENCE: 40
ttctgtgaac cttcaaaatc gttttagagc tagaaatagc aagttaaaat aaggctagtc 60
cgttatcaac ttgaaaaagt ggcaccgagt cggtgctttt ttt 103

<210> SEQ ID NO 41
<211> LENGTH: 103
<212> TYPE: DNA
<213> ORGANISM: Artificial sequence
<220> FEATURE:
<223> OTHER INFORMATION: gRNA_1147f

<400> SEQUENCE: 41
agattttgaa ggttcacaga gttttagagc tagaaatagc aagttaaaat aaggctagtc 60
cgttatcaac ttgaaaaagt ggcaccgagt cggtgctttt ttt 103

<210> SEQ ID NO 42
<211> LENGTH: 103
<212> TYPE: DNA
<213> ORGANISM: Artificial sequence
<220> FEATURE:
<223> OTHER INFORMATION: gRNA_1155f

<400> SEQUENCE: 42
aaggttcaca gaaggagaga gttttagagc tagaaatagc aagttaaaat aaggctagtc 60
cgttatcaac ttgaaaaagt ggcaccgagt cggtgctttt ttt 103

<210> SEQ ID NO 43
<211> LENGTH: 51
<212> TYPE: DNA
<213> ORGANISM: Artificial sequence
<220> FEATURE:
<223> OTHER INFORMATION: crRNA_1151f

<400> SEQUENCE: 43
taatttctac taagtgtaga taaggttcac agaaggagag atggtttttt t 51

<210> SEQ ID NO 44
<211> LENGTH: 1992
<212> TYPE: DNA
<213> ORGANISM: Zea mays

<400> SEQUENCE: 44
gtgcagcgtg acccggtcgt gcccctctct agagataatg agcattgcat gtctaagtta 60
taaaaaatta ccacatattt tttttgtcac acttgtttga agtgcagttt atctatcttt 120
atacatatat ttaaacttta ctctacgaat aatataatct atagtactac aataatatca 180
gtgttttaga gaatcatata aatgaacagt tagacatggt ctaaaggaca attgagtatt 240
ttgacaacag gactctacag ttttatcttt ttagtgtgca tgtgttctcc tttttttttg 300
caaatagctt cacctatata atacttcatc cattttatta gtacatccat ttagggttta 360
gggttaatgg tttttataga ctaatttttt tagtacatct attttattct attttagcct 420
ctaaattaag aaaactaaaa ctctatttta gtttttttat ttaataattt agatataaaa 480
tagaataaaa taaagtgact aaaaattaaa caaataccct ttaagaaatt aaaaaaacta 540
aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840
ttcgctttcc cttcctcgcc cgcccgtaata aatagacacc ccctccacac cctctttccc 900
caacctcgtg ttgttcggag cgcacacaca cacaaccaga tctcccccaa atccacccgt 960
cggcacctcc gcttcaaggt acgccgctcg tcctcccccc cccccctct ctaccttctc 1020 tagatcggcg ttccggtcca tggttagggc ccggtagttc tacttctgtt catgtttgtg 1080

```
ttagatccgt gtttgtgtta gatccgtgct gctagcgttc gtacacggat gcgacctgta   1140
cgtcagacac gttctgattg ctaacttgcc agtgtttctc tttggggaat cctgggatgg   1200
ctctagccgt tccgcagacg ggatcgattt catgattttt tttgtttcgt tgcatagggt   1260
ttggtttgcc cttttccttt atttcaatat atgccgtgca cttgtttgtc gggtcatctt   1320
ttcatgcttt tttttgtctt ggttgtgatg atgtggtctg gttgggcggt cgttctagat   1380
cggagtagaa ttaattctgt ttcaaactac ctggtggatt tattaatttt ggatctgtat   1440
gtgtgtgcca tacatattca tagttacgaa ttgaagatga tggatggaaa tatcgatcta   1500
ggataggtat acatgttgat gcgggtttta ctgatgcata tacagagatg ctttttgttc   1560
gcttggttgt gatgatgtgg tgtggttggg cggtcgttca ttcgttctag atcggagtag   1620
aatactgttt caaactacct ggtgtattta ttaattttgg aactgtatgt gtgtgtcata   1680
catcttcata gttacgagtt taagatggat ggaaatatcg atctaggata ggtatacatg   1740
ttgatgtggg ttttactgat gcatatacat gatggcatat gcagcatcta ttcatatgct   1800
ctaaccttga gtacctatct attataataa acaagtatgt tttataatta ttttgatctt   1860
gatatacttg gatgatggca tatgcagcag ctatatgtgg attttttag ccctgccttc   1920
atacgctatt tatttgcttg gtactgtttc ttttgtcgat gctcaccctg ttgtttggtg   1980
ttacttctgc ag                                                        1992
```

<210> SEQ ID NO 45
<211> LENGTH: 4206
<212> TYPE: DNA
<213> ORGANISM: Artificial sequence
<220> FEATURE:
<223> OTHER INFORMATION: NLS-Cas9-NLS

<400> SEQUENCE: 45

```
atggctccta agaagaagcg caaggttggg atccacgggg ttccggcggc tatggacaag     60
aagtacagca tcgggctcga catcgggacg aacagcgttg ggtgggcggt catcacggac    120
gagtacaagg ttccctccaa gaagttcaag gtgctgggga acaccgaccg ccactccatc    180
aagaagaacc tcatcggggc cctcctgttc gacagcgggg agaccgctga ggctacgagg    240
ctcaagagaa ccgcgaggcg cagatacacg agaaggaaga acaggatctg ctacctccaa    300
gagatcttct ccaacgagat ggccaaggtt gacgattcat tcttccaccg cctggaggag    360
tctttcctcg tggaggagga caagaagcac gagcggcatc ccatcttcgg gaacatcgtc    420
gacgaggttg cctaccacga gaagtaccct acgatctacc atctgcggaa gaagctcgtg    480
gacagcaccg ataaggcgga cctcagactg atctacctcg ccctggcgca catgatcaag    540
ttccgcgggc atttcctgat cgagggggat ctcaacccag acaactccga tgttgacaag    600
ctgttcatcc aactcgtgca gacctacaac caactcttcg aggagaaccc gatcaacgct    660
tcgggggtcg acgctaaggc catcctgtca gcccgcctct cgaagtcacg caggctggag    720
aacctgatcg cgcagctccc aggggagaag aagaacgggc tgttcgggaa cctcatcgct    780
ctctctctgg ggctcacgcc gaacttcaag tccaacttcg atctcgccga ggacgcgaag    840
ctgcaactca gcaaggacac ctacgacgat gacctcgata acctcctggc gcagatcggg    900
gatcaatacg ctgacctgtt cctcgccgcg aagaacctgt cggacgccat cctcctgtca    960
gatatcctcc gcgtgaacac cgagatcacg aaggccccac tctctgcgtc catgatcaag   1020
cgctacgacg agcaccatca ggatctgacc ctcctgaagg cgctggtccg ccaacagctc   1080
ccggagaagt acaaggagat cttcttcgat cagtcgaaga acgggtacgc tgggtacatc   1140
```

gacgggggggg cgtcacaaga ggagttctac aagttcatca agccaatcct ggagaagatg 1200
gacgggacgg aggagctcct ggtgaagctc aacagggagg acctcctgcg gaagcagaga 1260
accttcgata acgggtccat cccccaccaa atccatctcg ggagctgca cgccatcctg 1320
agaaggcaag aggacttcta ccctttcctc aaggataacc gggagaagat cgagaagatc 1380
ctgaccttca gaatcccata ctacgtcggg ccgctcgctc gggggaacag cagattcgcc 1440
tggatgaccc gcaagtcgga ggagaccatc acgccgtgga acttcgagga ggtggtcgac 1500
aagggggcga gcgctcagtc gttcatcgag aggatgacca acttcgacaa gaacctgccc 1560
aacgagaagg tgctccctaa gcactcgctc ctgtacgagt acttcaccgt ctacaacgag 1620
ctcacgaagg tgaagtatgt gaccgagggg atgagaaagc ctgccttcct gtccggggag 1680
cagaagaagg cgatcgtgga cctcctgttc aagaccaacc ggaaggtcac ggttaagcaa 1740
ctcaaggagg actacttcaa gaagatcgag tgcttcgatt cggtggagat ctcaggggtc 1800
gaggacaggt tcaacgcctc cctcgggacc taccacgatc tcctgaagat catcaaggat 1860
aaggacttcc tggacaacga ggagaacgag gacatcctgg aggacatcgt gctgaccctc 1920
acgctgttcg aggacaggga gatgatcgag gagcgcctga agacgtacgc ccatctcttc 1980
gatgacaagg tcatgaagca actcaagaga agaagataca ccgggtgggg gaggctgtcc 2040
cgcaagctca tcaacgggat ccgggacaag cagtcaggga agaccatcct cgacttcctg 2100
aagtctgatg ggttcgccaa caggaacttc atgcaactga tccacgatga ctcactcacc 2160
ttcaaggagg atatccaaaa ggctcaggtg agcgggcagg gggactcgct gcacgagcat 2220
atcgctaacc tcgctgggtc ccctgcgatc aagaagggga tcctgcagac cgtgaaggtt 2280
gtggacgagc tcgtgaaggt catggggcgg cataagcctg agaacatcgt catcgagatg 2340
gccagagaga accaaaccac gcagaagggg caaaagaact ctagggagcg catgaagcgc 2400
atcgaggagg ggatcaagga gctggggtcc caaatcctca aggagcaccc agttgagaac 2460
acccaactgc agaacgagaa gctctacctg tactacctcc agaacgggag ggatatgtat 2520
gtggaccaag agctggatat caaccgcctc agcgattacg acgttgatca tatcgtgccc 2580
cagtctttcc tgaaggatga ctccatcgac aacaaggtcc tcaccaggtc ggacaagaac 2640
cgcgggaagt cagataacgt tccatctgag gaggtcgtta agaagatgaa gaactactgg 2700
aggcagctcc tgaacgccaa gctgatcacg caaaggaagt tcgacaacct caccaaggct 2760
gagagagggg ggctctcaga gctggacaag gctgggttca tcaagcggca gctggtcgag 2820
accagacaaa tcacgaagca cgttgcgcaa atcctcgact ctcggatgaa cacgaagtac 2880
gatgagaacg acaagctgat cagggaggtg aaggtcatca ccctgaagtc taagctcgtc 2940
tccgacttcc gcaaggactt ccagttctac aaggttcgcg agatcaacaa ctaccaccat 3000
gcgcatgacg cttacctcaa cgctgtggtc gggaccgccc tgatcaagaa gtacccgaag 3060
ctggagagcg agttcgtgta cggggactac aaggtttacg atgtgcgcaa gatgatcgcc 3120
aagtcggagc aagagatcgg gaaggccacc gccaagtact tcttctactc aaacatcatg 3180
aacttcttta agaccgagat cacgctggcc aacggggaga tccggaagag acccctcatc 3240
gagaccaacg gggagacggg ggagatcgtg tgggacaagg ggagggattt cgcgaccgtc 3300
cgcaaggttc tctccatgcc ccaggtgaac atcgtcaaga agaccgaggt ccaaacgggg 3360
gggttctcaa aggagtctat cctgcctaag cggaacagcg acaagctcat cgccagaaag 3420
aaggactggg atccaaagaa gtacgggggg ttcgacagcc ctaccgtcgc gtactcggtt 3480
ctggttgtgg ctaaggttga gaaggggaag tccaagaagc tcaagagcgt gaaggagctc 3540
ctggggatca ccatcatgga gcgctccagc ttcgagaaga acccaatcga cttcctggag 3600
gccaaggggt acaaggaggt gaagaaggac ctgatcatca agctcccgaa gtactctctc 3660
ttcgagctgg agaacgggag gaagcgcatg ctggcttccg ctggggagct ccaaaagggg 3720
aacgagctcg ccctgccatc caagtatgtg aacttcctct acctggcgtc ccactacgag 3780
aagctcaagg ggagcccgga ggacaacgag caaaagcagc tgttcgtcga gcagcacaag 3840
cattacctcg acgagatcat cgagcaaatc tccgagttct ccaagcgcgt gatcctcgcg 3900
gacgctaacc tggataaggt cctctccgct tacaacaagc accgggacaa gcccatcaga 3960
gagcaggccg agaacatcat ccatctcttc accctgacga acctcggggc ccctgctgcc 4020
ttcaagtact tcgacaccac gatcgatcgg aagagataca ccagcacgaa ggaggtcctg 4080
gacgcgaccc tcatccacca atctatcacg ggctgtacg agacgagaat cgacctgtca 4140
caactggggg gggacaagag gccggcggca accaagaagg cgggccaggc caagaagaag 4200
aagtga 4206

<210> SEQ ID NO 46
<211> LENGTH: 3873
<212> TYPE: DNA
<213> ORGANISM: Artificial sequence
<220> FEATURE:
<223> OTHER INFORMATION: NLS-Cas12a-NLS

<400> SEQUENCE: 46
atggccccga agaagaagag gaaagtgggc atccacggcg tgcctgcagc aatgtccaag 60
ctggagaagt tcaccaactg ctactccctg agcaagaccc tccgcttcaa ggccatcccc 120
gtgggcaaga cccaggagaa catcgacaac aagaggctcc tggtggagga tgagaagagg 180
gcagaggact acaagggcgt caagaagctg ctcgacaggt actacctgtc cttcatcaac 240
gacgtcctcc acagcatcaa gctgaagaac ctcaacaact acatctccct cttcaggaag 300
aagacccgca ccgagaagga gaacaaggag ctggagaacc tcgagatcaa cctgcgcaag 360
gagatcgcca aggccttcaa gggcaacgag ggctacaaga gcctcttcaa gaaggacatc 420
atcgagacca tcctgcctga gttcctcgac gacaaggatg aaatcgccct ggtgaactcc 480
ttcaacggct tcaccaccgc cttcaccggc ttcttcgaca acagggagaa catgttcagc 540
gaggaagcca aatcaacctc catcgccttc aggtgcatca acgagaacct cacccgctac 600
atctccaaca tggacatctt cgagaaggtc gacgccatct tcgacaagca cgaggtgcag 660
gagatcaagg agaagatcct gaacagcgac tacgacgtgg aggacttctt cgagggcgag 720
ttcttcaact tcgtcctcac ccaagagggc atcgacgtgt acaacgccat catcggcggc 780
ttcgtcaccg agtccggcga gaagatcaag ggcctgaacg agtacatcaa cctctacaac 840
cagaagacca agcagaagct gccgaagttc aagccactgt acaagcaggt gctctccgac 900
agggagtccc tcagcttcta cggcgagggc tacaccagcg acgaggaagt gctggaggtg 960
ttccgcaaca ccctcaacaa gaacagcgag atcttctcca gcatcaagaa gctggagaag 1020
ctgttcaaga acttcgacga gtactccagc gccggcatct tcgtgaagaa cggcccggcc 1080
atctccacca tcagcaagga catcttcggc gagtggaacg tcatccgcga caagtggaac 1140
gccgagtacg acgacatcca cctgaagaag aaggccgtgg tcaccgagaa gtacgaggac 1200
gacaggcgca agtccttcaa gaagatcggc tccttcagcc tggagcagct ccaggagtac 1260
gccgacgccg acctgagcgt ggtcgagaag ctcaaggaga tcatcatcca gaaggtcgac 1320

```
gagatctaca aggtgtacgg ctccagcgag aagctgttcg acgccgactt cgtgctggag   1380
aagtccctca agaagaacga cgccgtggtc gccatcatga aagacctgct cgactccgtc   1440
aagagcttcg agaactacat caaggccttc ttcggcgagg gcaaggagac caacagggac   1500
gagtccttct acggcgactt cgtcctggcc tacgacatcc tgctcaaggt ggaccacatc   1560
tacgacgcca tcaggaacta cgtgacccag aagccgtaca gcaaggacaa gttcaagctc   1620
tacttccaga acccacagtt catgggcggc tgggacaagg acaaggagac cgactacagg   1680
gccaccatcc tgcgctacgg cagcaagtac tacctcgcca tcatggacaa gaagtacgcc   1740
aagtgcctgc agaagatcga caaggacgac gtgaacggca actacgagaa gatcaactac   1800
aagctgctcc cgggcccaaa caagatgctc cccaaggtct tcttctccaa gaagtggatg   1860
gcctactaca accctagcga ggacatccag aagatctaca agaacggcac cttcaagaag   1920
ggcgacatgt tcaacctgaa cgactgccac aagctcatcg acttcttcaa ggactccatc   1980
agcaggtacc cgaagtggtc caacgcctac gacttcaact tcagcgagac cgagaagtac   2040
aaggacatcg ccggcttcta ccgcgaggtc gaggagcagg gctacaaggt gtccttcgag   2100
tccgcctcca agaaggaagt ggacaagctg gtggaggaag gcaagctgta catgttccag   2160
atctacaaca aggacttctc cgacaagagc cacggcaccc caaacctgca caccatgtac   2220
ttcaagctgc tgttcgacga gaacaaccac ggccagatca ggctctccgg cggcgccgag   2280
ctgttcatgc gtagagccag cctgaagaaa gaggagctgg tggtccaccc agcaaacagc   2340
cctatcgcca acaagaaccc cgacaaccct aagaagacca ccaccctgtc ctacgacgtg   2400
tacaaggaca agaggttcag cgaggaccag tacgagctcc acatccccat cgccatcaac   2460
aagtgcccta agaacatctt caagatcaac accgaggtcc gcgtgctgct caagcacgac   2520
gacaacccat acgtgatcgg catcgacagg ggcgagcgca acctgctcta catcgtggtc   2580
gtggacggca agggcaacat cgtcgagcag tactccctca acgagatcat caacaacttc   2640
aacggcatca ggatcaagac cgactaccac agcctgctcg acaagaagga gaaggagagg   2700
ttcgaggccc gccagaactg gacctccatc gagaacatca aggagctgaa ggccggctac   2760
atcagccagg tcgtgcacaa gatctgcgag ctcgtcgaga agtacgacgc cgtgatcgcc   2820
ctggaggacc tcaactccgg cttcaagaac agccgcgtca aggtggagaa gcaggtgtac   2880
cagaagttcg agaagatgct gatcgacaag ctcaactaca tggtcgacaa gaagtccaac   2940
ccctgcgcaa ccggcggcgc cctgaagggc taccagatca ccaacaagtt cgagagcttc   3000
aagtccatga gcacccagaa cggcttcatc ttctacatcc cggcctggct cacctccaag   3060
atcgacccaa gcaccggctt cgtgaacctg ctcaagacca agtacacctc catcgccgac   3120
agcaagaagt tcatctccag cttcgacagg atcatgtatg tgcccgagga agacctgttc   3180
gagttcgccc tcgactacaa gaacttctcc cgcaccgacg ccgattacat caagaagtgg   3240
aagctgtaca gctacggcaa caggatccgc atcttcagga accctaagaa gaacaacgtc   3300
ttcgactggg aggaagtgtg cctgacctcc gcctacaagg agctgttcaa caagtacggc   3360
atcaactacc agcagggcga catcagggcc ctgctctgcg agcagagcga caaggccttc   3420
tactccagct tcatggccct gatgtccctg atgctccaga tgaggaacag catcaccggc   3480
cgcaccgacg tcgacttcct catctccccg gtgaagaaca gcgacggcat cttctacgac   3540
tccaggaact acgaggccca ggagaacgcc atcctgccaa agaacgccga cgccaacggc   3600
gcctacaaca tcgcaaggaa ggtgctctgg gcaatcggcc agttcaagaa ggccgaggac   3660
```

gagaagctgg acaaggtgaa gatcgccatc tccaacaagg agtggctcga gtacgcccag 3720
acctctgtca agcacaagag gccagcagca accaagaagg cgggccaggc caagaagaag 3780
aagggcagct acccgtacga cgtcccagac tacgcctacc cctacgacgt gcctgactac 3840
gcttacccat acgatgtgcc agactacgcc tga 3873

<210> SEQ ID NO 47
<211> LENGTH: 250
<212> TYPE: DNA
<213> ORGANISM: Agrobacterium tumefaciens

<400> SEQUENCE: 47
gatcgttcaa acatttggca ataaagtttc ttaagattga atcctgttgc cggtcttgcg 60
atgattatca tataatttct gttgaattac gttaagcatg taataattaa catgtaatgc 120
atgacgttat ttatgagatg ggtttttatg attagagtcc cgcaattata catttaatac 180
gcgatagaaa acaaaatata gcgcgcaaac taggataaat tatcgcgcgc ggtgtcatct 240
atgttactag 250

<210> SEQ ID NO 48
<211> LENGTH: 903
<212> TYPE: DNA
<213> ORGANISM: Triticum aestivum (var. Chinese Spring)

<400> SEQUENCE: 48
atggccacgg cggcggcggc ggcggcgacg atgcgtctgt cttccccgtt cagggccccg 60
cctctccgtc ctccctgcca ccgcgtcgtc ccgtcgatgc ggggccccag gcgggccggg 120
ctggccgtct cggcggccgc cgccgggtcg ccccccaccg tgctcgtcac cggcgccgga 180
ggacggacag gccaaattgt gtacaagaag ctgaaggaga gggcagacca gtttgtggcc 240
agagggctgg tcaggacgcc ggacagcaag ggtaagatag gcggcggcga cgacgtgttc 300
atcggcgaca tcagggatcc tgggagcatt gctccggcga ttgagggcat cgacgcgctc 360
atcatcctca ccagtggggt cccgaagatg aagcccgggt tcgatcctag caagggtgga 420
cggccggagt tttactttga ggaagggtct gatcctgagc aggtggattg gataggccaa 480
aagaaccaaa ttgatgctgc caagagcatt ggtgtaaagc agatagtttt ggttggatcc 540
atgggcggaa cagatatcaa ccatccatta aacaagcttg ggaatgggaa tatactggtg 600
tggaaacgga aggcagagca gtacctagcg gactctggtc taccatacac aattataagg 660
gctggaggac tacaagacaa agatggtggg gtgcgtgagt tgattgttgg aaaggatgac 720
gagatcttga agacggaaac aaaaactatt gccagggcag atgttgcaga agtttgcata 780
caggccttgc tatttgagga agcaaagttc aaggcgtttg atctggcttc aaaacctgaa 840
ggtgaaggaa caccgatgac agattttaag tctgtttttg cacaaattgc tactcgcttc 900
taa 903

<210> SEQ ID NO 49
<211> LENGTH: 300
<212> TYPE: PRT
<213> ORGANISM: Triticum aestivum (var. Chinese Spring)

<400> SEQUENCE: 49

Met Ala Thr Ala Ala Ala Ala Ala Ala Thr Met Arg Leu Ser Ser Pro
1 5 10 15

Phe Arg Ala Pro Pro Leu Arg Pro Pro Cys His Arg Val Val Pro Ser
20 25 30

```
Met Arg Gly Pro Arg Arg Ala Gly Leu Ala Val Ser Ala Ala Ala Ala
        35                  40                  45

Gly Ser Pro Pro Thr Val Leu Val Thr Gly Ala Gly Gly Arg Thr Gly
    50                  55                  60

Gln Ile Val Tyr Lys Lys Leu Lys Glu Arg Ala Asp Gln Phe Val Ala
65                  70                  75                  80

Arg Gly Leu Val Arg Thr Pro Asp Ser Lys Gly Lys Ile Gly Gly Gly
                85                  90                  95

Asp Asp Val Phe Ile Gly Asp Ile Arg Asp Pro Gly Ser Ile Ala Pro
            100                 105                 110

Ala Ile Glu Gly Ile Asp Ala Leu Ile Ile Leu Thr Ser Gly Val Pro
        115                 120                 125

Lys Met Lys Pro Gly Phe Asp Pro Ser Lys Gly Gly Arg Pro Glu Phe
    130                 135                 140

Tyr Phe Glu Glu Gly Ser Asp Pro Glu Gln Val Asp Trp Ile Gly Gln
145                 150                 155                 160

Lys Asn Gln Ile Asp Ala Ala Lys Ser Ile Gly Val Lys Gln Ile Val
                165                 170                 175

Leu Val Gly Ser Met Gly Gly Thr Asp Ile Asn His Pro Leu Asn Lys
            180                 185                 190

Leu Gly Asn Gly Asn Ile Leu Val Trp Lys Arg Lys Ala Glu Gln Tyr
        195                 200                 205

Leu Ala Asp Ser Gly Leu Pro Tyr Thr Ile Ile Arg Ala Gly Gly Leu
    210                 215                 220

Gln Asp Lys Asp Gly Gly Val Arg Glu Leu Ile Val Gly Lys Asp Asp
225                 230                 235                 240

Glu Ile Leu Lys Thr Glu Thr Lys Thr Ile Ala Arg Ala Asp Val Ala
                245                 250                 255

Glu Val Cys Ile Gln Ala Leu Leu Phe Glu Glu Ala Lys Phe Lys Ala
            260                 265                 270

Phe Asp Leu Ala Ser Lys Pro Glu Gly Glu Gly Thr Pro Met Thr Asp
        275                 280                 285

Phe Lys Ser Val Phe Ala Gln Ile Ala Thr Arg Phe
    290                 295                 300
```

```
<210> SEQ ID NO 50
<211> LENGTH: 3063
<212> TYPE: DNA
<213> ORGANISM: Triticum aestivum (var. Chinese Spring)

<400> SEQUENCE: 50

cgccttagat gccgtcgcct cctagccata agcgtcagaa ggcggtatat aggttatctc      60

cgccggaaaa agggtaaggt ttgcctcgag aatgttttgt ttgactatat cctatgtgga     120

accaaggcta ggtttgcatg caatgaaaaa atgtaattgt aggaggagaa gggagggtgg     180

tagatgtgcg cgacaacaac acacacgcca tatatatata gttggaggag gtggaaaaca     240

aggaggcgat aagaaaaagg gggggaatat ggagaatgtt tgaaatagcg tccaacccga     300

gtttccatta ttaattgtcg gccaaaaaaa gaaggcatgt tactcatgat ggtagtttca     360

agggaagtgg agcctcccag ctagtttgaa cacttaaaaa acaagctaca acagaaagta     420

gtttcaaggg gagtggagcc taaaacttgc atttaaaaag gaaatgcgca cactaagccg     480

aaagtgtgaa cactttgtgc cgacatttcc gaggaagtag gttttatgcg cataacattt     540

tttttgagac aattttatgc gcataactag ggttgactgc tgtggggaag atgaaatttg     600
```

aactgccatt gtgacgcaaa gatttggtga tccaaatttg tatatggacc atgcctgtag 660
gttgggctaa gtatactttt cgaagaaaat aggcccatgt taacttggga agtgggccta 720
ggcccacaaa cctgaaatcc ctgtgaagcc cacattcaca cgcgggccca ccgtcgaagc 780
gataaggaga gtgacagccg ctcagcccgc cggcacaccc gacaacaact ctcgcttcac 840
tcgccggagg gggacggagc aaatatggcc acggcggcgg cggcggcggc gacgatgcgt 900
ctgtcttccc cgttcagggc cccgcctctc cgtcctccct gccaccgcgt cgtcccgtcg 960
atgcggggcc ccaggcgggc cgggctggcc gtctcggcgg ccgccgccgg gtcgcccccc 1020
accgtgctcg tcaccggcgc cggaggacgg acaggtagat actacacatc ccgctagctt 1080
ctttaccttc gcgtcctgta gccgcacatt gttgcacgat gccgccttct cttgctgttc 1140
caatgggatt cagtttgcat ttgtgggaga atttaccggc ggaggcggcg gtttcttgga 1200
atcaagatgc ttcacaacct atggaacctc ctattgattt aaaatttaca ctgccgttta 1260
cgtgctgtga tccggcgtgc gcctctgacc cttgcgctgt ggtgacccag gccaaattgt 1320
gtacaagaag ctgaaggaga gggcagacca gtttgtggcc agagggctgg tcaggacgcc 1380
ggacagcaag ggtaagatag gcggcggcga cgacgtgttc atcggcgaca tcagggatcc 1440
tgggagcatt gctccggcga ttgagggcat cgacgcgctc atcatcctca ccagtggggt 1500
cccgaagatg aagcccgggt tcgatcctag caagggtgga cggccggagt tttactttga 1560
ggaagggtct gatcctgagc aggtaaccgg caaaaatcgc ttggcaatga cattagtcac 1620
attagcaatg acaacttatg catttctttt agagttaatt aatgtccttt gctgttttcc 1680
cttgatttaa ggtggattgg ataggccaaa agaaccaaat tgatgctggt aaatcttcac 1740
cttcttcttg ttctgttaga gcattataca atgtttagca tgttcattga aacgattgat 1800
tggtgaagca tcgatgtgtc attttctctc cggtcgacct ttttcttgtc tgctctctaa 1860
gtttcccatc tttaattatc catgcagcca agagcattgg tgtaaagcag atagttttgg 1920
ttggatccat gggcggaaca gatatcaacc atccattaaa caagcttggg aatgggaata 1980
tactggtata tagcatgctc gacgattttt gtatatgttc taattcccta tacttgtgtg 2040
tgcataaaca tataatatgt accattttga aacttagaat ggccaattgc tcttctaatt 2100
tgcaggtgtg gaaacggaag gcagagcagt acctagcgga ctctggtcta ccatacacaa 2160
ttataaggtt ataacacaga ctcattcggt agtgctattc ttgccatgtt ctgcaaagat 2220
tttttttttg tcacatttga gttatgtaat aggctgacag tcactgtttt ctccaaagat 2280
gcacagtcat agaaataatt ttatatatgt gatgaatgaa gaaaacaaca aaacaacaga 2340
agtgcattat ggagtatgaa gcaccacaaa gaacattaat tttgtataag aaataaaaaa 2400
ttccaattta tttcataggg acattaatcg ttggagtatt ttccaccaac aatcgtgtgc 2460
tgataaaata cctttcccat atcccatctc tttccagggc tggaggacta caagacaaag 2520
atggtggggt gcgtgagttg attgttggaa aggatgacga gatcttgaag acggaaacaa 2580
aaactattgc cagggcagat gttgcagaag tttgcataca ggtaccttta tagaacaaaa 2640
cacatgtttc tgtagataaa ctactgctca atattttttt catcatctac caaatatatt 2700
tcttgcatct atttatgtct tactagctag tggtcatacc actgatccat ctgtgccttt 2760
cctgagtagg ccttgctatt tgaggaagca aagttcaagg cgtttgatct ggcttcaaaa 2820
cctgaaggtg aaggaacacc gatgacagat tttaagtctg tttttgcaca aattgctact 2880
cgcttctaag aggacaagat cattctggcc aatgaaatgg gacagtatct ttaattaggc 2940

```
gatatggaat ttgtactggg tcaggttagt gttctgttta ttaattgagg aaatgcaaca   3000

ttttattcta cgcactatta ttccatagta aattttgtgt ttatctcttt tctttgtggt   3060

caa                                                                 3063
```

<210> SEQ ID NO 51
<211> LENGTH: 960
<212> TYPE: DNA
<213> ORGANISM: Triticum aestivum (var. Spelt)

<400> SEQUENCE: 51

```
atggccacgg cggcggcggc ggcggcgacg atgcgtctgt cttccccgtt cagggccccg     60

cctctccgtc ctccctgcca ccgcgtcgtc ccgtcgatgc ggggccccag gcgggccggg    120

ctggccgtct cggcggccgc cgccgggtcg ccccccaccg tgctcgtcac cggcgccgga    180

ggacggacag gccaaattgt gtacaagaag ctgaaggaga gggcagacca gtttgtggcc    240

agagggctgg tcaggacgcc ggacagcaag ggtaagatag gcggcggcga cgacgtgttc    300

atcggcgaca tcagggatcc tgggagcatt gctccggcga ttgagggcat cgacgcgctc    360

atcatcctca ccagtggggt cccgaagatg aagcccgggt tcgatcctag caagggtgga    420

cggccggagt tttactttga ggaagggtct gatcctgagc aggtggattg gataggccaa    480

aagaaccaaa ttgatgctgc caagagcatt ggtgtaaagc agatagtttt ggttggatcc    540

atgggcggaa cagatatcaa ccatccatta aacaagcttg ggaatgggaa tatactggtg    600

tggaaacgga aggcagagca gtacctagcg gactctggga cattaatcgt tggagtattt    660

tccaccaaca atcgtgtgct gataaaatac ctttcccata tcccatctct ttccagggct    720

ggaggactac aagacaaaga tggtggggtg cgtgagttga ttgttggaaa ggatgacgag    780

atcttgaaga cggaaacaaa aactattgcc agggcagatg ttgcagaagt ttgcatacag    840

gccttgctat ttgaggaagc aaagttcaag gcgtttgatc tggcttcaaa acctgaaggt    900

gaaggaacac cgatgacaga ttttaagtct gtttttgcac aaattgctac tcgcttctaa    960
```

<210> SEQ ID NO 52
<211> LENGTH: 319
<212> TYPE: PRT
<213> ORGANISM: Triticum aestivum (var. Spelt)

<400> SEQUENCE: 52

```
Met Ala Thr Ala Ala Ala Ala Ala Ala Thr Met Arg Leu Ser Ser Pro
1               5                   10                  15

Phe Arg Ala Pro Pro Leu Arg Pro Pro Cys His Arg Val Val Pro Ser
            20                  25                  30

Met Arg Gly Pro Arg Arg Ala Gly Leu Ala Val Ser Ala Ala Ala Ala
        35                  40                  45

Gly Ser Pro Pro Thr Val Leu Val Thr Gly Ala Gly Gly Arg Thr Gly
    50                  55                  60

Gln Ile Val Tyr Lys Lys Leu Lys Glu Arg Ala Asp Gln Phe Val Ala
65                  70                  75                  80

Arg Gly Leu Val Arg Thr Pro Asp Ser Lys Gly Lys Ile Gly Gly Gly
                85                  90                  95

Asp Asp Val Phe Ile Gly Asp Ile Arg Asp Pro Gly Ser Ile Ala Pro
            100                 105                 110

Ala Ile Glu Gly Ile Asp Ala Leu Ile Ile Leu Thr Ser Gly Val Pro
        115                 120                 125

Lys Met Lys Pro Gly Phe Asp Pro Ser Lys Gly Gly Arg Pro Glu Phe
```

```
    130                 135                 140

Tyr Phe Glu Glu Gly Ser Asp Pro Glu Gln Val Asp Trp Ile Gly Gln
145                 150                 155                 160

Lys Asn Gln Ile Asp Ala Ala Lys Ser Ile Gly Val Lys Gln Ile Val
                165                 170                 175

Leu Val Gly Ser Met Gly Gly Thr Asp Ile Asn His Pro Leu Asn Lys
            180                 185                 190

Leu Gly Asn Gly Asn Ile Leu Val Trp Lys Arg Lys Ala Glu Gln Tyr
        195                 200                 205

Leu Ala Asp Ser Gly Thr Leu Ile Val Gly Val Phe Ser Thr Asn Asn
    210                 215                 220

Arg Val Leu Ile Lys Tyr Leu Ser His Ile Pro Ser Leu Ser Arg Ala
225                 230                 235                 240

Gly Gly Leu Gln Asp Lys Asp Gly Gly Val Arg Glu Leu Ile Val Gly
                245                 250                 255

Lys Asp Asp Glu Ile Leu Lys Thr Glu Thr Lys Thr Ile Ala Arg Ala
            260                 265                 270

Asp Val Ala Glu Val Cys Ile Gln Ala Leu Leu Phe Glu Glu Ala Lys
        275                 280                 285

Phe Lys Ala Phe Asp Leu Ala Ser Lys Pro Glu Gly Glu Gly Thr Pro
    290                 295                 300

Met Thr Asp Phe Lys Ser Val Phe Ala Gln Ile Ala Thr Arg Phe
305                 310                 315


<210> SEQ ID NO 53
<211> LENGTH: 5510
<212> TYPE: DNA
<213> ORGANISM: Triticum aestivum (var. Spelt)

<400> SEQUENCE: 53

ggagtcgtgt cttatttggt ggcgtttgtc gactatctcc tgtgtggagc caatgcttgg     60

ctcgcacgca agtcgaaaag aactgcaatg gtaggaggag aagggagagg gtgtggtaga    120

tgcgcacgac aacaacaaca cacgacaaat atatatagtt ggagtaagtg gaaaacaagg    180

acgcgacaag aaagggggag aatgttcgaa atagcgtcca acctaagttc agagaattaa    240

ttgtcaacca aaaattgggc aagggctcag tataccggcc tagaagtgaa aattgcgatc    300

aaaagtttgc accgccgaag aagagaaaag caaaaacttc tcatattttt caaaggattg    360

aacatttttt attgtcatgt tatcccgtag gcaggatatt gacctagcaa ctttggtgta    420

gcctattgta ttactcatat tcatcgagca gtatattatt gaaggggctt ttattgactc    480

taaatgtagc attgttgtaa tgcatttgca taattaaggg tgtgtttggt tgtgtggcta    540

aggatagcca ctttttaagt ggttgccatg tgtttgattt taaaatttgt gtagttcagg    600

atagccatat ccaaggaata ttccataaaa tgtggcacag cggaagcgcc aaaaagtgat    660

gggtaaggtc aaccacccta tgcttgcatg ctcacctcac catctgaatc atttacaacc    720

tgttctgacc ccctccccca aaggaatttt atcaggcttt tggtgagggc attcgcatgt    780

ctgcacttgt catccaatga actgtgacga atactagggt gttagaaagg aaacggcaac    840

tcatgaaata taaccgacaa acatatatat ctataaatca tgcaacaaag aaaccgaaag    900

attacaacaa aaaccatata tggatctgat cataaagggg caattcatca cacggaaaca    960

aacacaccga gaattacatc agatggaaca caatcatgta gagcagcgca tgtgaccatt   1020

gattgaaaag caagggagag aaggaaaagc aagggagaga agatgccaac tagctactgt   1080
```

-continued tatggaccca tagttcaaag aggactattc acacatggtc atggtggcaa cgaggttgct 1140
ggagatgcat ccggcgatga tttatccctc caggaaagta ccggaaaaag gtctccggat 1200
tggatcatcg cgaaacaagt ggtggcgaca gcagaaaaat ccttgataaa caaatcacgt 1260
gagagagctc cgaaattagg gagcatactg aatttaaaga tactagatga taccccgcat 1320
gttattgtga actctggtct accatacaca attataaggt tataacacag actcattcgg 1380
tagtgctatt tgtggtatga gacttattct tgccatgttc tgcaaagaat tttttttgtc 1440
acatttgagt tatgtaatag gctgacagtc actgttttct ccaaagacgc acagtcataa 1500
aagtaatttg aaaaaactgt gcattttgaa aaaaatgttc gcggaatcaa aaaatgtttg 1560
tgattttaca aaaaaatatt cacatattca gaaaatgttg gcgtattcag aaaatgttat 1620
ggaattgaga aattttctgc aaagtttaaa atttttcatg tattttaaaa aggcttcaca 1680
aaatttaaaa aatgtccatt cattacaaaa atgatcctcg attcaaaaat gctcattcaa 1740
ataaaaaaat gttcatgaat tacaaaatta attcccccaa tttttaaaag tgtttcgctg 1800
attcaaaaca aatattcaca ggcttaaaag atgttcacaa ttcctagaaa tgtacacaaa 1860
tttgtaaaaa atcctcgtca atttaaaaaa tgttcgtcaa ttaaaaaaat gtaatgtagt 1920
agtagtatgt tgagtagtcc aaccgaagga tattaattct catctcagtc atcactcctc 1980
ttcctcggat caccggcgat ggcaatggca ttgtccctcc ccaccacggt cttgctcctc 2040
ctcctcctcc tcctcctccc cgtcgcctta gatgccgtcg cctcctagcc ataagcgtca 2100
gaaggcggta tataggttat ctccgccgga aaaagggtaa ggtttgcctc gagaatgttt 2160
tgtttgacta tatcctatgt ggaaccaagg ctaggtttgc atgcaatgaa aaaatgtaat 2220
tgtaggagga gaagggaggg tggtagatgt gcgcgacaac aacacacacg ccatatatat 2280
atagttggag gaggtggaaa acaaggaggc gataagaaaa aggggggggg ggaatatgga 2340
gaatgtttga aatagcgtcc aacccgagtt tccattatta attgtcggcc aaaaaaagaa 2400
ggcatgttac tcatgatggt agtttcaagg gaagtggagc ctcccagcta gtttgaacac 2460
ttaaaaaaac aagctacaac agaaagtagt ttcaagggga gtggagccta aaacttgcat 2520
ttaaaaagga aatgcgcaca ctaagccgaa agtgtgaaca ctttgtgccg acatttccga 2580
ggaagtaggt tttatgcgca taacattttt ttgagacaat tttatgcgca taactagggt 2640
tgactgctgt ggggaagatg aaatttgaac tgccattgtg acgcaaagat ttggtgatcc 2700
aaatttgtat atggaccatg cctgtaggtt gggctaagta tacttttcga agaaaatagg 2760
cccatgttaa cttgggaagt gggcctaggc ccacaaacct gaaatccctg tgaagcccac 2820
attcacacgc gggcccaccg tcgaagcgat aaggagagtg acagccgctc agcccgccgg 2880
cacacccgac aacaactctc gcttcactcg ccggaggggg acggagcaaa tatggccacg 2940
gcggcggcgg cggcggcgac gatgcgtctg tcttccccgt tcagggcccc gcctctccgt 3000
cctccctgcc accgcgtcgt cccgtcgatg cggggcccca ggcgggccgg gctggccgtc 3060
tcggcggccg ccgccgggtc gccccccacc gtgctcgtca ccggcgccgg aggacggaca 3120
ggtagatact acacatcccg ctagcttctt taccttcgcg tcctgtagcc gcacattgtt 3180
gcacgatgcc gccttctctt gctgttccaa tgggattcag tttgcatttg tgggagaatt 3240
taccggcgga ggcggcggtt tcttggaatc aagatgcttc acaacctatg gaacctccta 3300
ttgatttaaa atttacactg ccgtttacgt gctgtgatcc ggcgtgcgcc tctgaccctt 3360
gcgctgtggt gacccaggcc aaattgtgta caagaagctg aaggagaggg cagaccagtt 3420
tgtggccaga gggctggtca ggacgccgga cagcaagggt aagataggcg gcggcgacga 3480
cgtgttcatc ggcgacatca gggatcctgg gagcattgct ccggcgattg agggcatcga 3540
cgcgctcatc atcctcacca gtggggtccc gaagatgaag cccgggttcg atcctagcaa 3600
gggtggacgg ccggagtttt actttgagga agggtctgat cctgagcagg taaccggcaa 3660
aaatcgcttg gcaatgacat tagtcacatt agcaatgaca acttatgcat ttcttttaga 3720
gttaattaat gtcctttgct gttttccctt gatttaaggt ggattggata ggccaaaaga 3780
accaaattga tgctggtaaa tcttcacctt cttcttgttc tgttagagca ttatacaatg 3840
tttagcatgt tcattgaaac gattgattgg tgaagcatcg atgtgtcatt ttctctccgg 3900
tcgacctttt tcttgtctgc tctctaagtt tcccatcttt aattatccat gcagccaaga 3960
gcattggtgt aaagcagata gttttggttg gatccatggg cggaacagat atcaaccatc 4020
cattaaacaa gcttgggaat gggaatatac tggtatatag catgctcgac gatttttgta 4080
tatgttctaa ttccctatac ttgtgtgtgc ataaacatat aatatgtacc attttgaaac 4140
ttagaatggc caattgctct tctaatttgc aggtgtggaa acggaaggca gagcagtacc 4200
tagcggactc tggtctacca tacacaatta taaggttata acacagactc attcggtagt 4260
gctattcttg ccatgttctg caaagatttt tttttgtca catttgagtt atgtaatagg 4320
ctgacagtca ctgttttctc caaagatgca cagtcataga aataatttta tatatgtgat 4380
gaatgaagaa aacaacaaaa caacagaagt gcattatgga gtatgaagca ccacaaagaa 4440
cattaatttt gtataagaaa taaaaaattc caatttattt catagggaca ttaatcgttg 4500
gagtattttc caccaacaat cgtgtgctga taaaatacct ttcccatatc ccatctcttt 4560
ccagggctgg aggactacaa gacaaagatg gtggggtgcg tgagttgatt gttggaaagg 4620
atgacgagat cttgaagacg gaaacaaaaa ctattgccag ggcagatgtt gcagaagttt 4680
gcatacaggt acctttatag aacaaaacac atgtttctgt agataaacta ctgctcaata 4740
tttttatcat catctaccaa atatatttct tgcatctatt tatgtcttac tagctagtgg 4800
tcataccact gatccatctg tgcctttcct gagtaggcct tgctatttga ggaagcaaag 4860
ttcaaggcgt ttgatctggc ttcaaaacct gaaggtgaag gaacaccgat gacagatttt 4920
aagtctgttt ttgcacaaat tgctactcgc ttctaagagg acaagatcat tctggccaat 4980
gaaatgggac agtatcttta attaggcgat atggaatttg tactgggtca ggttagtgtt 5040
ctgtttatta attgaggaaa tgcaacattt tattctacgc actattattc catagtaaat 5100
tttgtgttta tctcttttct ttgtggtcaa tggattctgc ataaaatgtt tatggccctt 5160
ctgttacctg gttgatctgt cctaatttgg atgtacacac ttagtatttg cagttagttt 5220
attttgtaac taaaggtcgg acatgcttgg ggtcatgcgg tcatgatgtt ctggttgatc 5280
tagttttaag ttaatccatt tgctagttta aacaacgttt agggttatcc atgttgcgta 5340
tttatagtcc caccaaatcg ttggttagta taatctggat tgtaaatttg ttagggctat 5400
aaacacccaa cttcacatgc tccttctgta gcaaaagtag aagtggcatg tcctctcctt 5460
ccagattgtc tccgatgctc tgccaacaaa acaacaacaa caacaacaac 5510

<210> SEQ ID NO 54
<211> LENGTH: 23
<212> TYPE: DNA
<213> ORGANISM: Triticum aestivum (var. Spelt)

<400> SEQUENCE: 54
cttcactcgc cggaggggga cgg 23

<210> SEQ ID NO 55
<211> LENGTH: 23
<212> TYPE: DNA
<213> ORGANISM: Triticum aestivum (var. Spelt)

<400> SEQUENCE: 55
ggagggggac ggagcaaata tgg 23

<210> SEQ ID NO 56
<211> LENGTH: 103
<212> TYPE: DNA
<213> ORGANISM: Triticum aestivum (var. Spelt)

<400> SEQUENCE: 56
cttcactcgc cggaggggga gttttagagc tagaaatagc aagttaaaat aaggctagtc 60
cgttatcaac ttgaaaaagt ggcaccgagt cggtgctttt ttt 103

<210> SEQ ID NO 57
<211> LENGTH: 103
<212> TYPE: DNA
<213> ORGANISM: Triticum aestivum (var. Spelt)

<400> SEQUENCE: 57
ggagggggac ggagcaaata gttttagagc tagaaatagc aagttaaaat aaggctagtc 60
cgttatcaac ttgaaaaagt ggcaccgagt cggtgctttt ttt 103

<210> SEQ ID NO 58
<211> LENGTH: 2379
<212> TYPE: DNA
<213> ORGANISM: Triticum aestivum

<400> SEQUENCE: 58
atgcctcgct tctcctccac cacgccaatg tcgccacccc gcctcctcct ccggctcggc 60
gcccgccact cctcctccac ctctcatccc tcacgcatct gggatcccca cgccgccttc 120
gccgctgcga cgcagcgggc gcgctctggc acgctcacca cggaggacgc acaccacctg 180
tttgatgaat tgctgcggca gggcaatcct gtccaggagc gtcccttgac taactttctg 240
gctgccctcg cccgcgcgcc cgcgtccgca ttctgcagcg atggccctgc cctggccgtc 300
gccctcttcg gccgtttgtc ccgaggcgcc ggacgacggg tggcgcagcc aaatgtcttc 360
acctatggcg tcctcatgga ctgctgctgc cgtgcgcgcc gcctggatct agcgatcgcc 420
ttcttcgccc gtctcctcaa gacgggactg gaggcaaacc aagtcatctt ctgcaccctc 480
ctcaagggac tctgccacgc aaagcgctca gatgaggctt tggacgtggt gcttcacagg 540
atgcctgagc taggctgcac ccccaacgtg gtggcctata ccacggtcat ccacggcttc 600
ttgaaggaag gccaagtagg caaggcatgc aatctattcc atggaatggc gcagcagggc 660
gttgcgcctg atgtggtgac atataactcg gttatcgatg cgttgtgcaa ggccagagca 720
atggacaagg cagagtattt ccttcgtgaa atggttgata atggtgtcgt acctaataat 780
gtgacatata atagcctcat ccatggatat tcctctttgg gccatcagaa ggaggctgtt 840
agggtgctga aagaaatgac aagacagggt atcataccag atgtcattac ctgcacctca 900
ctcatgacct tcctttgcaa gaatggaaaa agcaaggaag ctgcagaaat ttttgattca 960
atggccacga agggcctgaa acatgacgcc gtttcatatg ctattctcct tcatgggtat 1020
gccactgaag gatgcttggt tgatatgatt aatctcttca attcgatgga cagagactgt 1080
attctaccta actgtcatat cttcaacata ctgatttatg catatgctaa atctgggaag 1140
cttgataagg ctatgcttat atttagagat atgcagaaac aaggagtgag cccagatgca 1200
ttcacatatt caaccttaat acatgcattt tgtaaaaagg gtcggttgga cgatgctatg 1260
ataaagttta atcagatggt tgatacagga gtacgacagg gcacagctgt ttatggttct 1320
ctaatccagg gtttttgtac acacggcgat ttggtgaaag gaaaggaatt ggttactgaa 1380
atgatgaaca aaggtatacc tcctcctgac attatgttct tccattcaat catgcagaac 1440
ctatgcacag aaggaagggt agtagaagca cgggatatcc ttggcttgat agcacacata 1500
ggtatgaggc ctaatgtttg cacatttaat atactgattg gtggatactg cctagtccgc 1560
aagatggagg atgcctcaaa aatatttcat gatatgatgt catatggttt agaaccttct 1620
aatgttacgt atggtattct tattaatggc tattgcaaaa acagaaggat tgatgacggg 1680
ctgattctgt tcaaagaaat gttgcgcaag ggacttaaac ctacaacttt taattacaac 1740
atcatactgg atggattatt tctggctgga cgaactgttg ctgcaaagga aaagtttgat 1800
gagatggttg aatctggagt aagtatgtgc atcagtactt actctatagt tcttcgtgga 1860
ctttgtagaa ataattgtag cggcgaagcc atcacgctat tccagacatt aagcgcaatg 1920
gatgtgaaat tcaatattag aattgtcaat atcatgattg atgccttctt cagggttcag 1980
cgaaagcaag aagctaagga tttgtttgct gcaataacag ccaatgggtt ggttgctaat 2040
gtttttacct acagcctaat gatgacaaat cttataaaag aagggtcagt ggaagaggct 2100
gacacactct ttttatcgat ggagatgagc ggctgtactt cgaactcgtg gatgttaaat 2160
cttattatca gagggttgct ggaaaaagga gagatagtca aggctggatg ttatatgtct 2220
aaagttgatg ccaagagcta ctcacttgaa gctaaaactg tttcgttgct gatctatctc 2280
ttttcaggga aagggaaata cagagaacac ataagattgc tacctacaaa gtatcagttt 2340
ctcgaagaag cagccacagt tgaatggttt gctatatag 2379

<210> SEQ ID NO 59
<211> LENGTH: 2880
<212> TYPE: DNA
<213> ORGANISM: Triticum aestivum (var. Chinese Spring)

<400> SEQUENCE: 59
gagtcgtgtc ttatttggtg gcgtttgtcg actatctcct gtgtggagcc aatgcttggc 60
tcgcacgcaa gtcgaaaaga actgcaatgg taggaggaga agggagaggg tgtggtagat 120
gcgcacgaca acaacaacac acgacaaata tatatagttg gagtaagtgg aaaacaagga 180
cgcgacaaga aagggggaga atgttcgaaa tagcgtccaa cctaagttca gagaattaat 240
tgtcaaccaa aaattgggca agggctcagt ataccggcct agaagtgaaa attgcgatca 300
aaagtttgca ccgccgaaga agagaaaagc aaaaacttct catatttttc aaaggattga 360
acatttttta ttgtcatgtt atcccgtagg caggatattg acctagcaac tttggtgtag 420
cctattgtat tactcatatt catcgagcag tatattattg aaggggcttt tattgactct 480
aaatgtagca ttgttgtaat gcatttgcat aattaagggt gtgtttggtt gtgtggctaa 540
ggatagccac tttttaagtg gttgccatgt gtttgatttt aaaatttgtg tagttcagga 600
tagccatatc caaggaatat tccataaaat gtggcacagc ggaagcgcca aaaagtgatg 660
ggtaaggtca accaccctat gcttgcatgc tcacctcacc atctgaatca tttacaacct 720
gttctgaccc cctcccccaa aggaatttta tcaggctttt ggtgagggca ttcgcatgtc 780
tgcacttgtc atccaatgaa ctgtgacgaa tactagggtg ttagaaagga aacggcaact 840

-continued catgaaatat aaccgacaaa catatatatc tataaatcat gcaacaaaga aaccgaaaga 900
ttacaacaaa aaccatatat ggatctgatc ataaaggggc aattcatcac acggaaacaa 960
acacaccgag aattacatca gatggaacac aatcatgtag agcagcgcat gtgaccattg 1020
attgaaaagc aagggagaga aggaaaagca agggagagaa gatgccaact agctactgtt 1080
atggacccat agttcaaaga ggactattca cacatggtca tggtggcaac gaggttgctg 1140
gagatgcatc cggcgatgat ttatccctcc aggaaagtac cggaaaaagg tctccggatt 1200
ggatcatcgc gaaacaagtg gtggcgacag cagaaaaatc cttgataaac aaatcacgtg 1260
agagagctcc gaaattaggg agcatactga atttaaagat actagatgat accccgcatg 1320
ttattgtgaa ctctggtcta ccatacacaa ttataaggtt ataacacaga ctcattcggt 1380
agtgctattt gtggtatgag acttattctt gccatgttct gcaaagaatt ttttttgtca 1440
catttgagtt atgtaatagg ctgacagtca ctgttttctc caaagacgca cagtcataaa 1500
agtaatttga aaaaactgtg cattttgaaa aaaatgttcg cggaatcaaa aaatgtttgt 1560
gattttacaa aaaaatattc acatattcag aaaatgttgg cgtattcaga aaatgttatg 1620
gaattgagaa attttctgca aagtttaaaa tttttcatgt attttaaaaa ggcttcacaa 1680
aatttaaaaa atgtccattc attacaaaaa tgatcctcga ttcaaaaatg ctcattcaaa 1740
taaaaaaatg ttcatgaatt acaaaattaa ttccccccaat ttttaaaagt gtttcgctga 1800
ttcaaaacaa atattcacag gcttaaaaga tgttcacaat tcctagaaat gtacacaaat 1860
ttgtaaaaaa tcctcgtcaa tttaaaaaat gttcgtcaat taaaaaaatg taatgtagta 1920
gtagtatgtt gagtagtcca accgaaggat attaattctc atctcagtca tcactcctct 1980
tcctcggatc accggcgatg gcaatggcat tgtccctccc caccacggtc ttgctcctcc 2040
tcctcctcct cctcctcccc gtcgccttag atgccgtcgc ctcctagcca taagcgtcag 2100
aaggcggtat ataggttatc tccgccggaa aaagggtaag gtttgcctcg agaatgtttt 2160
gtttgactat atcctatgtg gaaccaaggc taggtttgca tgcaatgaaa aaatgtaatt 2220
gtaggaggag aagggagggt ggtagatgtg cgcgacaaca acacacacgc catatatata 2280
tagttggagg aggtggaaaa caaggaggcg ataagaaaaa gggggggggg gaatatggag 2340
aatgtttgaa atagcgtcca acccgagttt ccattattaa ttgtcggcca aaaaaagaag 2400
gcatgttact catgatggta gtttcaaggg aagtggagcc tcccagctag tttgaacact 2460
taaaaaaaca agctacaaca gaaagtagtt tcaaggggag tggagcctaa aacttgcatt 2520
taaaaaggaa atgcgcacac taagccgaaa gtgtgaacac tttgtgccga catttccgag 2580
gaagtaggtt ttatgcgcat aacatttttt tgagacaatt ttatgcgcat aactagggtt 2640
gactgctgtg gggaagatga aatttgaact gccattgtga cgcaaagatt tggtgatcca 2700
aatttgtata tggaccatgc ctgtaggttg ggctaagtat acttttcgaa gaaaataggc 2760
ccatgttaac ttgggaagtg ggcctaggcc cacaaacctg aaatccctgt gaagcccaca 2820
ttcacacgcg ggcccaccgt cgaagcgata aggagagtga cagccgctca gcccgccggc 2880

<210> SEQ ID NO 60
<211> LENGTH: 80
<212> TYPE: DNA
<213> ORGANISM: Triticum aestivum

<400> SEQUENCE: 60
gccccgtcgt cctgctccca gttgagttcg cgacctacac accggccatg ccccgcttct 60
cctccaccac gccaatgtcg 80

-continued

```
<210> SEQ ID NO 61
<211> LENGTH: 80
<212> TYPE: DNA
<213> ORGANISM: Triticum aestivum

<400> SEQUENCE: 61

ggttcgtgtc cggcggctcg atttgagggc cggacggtcc tcgccatggg gaactgctgg     60

ggcgccaaga tcagctccga                                                  80


<210> SEQ ID NO 62
<211> LENGTH: 80
<212> TYPE: DNA
<213> ORGANISM: Triticum aestivum

<400> SEQUENCE: 62

tggtcactgg actgatattt cttttccaga ttttgaaggt tcacagaagg agagatggca     60

gctctaacca gccttgcctc                                                  80


<210> SEQ ID NO 63
<211> LENGTH: 73
<212> TYPE: DNA
<213> ORGANISM: Triticum aestivum

<400> SEQUENCE: 63

acaactctcg cttcactcgc cggaggggga cggagcaaat atggccacgg cggcggcggc     60

ggcggcgacg atg                                                         73
```